(12) United States Patent
Mansfield, III et al.

(10) Patent No.: US 11,672,965 B2
(45) Date of Patent: Jun. 13, 2023

(54) MICRONEEDLE ENCLOSURE AND APPLICATOR DEVICE FOR MICRONEEDLE ARRAY BASED CONTINUOUS ANALYTE MONITORING DEVICE

(71) Applicant: Biolinq Incorporated, San Diego, CA (US)

(72) Inventors: George Albert Mansfield, III, San Diego, CA (US); David Michael Morelock, Escondido, CA (US); Mark Christopher Brister, San Diego, CA (US); Nathan Thomas Balcom, San Marcos, CA (US); Joshua David Doan, Oceanside, CA (US); Joshua Andrew Warner, Escondido, CA (US)

(73) Assignee: Biolinq Incorporated, San Diego, CA (US)

( * ) Notice: Subject to any disclaimer, the term of this patent is extended or adjusted under 35 U.S.C. 154(b) by 0 days.

(21) Appl. No.: 17/954,289

(22) Filed: Sep. 27, 2022

(65) Prior Publication Data
US 2023/0099617 A1 Mar. 30, 2023

Related U.S. Application Data

(60) Provisional application No. 63/355,987, filed on Jun. 27, 2022, provisional application No. 63/291,293,
(Continued)

(51) Int. Cl.
*A61M 37/00* (2006.01)
*A61B 5/145* (2006.01)

(52) U.S. Cl.
CPC ..... *A61M 37/0015* (2013.01); *A61B 5/14532* (2013.01); *A61M 2037/0061* (2013.01)

(58) Field of Classification Search
CPC ............ A61M 37/0015; A61M 5/3202; A61M 2037/0061; A61B 5/14532
See application file for complete search history.

(56) References Cited

U.S. PATENT DOCUMENTS

| 6,855,131 B2 | 2/2005 | Trautman et al. |
| 7,097,631 B2 | 8/2006 | Trautman et al. |

(Continued)

FOREIGN PATENT DOCUMENTS

| EP | 2532305 A1 | 12/2012 |
| WO | WO-2007097754 A1 | 8/2007 |

(Continued)

OTHER PUBLICATIONS

Abbot press release (2020). "New late-breaking data show use of abbott'sFreestyle® Libre System significantly reduces HBA1C levels in people with type 2 diabetes using insulin or not," 3 pages.
(Continued)

*Primary Examiner* — Amber R Stiles
(74) *Attorney, Agent, or Firm* — Cooley LLP

(57) ABSTRACT

An applicator for an analyte monitoring device may include an actuatable housing having a body defining a cavity therein and having a distal opening and a side opening. A cuff and a shuttle are received within the cavity and are separately translatable relative to the housing body. A base may removable engage the housing body at the distal opening. The housing body, the cuff, the shuttle, and/or the base may be engaged with one another with one or more releasable coupling features. The base may be removed from an engagement with the housing body, causing the cuff and the shuttle to be aligned and positioned in a configuration in which the analyte monitoring device, held by the shuttle, is ready for insertion into the skin.

29 Claims, 98 Drawing Sheets

Related U.S. Application Data filed on Dec. 17, 2021, provisional application No. 63/249,399, filed on Sep. 28, 2021.

(56) References Cited

U.S. PATENT DOCUMENTS

| | | |
|---|---|---|
| 7,582,059 B2 | 9/2009 | Funderburk et al. |
| 7,946,984 B2 | 5/2011 | Brister et al. |
| 8,094,009 B2 | 1/2012 | Allen et al. |
| 8,125,331 B2 | 2/2012 | Allen et al. |
| 8,130,095 B2 | 3/2012 | Allen et al. |
| 8,175,673 B2 | 5/2012 | Say et al. |
| 8,252,229 B2 | 8/2012 | Thomas et al. |
| 8,267,889 B2 | 9/2012 | Cantor et al. |
| 8,280,475 B2 | 10/2012 | Brister et al. |
| 8,284,046 B2 | 10/2012 | Allen et al. |
| 8,579,862 B2 | 11/2013 | Kobayashi et al. |
| 8,652,043 B2 | 2/2014 | Drucker et al. |
| 8,753,318 B2 | 6/2014 | Trautman et al. |
| 8,758,298 B2 | 6/2014 | Cantor et al. |
| 8,764,657 B2 | 7/2014 | Curry et al. |
| 8,821,446 B2 | 9/2014 | Trautman et al. |
| 9,008,745 B2 | 4/2015 | Pushpala et al. |
| 9,055,901 B2 | 6/2015 | Brister et al. |
| 9,101,305 B2 | 8/2015 | Larson et al. |
| 9,119,945 B2 | 9/2015 | Simons et al. |
| 9,174,035 B2 | 11/2015 | Ringsred et al. |
| 9,215,992 B2 | 12/2015 | Donnay et al. |
| 9,357,951 B2 | 6/2016 | Simpson et al. |
| 9,402,544 B2 | 8/2016 | Yee et al. |
| 9,402,570 B2 | 8/2016 | Pace et al. |
| 9,415,198 B2 | 8/2016 | McAllister |
| 9,492,647 B2 | 11/2016 | Stumber et al. |
| 9,610,401 B2 | 4/2017 | Antonio et al. |
| 9,615,779 B2 | 4/2017 | Pryor et al. |
| 9,636,060 B2 | 5/2017 | Feldman et al. |
| 9,642,568 B2 | 5/2017 | Shah et al. |
| 9,687,640 B2 | 6/2017 | Trautman et al. |
| 9,717,843 B2 | 8/2017 | Grucela et al. |
| 9,737,247 B2 | 8/2017 | Wang et al. |
| 9,743,870 B2 | 8/2017 | Wang et al. |
| 9,782,574 B2 | 10/2017 | Simmers |
| 9,789,249 B2 | 10/2017 | Frederickson et al. |
| 9,814,414 B2 | 11/2017 | Brister et al. |
| 9,844,328 B2 | 12/2017 | Simpson et al. |
| 9,933,387 B1 | 4/2018 | McCanna et al. |
| 9,949,642 B2 | 4/2018 | Love et al. |
| 9,968,742 B2 | 5/2018 | Van et al. |
| 10,010,280 B2 | 7/2018 | Donnay et al. |
| 10,010,707 B2 | 7/2018 | Colburn et al. |
| 10,092,207 B1 | 10/2018 | Windmiller |
| 10,136,846 B2 | 11/2018 | Wang et al. |
| 10,213,139 B2 | 2/2019 | Rao et al. |
| 10,213,141 B2 | 2/2019 | Cole et al. |
| 10,278,732 B2 | 5/2019 | Schoonmaker et al. |
| 10,300,260 B2 | 5/2019 | Wirtanen et al. |
| 10,405,339 B2 | 9/2019 | Yamada et al. |
| 10,406,339 B2 | 9/2019 | Simmers |
| 10,413,183 B2 | 9/2019 | Antonio et al. |
| 10,492,685 B2 | 12/2019 | Bernstein et al. |
| 10,492,708 B1 | 12/2019 | Windmiller |
| D875,254 S | 2/2020 | Cooke et al. |
| 10,574,944 B2 | 2/2020 | Adelson et al. |
| 10,595,754 B2 | 3/2020 | Pushpala et al. |
| 10,596,295 B2 | 3/2020 | Larson et al. |
| 10,709,834 B2 | 7/2020 | Chiu et al. |
| 10,863,944 B2 | 12/2020 | Gray et al. |
| 10,898,115 B2 | 1/2021 | Halac et al. |
| 10,932,699 B2 | 3/2021 | Lin et al. |
| 10,973,443 B2 | 4/2021 | Funderburk et al. |
| 10,993,646 B2 | 5/2021 | Scott et al. |
| 11,045,142 B1 | 6/2021 | Windmiller et al. |
| 11,058,329 B2 | 7/2021 | Simpson et al. |
| 11,071,478 B2 | 7/2021 | Rao et al. |
| 11,122,043 B2 | 9/2021 | Love et al. |
| 11,172,851 B2 | 11/2021 | Pushpala et al. |
| 2002/0087182 A1* | 7/2002 | Trautman ........... A61B 5/15194 606/186 |
| 2008/0114280 A1 | 5/2008 | Stafford |
| 2008/0183144 A1 | 7/2008 | Trautman et al. |
| 2008/0242961 A1 | 10/2008 | Brister et al. |
| 2010/0056873 A1 | 3/2010 | Allen et al. |
| 2011/0082484 A1 | 4/2011 | Saravia et al. |
| 2011/0106126 A1 | 5/2011 | Love et al. |
| 2011/0190603 A1 | 8/2011 | Stafford |
| 2011/0319729 A1 | 12/2011 | Donnay et al. |
| 2012/0197222 A1 | 8/2012 | Donnay et al. |
| 2012/0303043 A1 | 11/2012 | Donnay |
| 2014/0275907 A1 | 9/2014 | Feldman et al. |
| 2014/0330209 A1 | 11/2014 | Frederickson et al. |
| 2014/0336487 A1 | 11/2014 | Wang et al. |
| 2015/0173661 A1 | 6/2015 | Myles |
| 2015/0351674 A1 | 12/2015 | Thomas et al. |
| 2016/0029931 A1 | 2/2016 | Salas-Boni et al. |
| 2017/0361079 A1 | 12/2017 | Trautman et al. |
| 2018/0317820 A1 | 11/2018 | Pace et al. |
| 2019/0059796 A1 | 2/2019 | Larson et al. |
| 2019/0120785 A1 | 4/2019 | Halac et al. |
| 2019/0125223 A1 | 5/2019 | Wang et al. |
| 2019/0133501 A1 | 5/2019 | Rao et al. |
| 2019/0133510 A1 | 5/2019 | El Kaliouby et al. |
| 2019/0239825 A1 | 8/2019 | Kumar et al. |
| 2019/0309433 A1 | 10/2019 | Sattayasamitsathit et al. |
| 2019/0336053 A1 | 11/2019 | Halac et al. |
| 2019/0339224 A1 | 11/2019 | Bhavaraju et al. |
| 2020/0037939 A1 | 2/2020 | Castagna et al. |
| 2020/0085341 A1 | 3/2020 | Windmiller |
| 2020/0101286 A1 | 4/2020 | Windmiller et al. |
| 2020/0138346 A1 | 5/2020 | Brister et al. |
| 2020/0209179 A1 | 7/2020 | Bohm et al. |
| 2020/0214566 A1 | 7/2020 | Allen et al. |
| 2020/0254240 A1 | 8/2020 | Windmiller et al. |
| 2020/0297997 A1 | 9/2020 | Windmiller et al. |
| 2020/0330010 A1 | 10/2020 | Barry et al. |
| 2020/0375455 A1 | 12/2020 | Van Tassel et al. |
| 2021/0007651 A1 | 1/2021 | Donnay et al. |
| 2021/0038131 A1 | 2/2021 | Li et al. |
| 2021/0076987 A1 | 3/2021 | Stafford |
| 2021/0133126 A1 | 5/2021 | Yamakita et al. |
| 2021/0142912 A1 | 5/2021 | Belliveau et al. |
| 2021/0186425 A1 | 6/2021 | Rodriguez et al. |
| 2021/0187286 A1 | 6/2021 | Windmiller et al. |
| 2021/0196162 A1 | 7/2021 | Halac et al. |
| 2021/0204841 A1 | 7/2021 | Thomas et al. |
| 2021/0219877 A1 | 7/2021 | Baker et al. |
| 2021/0260257 A1 | 8/2021 | McCanless et al. |
| 2021/0308009 A1 | 10/2021 | Cho et al. |
| 2021/0315493 A1 | 10/2021 | Pace et al. |
| 2021/0321942 A1 | 10/2021 | Pushpala et al. |
| 2021/0393201 A1 | 12/2021 | Morelock et al. |
| 2022/0031209 A1 | 2/2022 | Windmiller et al. |
| 2022/0031244 A1 | 2/2022 | Windmiller et al. |
| 2022/0079481 A1 | 3/2022 | Pushpala et al. |
| 2022/0175278 A1 | 6/2022 | Campbell et al. |

FOREIGN PATENT DOCUMENTS

| | | |
|---|---|---|
| WO | WO-2013066854 A1 | 5/2013 |
| WO | WO-2014055456 A1 | 4/2014 |
| WO | WO-2018071265 A1 | 4/2018 |
| WO | WO-2019084023 A1 | 5/2019 |
| WO | WO-2019236859 A1 | 12/2019 |
| WO | WO-2019236876 A1 | 12/2019 |
| WO | WO-2021101857 A1 | 5/2021 |
| WO | WO-2021158372 A1 | 8/2021 |

OTHER PUBLICATIONS

American Diabetes Association® Press Release (2020). "American Diabetes Association®Applauds policymakers' Focus on Addressing High Costs of Insulin for Seven Million Americans," 4 pages.

Bantle, J.P. et al. (1997). "Glucose measurement in patients with diabetes mellitus with dermal interstitial fluid," J. Lab. Clin. Med. 130:436-441.

(56) References Cited

OTHER PUBLICATIONS

Beckles, G.L. et al. (2016). "Disparities in the prevalence of diagnosed diabetes—United States, 1999-2002 and 2011-2014," MMWR 65:1265-1269.

Cao, J. et al. (2017). "Validation of capillary blood analysis and capillary testing mode on the epoc Point of Care system," Pract. Lab. Med. 9:24-27.

Castle, J.R. et al. (2012). "The accuracy benefit of multiple amperometric glucose sensors in people with type 1 diabetes," Diabetes Care 35:706-710.

DEXCOM (2020). Analyst Day Presentation, 19 total pages.

DEXCOM (2020). Analyst Day Presentation, 27 total pages.

Diabetes Care (2021). "7. Diabetes Technology: Standards of Medical Care in Diabetes—2021," Diabetes Care 44(Supplement 1):S85-S99.

Fang, M. et al. (2021). "Trends in Diabetes Treatment and Control in U.S. Adults, 1999-2018," N. Engl. Med. 384:2219-2228.

French, D.P. et al. (2008). "Original Article: Psychological Care Self-monitoring of blood glucose changed non-insulin-treated Type 2 diabetes patients' beliefs about diabetes and self-monitoring in a randomized trial," Diav. Med. 25:1218-1228.

Grady, M. et al. (2017). "Examining the Impact of a Novel Blood Glucose Monitor with Color Range Indicator on Decision-Making in Patients With Type 1 and Type 2 Diabetes and its Association With Patient Numeracy Level," JMIR Diabetes 2:e24.

Grady, M. et al. (2018). "Use of Blood Glucose Meters Featuring Color Range Indicators Improves Glycemic Control in Patients with Diabetes in Comparison to Blood Glucose Meters Without Color (ACCENTS Study)," J. Diab. Sci. Tech. 12:1211-1219.

Groenendaal, W. et al. (2008). "Modeling Glucose and Water Dynamics in Human Skin," Diab. Tech. Therap. 10:283-293.

International Search Report dated Sep. 9, 2021, for PCT Application No. PCT/US2021/037511, filed on Jun. 15, 2021, 2 pages.—(023/02WO).

Juvenile Diabetes Research Foundation Continuous Glucose Monitoring Study Group (2008). "Continuous Glucose Monitoring and Intensive Treatment of Type 1 Diabetes," N. Engl. Med. 359:1464-1476.

Karter, A.J. et al. (2021). "Association of Real-time Continuous Glucose Monitoring With Glycemic Control and Acute Metabolic Events Among Patients With Insulin-Treated Diabetes," JAMA 325:2273-2284.

Martens, T. et al. (2021). "Effect of Continuous Glucose Monitoring on Glycemic Control in Patients with Type 2 Diabetes Treated with Basal Insulin A Randomized Clinical Trial," JAMA 325:2262-2272.

McClatchey, P.M. et al. (2019). "Fibrotic Encapsulation Is the Dominant Source of Continuous Glucose Monitor Delays," Diabetes 68:1892-1901.

Neerken, S. et al. (2004). "Characterization of age-related effects in human skin: A comparative study that applies confocal laser scanning microscopy and optical coherence tomography," J. Biomed. Optics 9:274-281.

Polonsky, W.H. et al. (2011). "A survey of blood glucose monitoring in patients with type 2 diabetes: Are recommendations from health care professionals being followed?" Curr. Med. Res. & Opinion 27:31-37.

Rigla, M. et al. (2018). "Human Subcutaneous Tissue Response to Glucose Sensors: Macrophages Accumulation Impact on Sensor Accuracy," Diabetes Technology & Therapeutics 20:296-302.

Sheikh, Z. et al. (2015). "Macrophages, Foreign Body Giant Cells and Their Response to Implantable Biomaterials," Materials 8:5671-5701.

Shi, T. et al. (2016). "Modeling and Measurement of Correlation between Blood and Interstitial Glucose Changes," J. Diab. Res. vol. 2016, 9 pages.

Written Opinion of the International Searching Authority dated Sep. 9, 2021, for PCT Application No. PCT/US2021/037511, filed on Jun. 15, 2021,6 pages.—(023/02WO).

International Search Report and Written Opinion dated Mar. 20, 2023, for PCT Application No. PCT/US2022/044950, filed Sep. 27, 2022, 26 pages.

Invitation to Pay Additional Fees dated Jan. 26, 2023, for PCT Application No. PCT/US2022/044950, filed Sep. 27, 2022, 22 pages.

\* cited by examiner

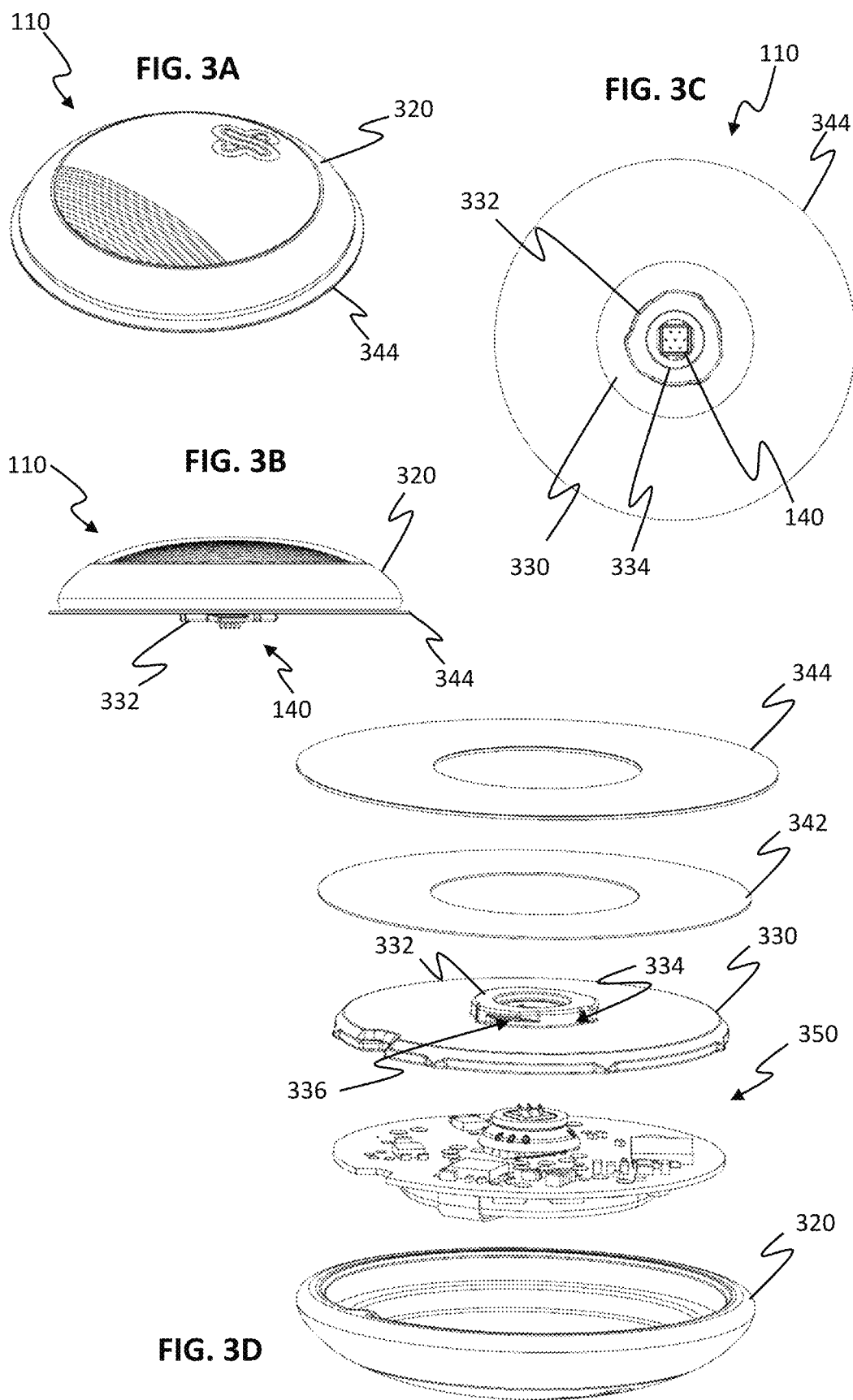

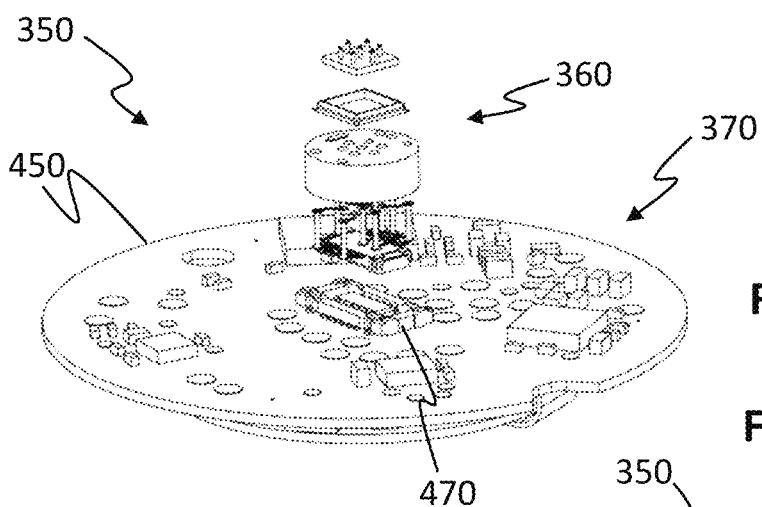
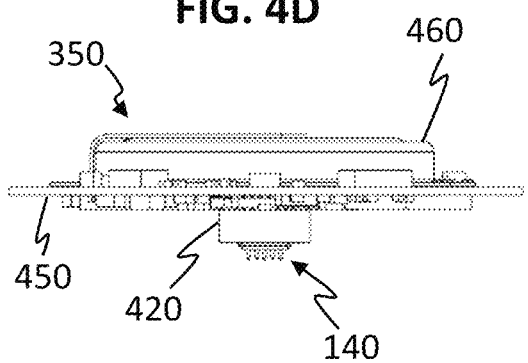
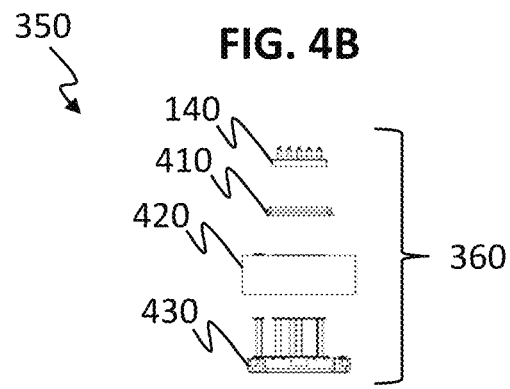
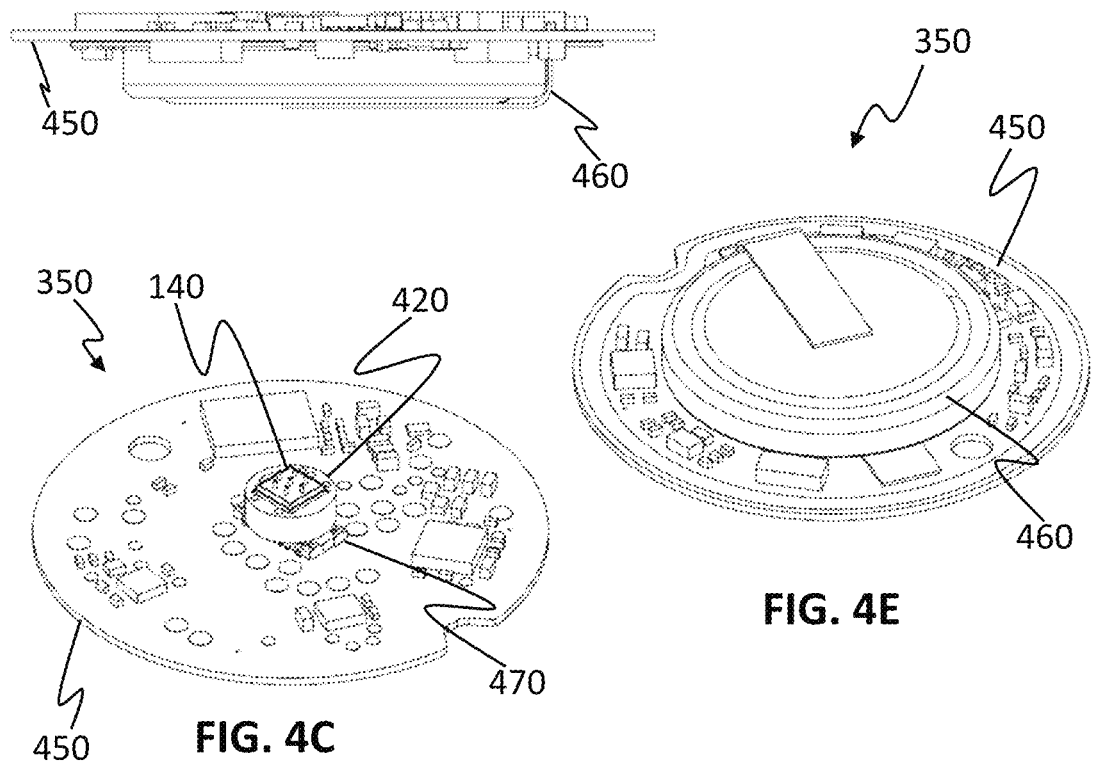
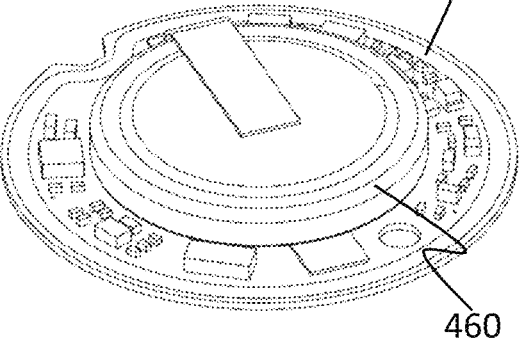

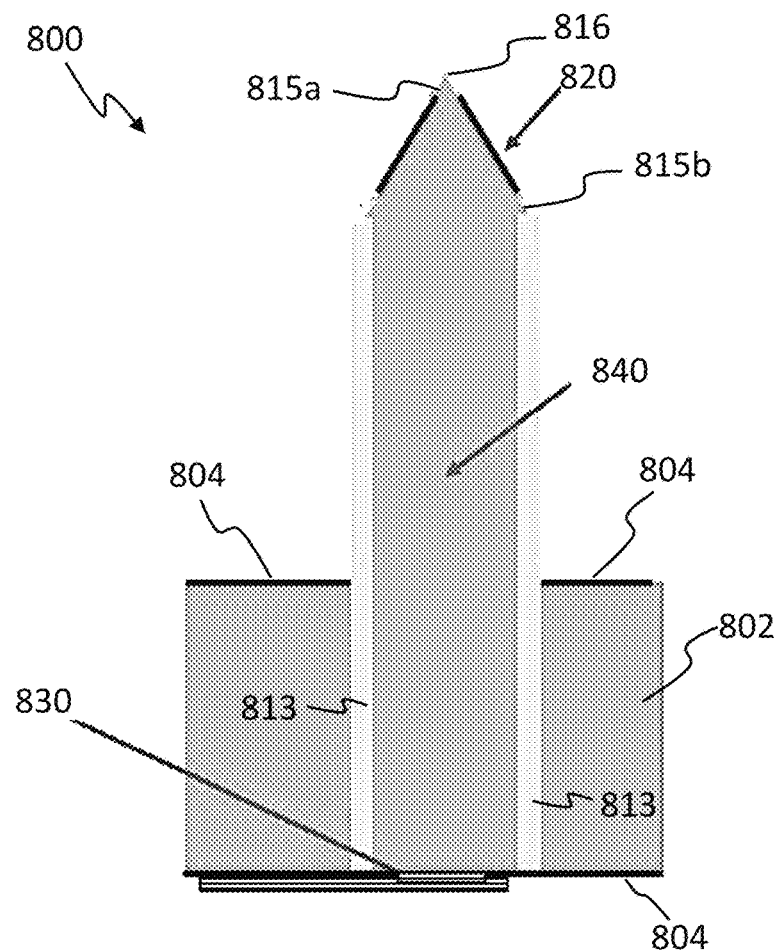
FIG. 8A
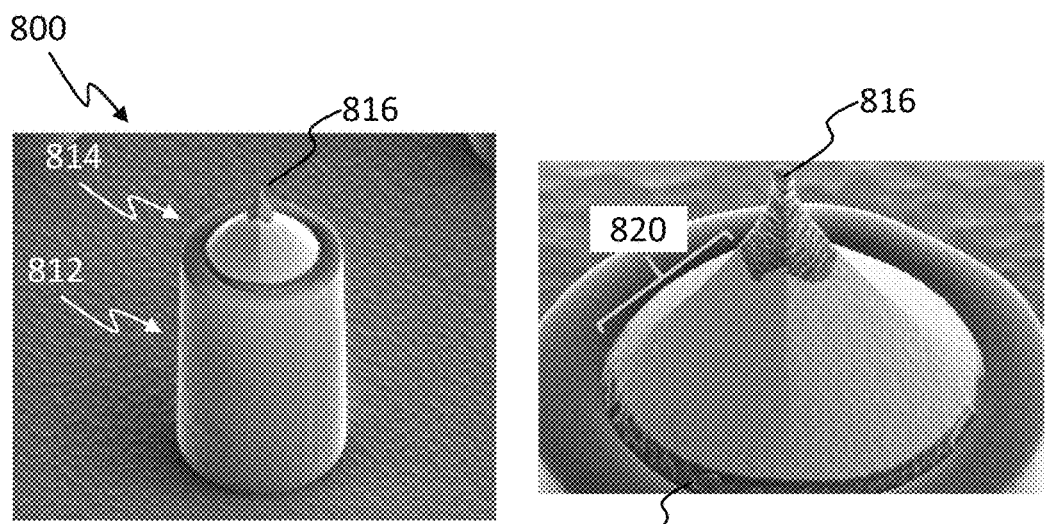
FIG. 8B
FIG. 8C

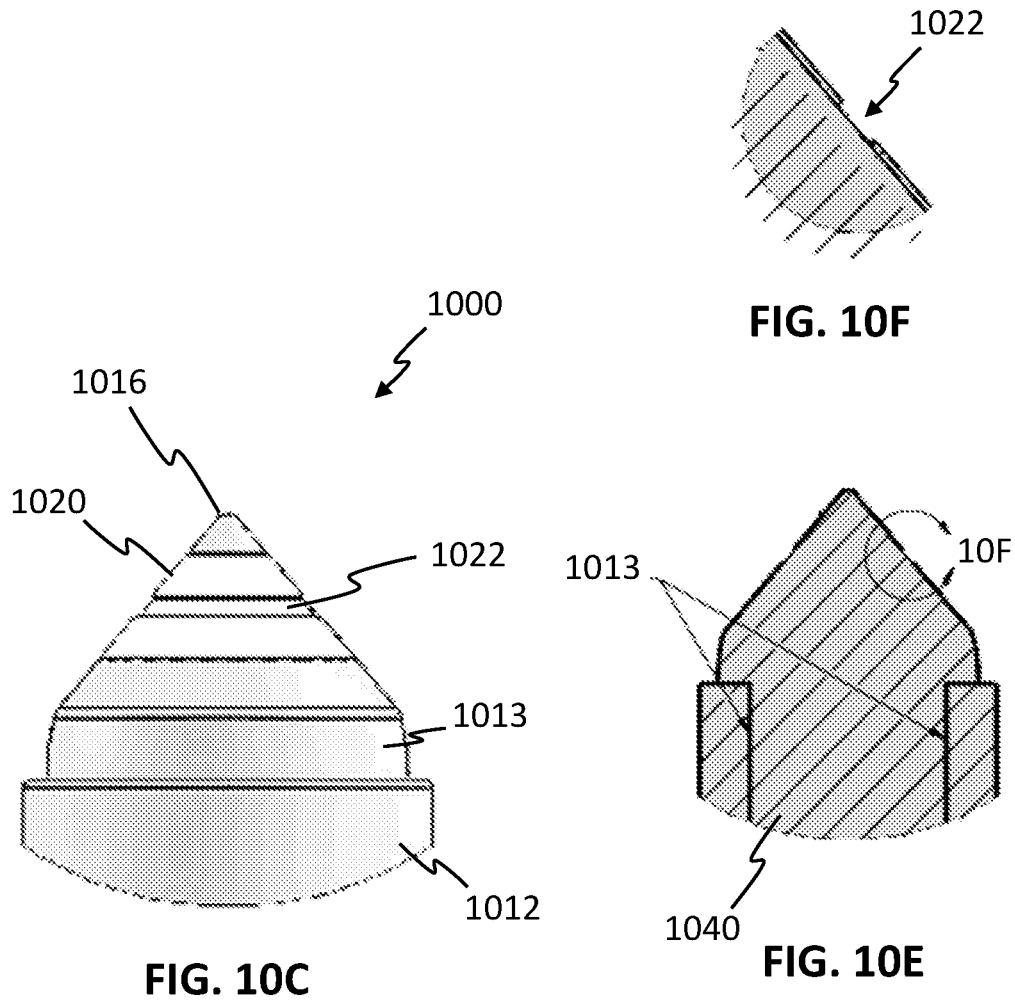
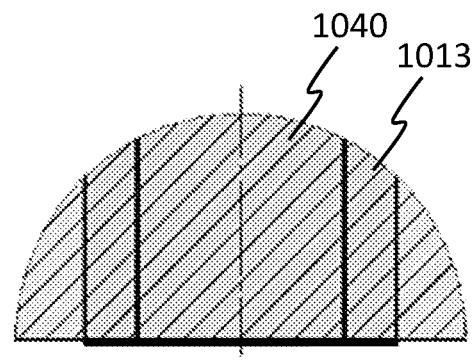

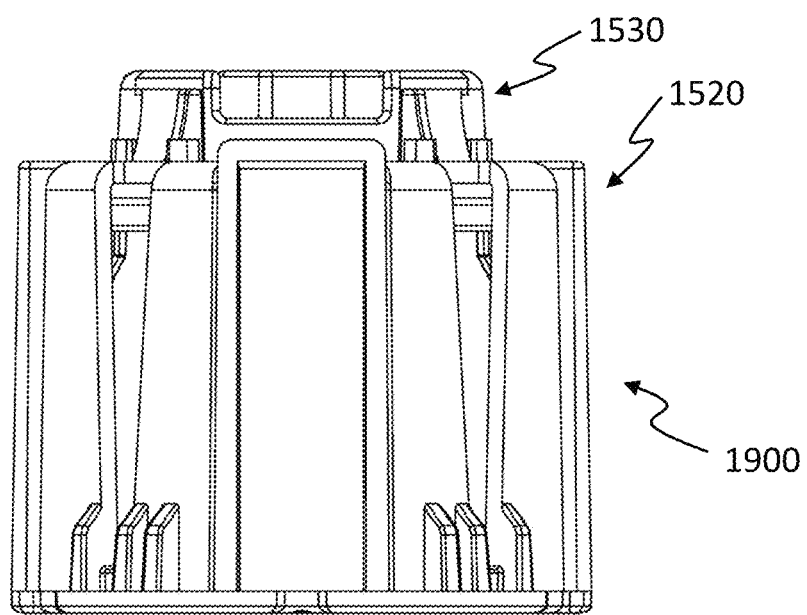
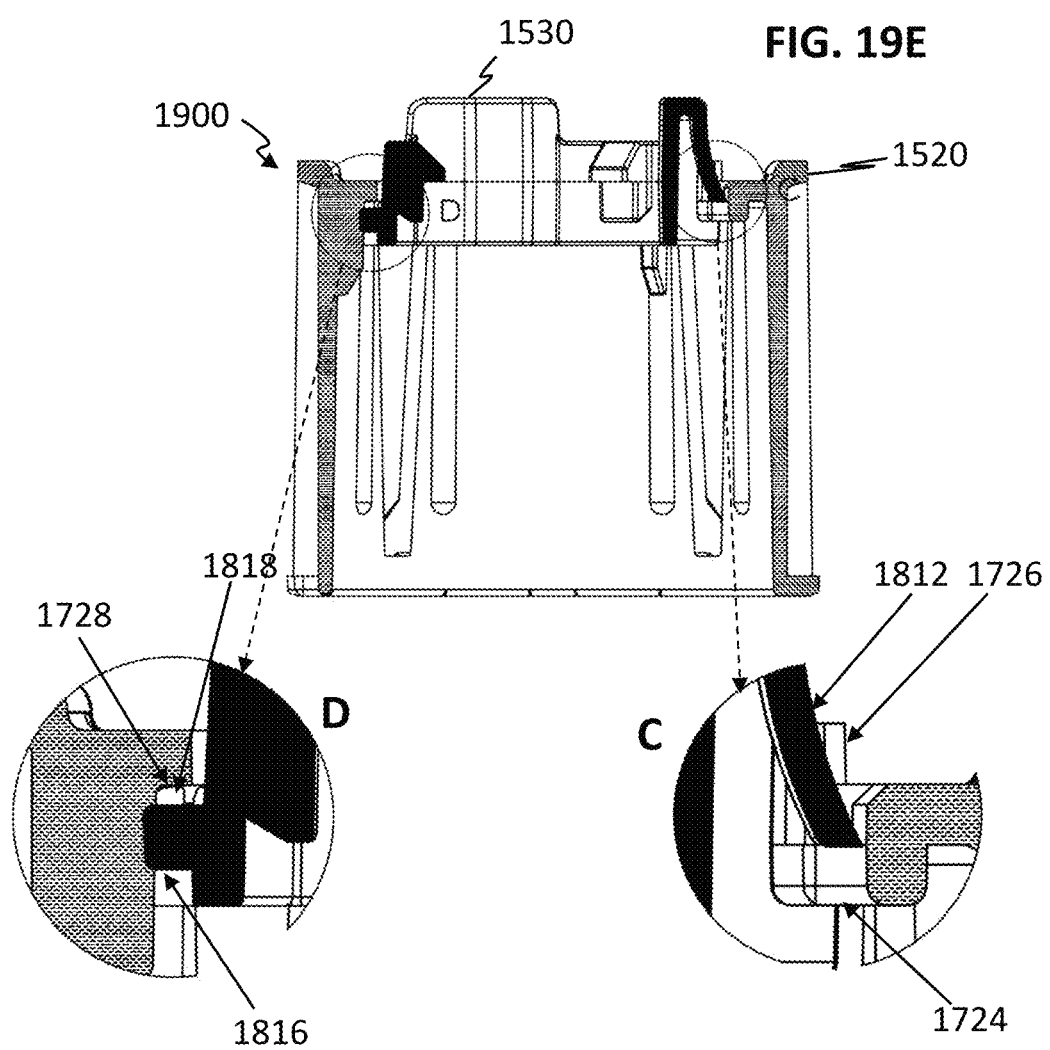
FIG. 19D
FIG. 19E

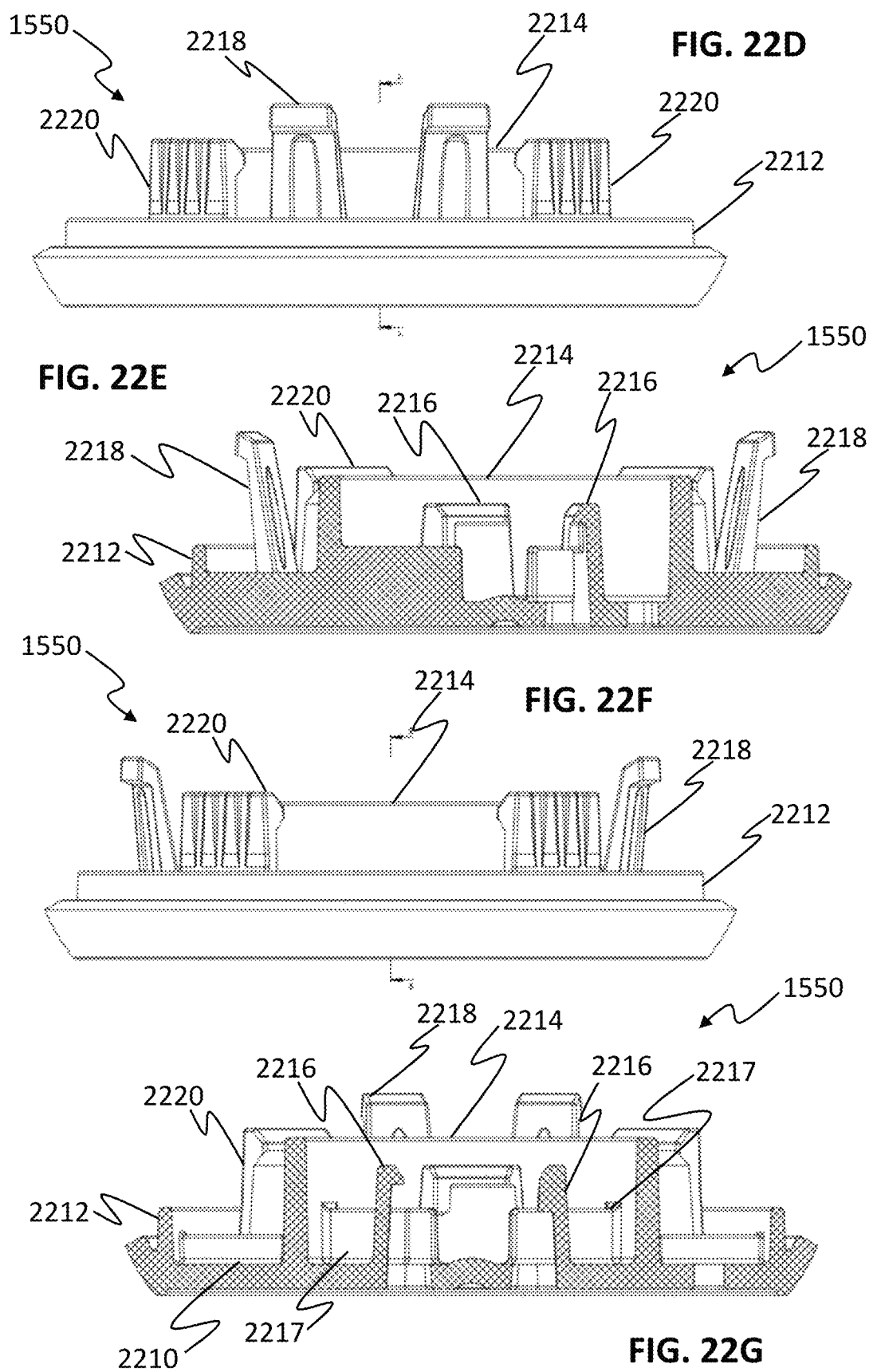

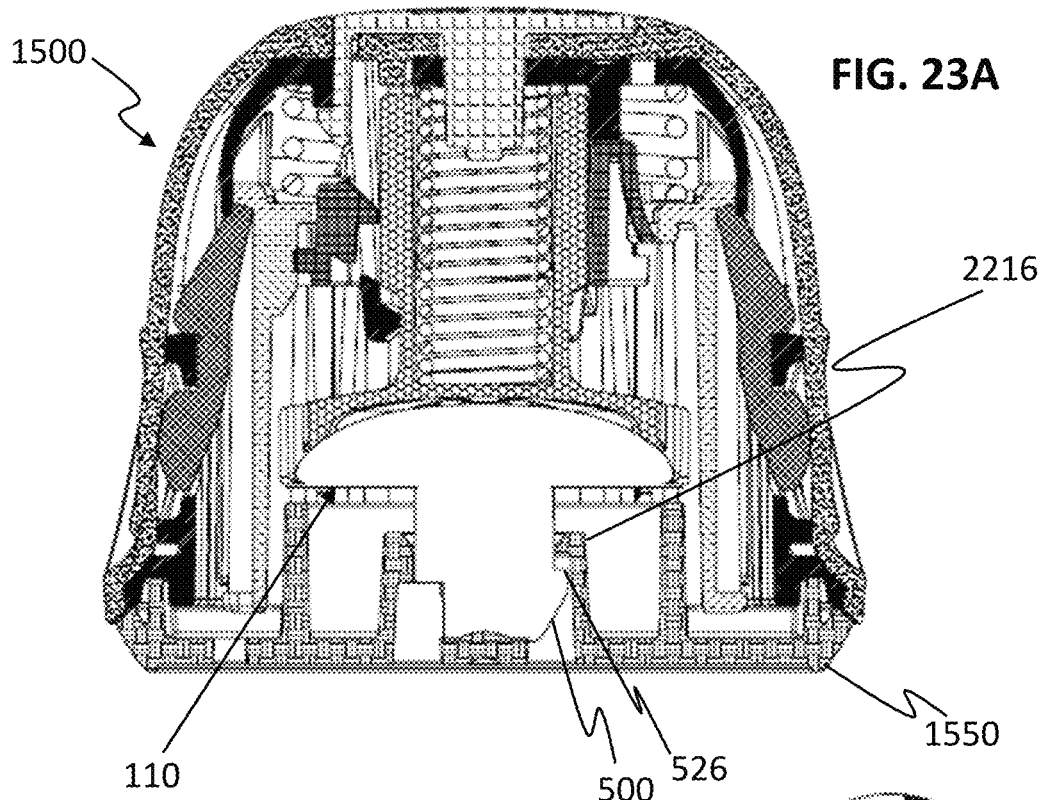
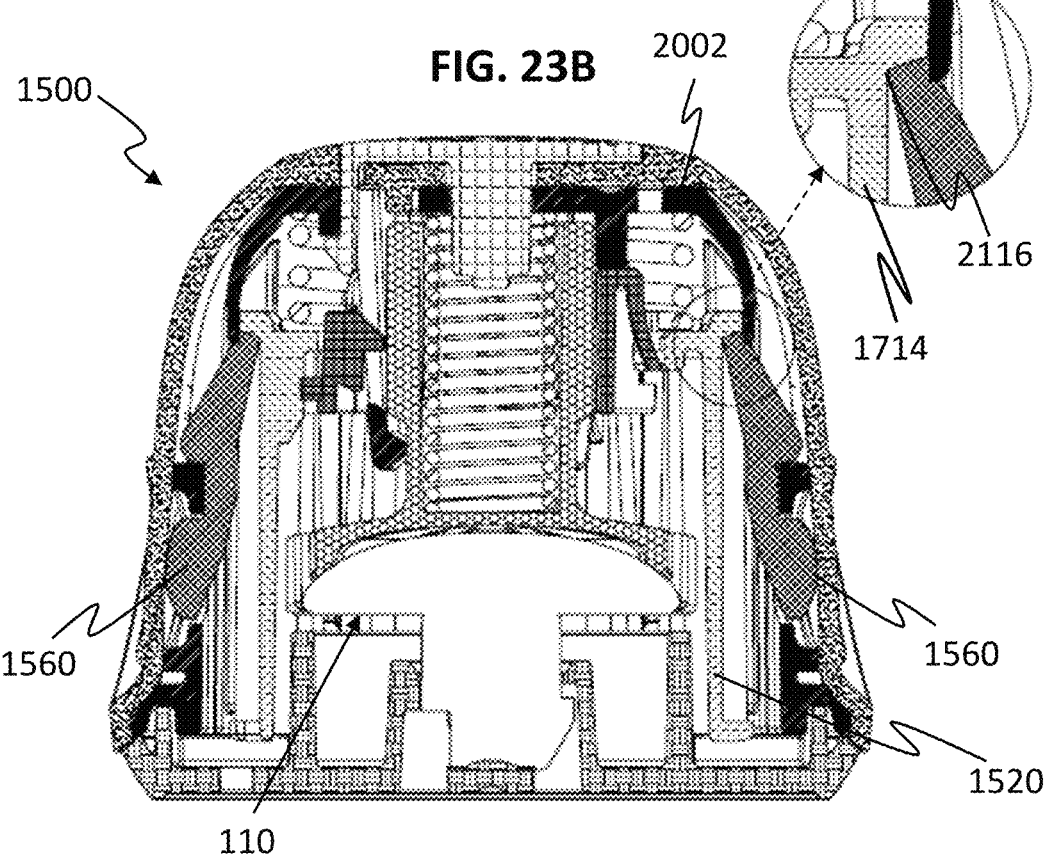

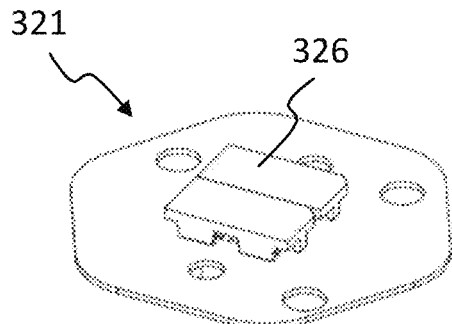
FIG. 27F
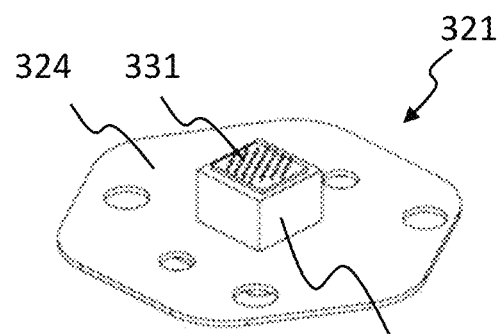
FIG. 27G
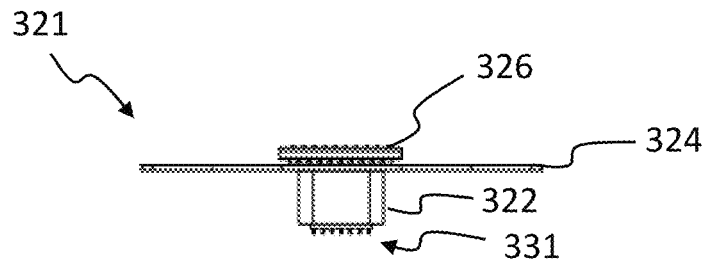
FIG. 27H
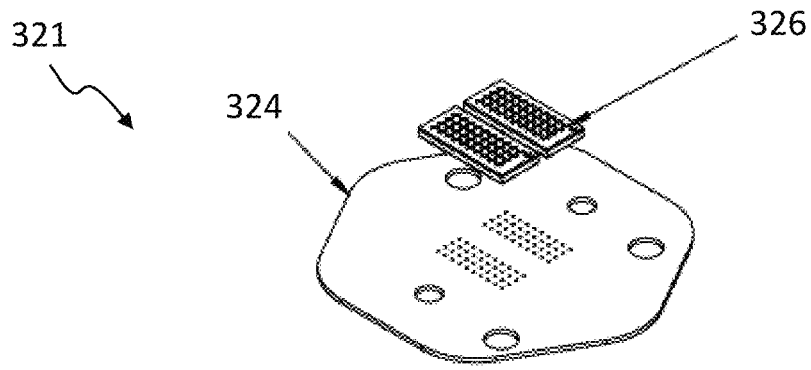
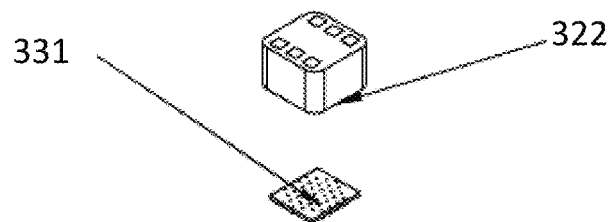
FIG. 27I

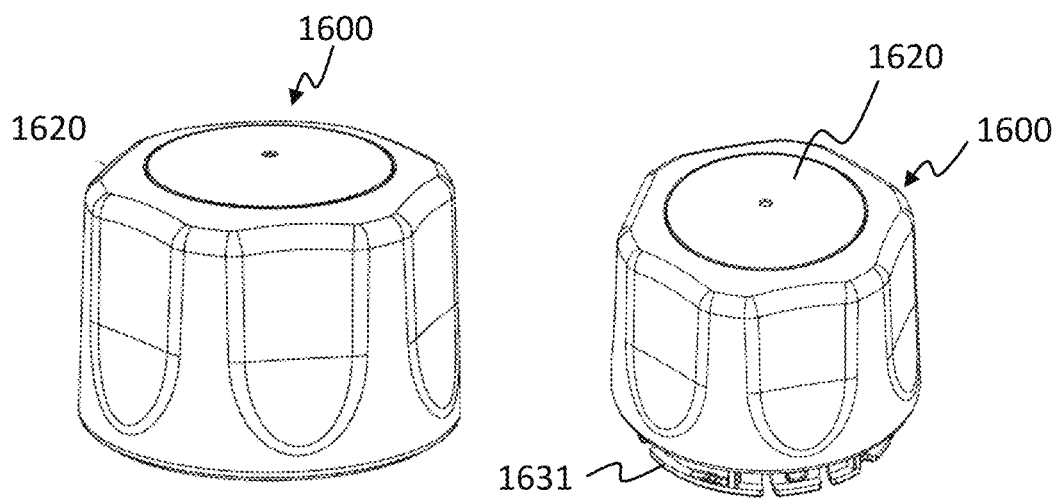
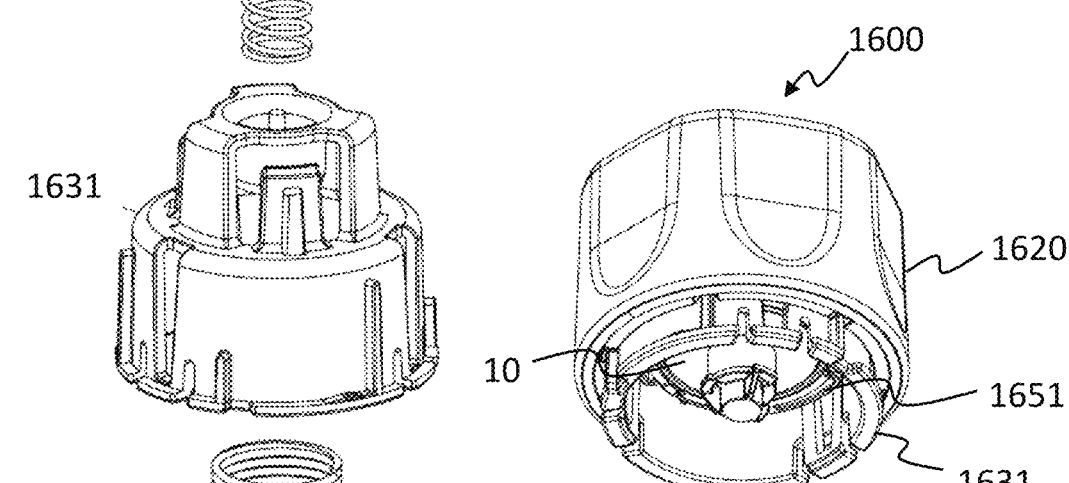
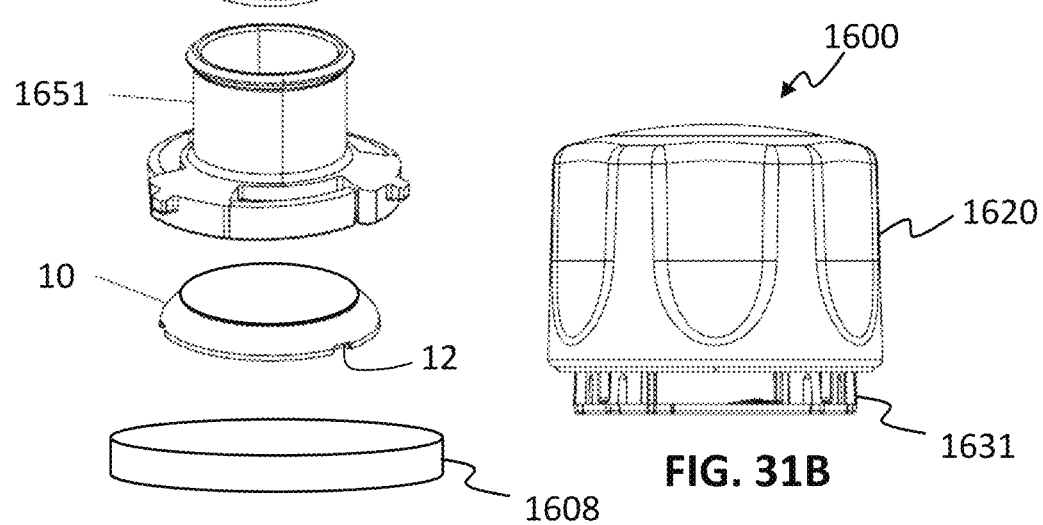
FIG. 31A
FIG. 31C
FIG. 31B
FIG. 31D

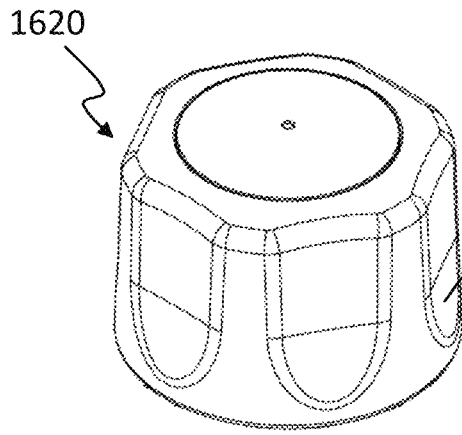
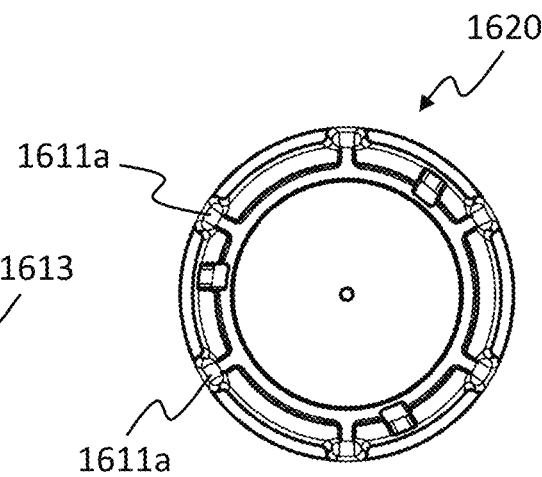
FIG. 34A
FIG. 34C
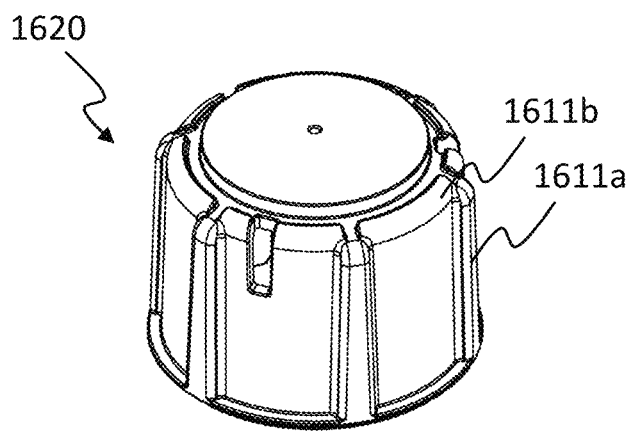
FIG. 34B
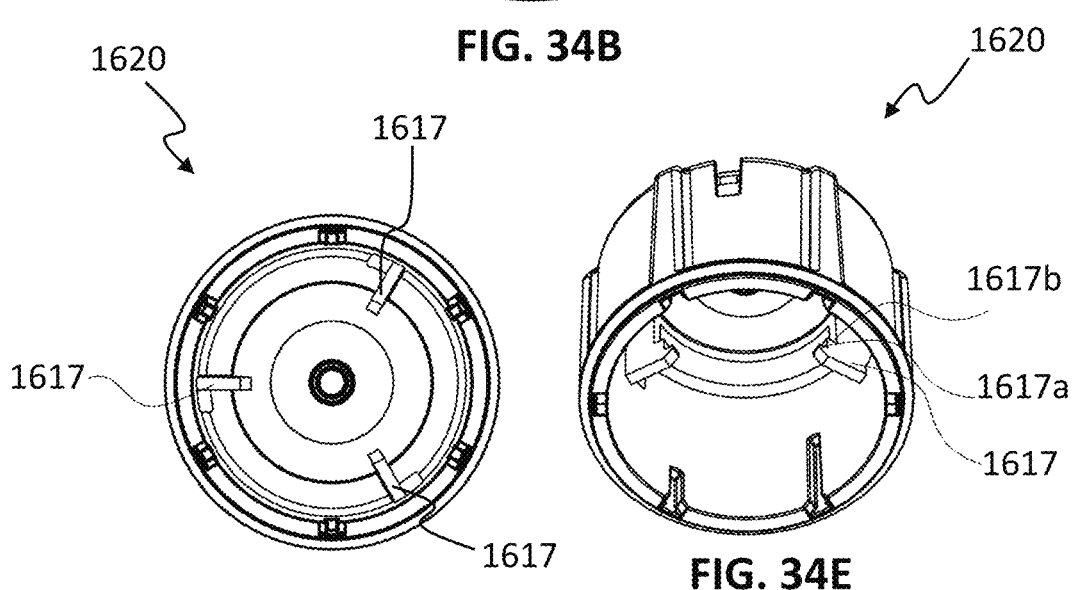
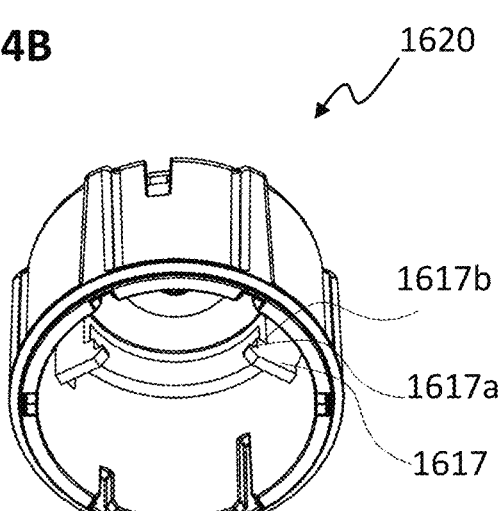
FIG. 34D
FIG. 34E

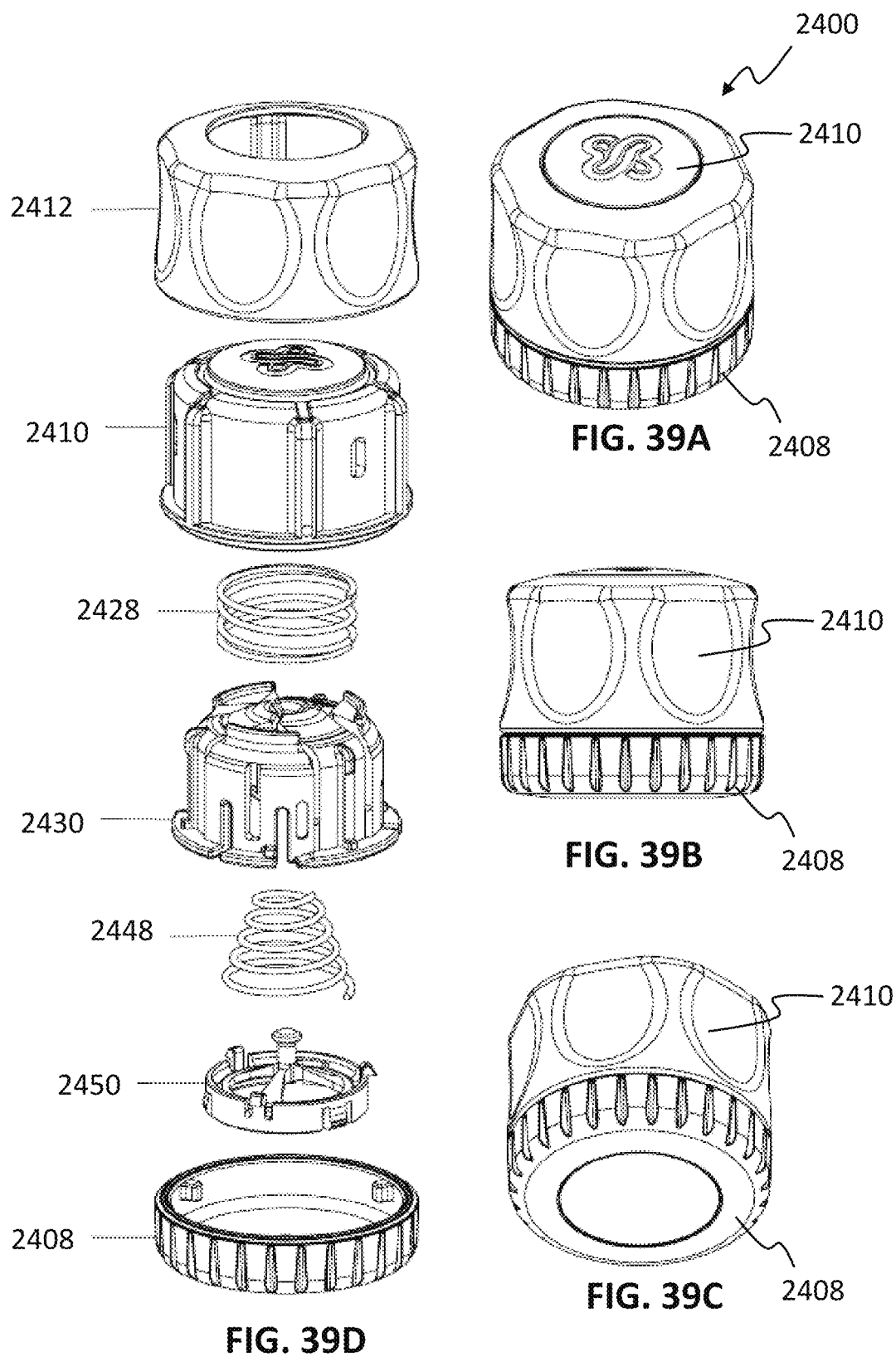

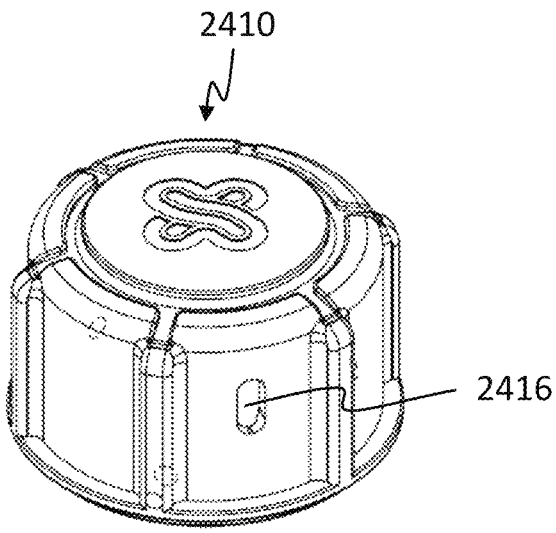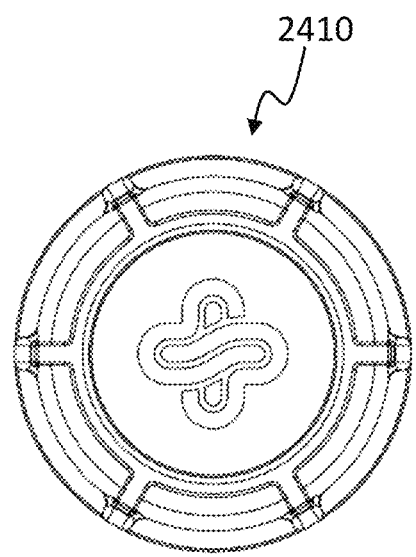
FIG. 42A     FIG. 42B
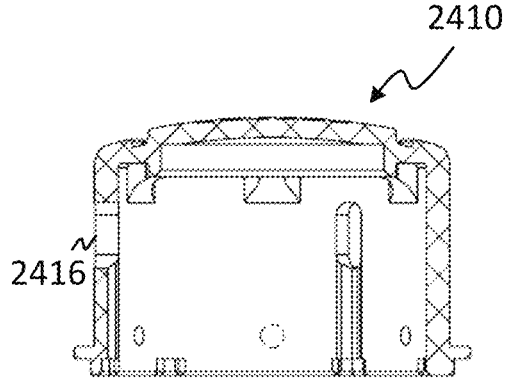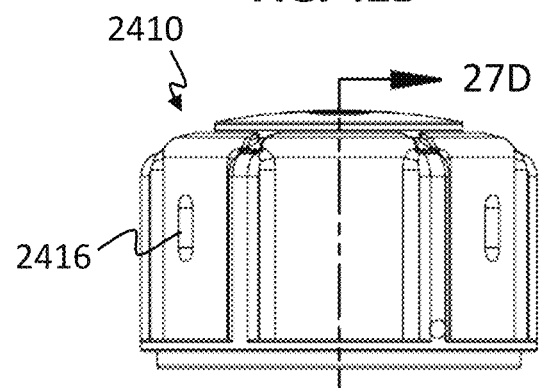
FIG. 42D     FIG. 42C
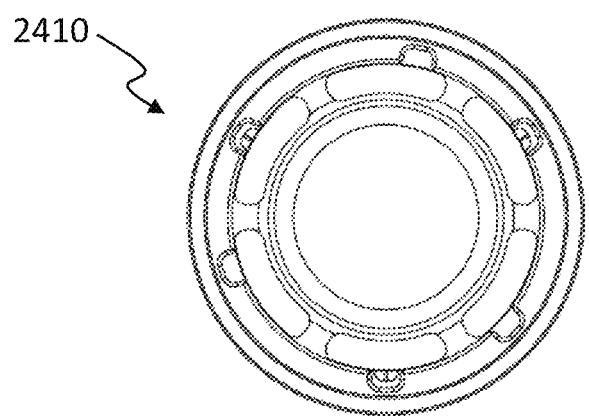
FIG. 42E

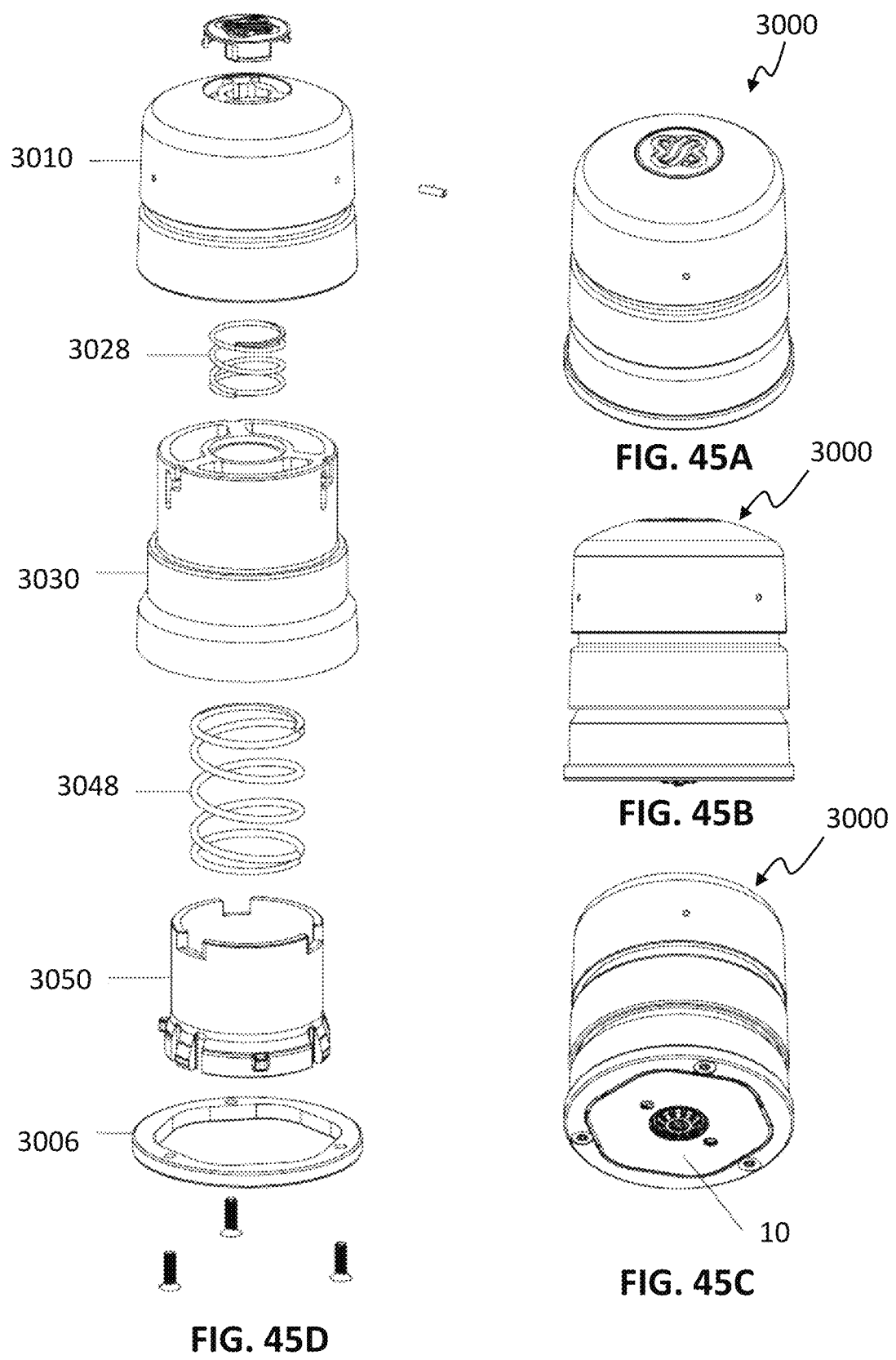

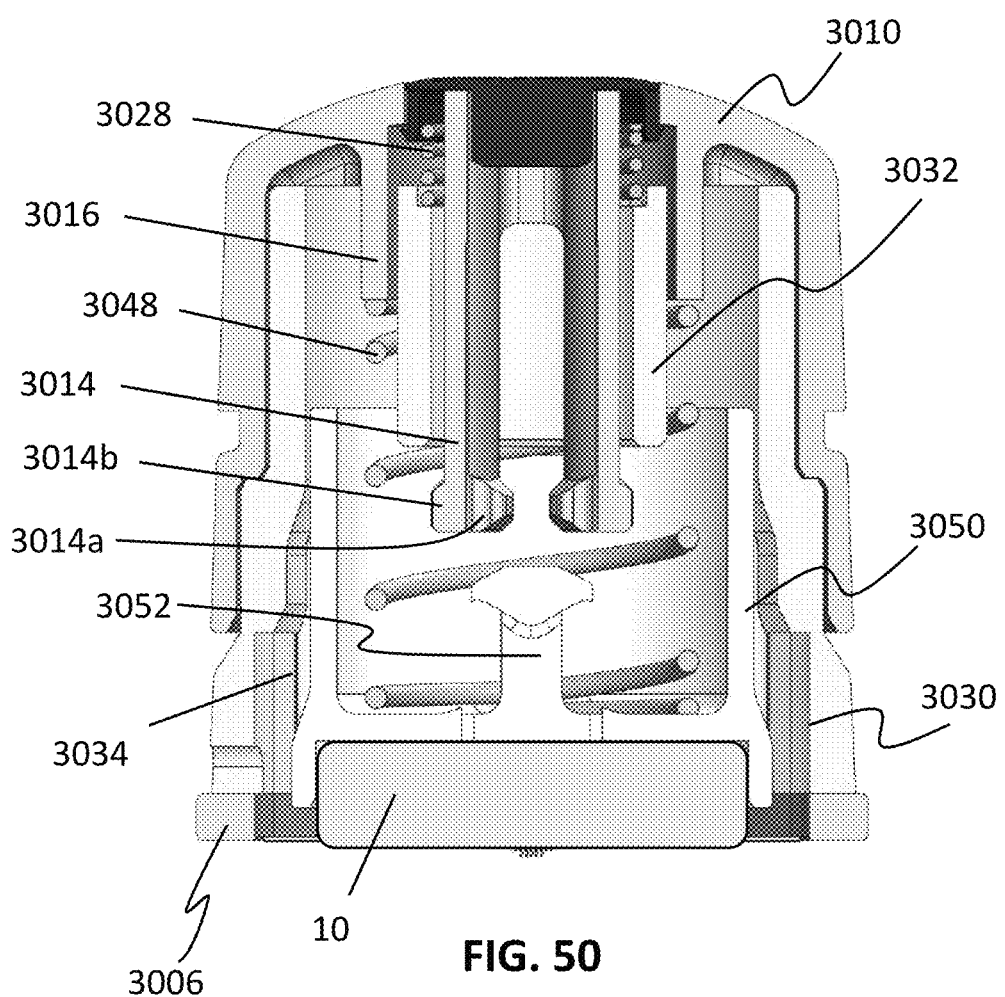

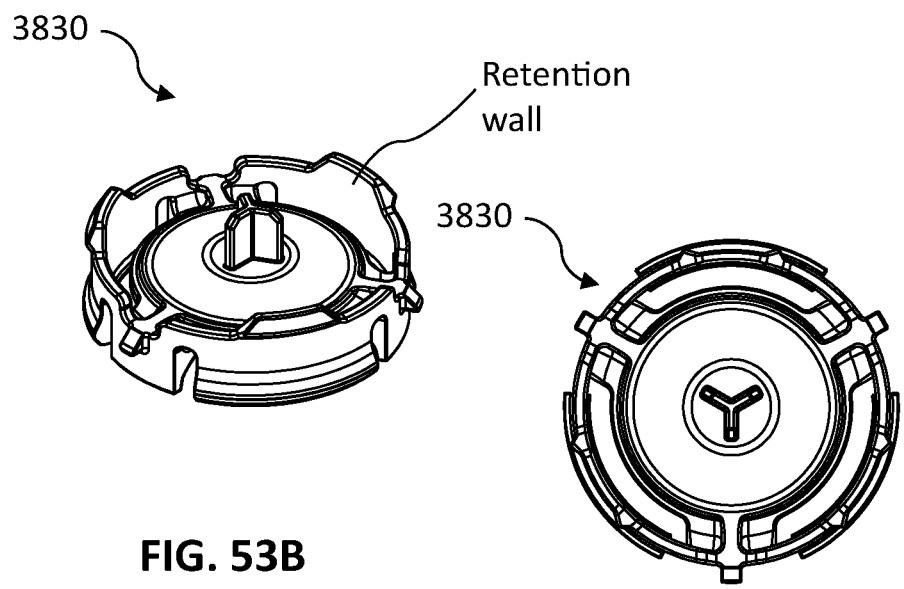
FIG. 53B
FIG. 53C
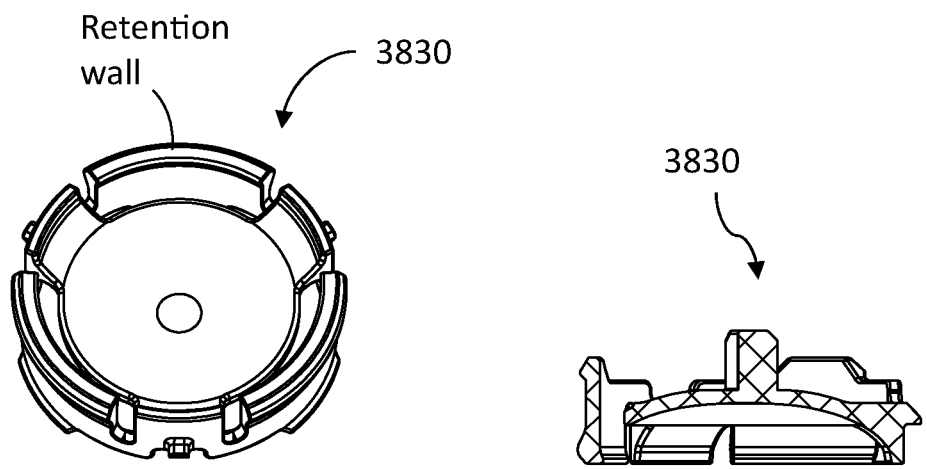
FIG. 53D
FIG. 53E

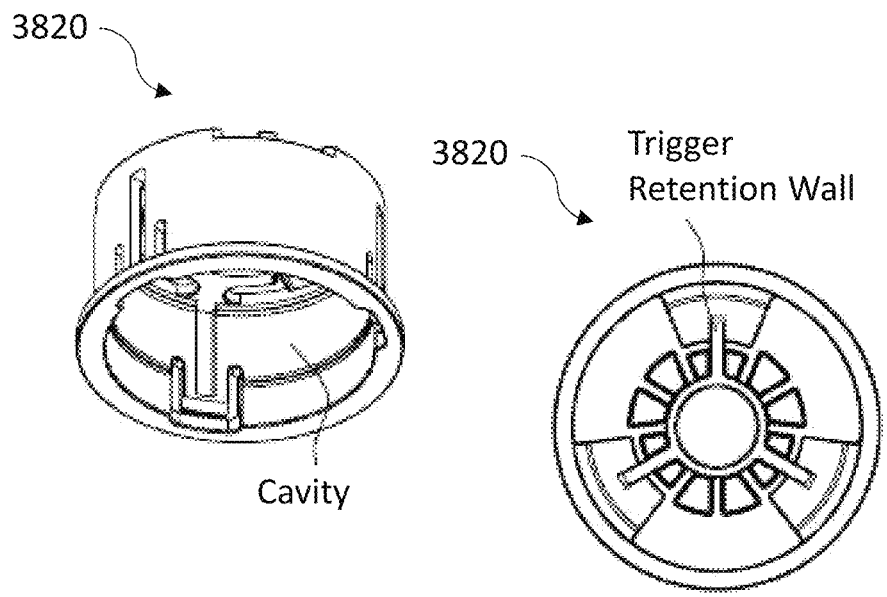
FIG. 53F
FIG. 53G
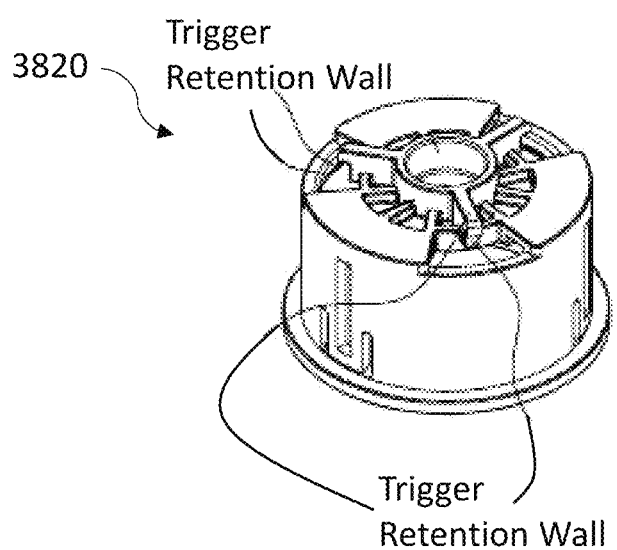
FIG. 53H

3900
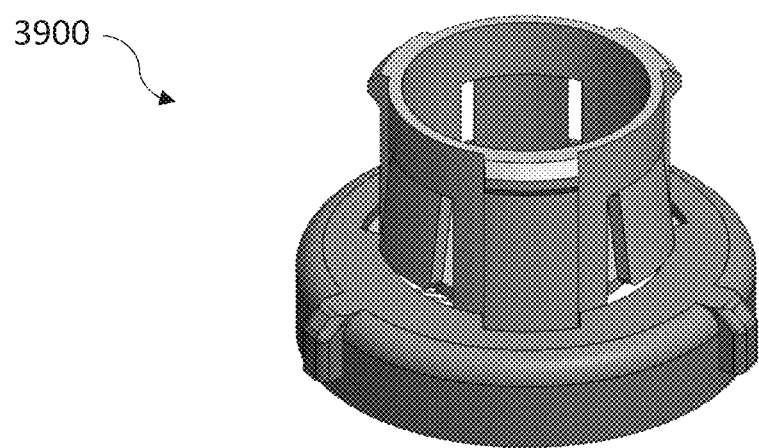
FIG. 54A
3900
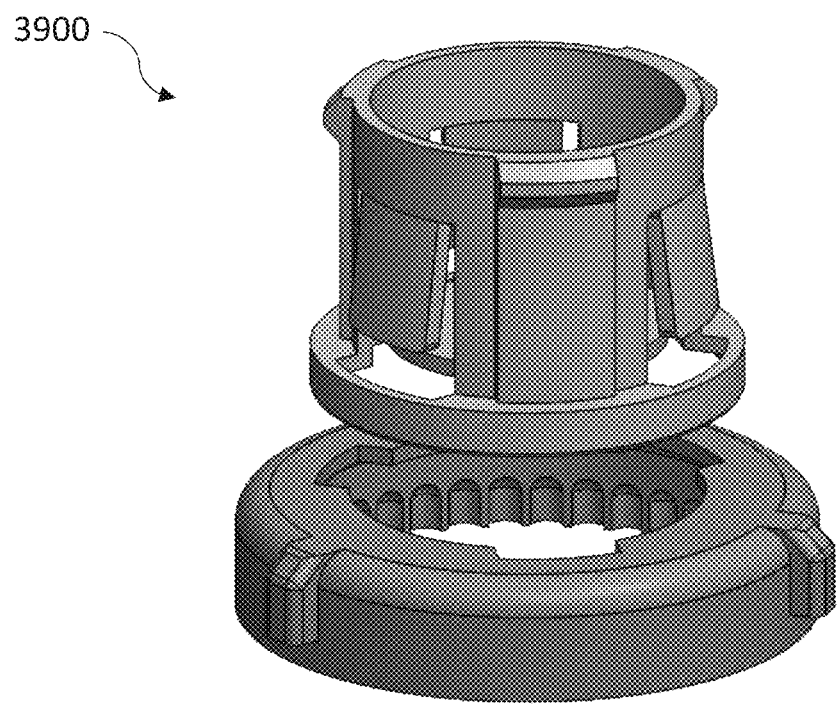
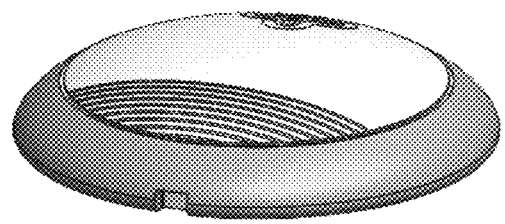
FIG. 54B

MICRONEEDLE ENCLOSURE AND APPLICATOR DEVICE FOR MICRONEEDLE ARRAY BASED CONTINUOUS ANALYTE MONITORING DEVICE

CROSS-REFERENCE TO RELATED APPLICATIONS

This application claims priority to U.S. Provisional Patent Application No. 63/249,399, filed Sep. 28, 2021, U.S. Provisional Patent Application No. 63/291,293, filed Dec. 17, 2021, and U.S. Provisional Patent Application No. 63/355,987, filed Jun. 27, 2022, the contents of which are hereby incorporated in their entirety by this reference.

TECHNICAL FIELD

This invention relates generally to the field of analyte monitoring, such as continuous glucose monitoring.

BACKGROUND

Diabetes is a chronic disease in which the body does not produce or properly utilize insulin, a hormone that regulates blood glucose. Insulin may be administered to a diabetic patient to help regulate blood glucose levels, though blood glucose levels must nevertheless be carefully monitored to help ensure that timing and dosage are appropriate. Without proper management of their condition, diabetic patients may suffer from a variety of complications resulting from hyperglycemia (high blood sugar levels) or hypoglycemia (low blood sugar levels).

Blood glucose monitors help diabetic patients manage their condition by measuring blood glucose levels from a sample of blood. For example, a diabetic patient may obtain a blood sample through a fingerstick sampling mechanism, transfer the blood sample to a test strip with suitable reagent(s) that react with the blood sample, and use a blood glucose monitor to analyze the test strip to measure glucose level in that blood sample. However, a patient using this process can typically only measure his or her glucose levels at discrete instances in time, which may fail to capture a hyperglycemia or hypoglycemia condition in a timely manner. Yet a more recent variety of glucose monitor is a continuous glucose monitor (CGM) device, which includes implantable transdermal electrochemical sensors that are used to continuously detect and quantify blood glucose levels by proxy measurement of glucose levels in the subcutaneous interstitial fluid. However, conventional CGM devices also have weaknesses including tissue trauma from insertion and signal latency (e.g., due to the time required for the glucose analyte to diffuse from capillary sources to the sensor). These weaknesses also lead to a number of drawbacks, such as pain experienced by the patient when electrochemical sensors are inserted, and limited accuracy in glucose measurements, particularly when blood glucose levels are changing rapidly. Accordingly, there is a need for a new and improved analyte monitoring system.

SUMMARY

According to an embodiment, the present disclosure relates to analyte monitoring.

In embodiments, the present disclosure further relates to an applicator for an analyte monitoring device, the applicator comprising a housing comprising a body defining a cavity therein, wherein the housing body comprises a distal opening, a cuff received within the cavity and comprising a lumen therethrough, and a shuttle slidably received within the lumen and configured to releasably retain the analyte monitoring device, wherein the applicator is movable between a collapsed configuration, an extended configuration, and a released configuration, and wherein in the collapsed configuration, the analyte monitoring device is retained within the shuttle, and the shuttle and a distal edge of the cuff are in a proximal most position, in the extended configuration, the distal edge of the cuff is in a distal most position and the shuttle is in an intermediate position, and in the released configuration, the analyte monitoring device is released from the shuttle, the distal edge of the cuff is in an intermediate position, and the shuttle is in a distal most position.

In embodiments, the present disclosure further relates to an applicator for an analyte monitoring device, the applicator comprising a housing comprising a body defining a cavity therein, wherein the housing body comprises a distal opening, a cuff received within the cavity and comprising a lumen therethrough, and a shuttle slidably received within the lumen and configured to releasably retain the analyte monitoring device, wherein the applicator is movable between a collapsed configuration, an extended configuration, and a released configuration, and wherein in the collapsed configuration, the analyte monitoring device is retained within the shuttle, the shuttle and a distal edge of the cuff are positioned proximal of the distal opening of the housing body, in the extended configuration, the distal edge of the cuff is positioned distal of the distal opening of the housing body, and the shuttle is positioned proximal of the distal opening of the housing body, and in the released configuration, the analyte monitoring device is released from the shuttle, the distal edge of the cuff is positioned distal of the distal opening of the housing body, and the shuttle is positioned distal of the distal opening of the housing body.

In embodiments, the present disclosure further relates to a method of applying an analyte monitoring device to a skin surface of a user, the method comprising providing an applicator in a collapsed configuration, wherein the applicator comprises a shuttle releasably retaining an analyte monitoring device, the shuttle being slidably received within a trigger cavity of a cuff, the cuff being received within a cavity of a housing comprising a body defining the cavity, the housing body comprising a distal opening, transitioning the applicator from the collapsed configuration to an extended configuration, and transitioning the applicator from the extended configuration to a released configuration, and wherein in the collapsed configuration, the shuttle and a distal edge of the cuff are in a proximal most position, in the extended configuration, the distal edge of the cuff is in a distal most position, and the shuttle is in an intermediate position, and in the released configuration, the analyte monitoring device is released from the shuttle, the distal edge of the cuff is in an intermediate position, and the shuttle is in a distal most position.

In embodiments, the present disclosure further relates to an applicator for an analyte monitoring device, the applicator comprising: a. a housing comprising a body defining a cavity therein, wherein the housing body comprises a distal opening and a side opening; b. a cuff received within the cavity; c. a shuttle received within the cavity and configured to releasably retain the analyte monitoring device; d. a locking member at least partially received in the side opening of the housing body, wherein the locking member is engaged with the cuff in a first configuration and disengaged from the cuff in a second configuration; and e. a base configured to removably couple to the housing body at the distal opening, wherein the base comprises a proximal surface, f wherein movement of the locking member from the first configuration to the second configuration releases the cuff thereby decoupling the proximal surface from the housing body.

In embodiments, the present disclosure further relates to a method of using an applicator for an analyte monitoring device, the method comprising transitioning a locking member of an applicator from a first configuration to a second configuration, wherein the applicator comprises a housing body defining a cavity therein, a cuff and a shuttle each received within the cavity, and a base removably coupled to the housing body, wherein the shuttle releasably retains the analyte monitoring device, and wherein transitioning the locking member disengages the locking member from the cuff, thereby allowing the cuff to move relative to the housing body and displace a base of the applicator relative to the housing body.

In embodiments, the present disclosure further relates to an applicator for an analyte monitoring device, the applicator comprising a housing comprising a body defining a cavity therein, a cuff received within the cavity and comprising a lumen, and a shuttle received within the lumen, wherein the shuttle comprises a shaft; and a base portion at a distal end of the shaft, wherein the base portion comprises a plurality of flexible leaves extending from the shaft and a plurality of petals extending from the shaft, and wherein the plurality of flexible leaves define a receptacle to retain the analyte monitoring device.

In embodiments, the present disclosure further relates to an applicator for an analyte monitoring device, the applicator comprising a housing comprising a housing body and a mount, a cuff-ring assembly comprising a cuff and a friction ring coupled to the cuff, and a shuttle configured to releasably retain the analyte monitoring device, wherein the shuttle and the cuff-ring assembly are separately translatable relative to the housing body, and wherein each of the shuttle and the cuff-ring assembly are releasably coupled to the mount.

In embodiments, the present disclosure further relates to an applicator for an analyte monitoring device, the applicator comprising a housing comprising a housing body defining a cavity therein and a mount extending from an internal surface of a proximal end of the housing body into the cavity, a cuff-ring assembly comprising a cuff having a lumen and a proximal opening, and a friction ring positioned within the lumen and extending through the proximal opening, wherein the cuff-ring assembly is positioned around the mount, and a shuttle configured to releasably retain the analyte monitoring device, wherein a portion of the shuttle extends through the mount.

In embodiments, the present disclosure further relates to an applicator for an analyte monitoring device, the applicator comprising a housing comprising a housing body defining a cavity therein and a mount extending into the cavity, a cuff-ring assembly comprising a cuff and a friction ring coupled to the cuff, a shuttle configured to releasably retain the analyte monitoring device, and a base removably coupled to the housing, wherein the mount is configured to 1) releasably engage the friction ring to prevent axial movement of the shuttle before removal of the base from the housing and 2) releasably engage with the shuttle to control axial movement of the shuttle after removal of the base from the housing.

In embodiments, the present disclosure further relates to In embodiments, the present disclosure further relates to method of applying an analyte monitoring device to a skin surface using an applicator, the method comprising providing an applicator comprising a housing defining a cavity, a cuff, and a shuttle, wherein the cuff and the shuttle are each received within the cavity, wherein the shuttle retains the analyte monitoring device, applying a distal surface of the cuff of the applicator to the skin surface, advancing the housing toward the skin surface, wherein advancing the housing moves the housing relative to the cuff and the shuttle, and disengages one or more retention features preventing movement of the shuttle independently of the housing, wherein disengagement of the one or more retention features releases the shuttle and advances the shuttle with the analyte monitoring device toward the skin surface, and releasing the analyte monitoring device from the shuttle.

In embodiments, the present disclosure further relates to an applicator for an analyte monitoring device, the applicator comprising a housing comprising a body defining a cavity therein and a distal opening, a cuff slidably received within the cavity and comprising a lumen therethrough, a shuttle slidably received within the lumen and configured to releasably retain the analyte monitoring device, a first biasing element arranged between the housing and the cuff, a second biasing element arranged between the housing and the shuttle, a microneedle enclosure releasably engaged with the analyte monitoring device and configured to enclose a portion of the analyte monitoring device when engaged, the microneedle enclosure comprising a third biasing element, and a base releasably engaged with the housing and coupled to the microneedle enclosure.

BRIEF DESCRIPTION OF THE DRAWINGS

FIGS. 3A-3D depict an upper perspective view, a side view, a bottom view, and an exploded view, respectively, of an analyte monitoring device.

FIGS. 4A-4E depict a perspective exploded view, a side exploded view, a lower perspective view, a side view, and an upper perspective view, respectively, of a sensor assembly in an analyte monitoring device.

FIG. 8A depicts a cross-sectional side view of a columnar microneedle having a tapered distal end. FIGS. 8B and 8C are images depicting perspective and detailed views, respectively, of an embodiment of the microneedle shown in FIG. 8A.

Figure 9:
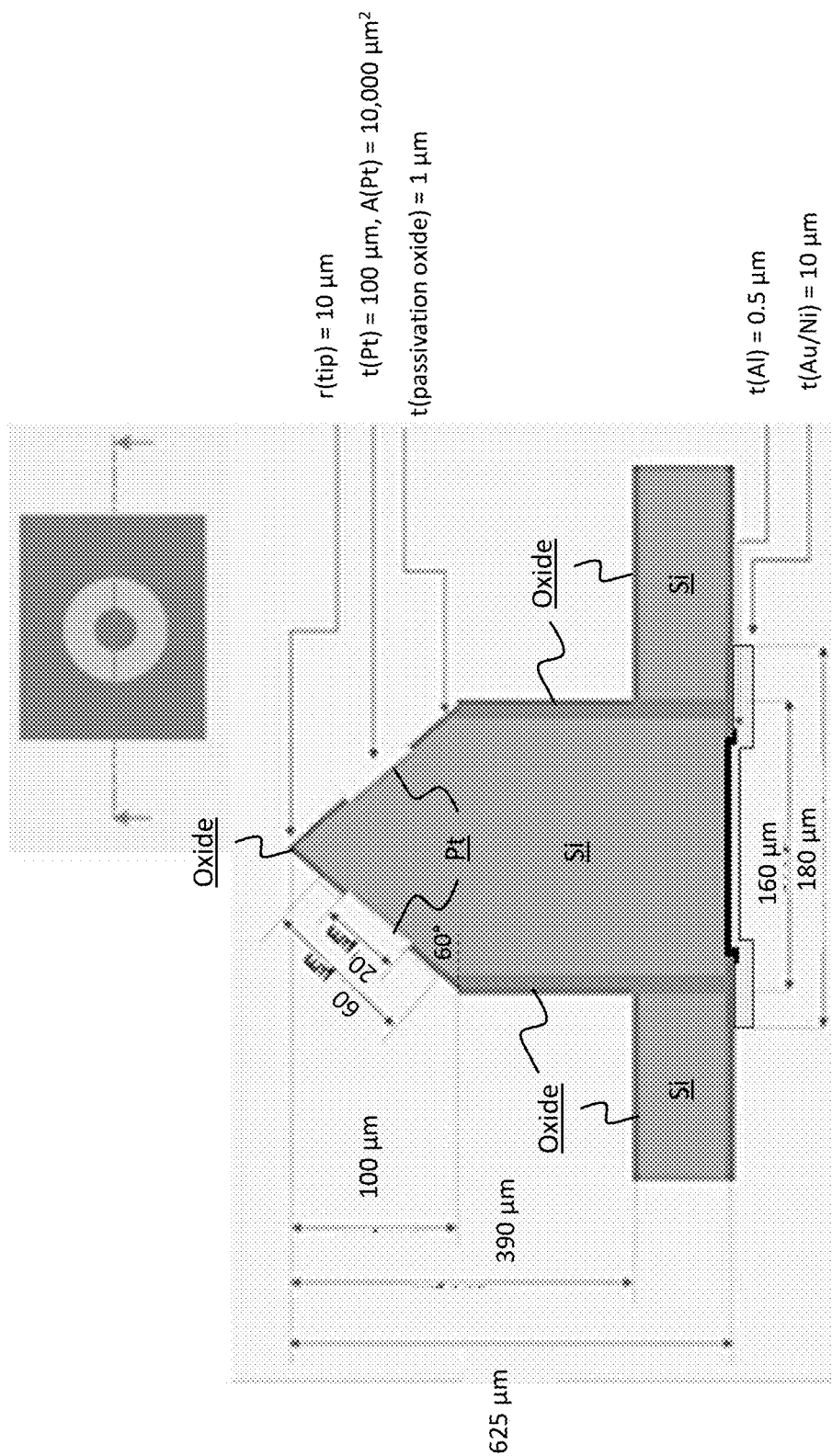

FIG. 9 depicts an illustrative schematic of a columnar microneedle having a tapered distal end.

Figure 10A:
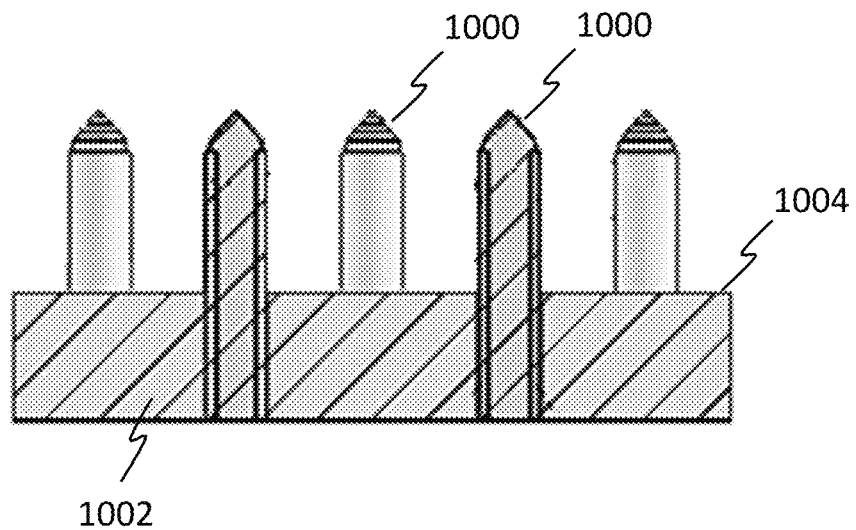
Figure 10B:
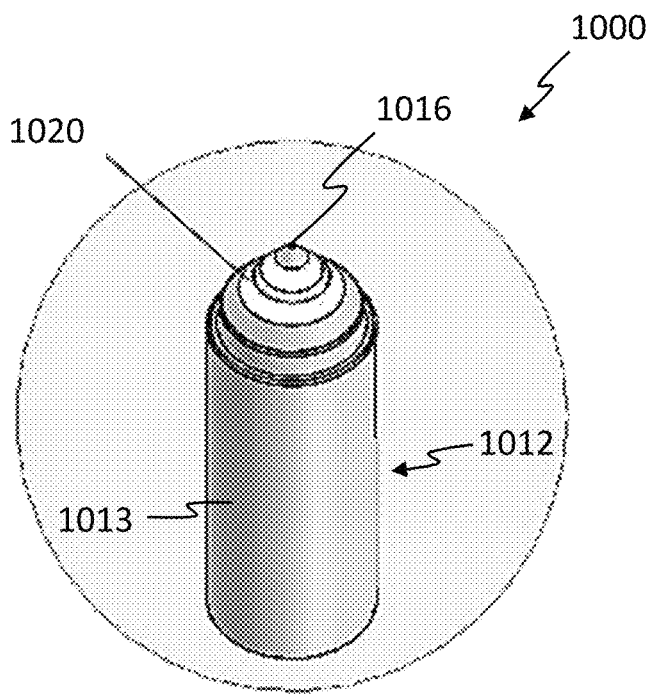

FIGS. 10A and 10B depict illustrative schematics of a microneedle array and a microneedle, respectively. FIGS. 10C-10F depict detailed partial views of an illustrative variation of a microneedle.

Figure 11A:
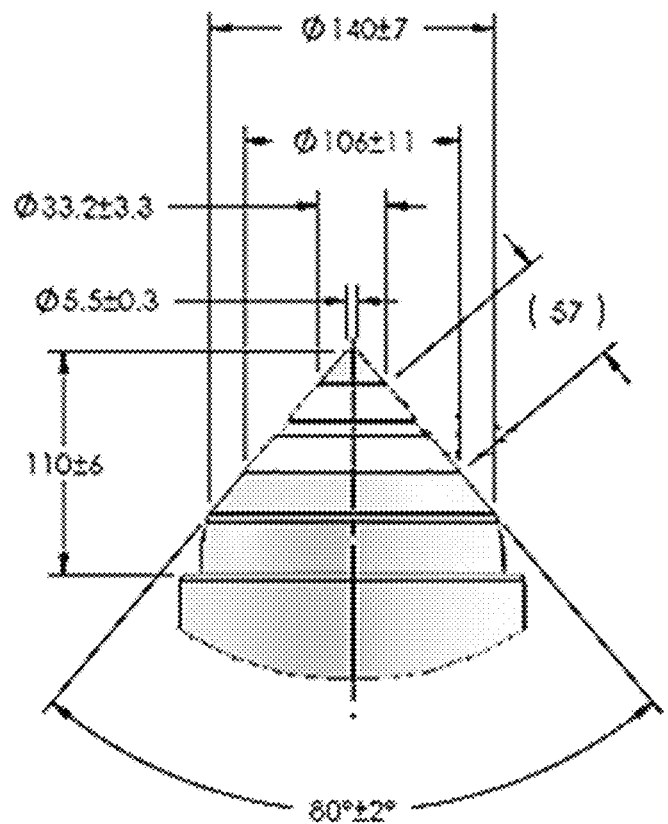
Figure 11B:
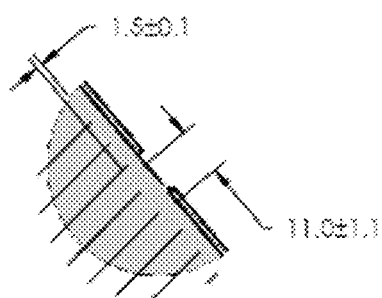

FIGS. 11A and 11B depict an illustrative variation of a microneedle.

Figure 12A:
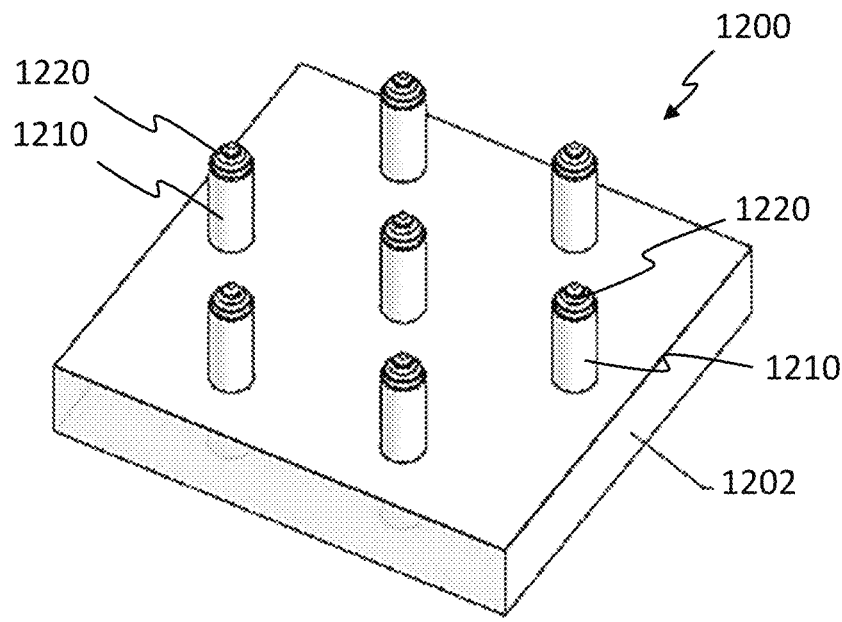
Figure 12B:
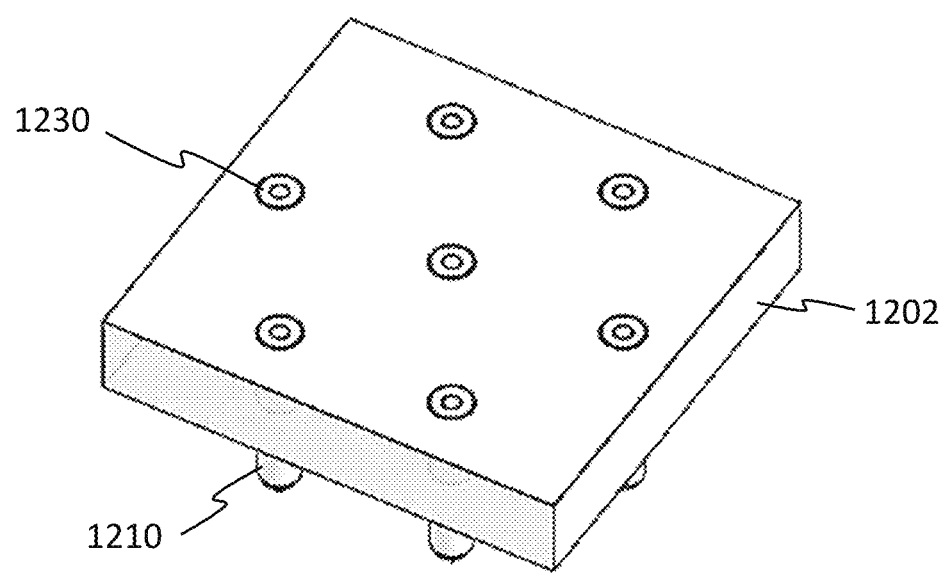

FIGS. 12A and 12B depict illustrative schematics of a microneedle array configuration.

Figure 12C:
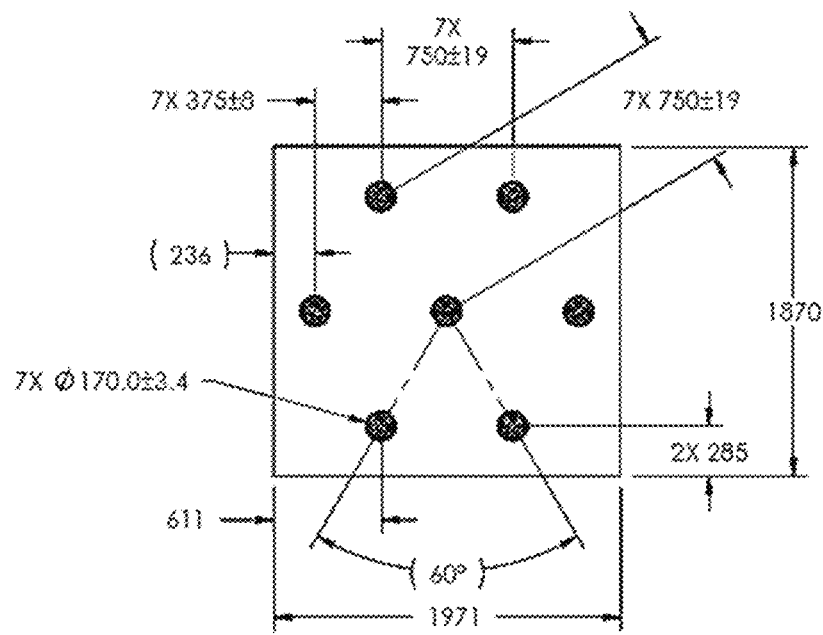
Figure 12D:
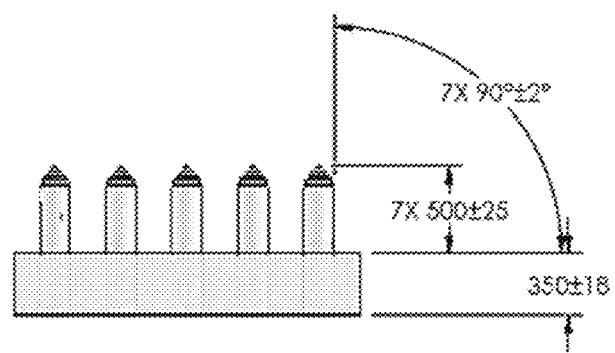

FIGS. 12C and 12D depict illustrative schematics of a microneedle array configuration.

Figure 13A:
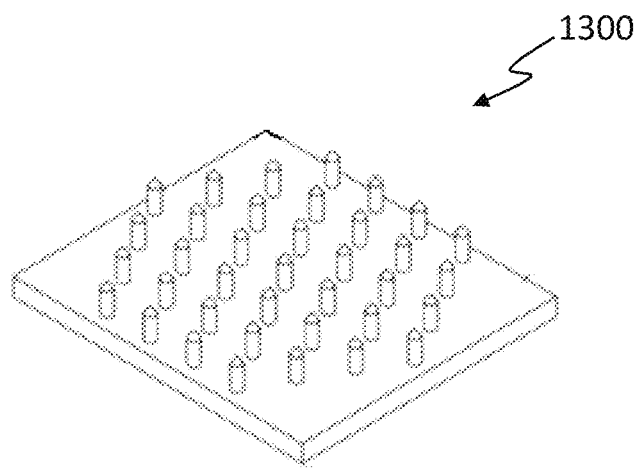
Figure 13B:
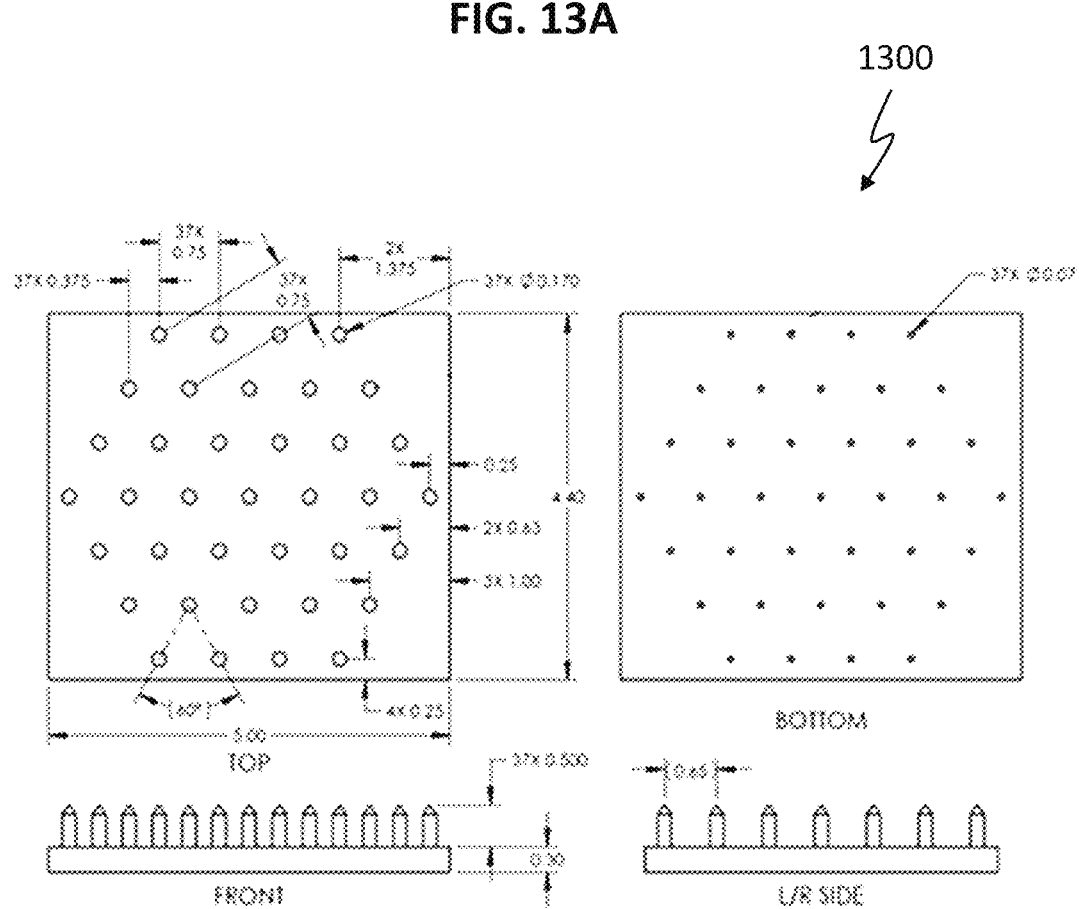

FIGS. 13A and 13B depict perspective and orthogonal views, respectively, of an illustrative variation of a die including a microneedle array.

FIGS. 14A-14J depict illustrative schematics of different variations of microneedle array configurations.

FIGS. 15A-15D depict aspects of an applicator for an analyte monitoring device in a first side view, a second side view, a top perspective view, and a bottom perspective view, respectively.

Figure 15A:
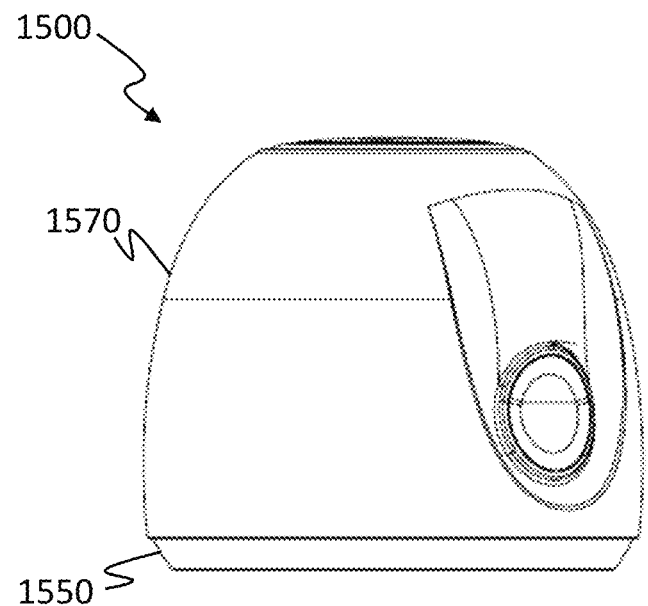
Figure 15B:
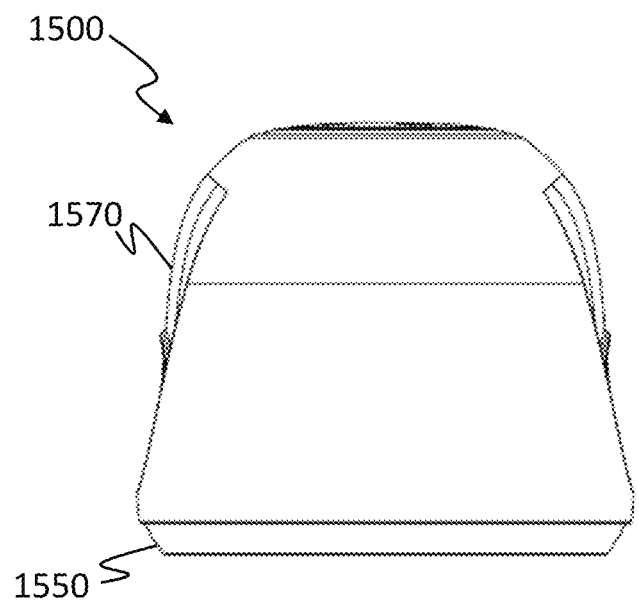
Figure 15C:
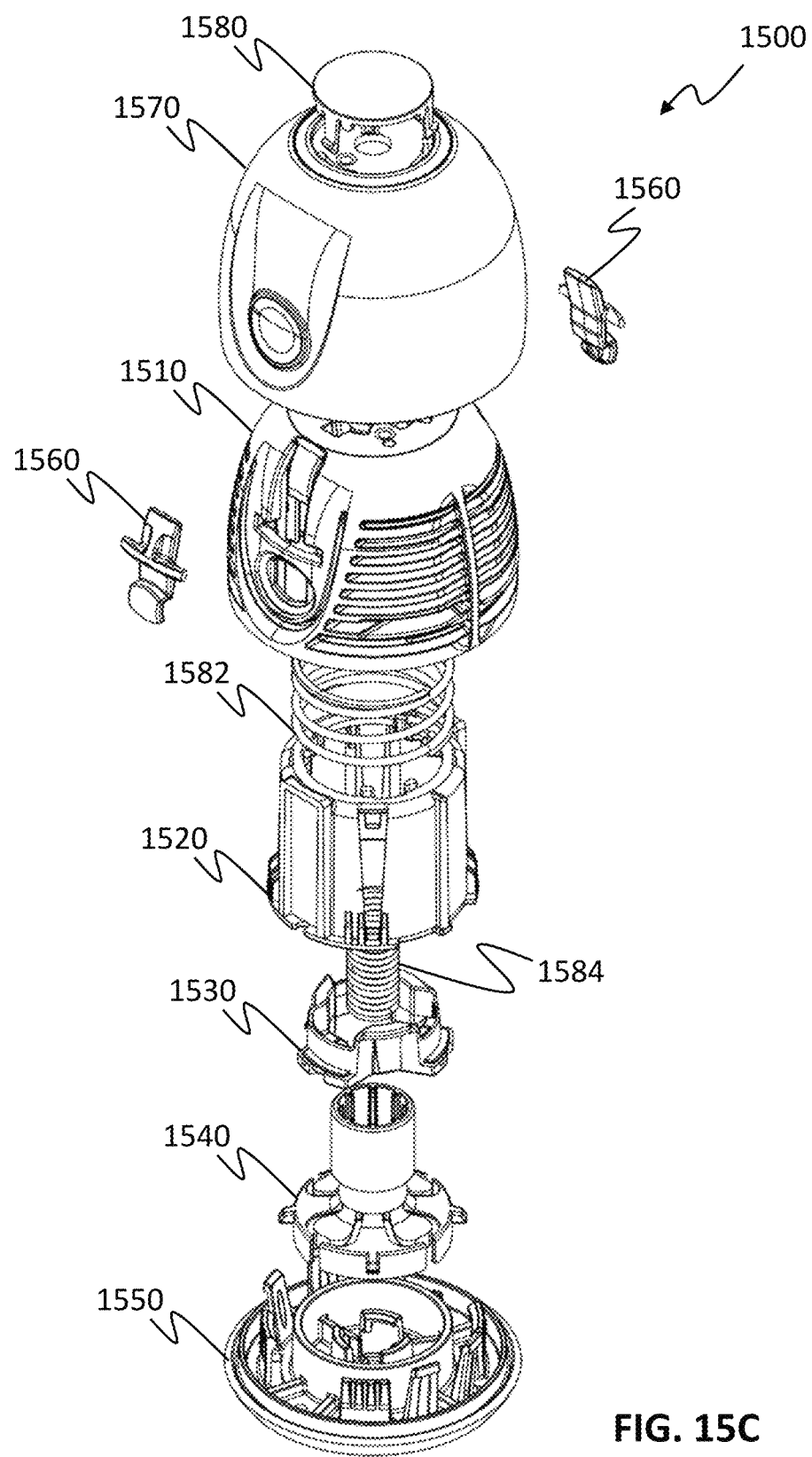
Figure 15D:
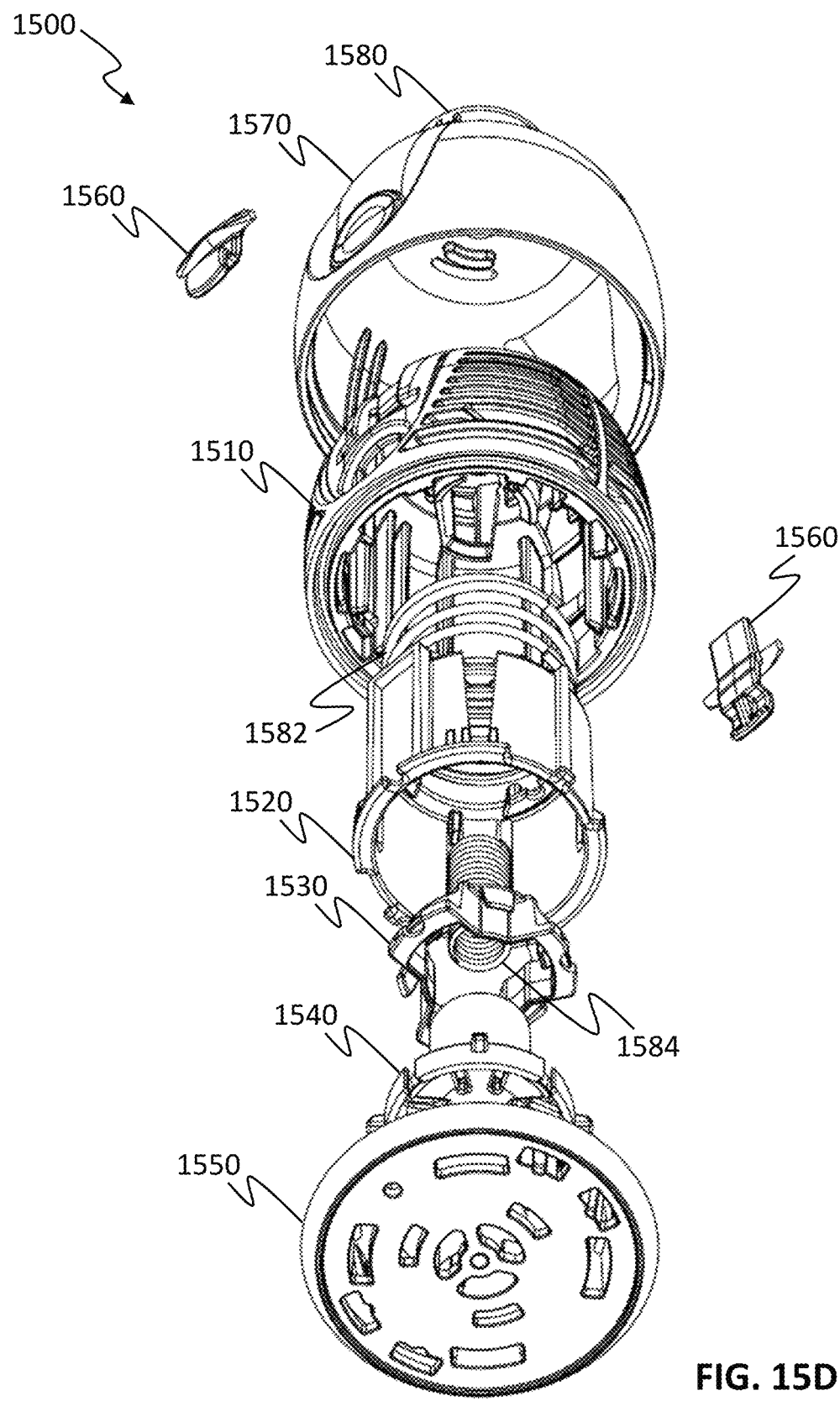
Figure 15E:
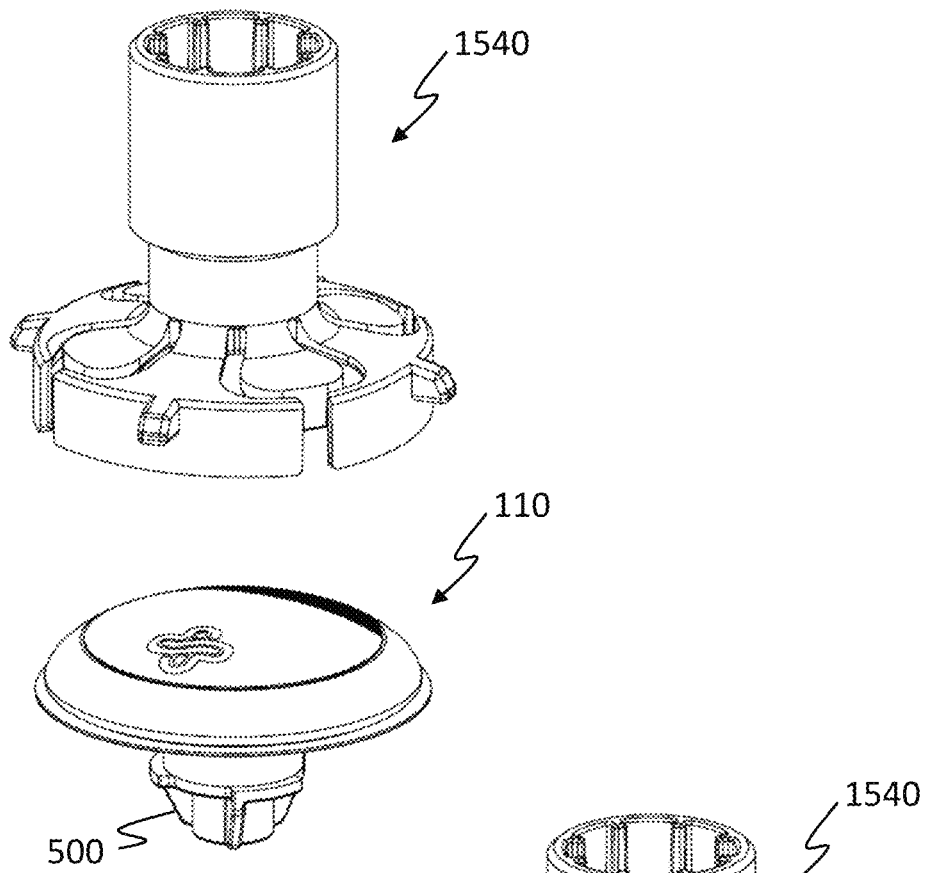
Figure 15F:
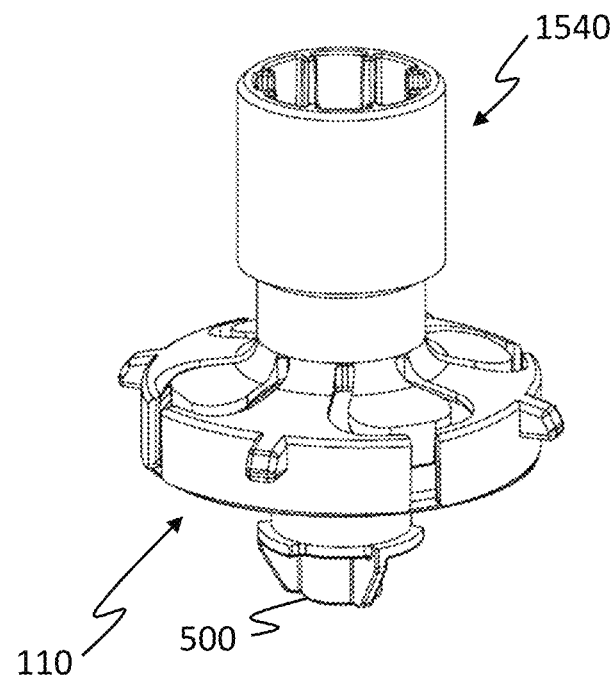

FIG. 15E and FIG. 15F depict aspects of an analyte monitoring device with respect to a shuttle of an applicator, in an exploded view and a perspective view, respectively FIGS. 16A-16D depicts aspects of a shuttle of an applicator for an analyte monitoring device in a top perspective view, a bottom view, a side view, and a side cross-sectional view, respectively.

Figure 16A:
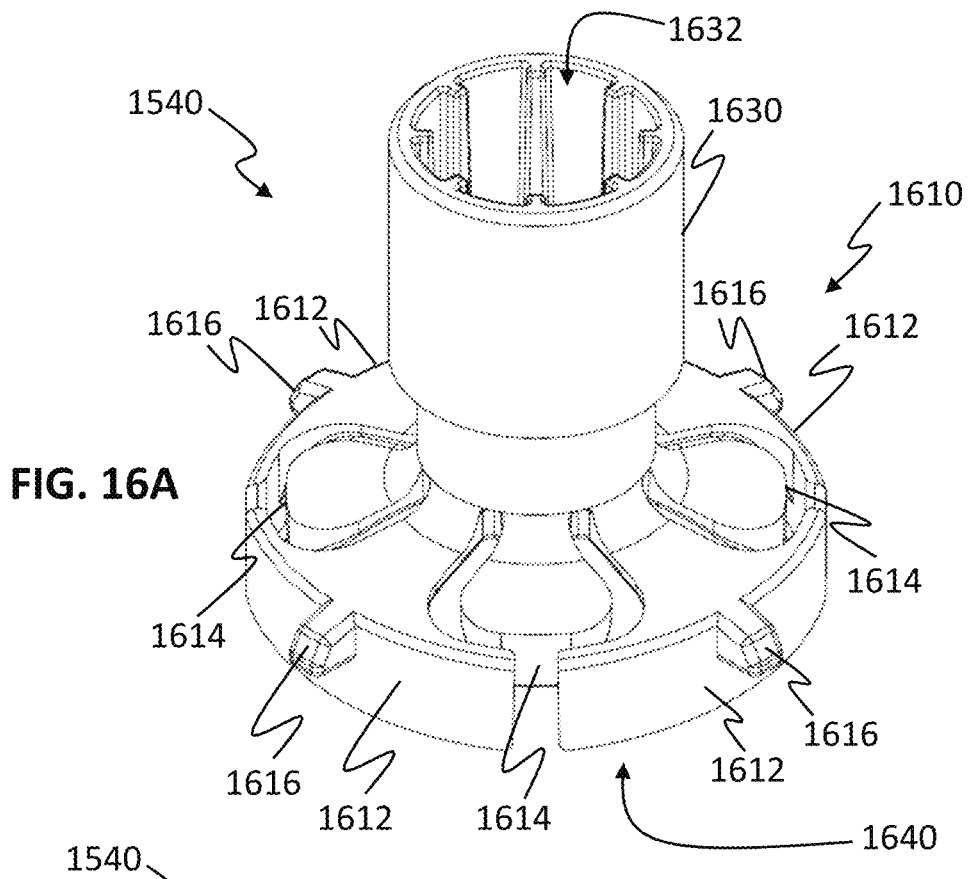
Figure 16B:
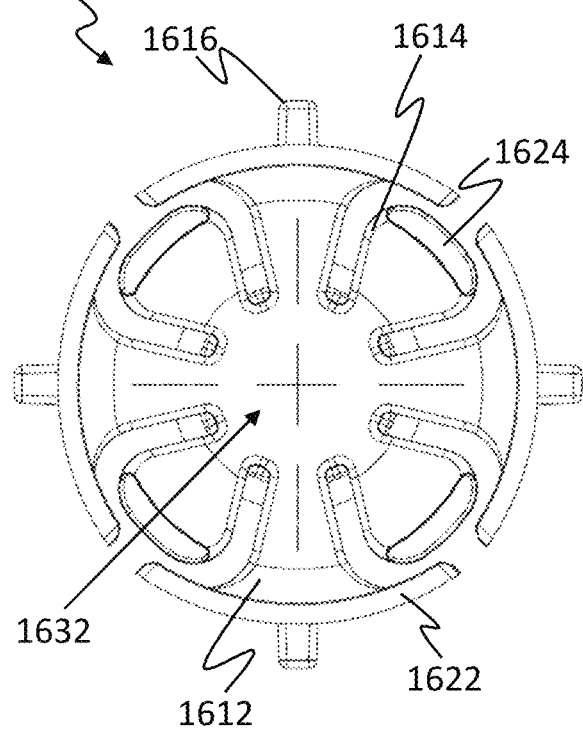
Figure 16C:
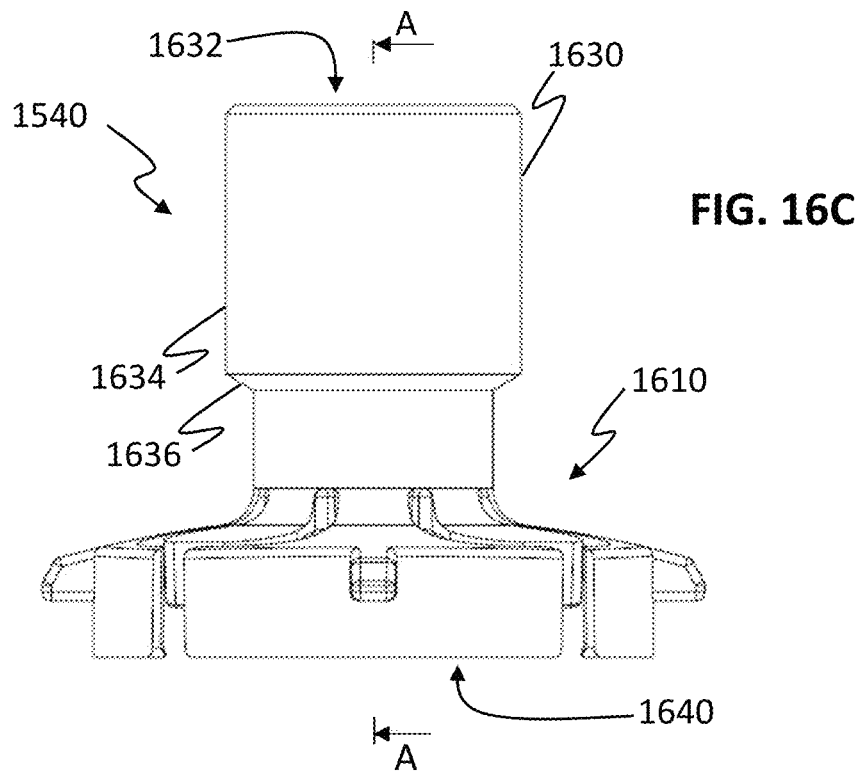
Figure 16D:
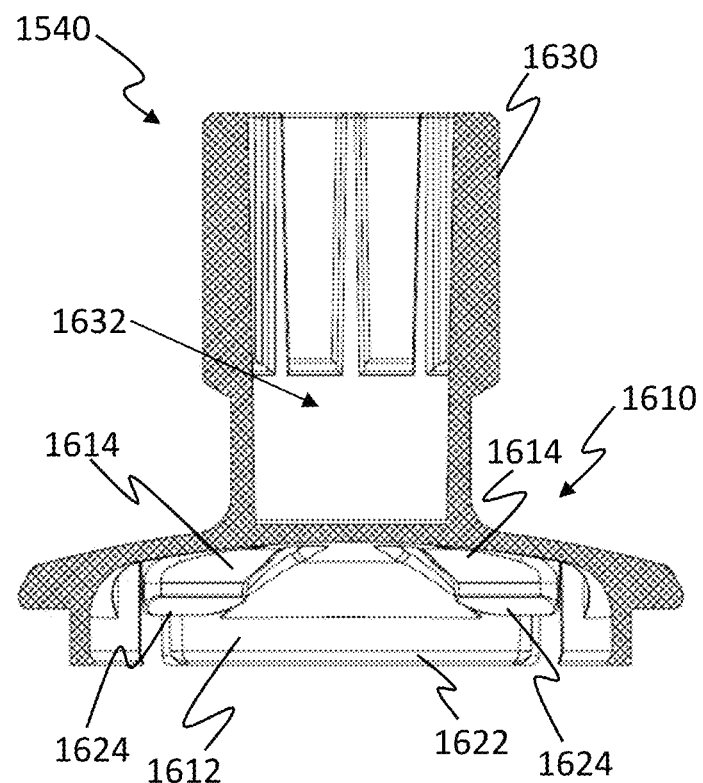
Figure 16E:
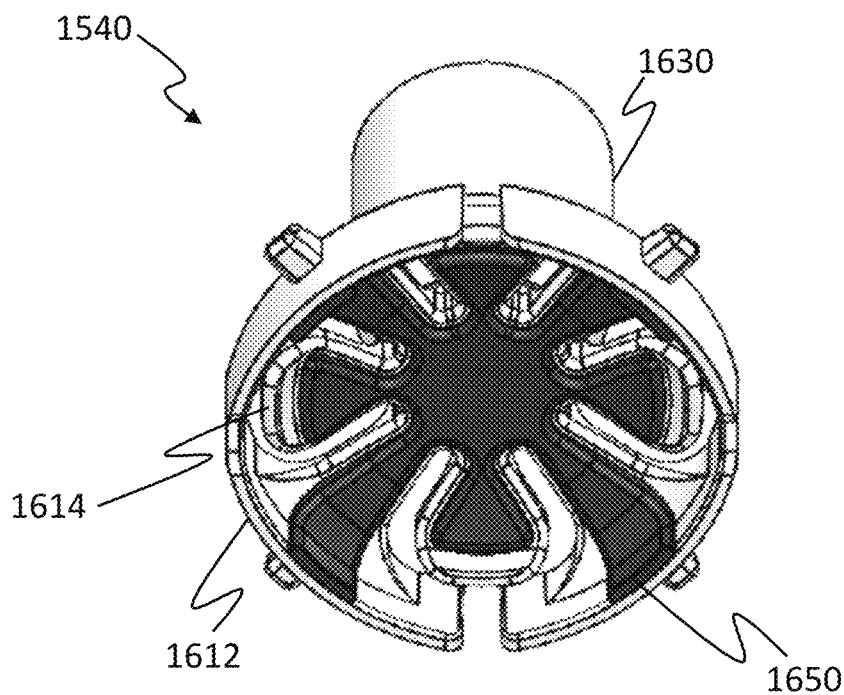
Figure 16F:
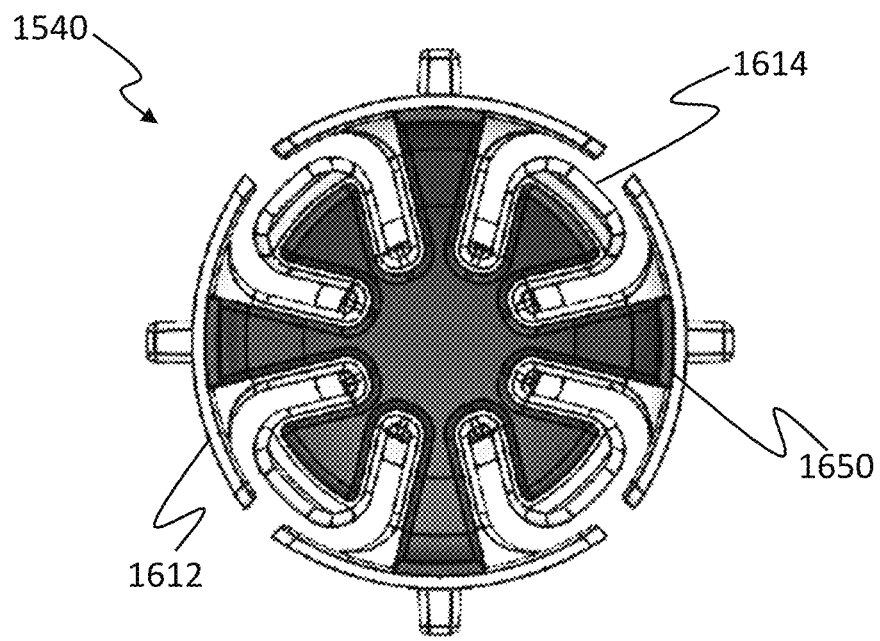

FIGS. 16E and 16F depict aspects of a shuttle of an applicator for an analyte monitoring device in a bottom perspective view and a bottom view, respectively.

Figure 16G:
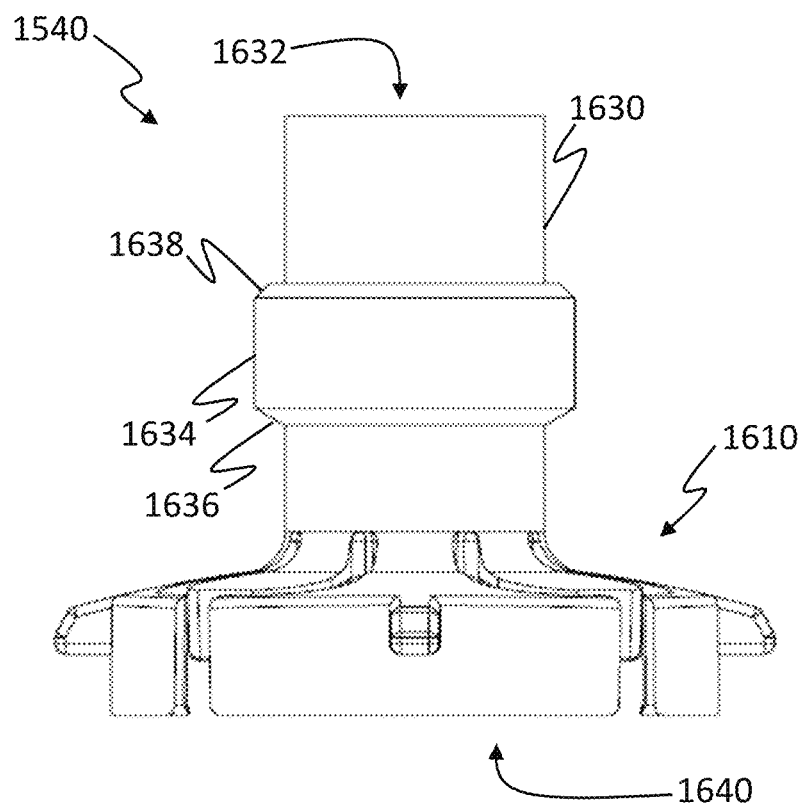
Figure 16H:
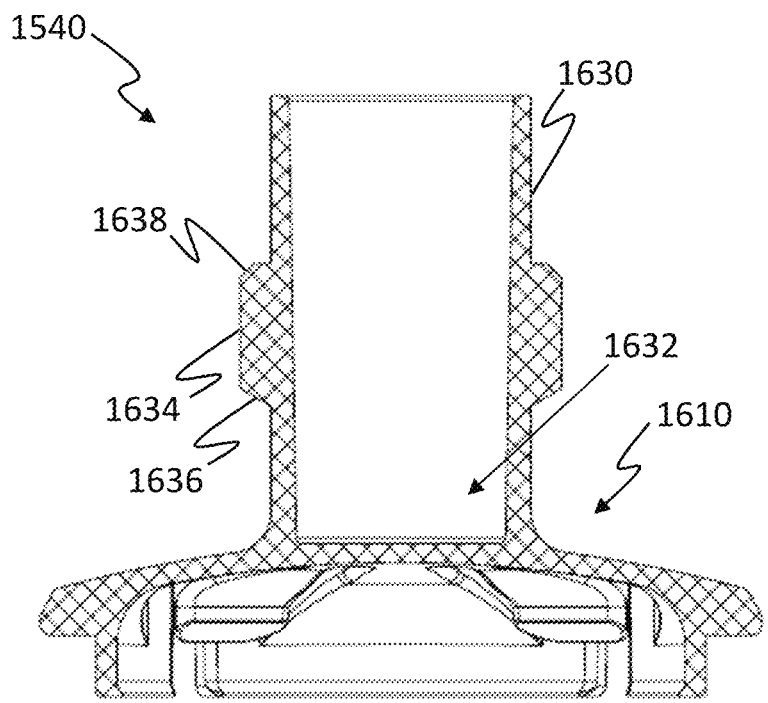

FIGS. 16G and 16H depict aspects of a shuttle of an applicator for an analyte monitoring device in a side view and a side cross-sectional view, respectively.

FIGS. 17A-17E depict aspects of a cuff of an applicator for an analyte monitoring device in a top perspective view, a bottom view, a top view, a first side and side cross-sectional view, and a second side and side cross-sectional view, respectively.

Figure 17A:
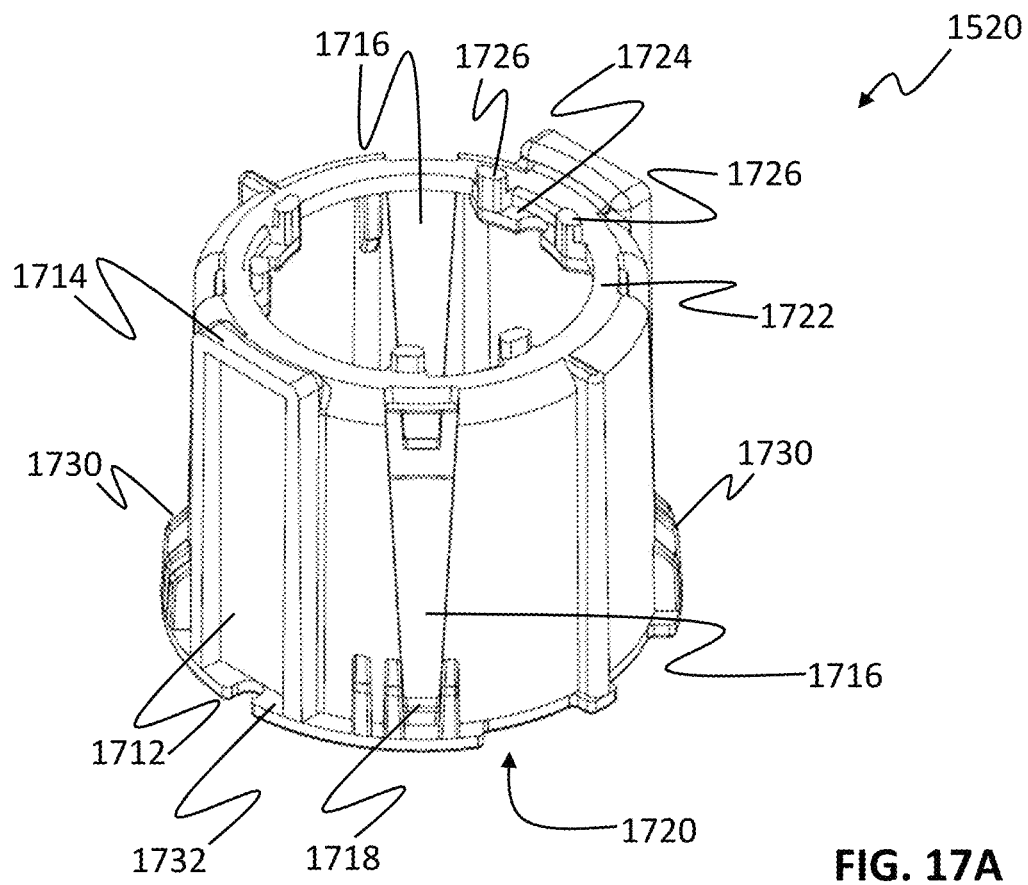
Figure 17B:
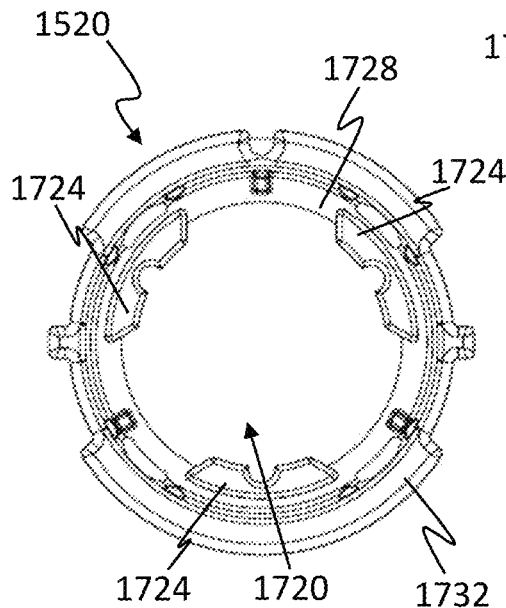
Figure 17C:
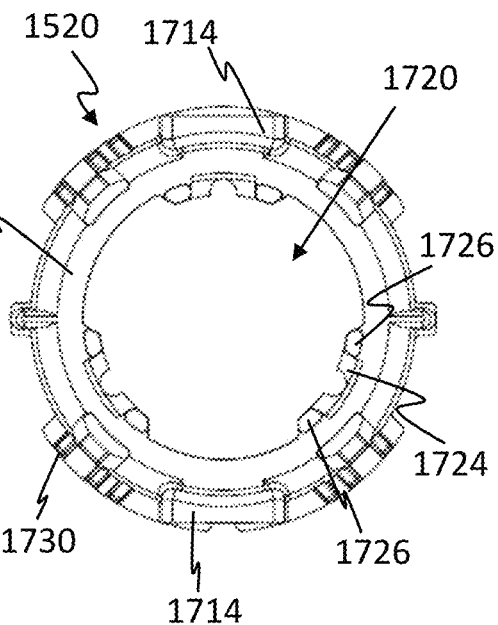
Figure 17D:
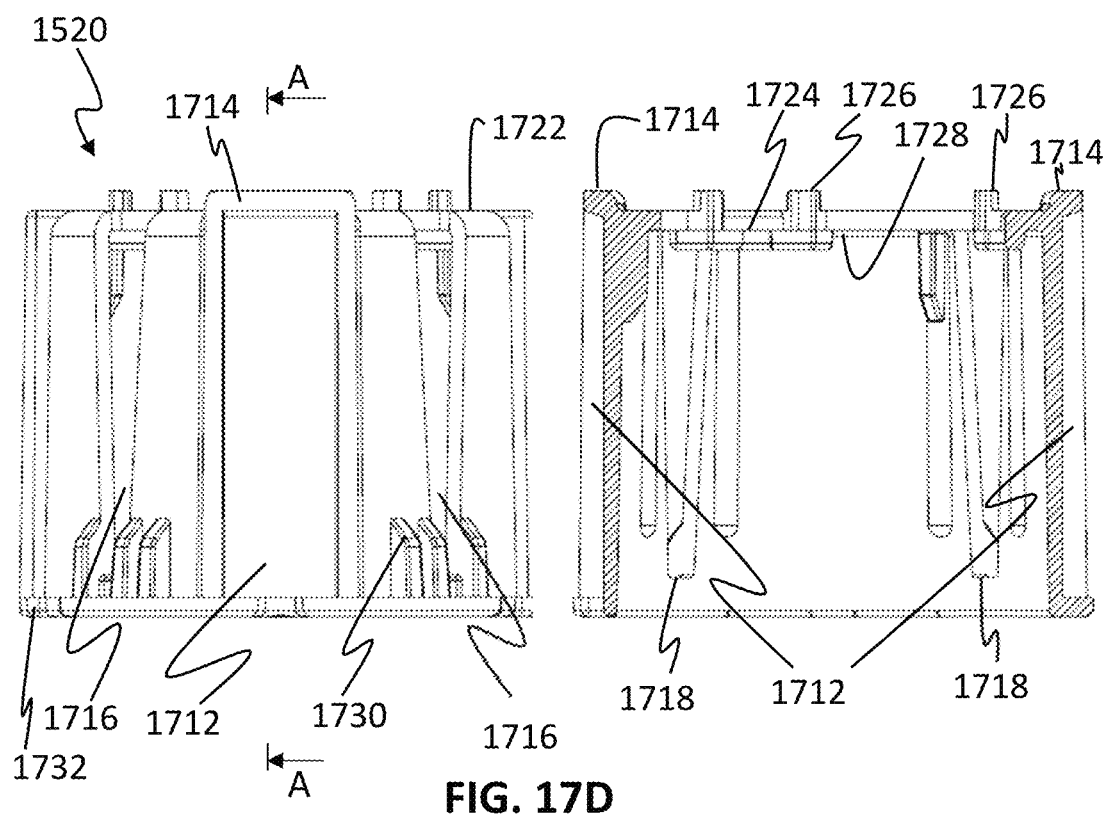
Figure 17E:
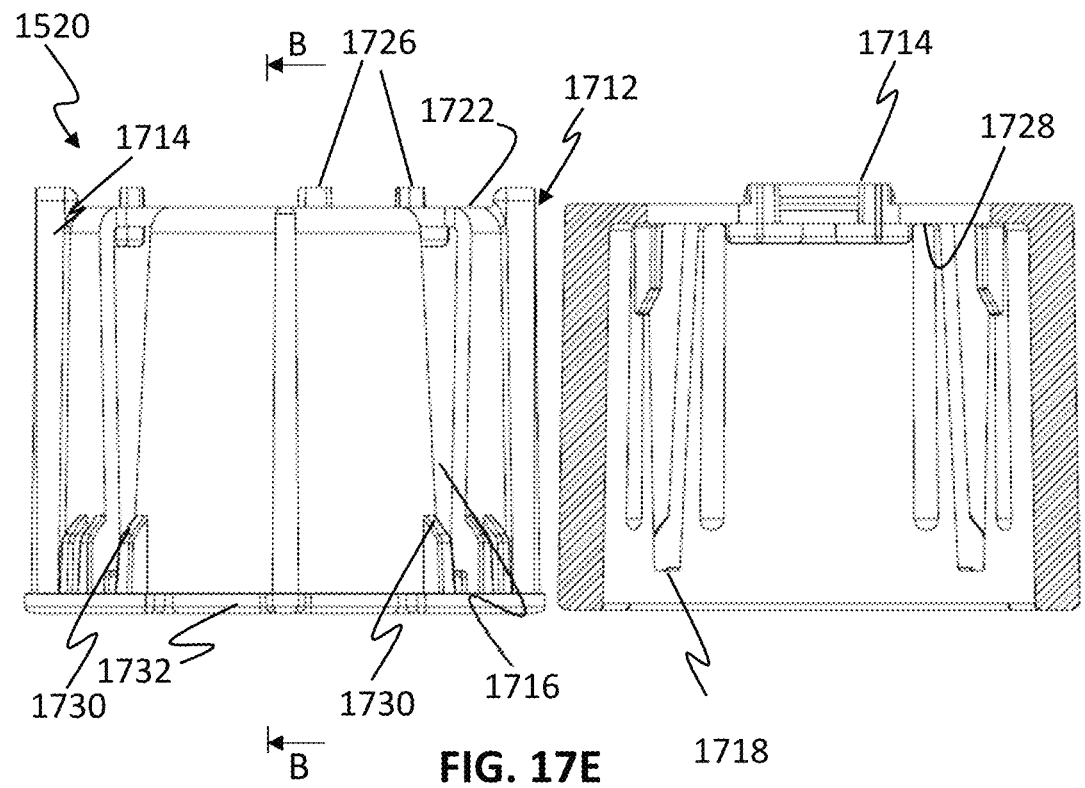
Figure 17F:
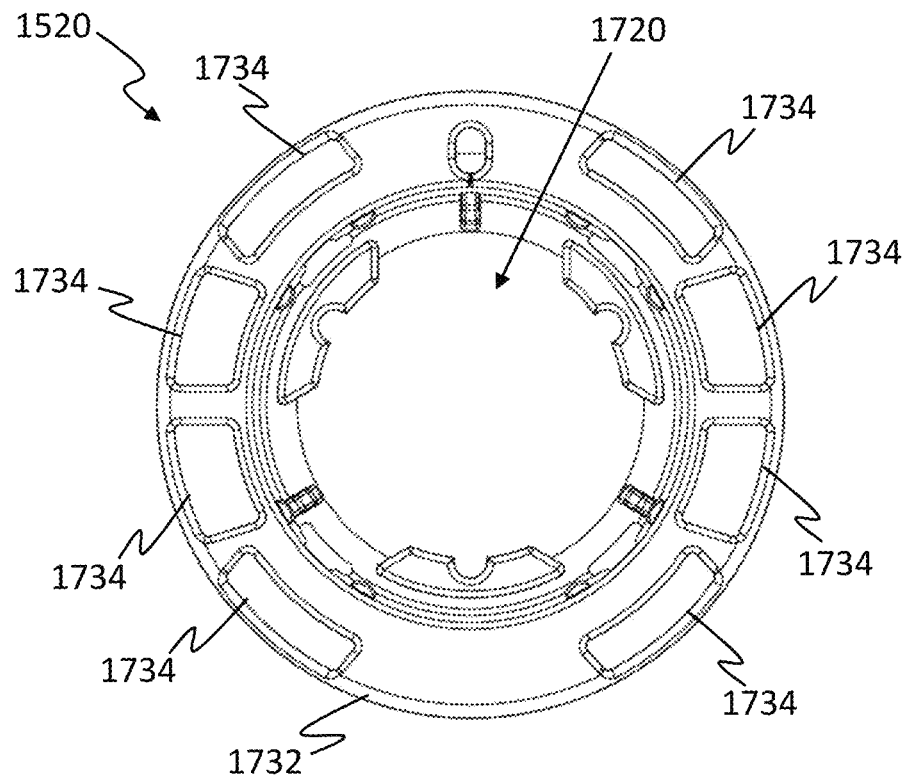
Figure 17G:
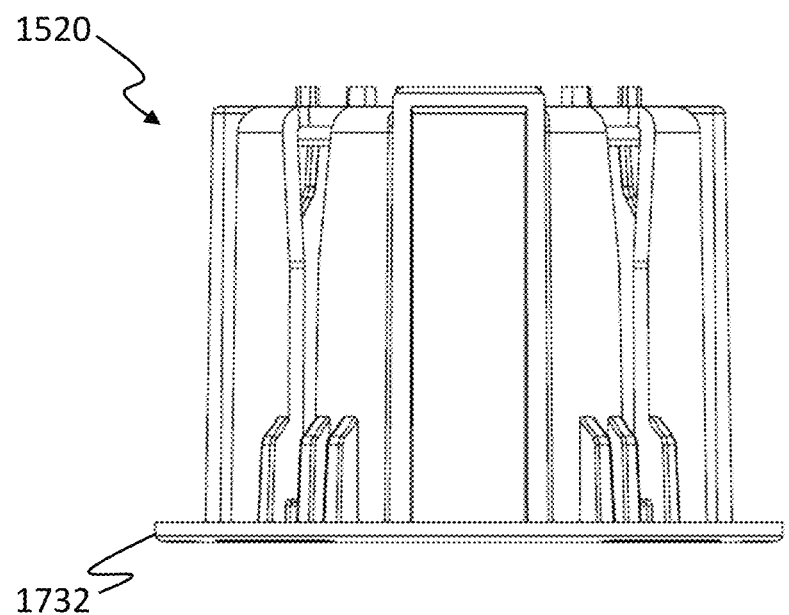

FIGS. 17F and 17G depict aspects of a cuff of an applicator for an analyte monitoring device in a bottom view and a side view, respectively.

FIGS. 18A-18D depict aspects of a locking friction ring of an applicator for an analyte monitoring device in a first top perspective view, a second top perspective view, a first bottom perspective view, and a second bottom perspective view, respectively.

FIGS. 19A-19E depict aspects of a cuff-ring assembly of an applicator for an analyte monitoring device in a top perspective view, a bottom view, a top view, a side view, and a side cross-sectional view with detailed views, respectively.

FIGS. 20A-20F depict aspects of a housing of an applicator for an analyte monitoring device in a first top perspective view, a second top perspective view, a first bottom perspective view, a second bottom perspective view, a first side cross-sectional view, and a second side cross-sectional view, respectively.

Figure 21A:
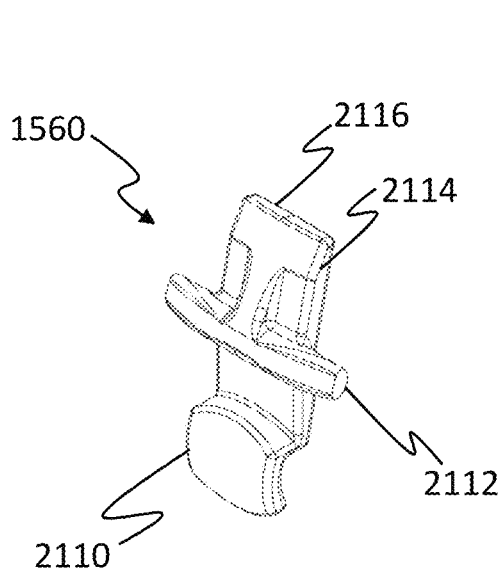
Figure 21B:
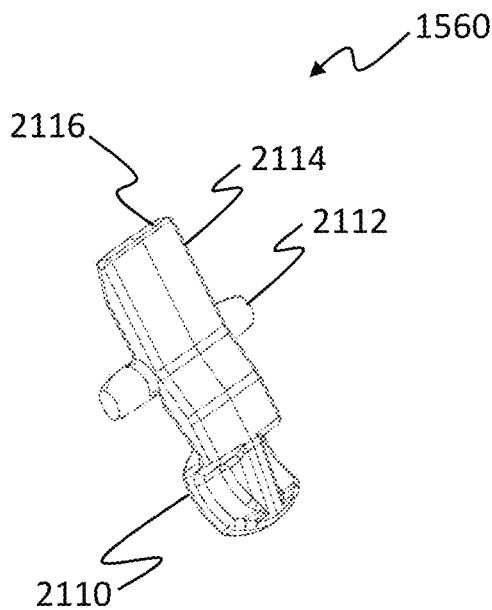

FIGS. 21A-21B depict aspects of a locking member of an applicator for an analyte monitoring device in a front perspective view and a back perspective view, respectively.

FIGS. 22A-22G depict aspects of a base of an applicator for an analyte monitoring device in a top perspective view, a top view, a bottom view, a first side view, a first side cross-sectional view, a second side view, and a second side cross-sectional view, respectively.

Figure 22A:
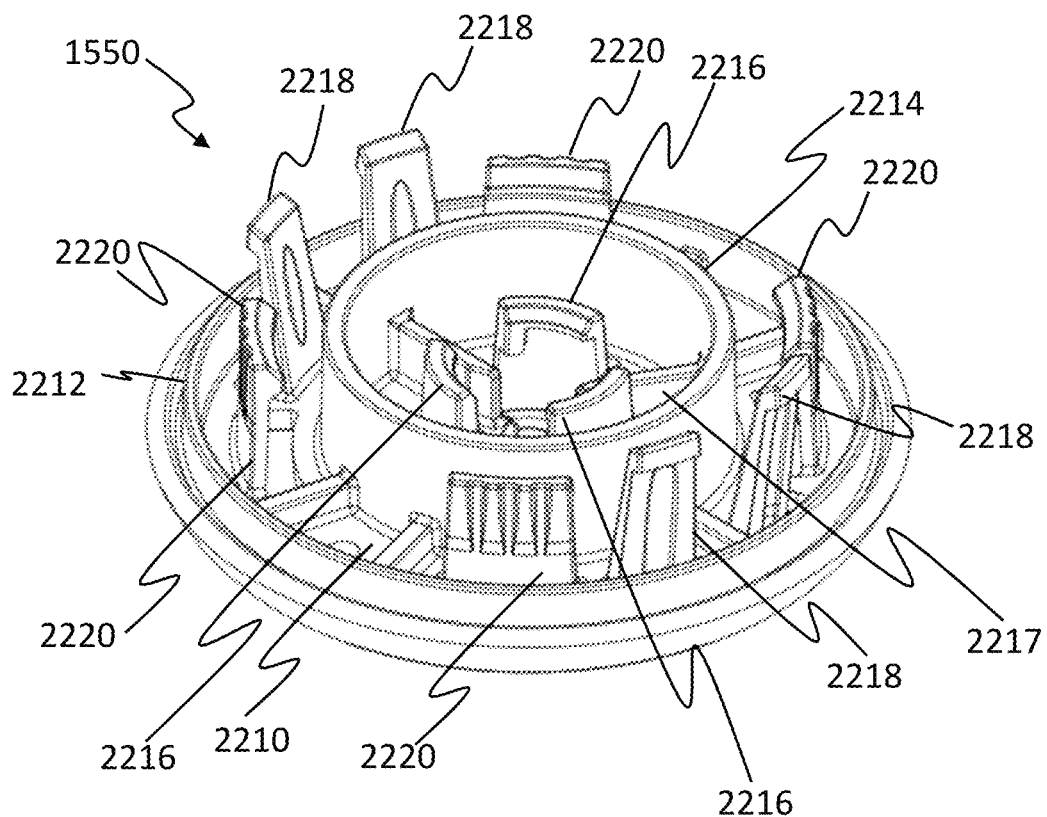
Figure 22B:
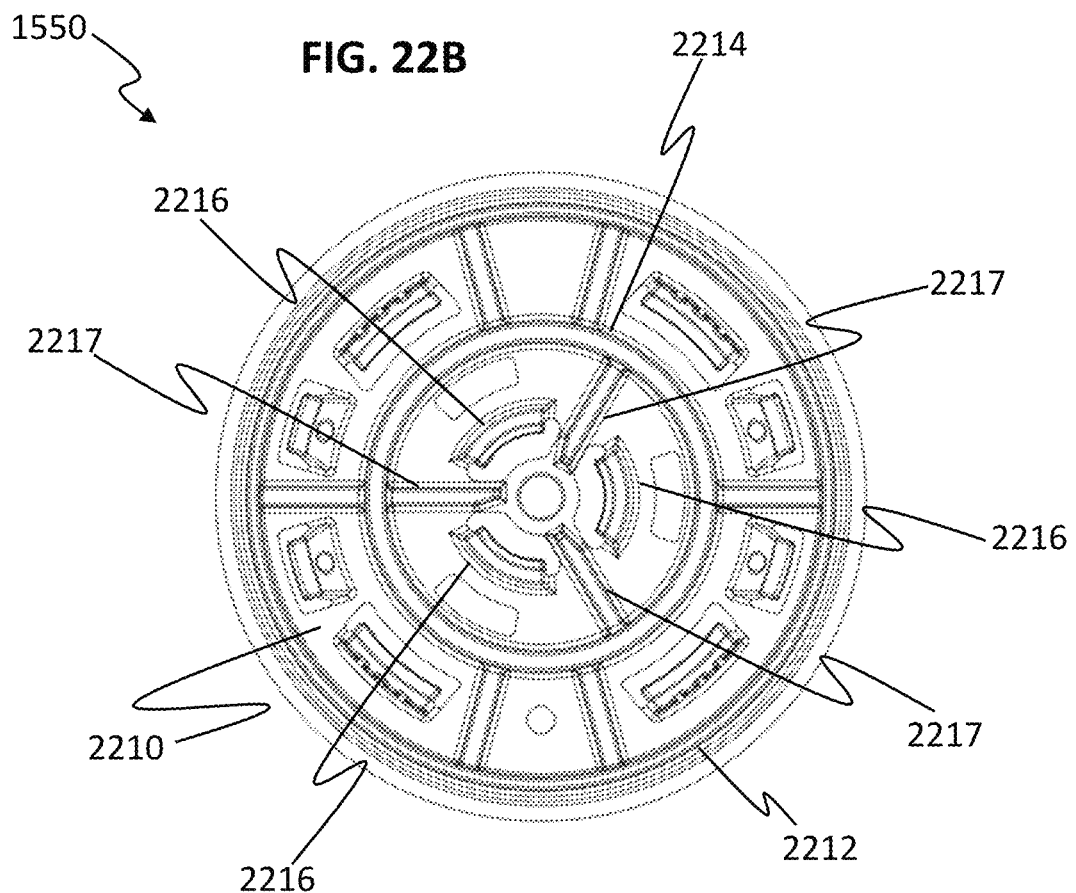
Figure 22C:
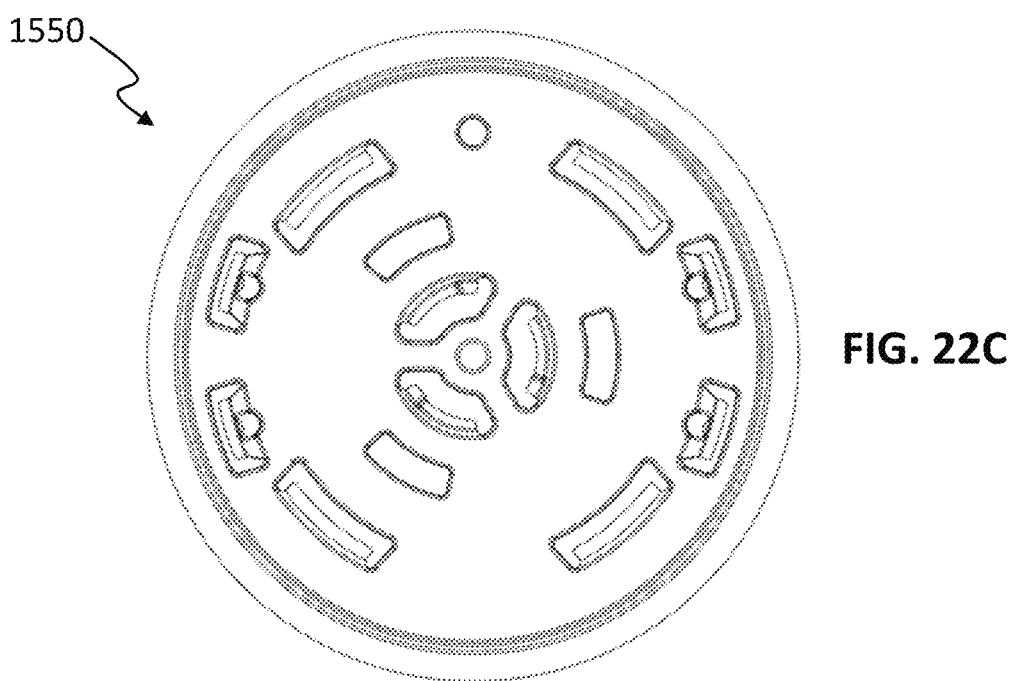
Figure 22H:
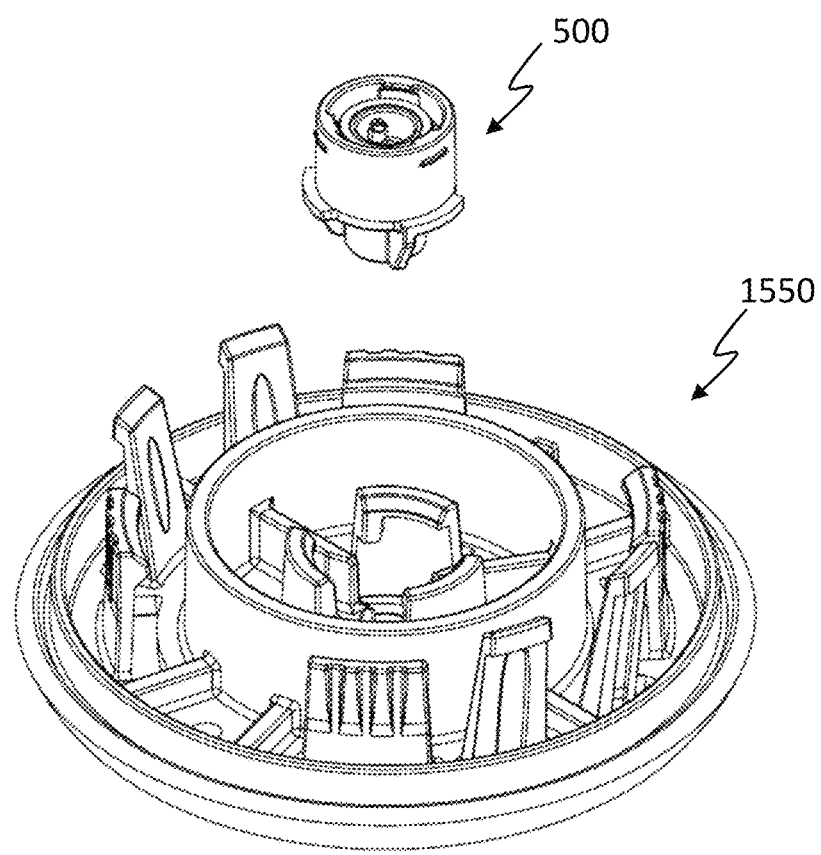
Figure 22I:
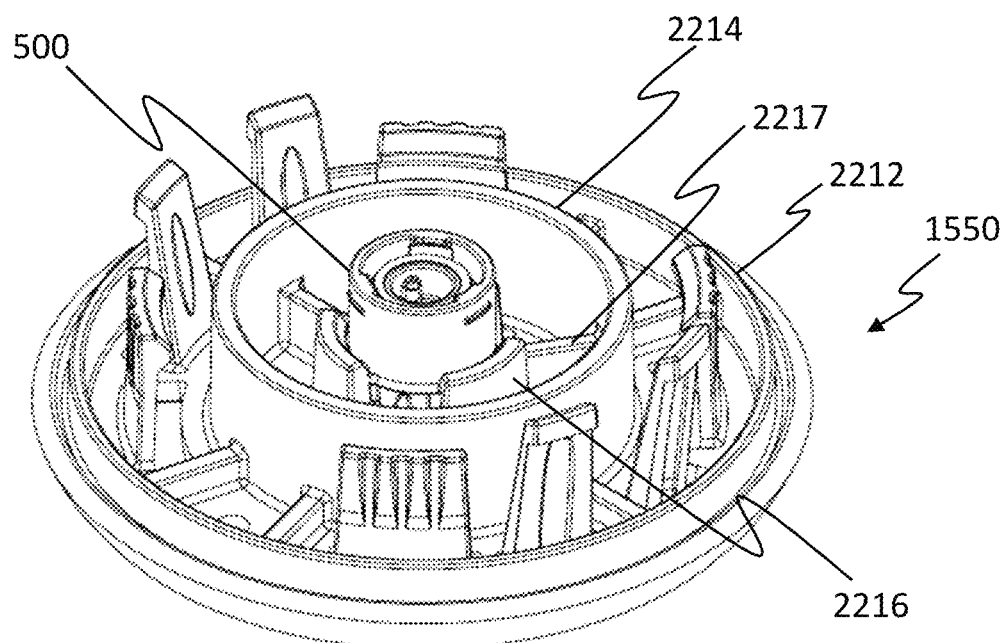
Figure 22J:
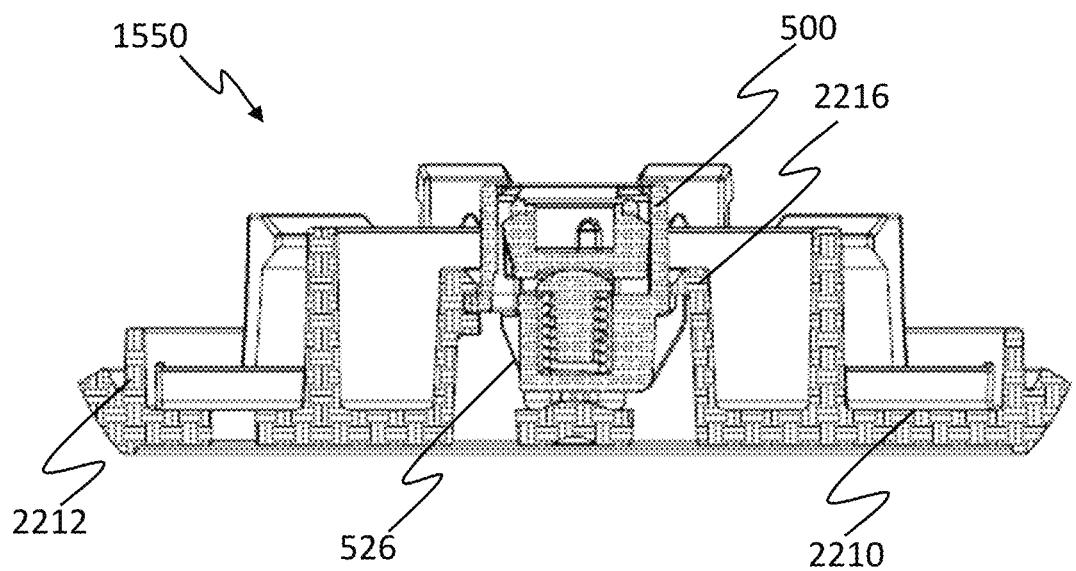

FIGS. 22H-22J depict aspects of a base of an applicator for an analyte monitoring device with a microneedle enclosure in an exploded view, a top perspective view, and a side cross-sectional view, respectively.

Figure 22K:
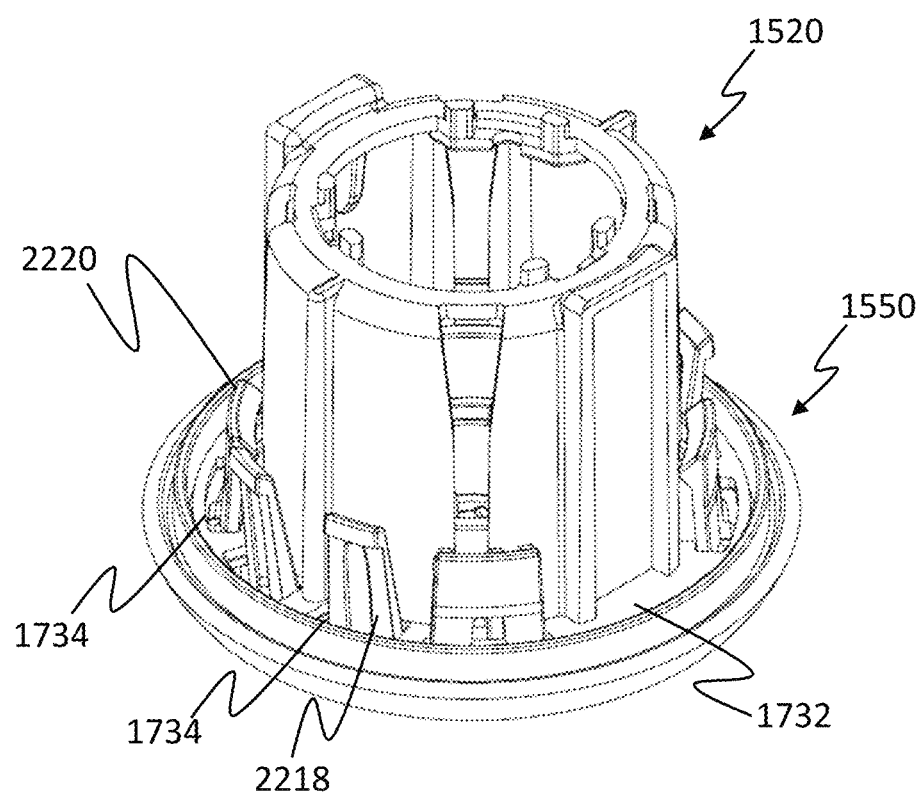

FIG. 22K depicts aspects of a base of an applicator for an analyte monitoring device engaged with a cuff of the applicator in a top perspective view.

Figure 23C:
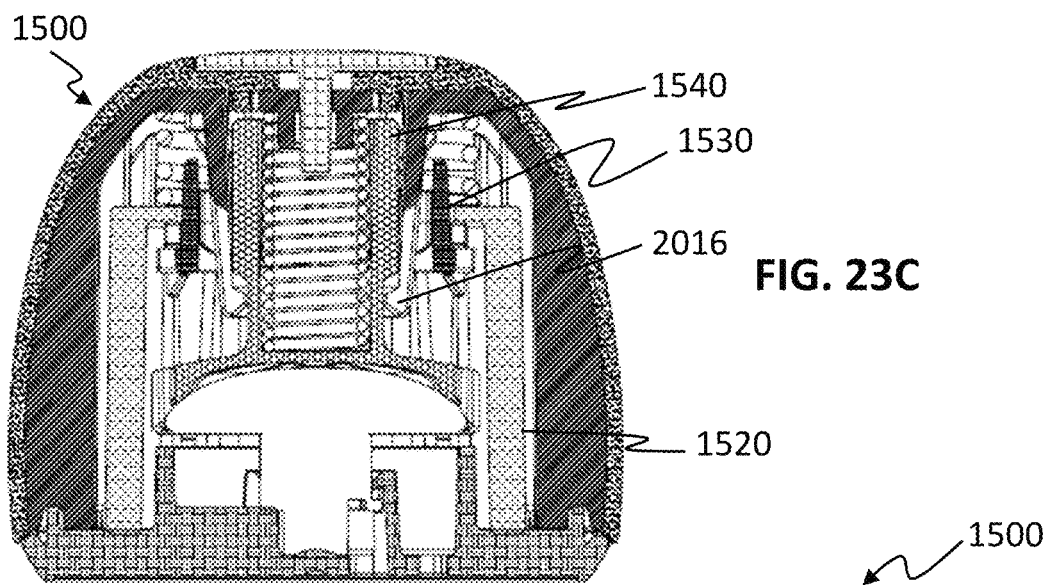
Figure 23D:
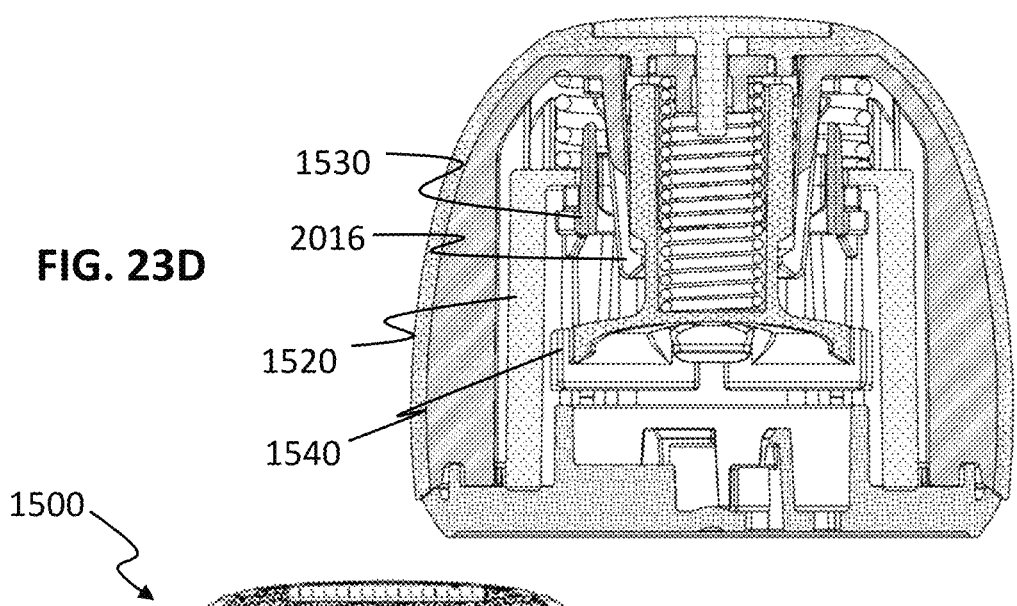
Figure 23E:
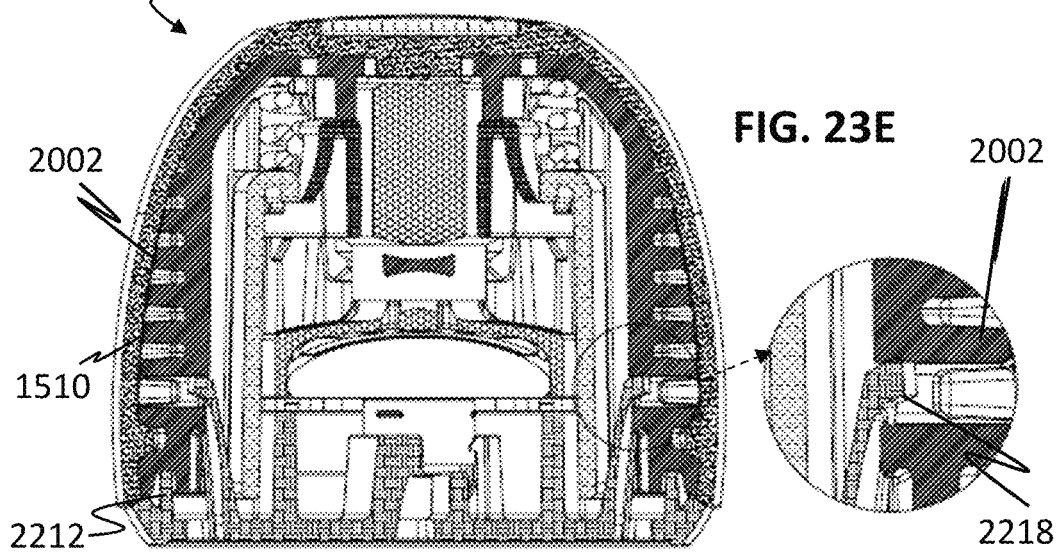
Figure 23F:
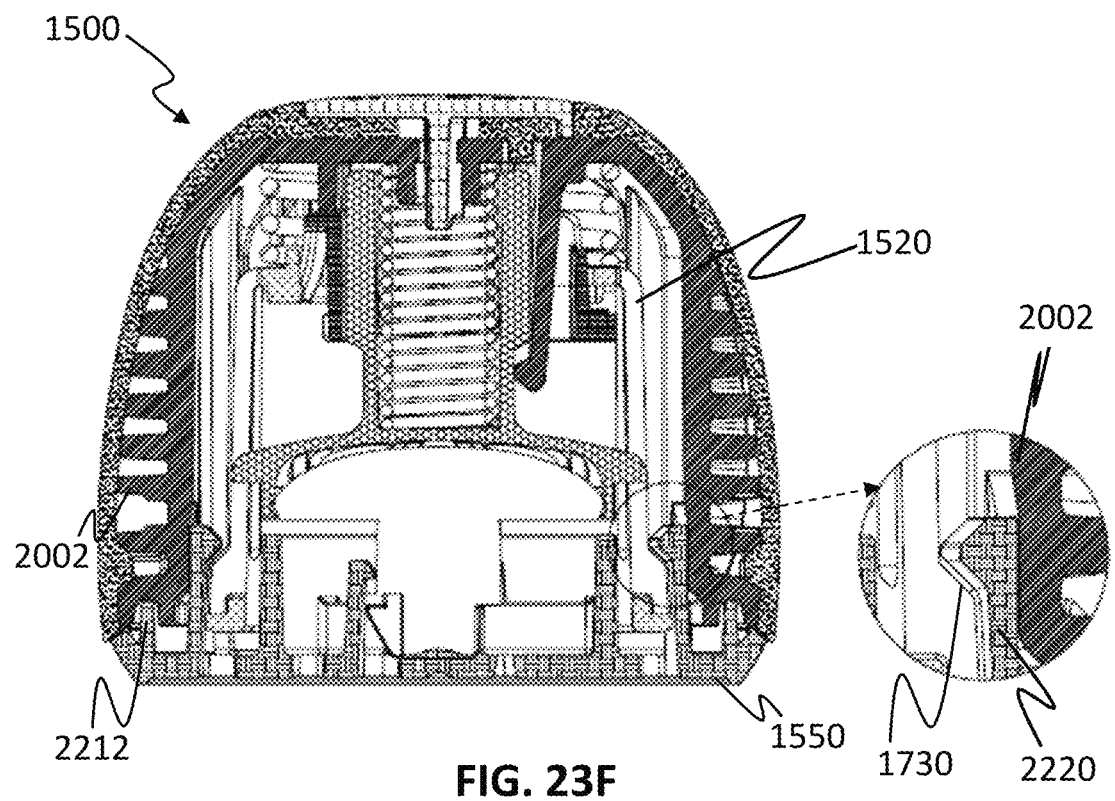
Figure 23G:
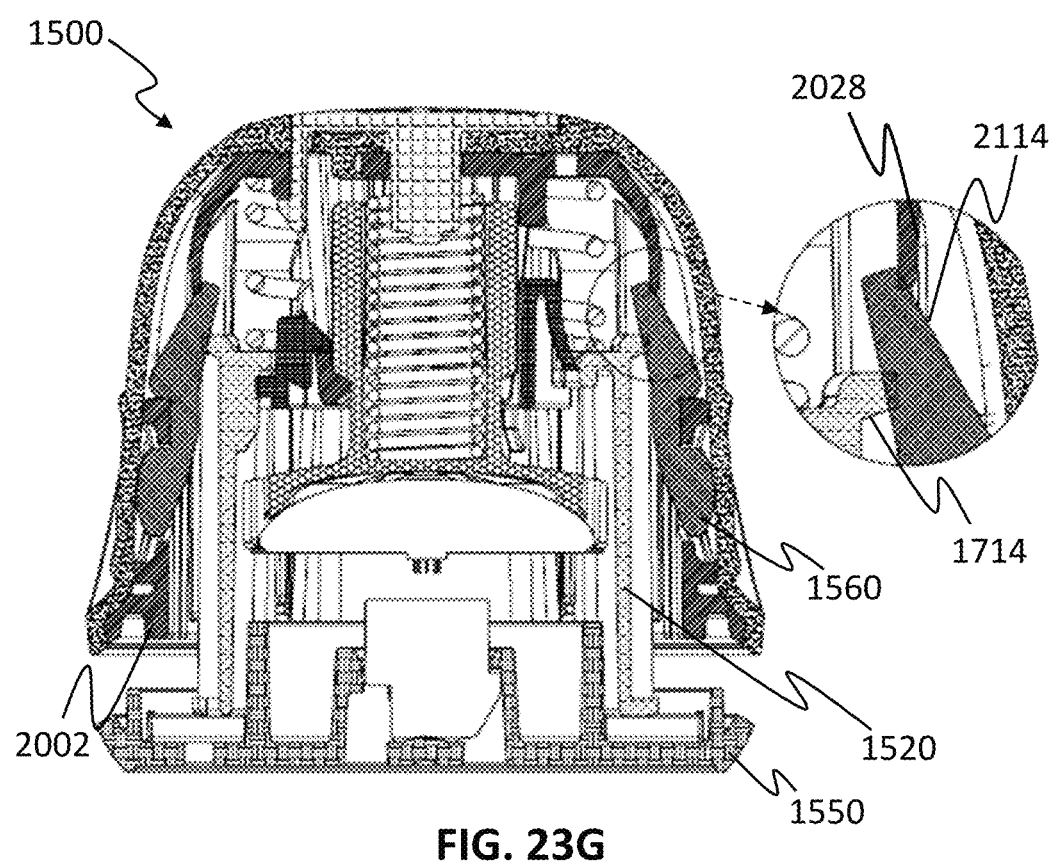
Figure 23H:
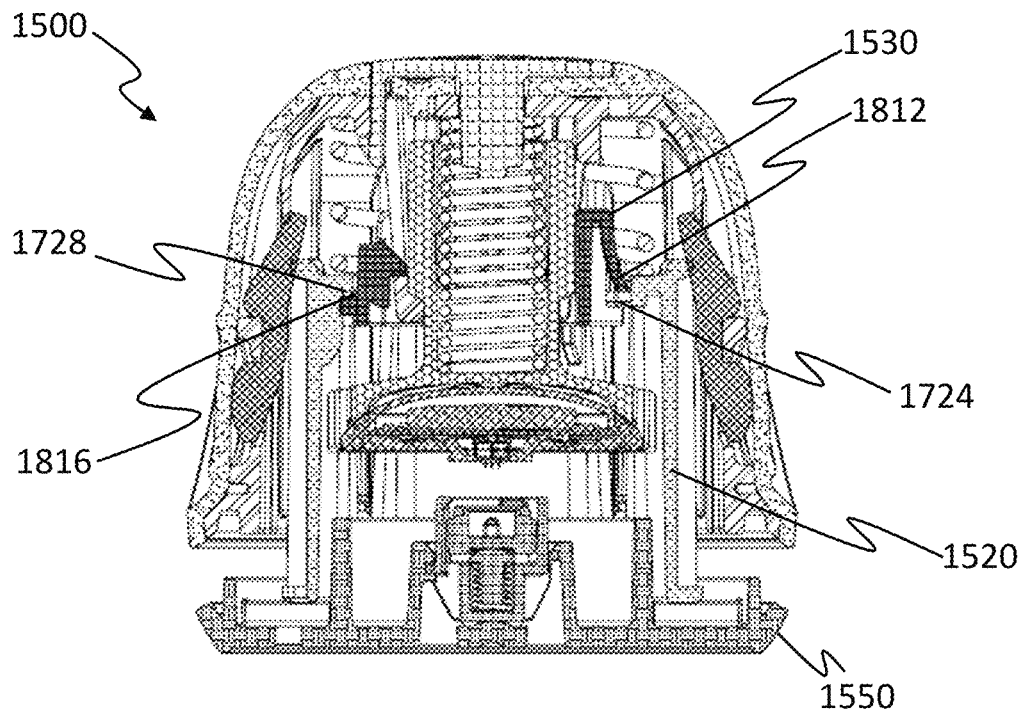
Figure 23I:
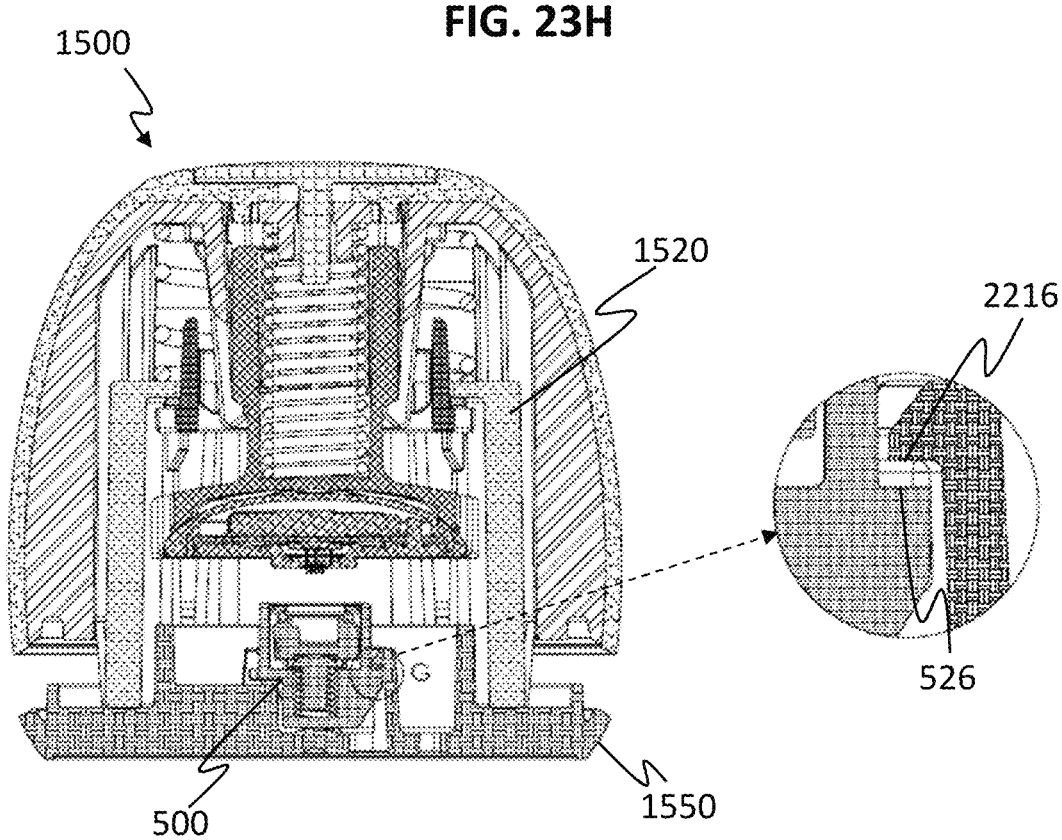
Figure 23J:
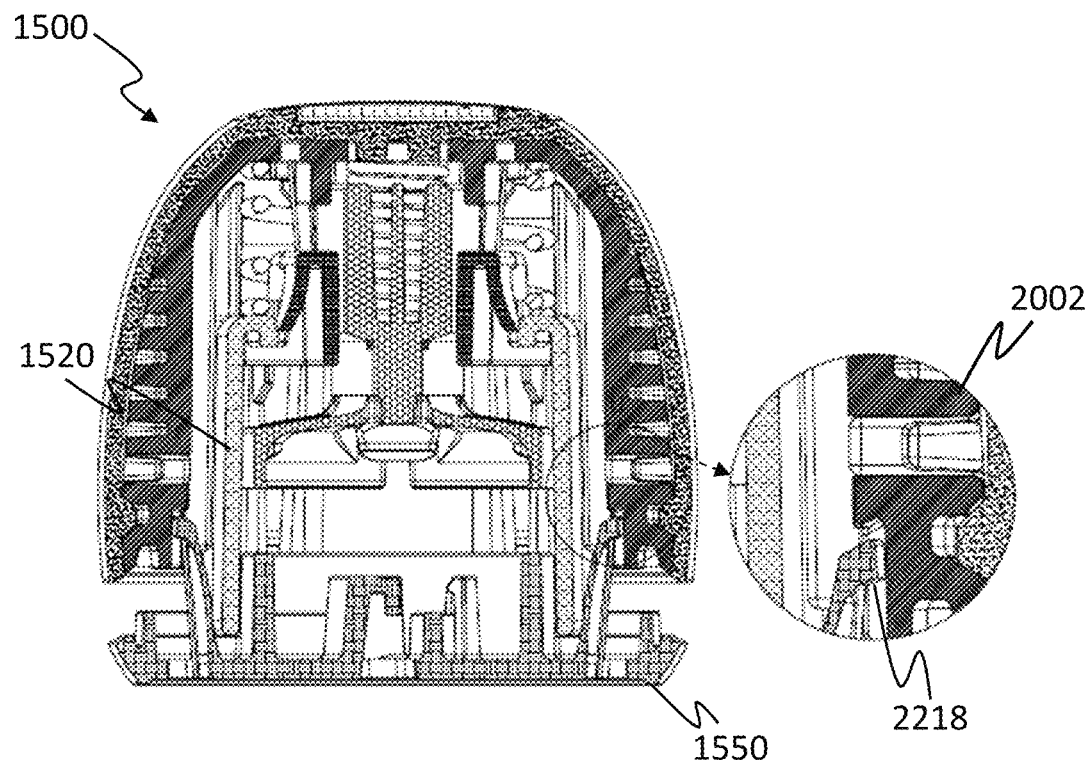
Figure 23K:
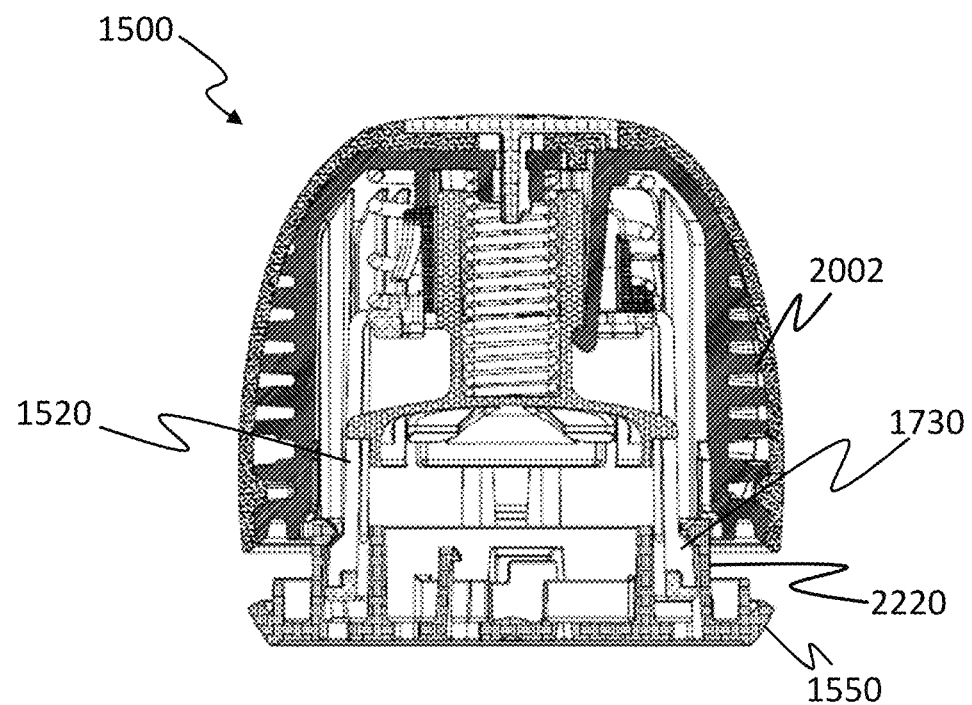
Figure 23L:
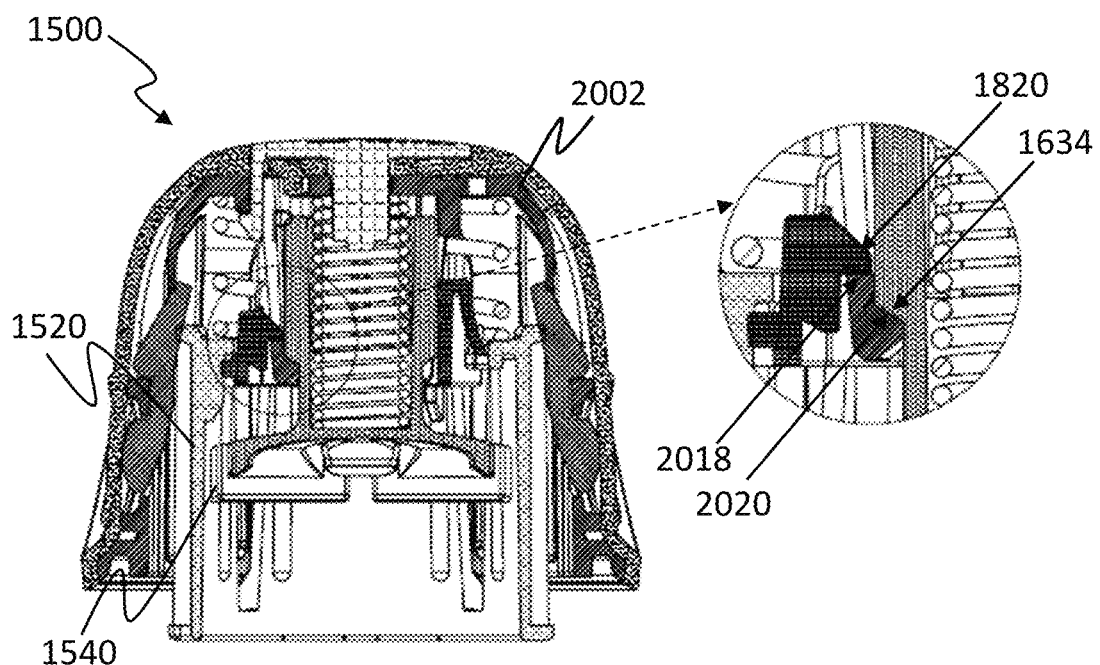
Figure 23M:
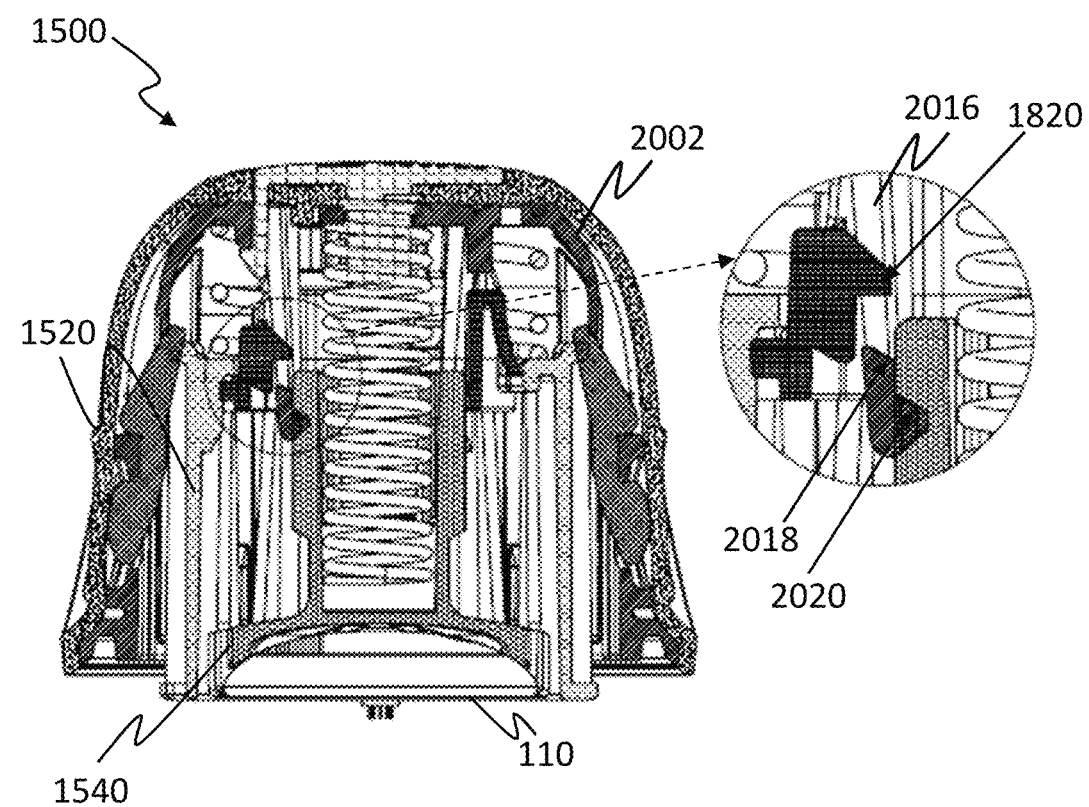
Figure 23N:
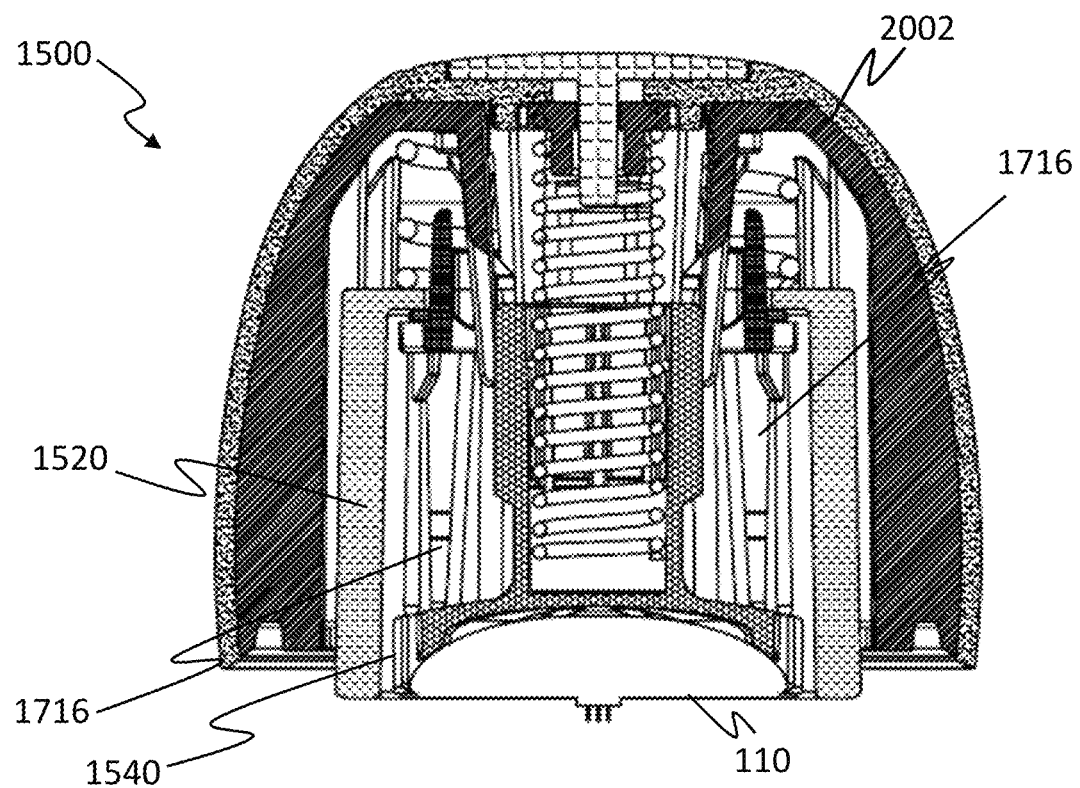
Figure 23O:
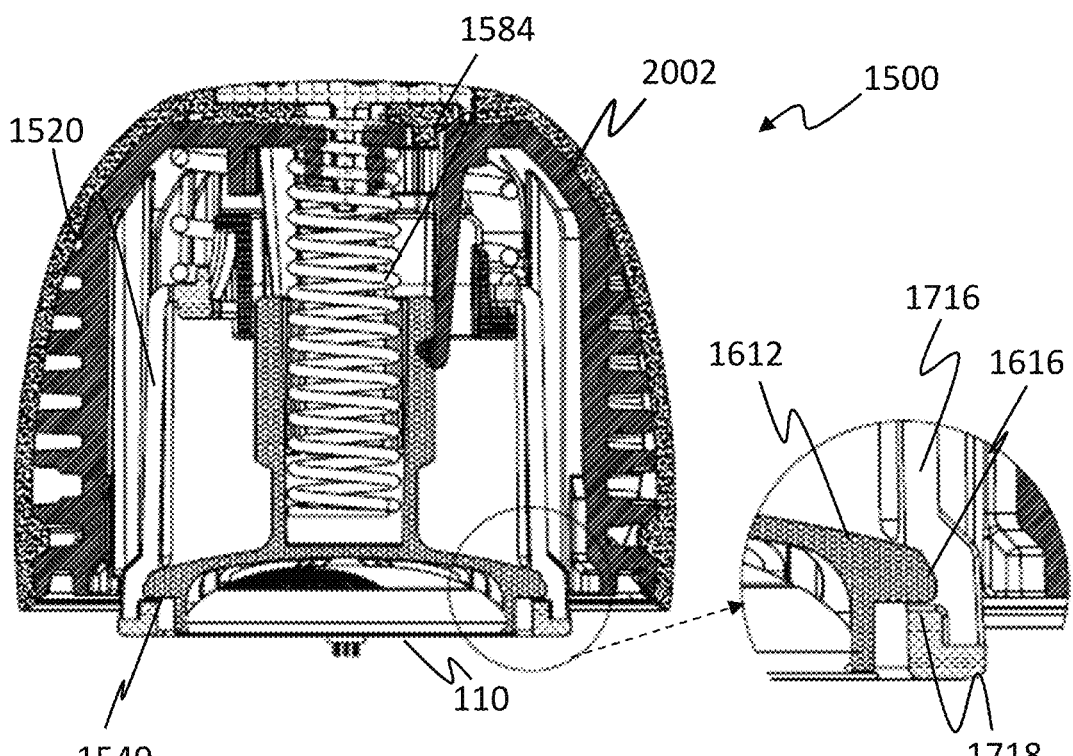

FIGS. 23A-23O depict, in cross-sectional and close-up views, views of an applicator for an analyte monitoring device in various configurations.

Figure 24:
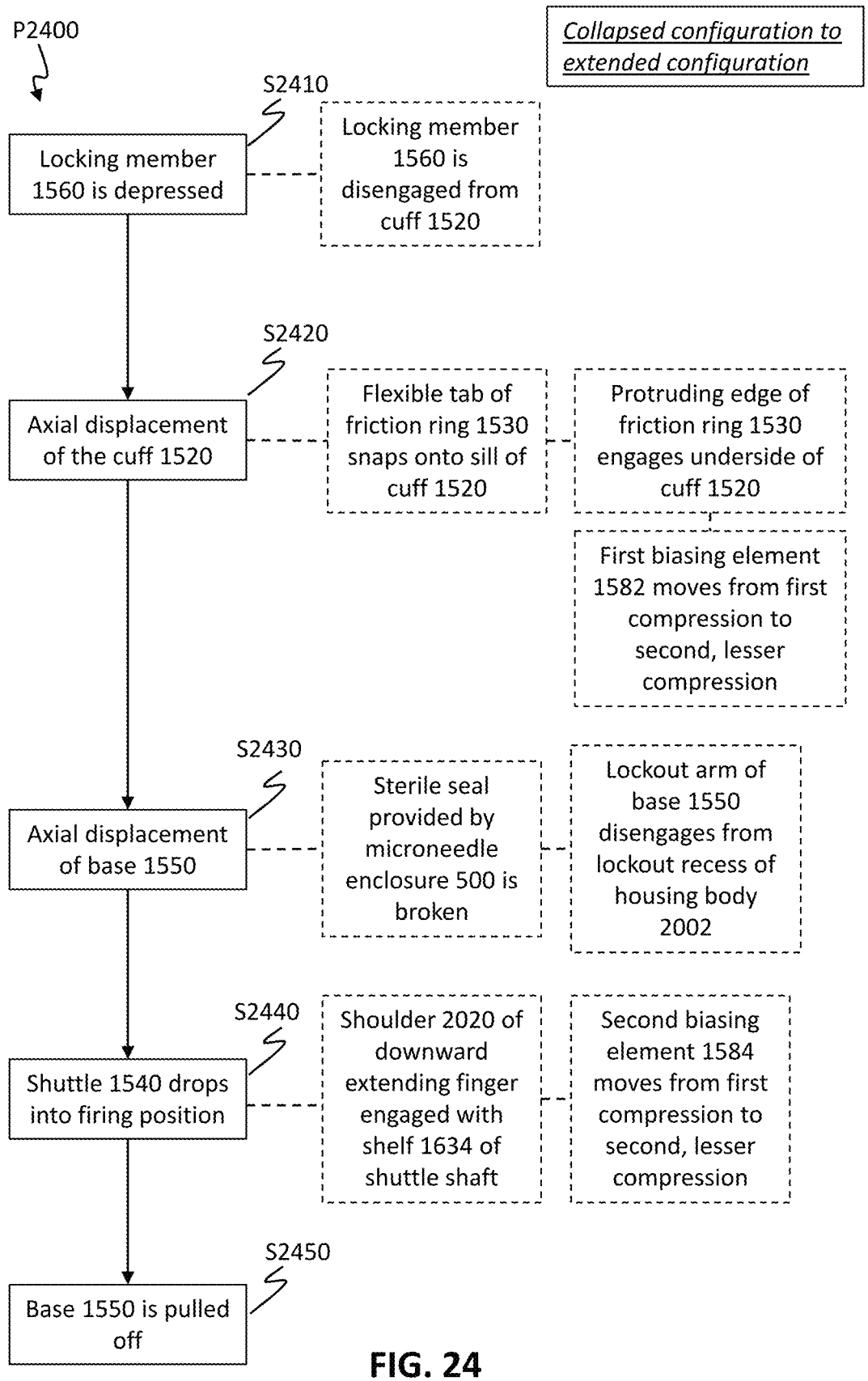

FIG. 24 is a process flowchart illustrating a process from a collapsed configuration to an extend configuration of an applicator.

Figure 25:
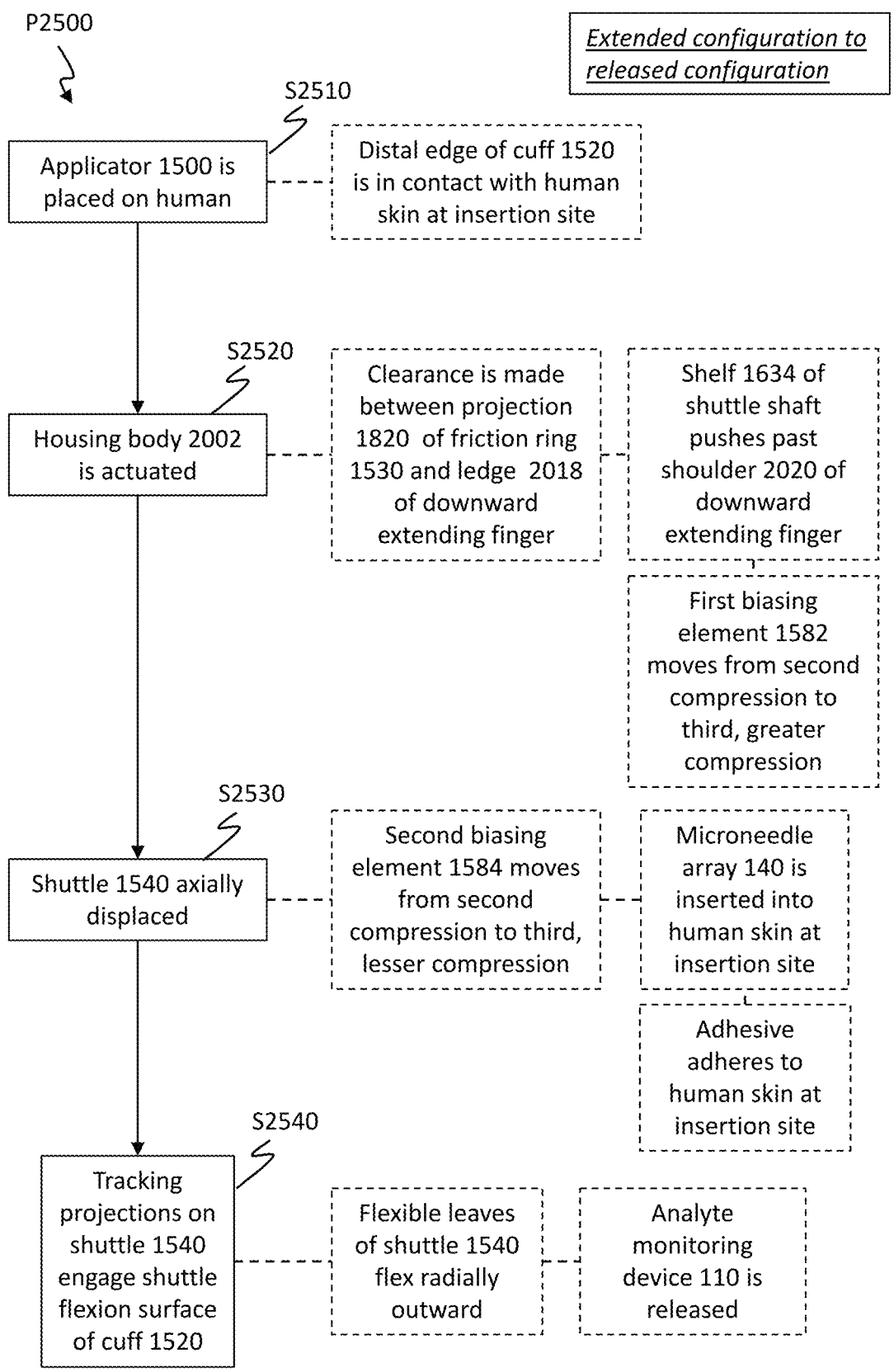

FIG. 25 is a process flowchart illustrating a process from an extended configuration to a released configuration of an applicator.

Figure 26A:
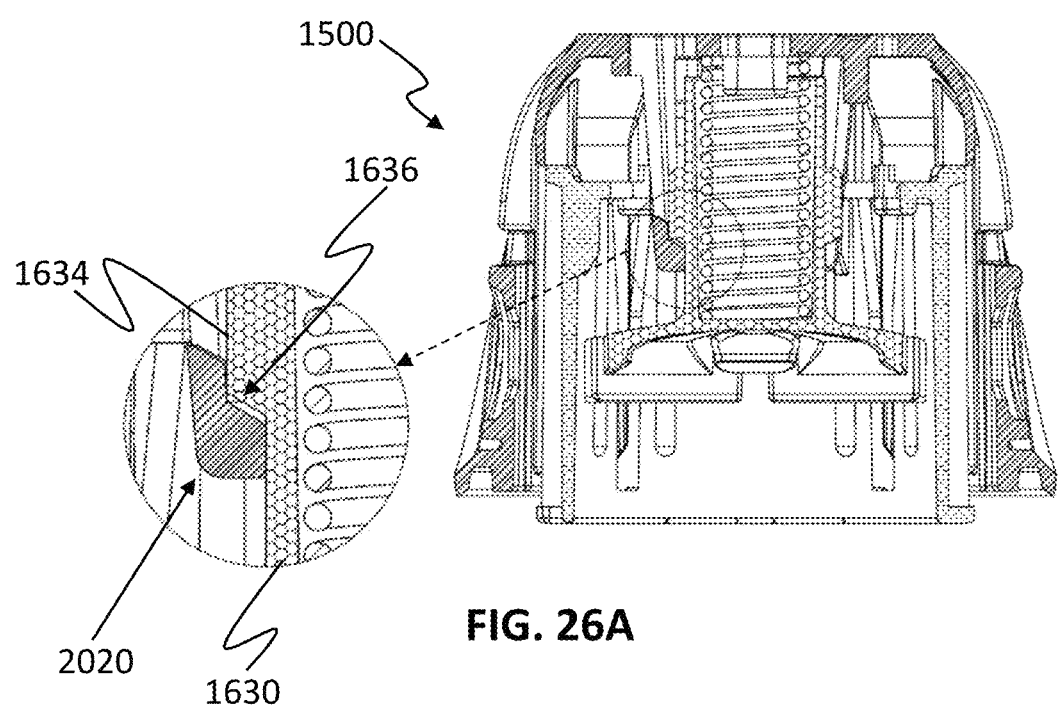
Figure 26B:
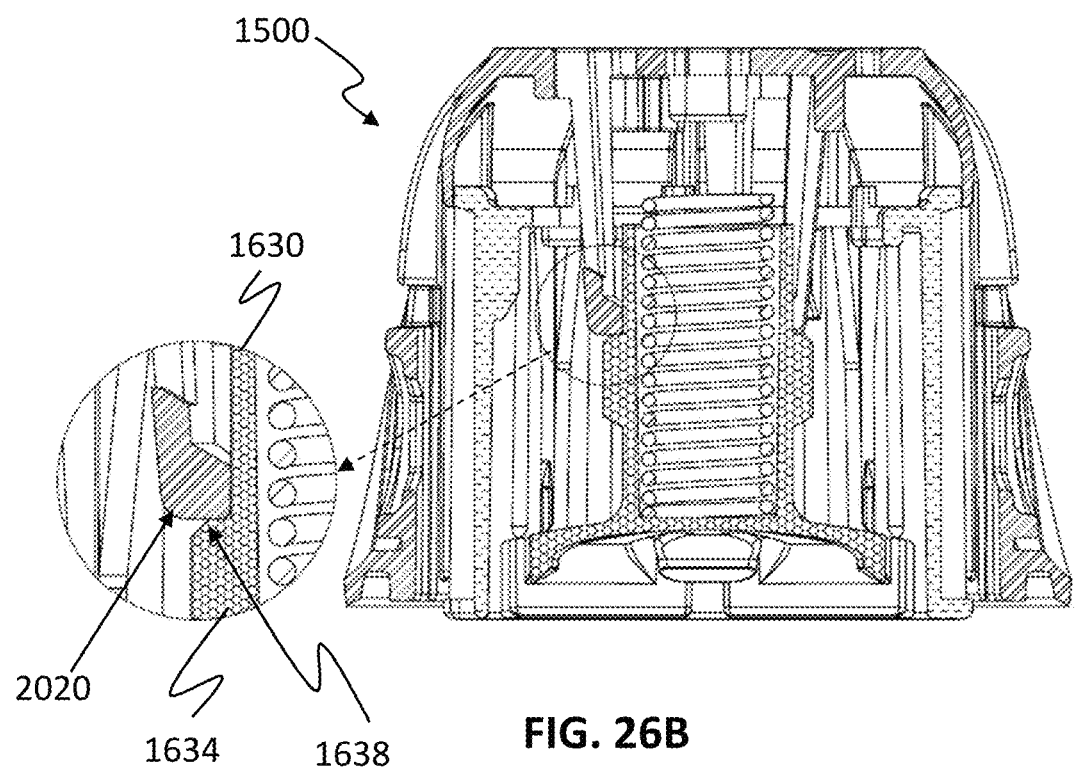

FIGS. 26A and 26B depict, in cross-sectional and close-up views, views of an applicator for an analyte monitoring device in various configurations.

Figure 27A:
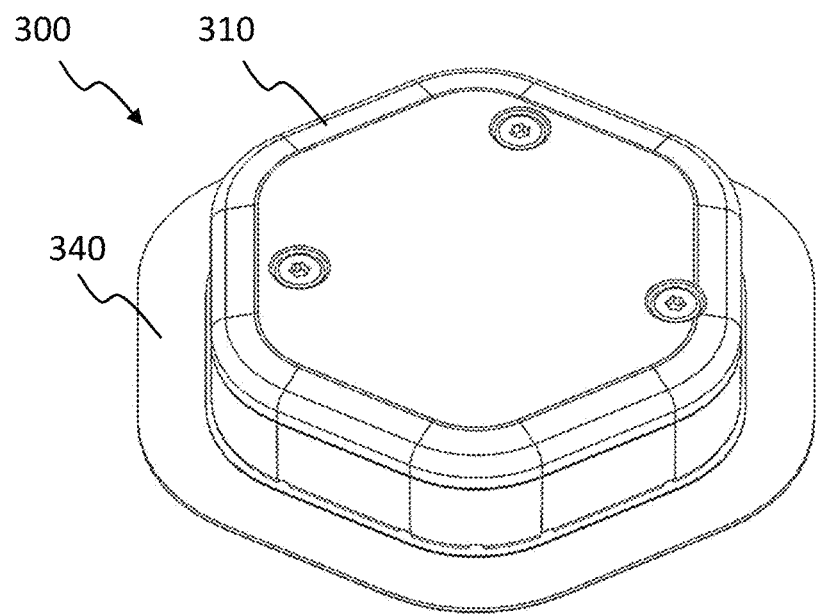
Figure 27B:
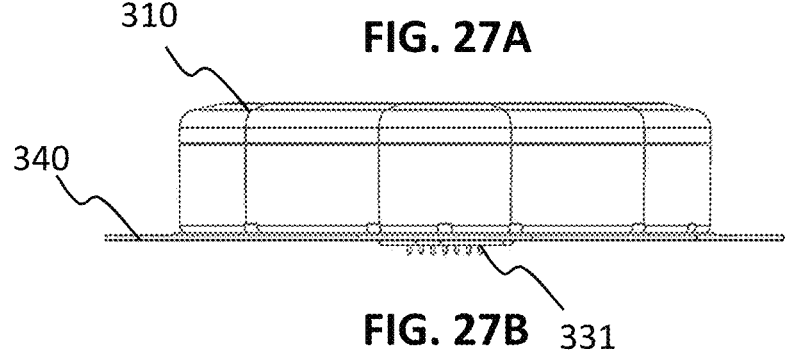
Figure 27C:
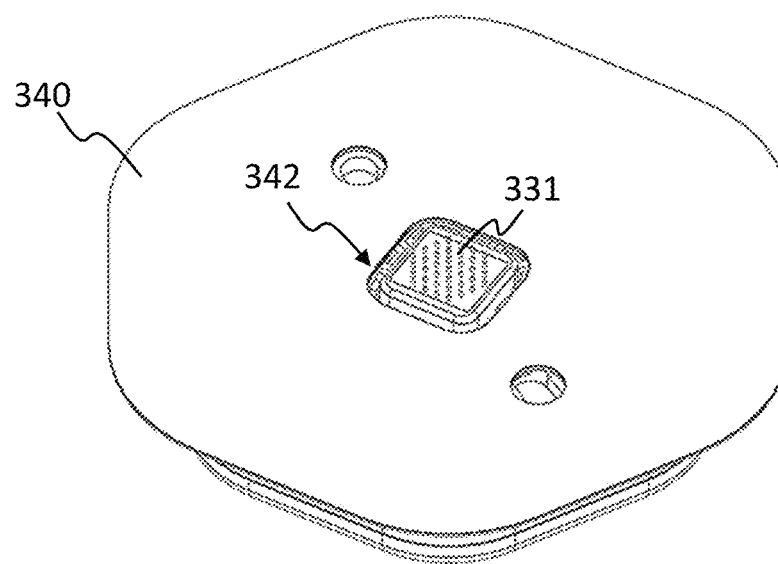
Figure 27D:
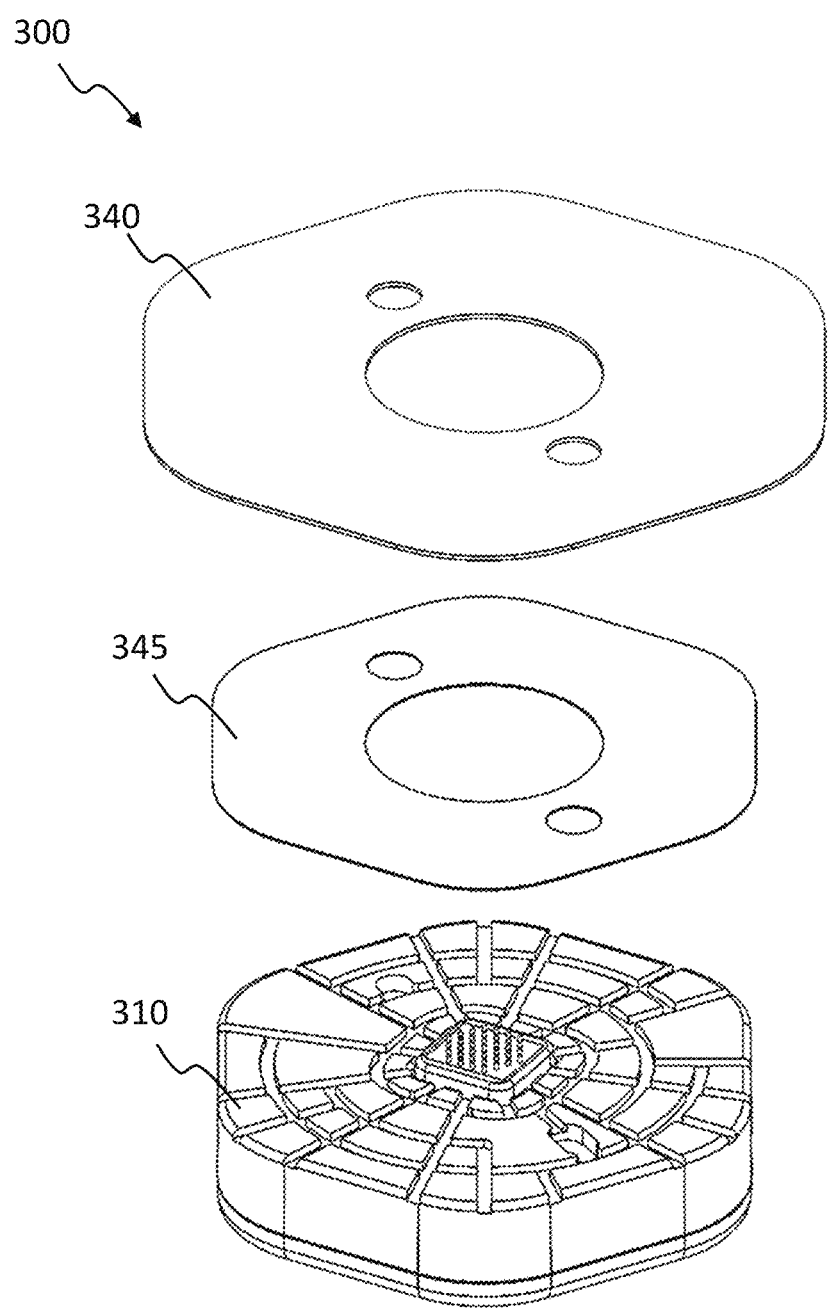
Figure 27E:
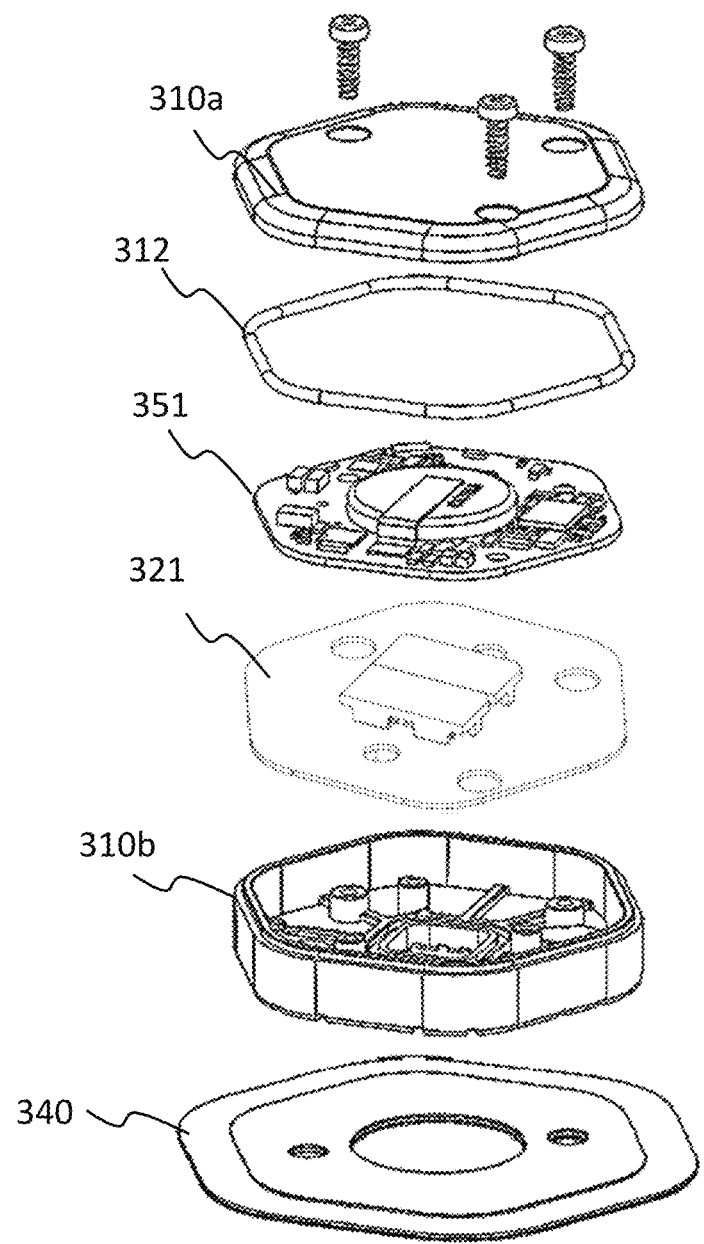

FIGS. 27A-27C depict an upper perspective view, a side view, and a lower perspective view, respectively, of an analyte monitoring device. FIG. 27D depicts a partially exploded view of the analyte monitoring device shown in FIG. 27A including an adhesive layer. FIG. 27E depicts an exploded view of the analyte monitoring device shown in FIG. 27A.

FIGS. 27F-27I depict an upper perspective view, a lower perspective view, a side view, and an exploded view, respectively, of a sensor assembly in an analyte monitoring device.

Figure 27J:
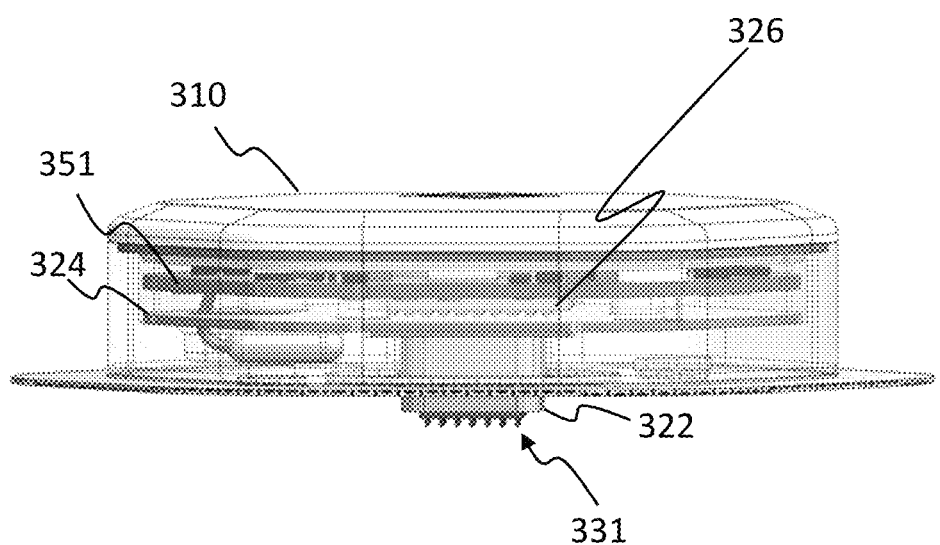

FIG. 27J depicts a transparent side view of a sensor assembly in an analyte monitoring device.

FIGS. 28A-28E depict a perspective view, a side view, a bottom view, a side cross-sectional view, and an upper perspective transparent view, respectively, of an analyte monitoring device.

Figure 29:
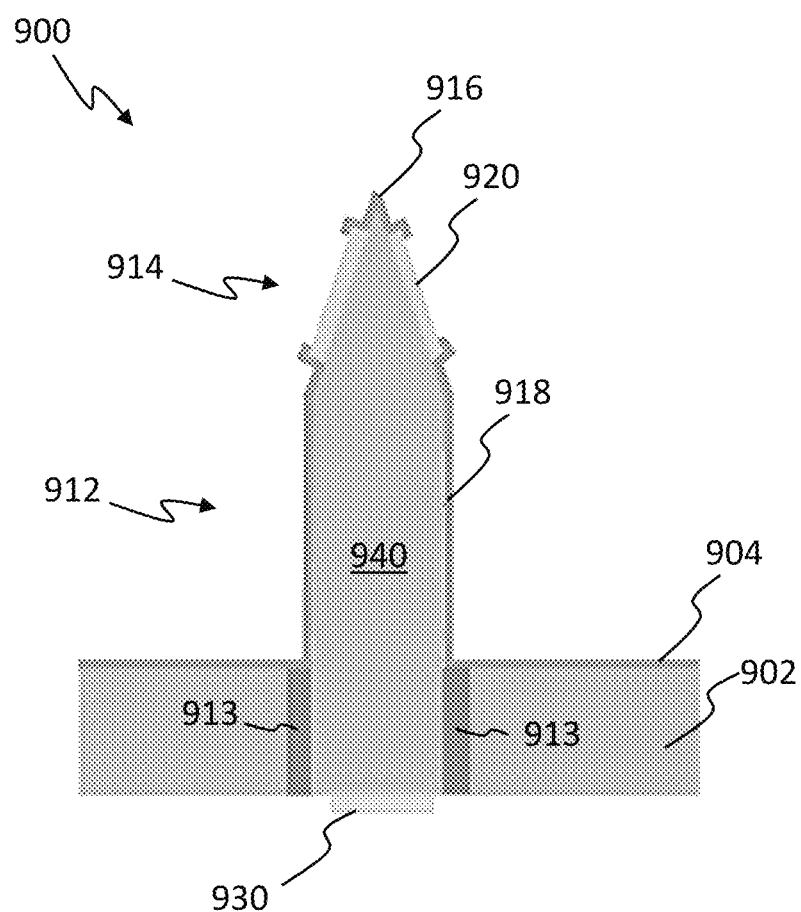

FIG. 29 depicts a cross-sectional side view of a columnar microneedle having a tapered distal end.

Figure 30:
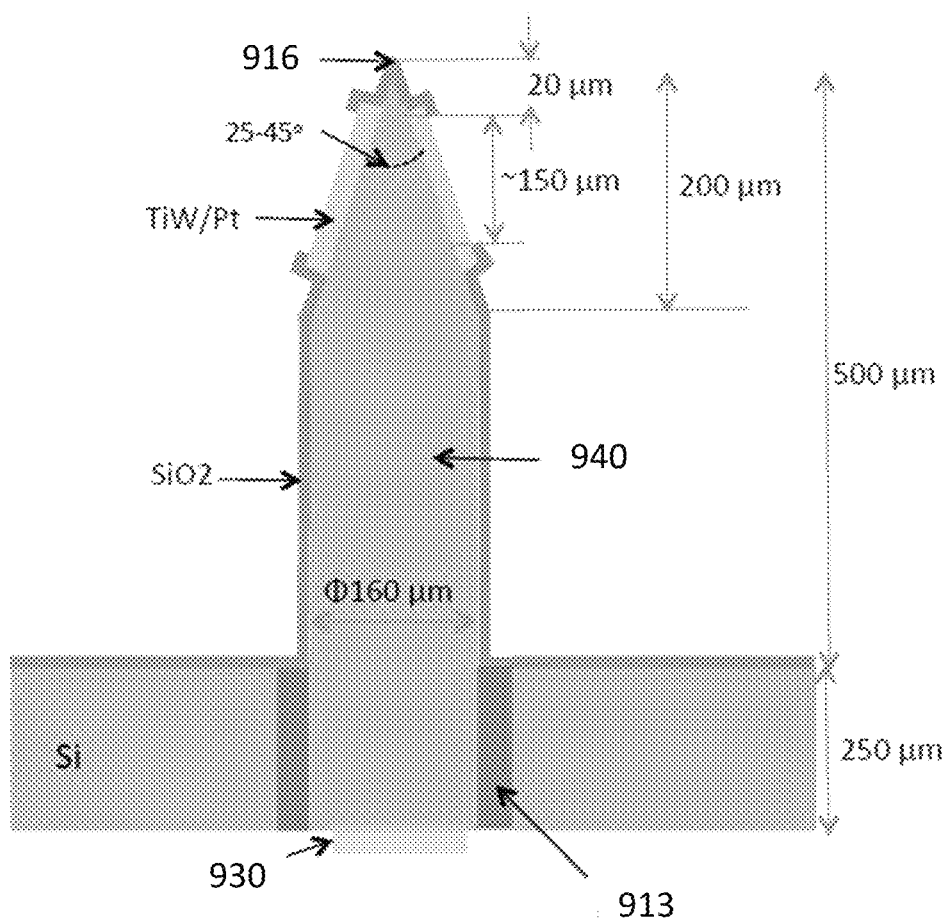

FIG. 30 depicts an illustrative schematic of a columnar microneedle having a tapered distal end.

FIGS. 31A-31C depict an upper perspective view, side view, and lower perspective view, respectively, of an applicator. FIG. 31D depicts an exploded view of the applicator shown in FIGS. 31A-31C.

FIGS. 32A-32G depict an upper perspective view, a lower perspective view, another upper perspective view, another lower perspective view, a top view, a side view, and a bottom view, respectively, of a shuttle of an applicator.

Figure 33B:
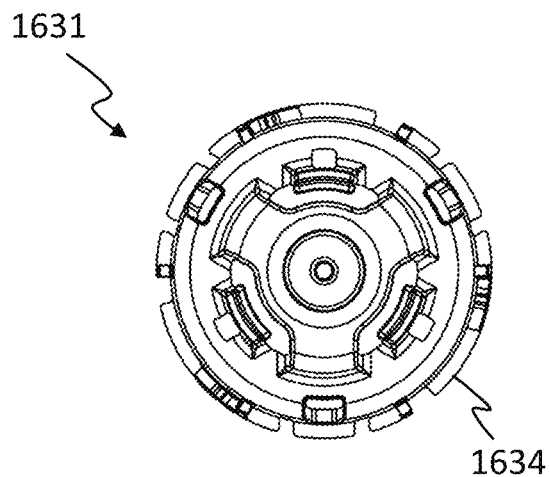
Figure 33A:
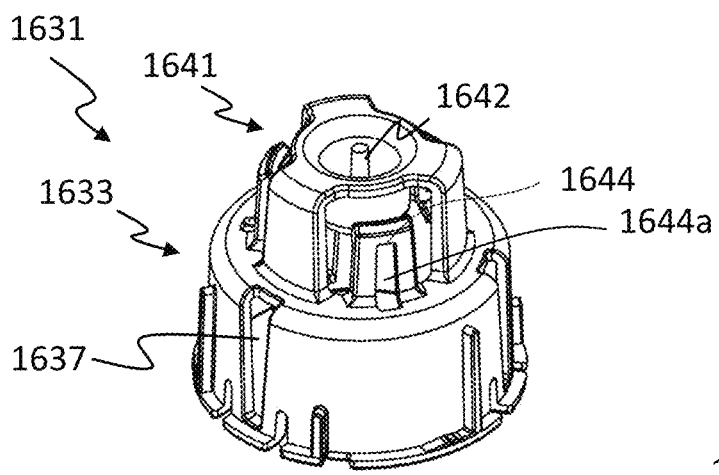
Figure 33C:
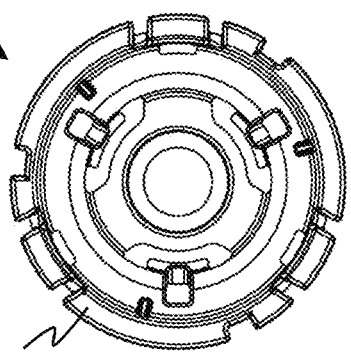
Figure 33D:
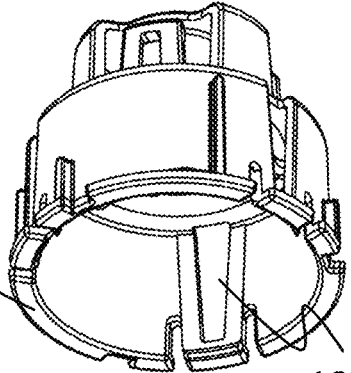
Figure 33E:
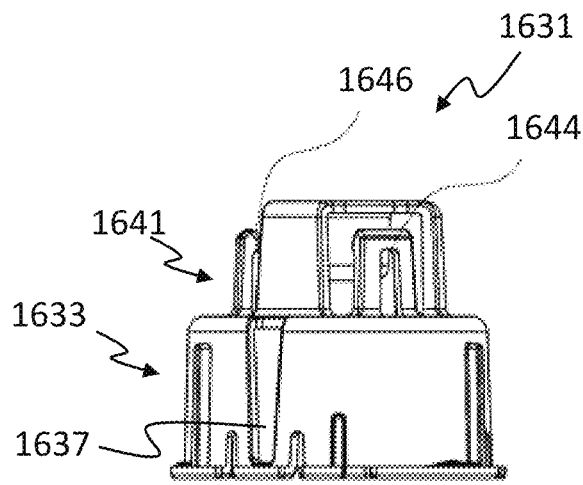
Figure 33F:
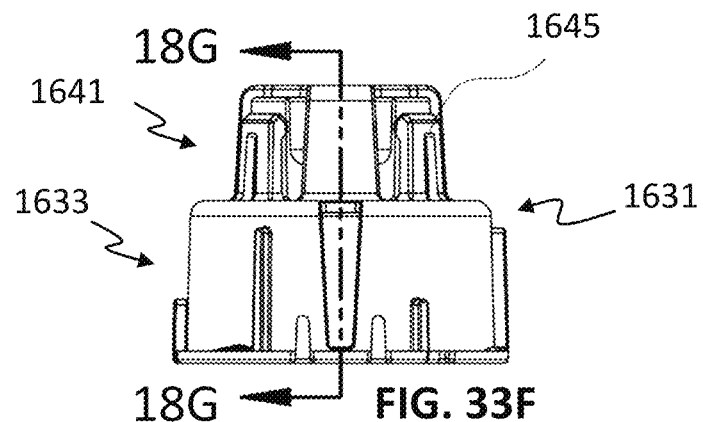

FIGS. 33A-33E depict an upper perspective view, a top view, a bottom view, a lower perspective view, and a side view, respectively, of a trigger of an applicator. FIG. 33F depicts another side view of the trigger shown in FIGS. 33A-33E, and FIG. 33G depicts a cross-sectional view of the trigger taken along the line 18G:18G shown in FIG. 33F.

Figure 34F:
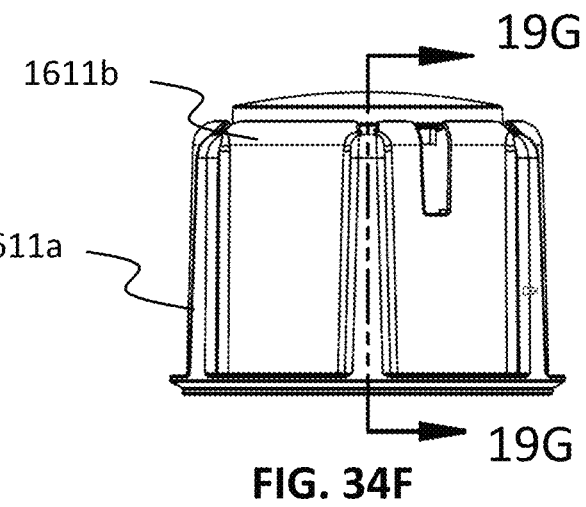
Figure 34G:
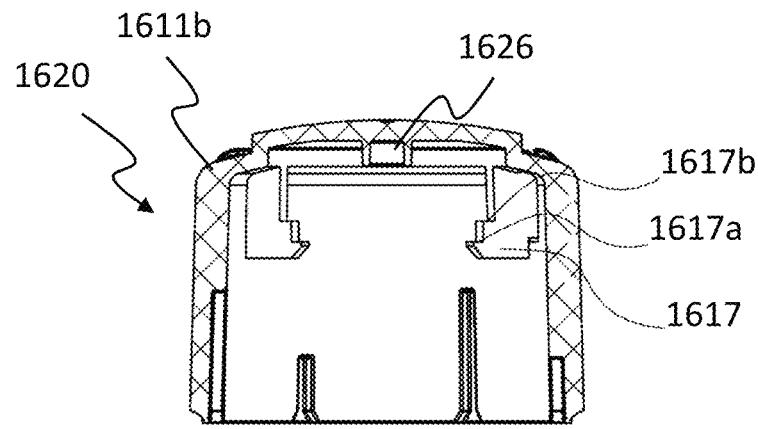

FIG. 34A depicts an upper perspective view of a housing of an applicator. FIGS. 34B-34F depict an upper perspective view, a top view, a bottom view, a lower perspective view, and a side view, respectively, of the housing shown in FIG. 34A. FIG. 34G depicts a side cross-sectional view of the housing taken along the line 19G:19G shown in FIG. 34F.

Figure 34H:
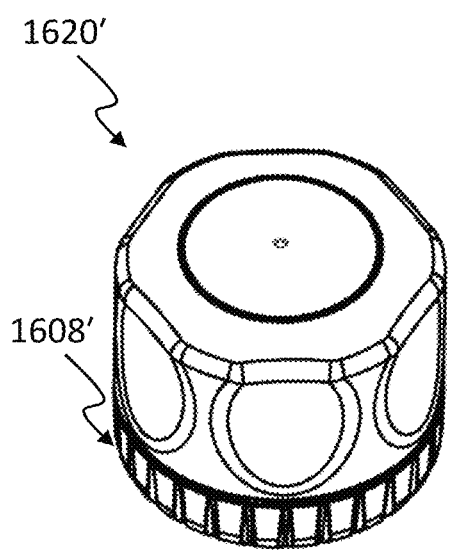
Figure 34I:
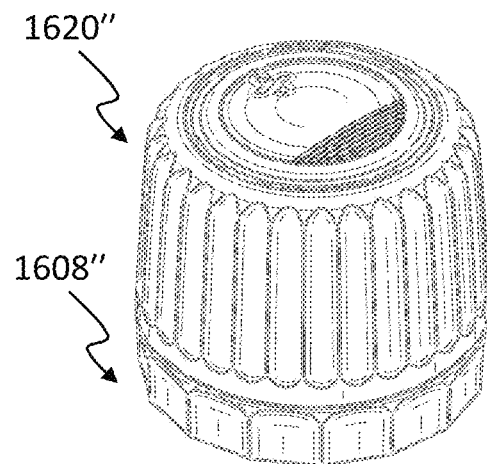

FIGS. 34H and 34I depict example variations of a housing of an applicator.

Figure 35A:
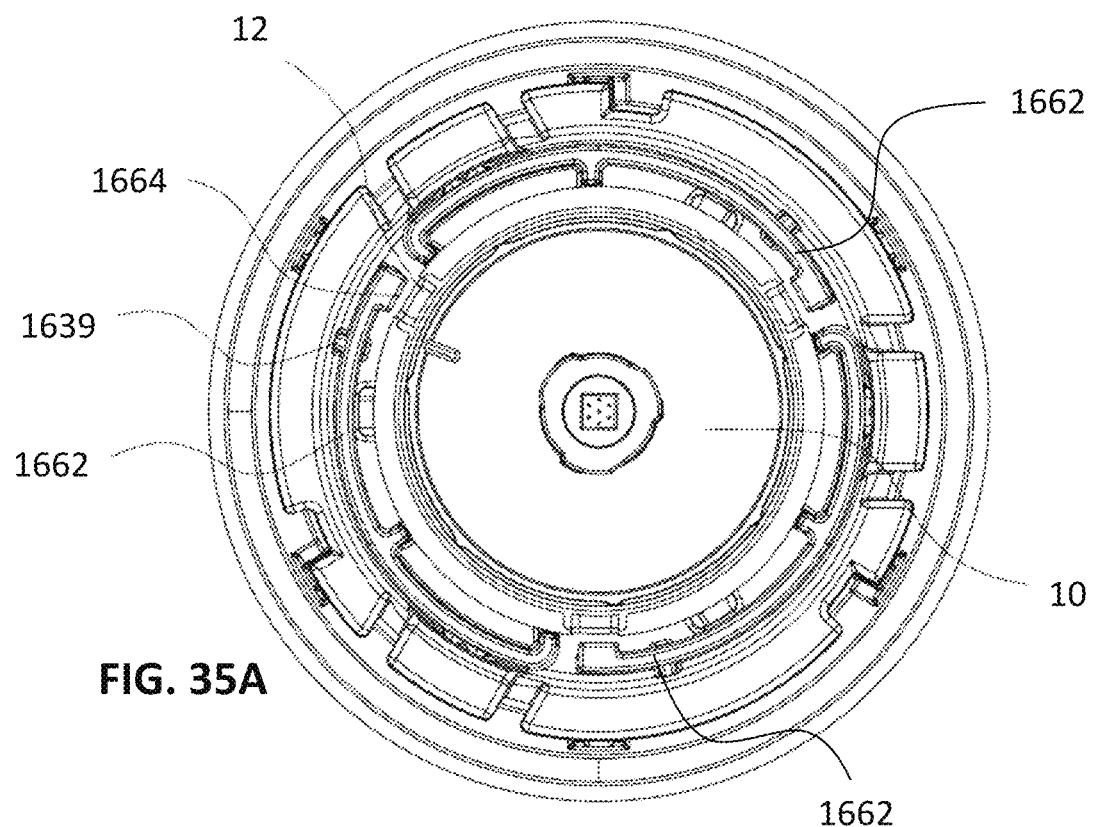
Figure 35B:
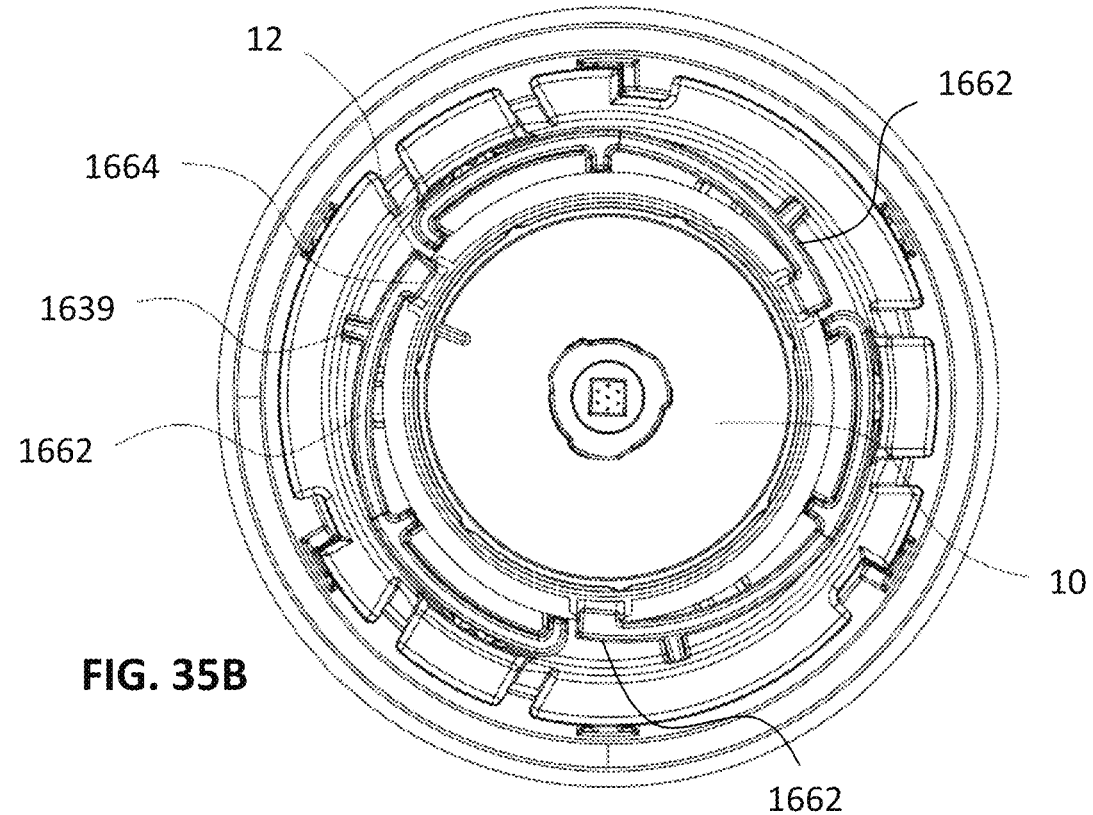

FIG. 35A depicts a bottom view of an applicator at the beginning of a loading process for loading an analyte monitoring device in the applicator. FIG. 35B depicts a bottom view of the applicator of FIG. 35A after an analyte monitoring device is loaded in the applicator.

Figure 36A:
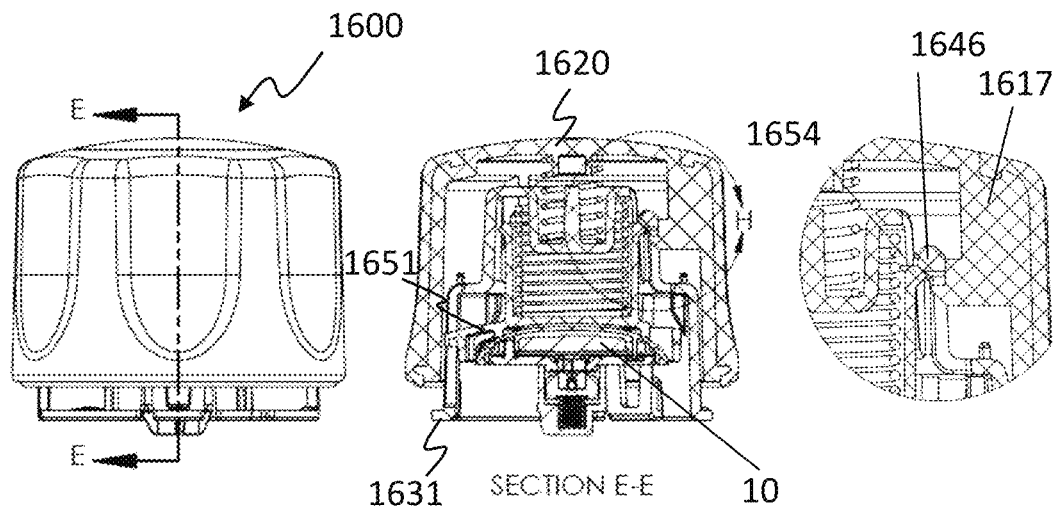
Figure 36B:
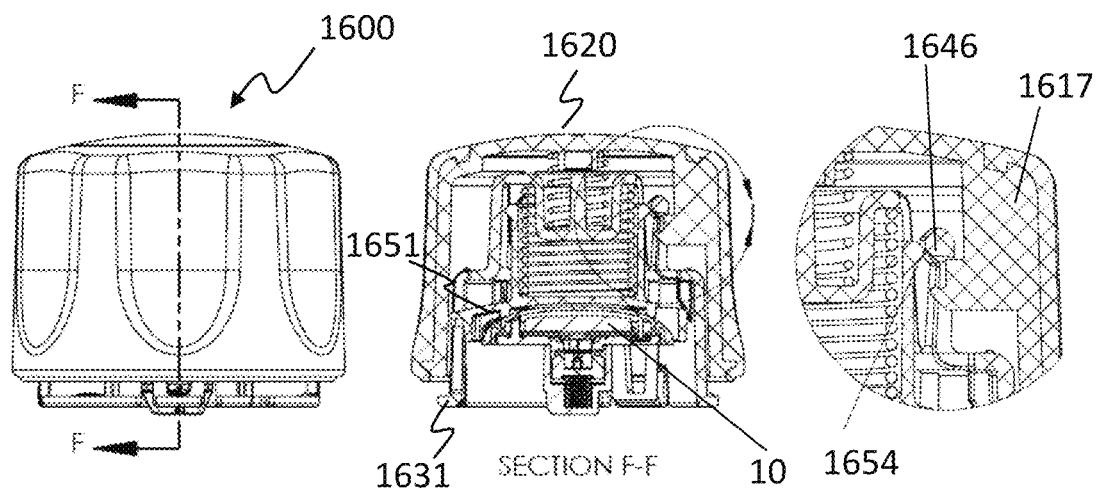
Figure 36C:
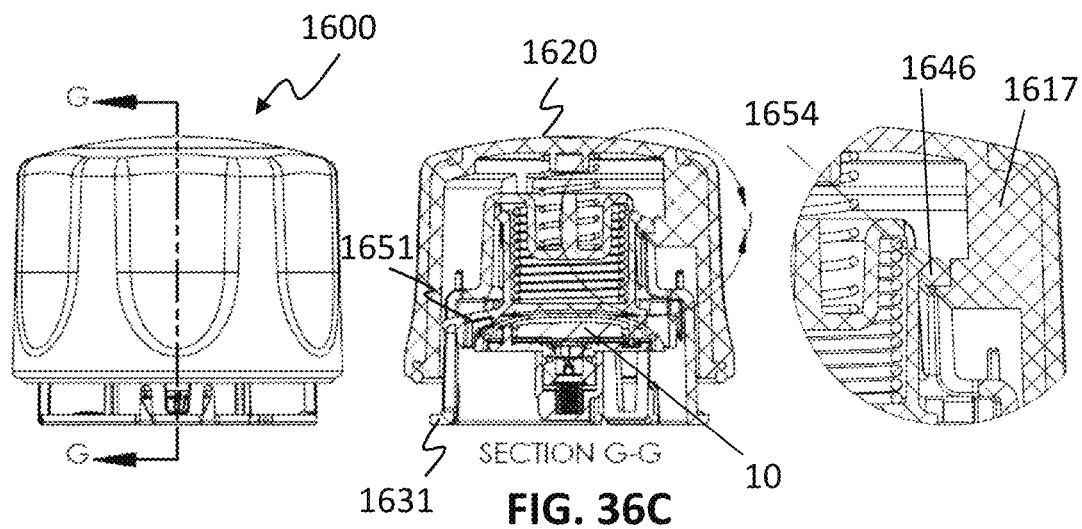

FIGS. 36A-36C depict a loading process for loading an analyte monitoring device in an applicator.

Figure 37A:
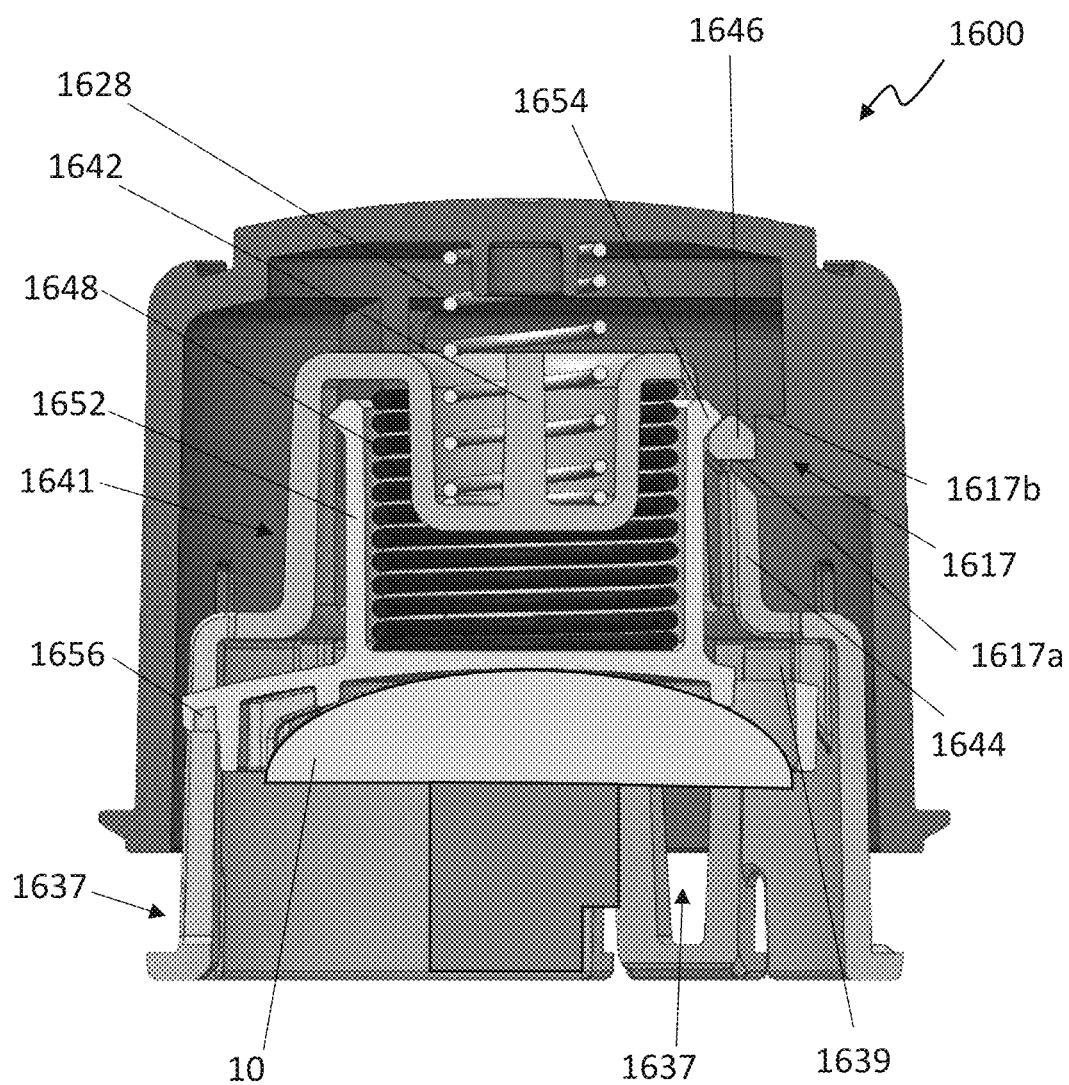
Figure 37B:
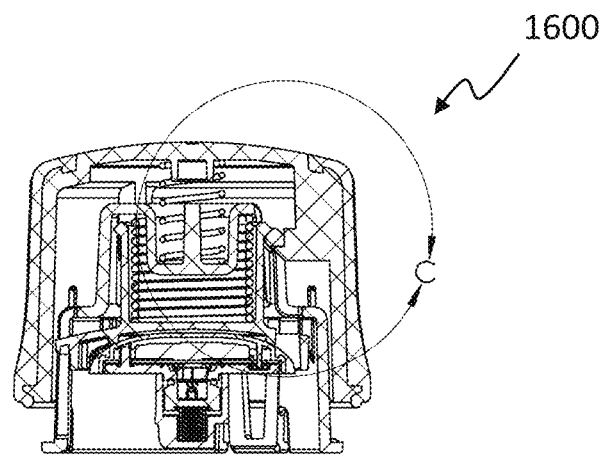
Figure 37C:
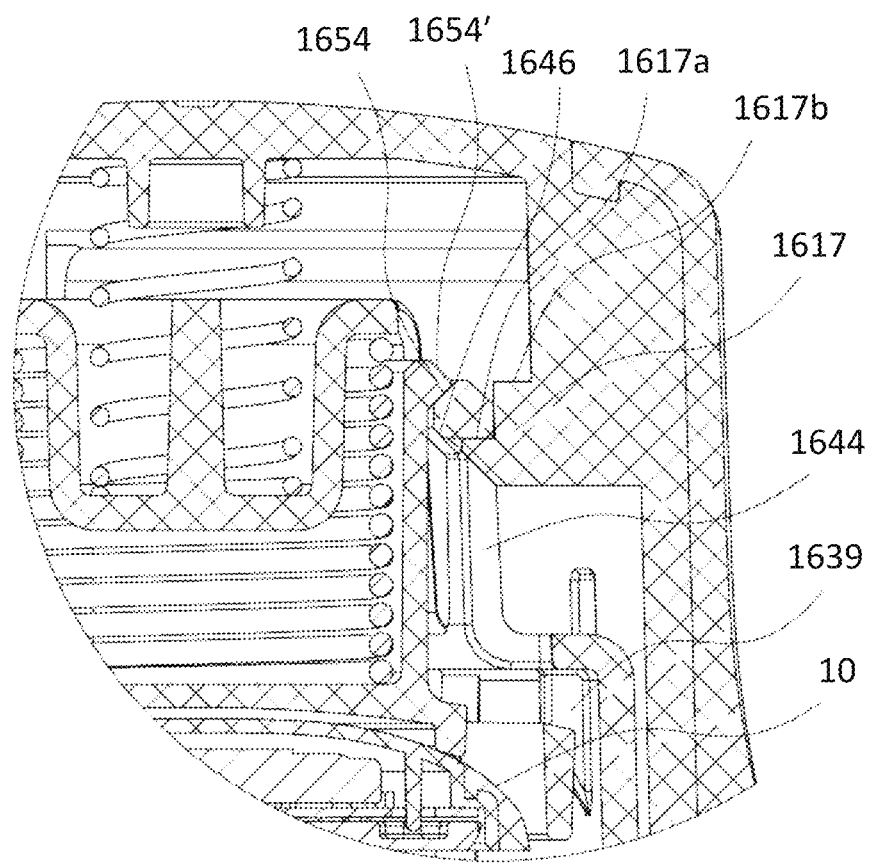
Figure 37D:
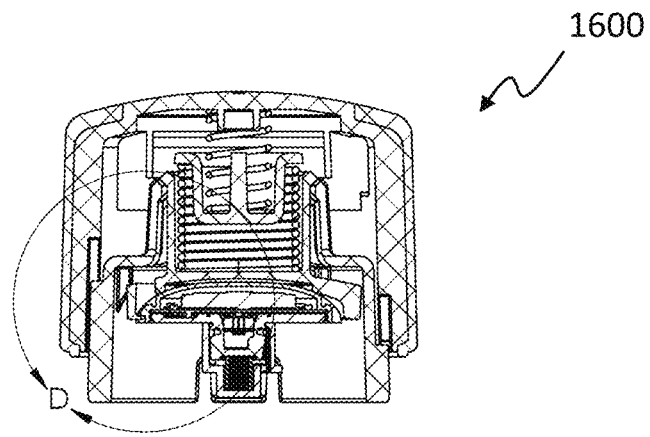
Figure 37E:
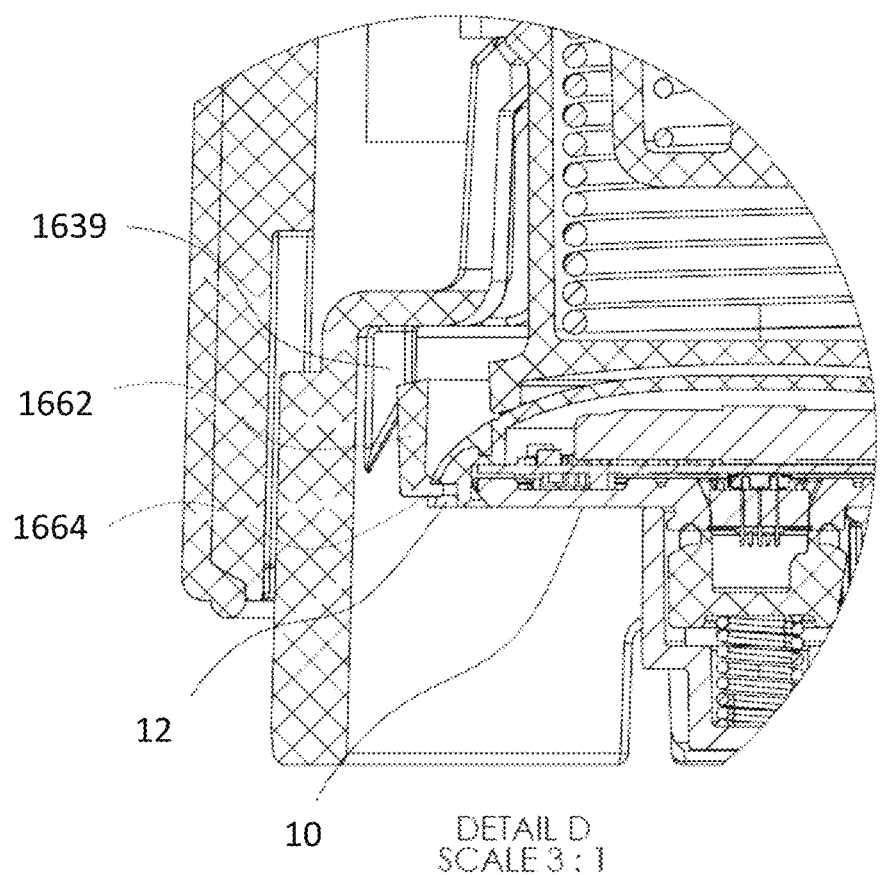

FIGS. 37A, 37B, and 37D depict a cross-sectional view of an applicator in a loaded configuration for deploying an analyte monitoring device from the applicator. FIG. 37C depicts a detailed cross-sectional view of the portion of the loaded applicator indicated by circle C in FIG. 37B. FIG. 37E depicts a detailed cross-sectional view of the portion of the loaded applicator indicated by circle D in FIG. 37D.

Figure 38:
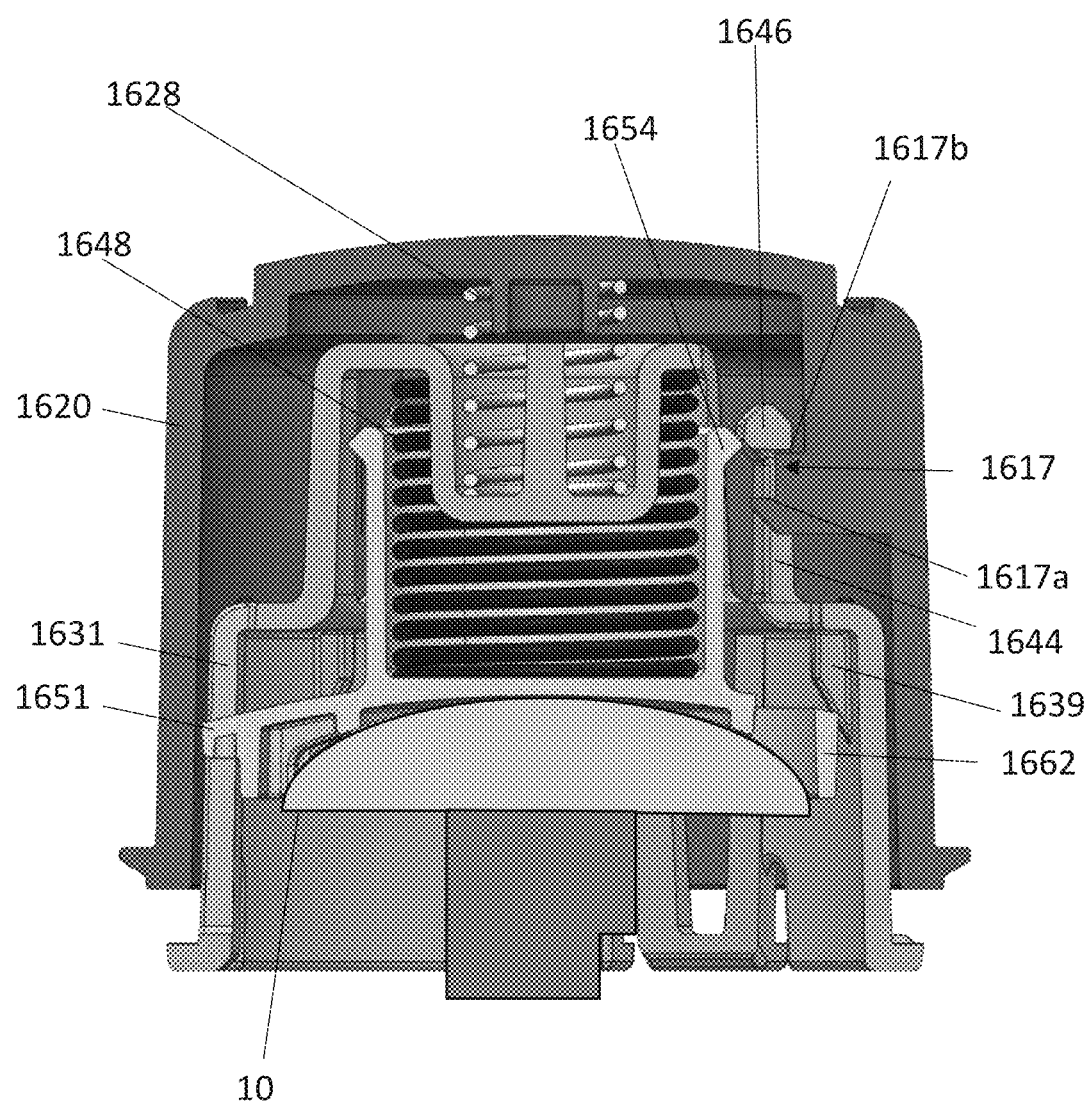

FIG. 38 depicts a cross-sectional view of an applicator in a fired configuration for deploying an analyte monitoring device from the applicator.

FIGS. 39A-39C depict an upper perspective view, a side view, and a lower perspective view, respectively, of an applicator. FIG. 39D depicts an exploded view of the applicator shown in FIGS. 39A-39C.

Figure 40A:
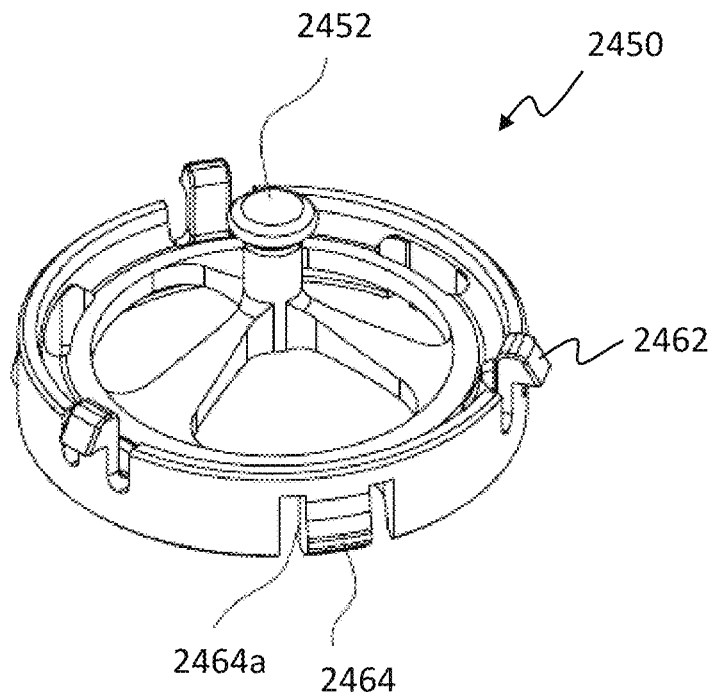
Figure 40B:
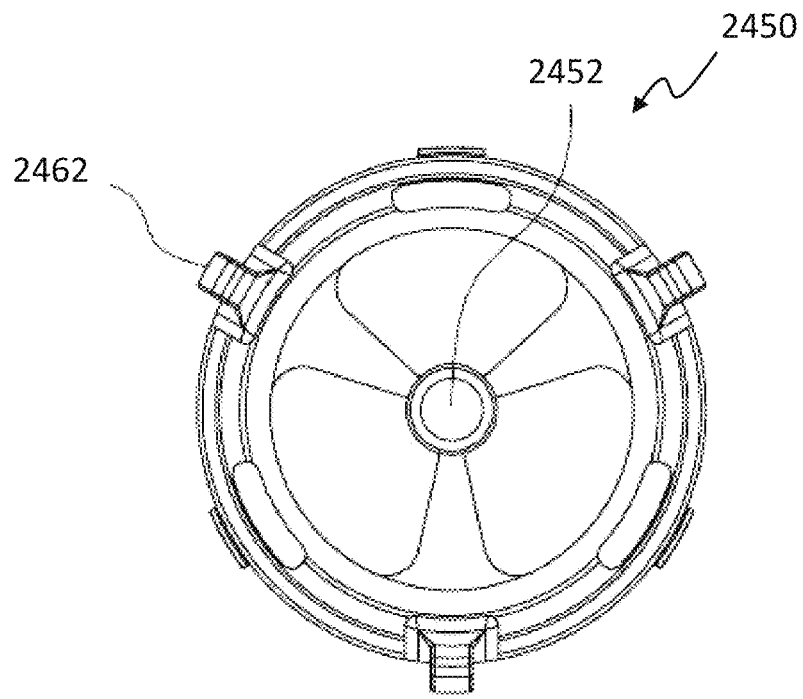

FIGS. 40A and 40B depict an upper perspective view and a top view, respectively, of a shuttle of an applicator.

Figure 41B:
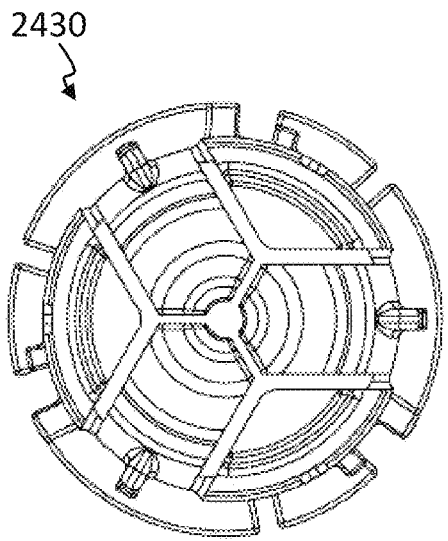
Figure 41D:
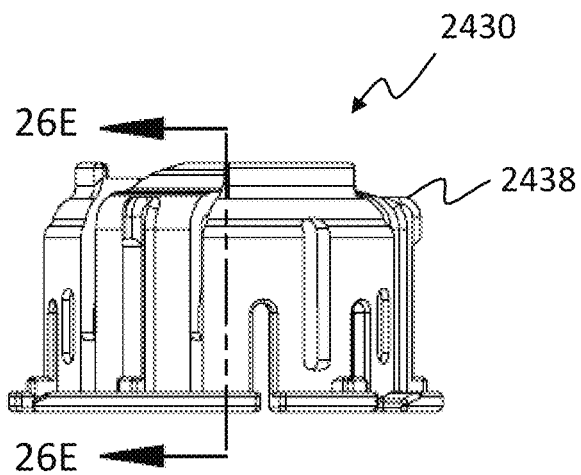
Figure 41A:
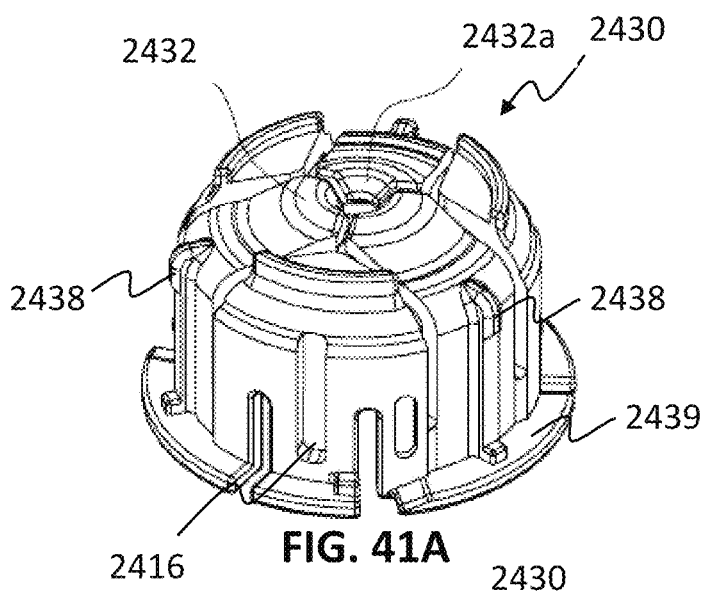
Figure 41C:
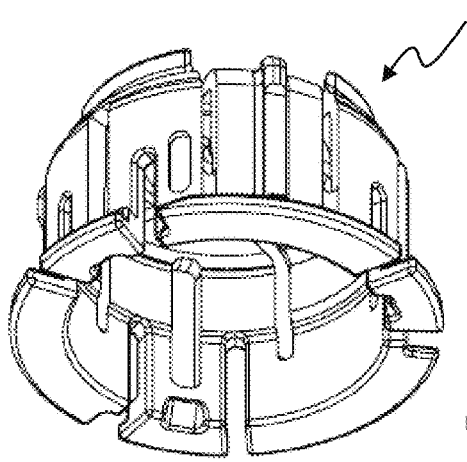
Figure 41E:
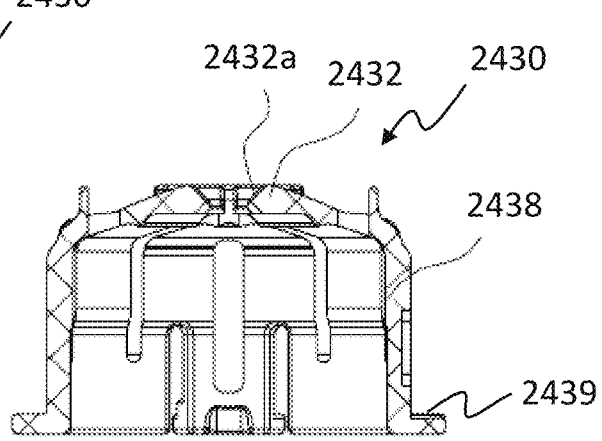

FIGS. 41A-41D depict an upper perspective view, a top view, a lower perspective view, and a side view, respectively, of a trigger of an applicator. FIG. 41E depicts a cross-sectional view of the trigger taken along the line 26E:26E shown in FIG. 41D.

FIGS. 42A-42C depict an upper perspective view, a top view, and a side view, respectively, of a housing of an applicator. FIG. 42D depicts a cross-sectional view of the housing taken along the line 27D: 27D shown in FIG. 42C. FIG. 42E depicts a bottom view of the housing shown in FIGS. 42A and 42B.

Figure 43:
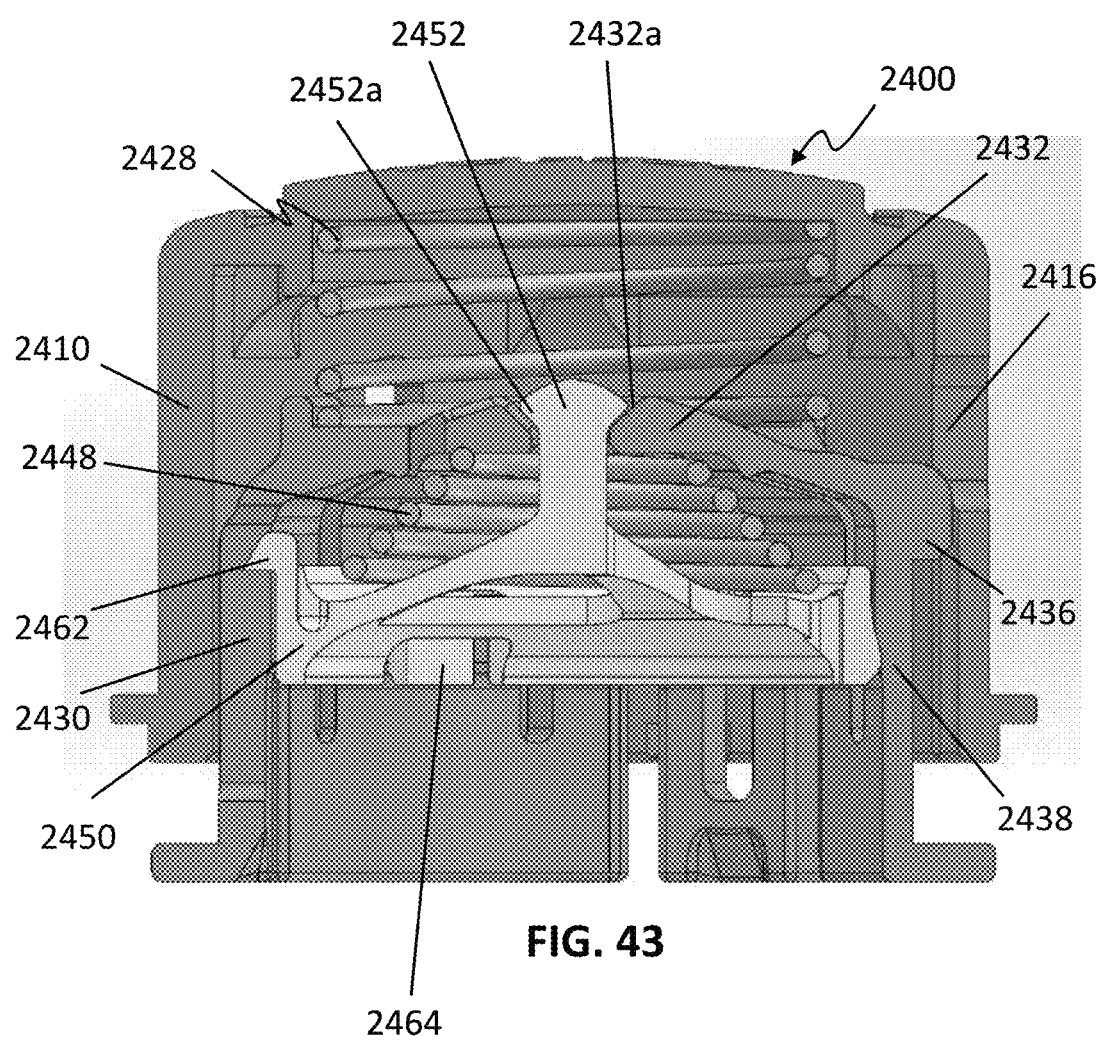

FIG. 43 depicts a cross-sectional view of an applicator in a loaded configuration for deploying an analyte monitoring device from the applicator.

Figure 44:
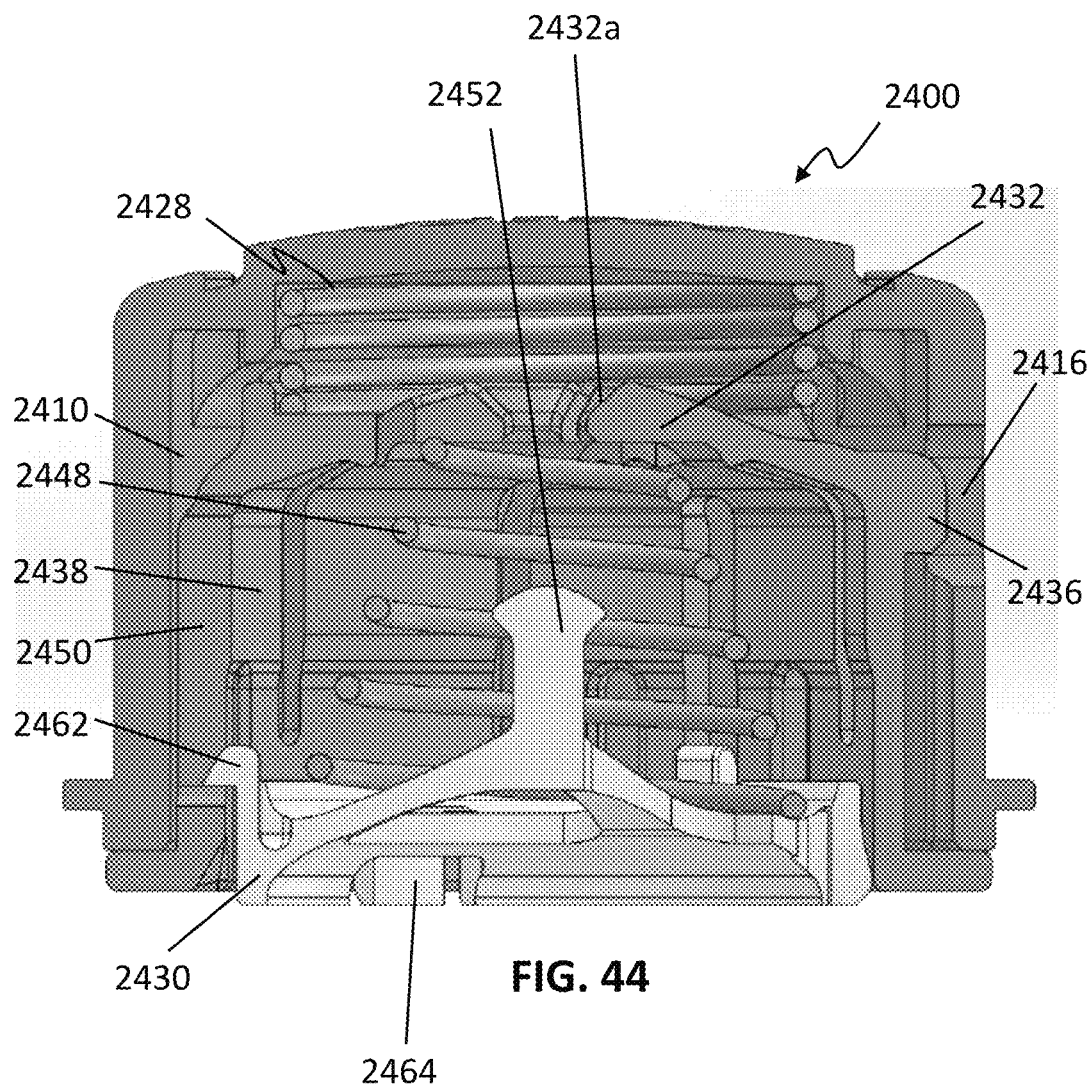

FIG. 44 depicts a cross-sectional view of an applicator in a fired configuration for deploying an analyte monitoring device from the applicator.

FIGS. 45A-45C depict an upper perspective view, a side view, and a lower perspective view, respectively, of an applicator. FIG. 45D depicts an exploded view of the applicator shown in in FIGS. 45A-45C.

Figure 46B:
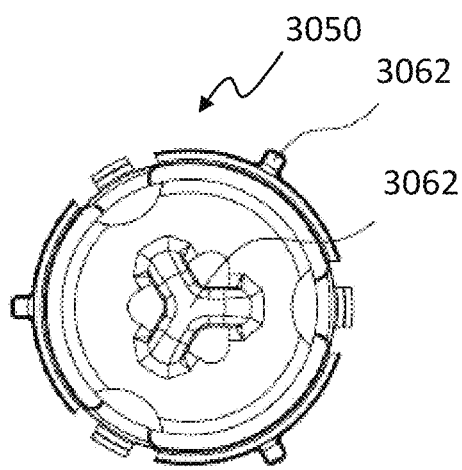
Figure 46A:
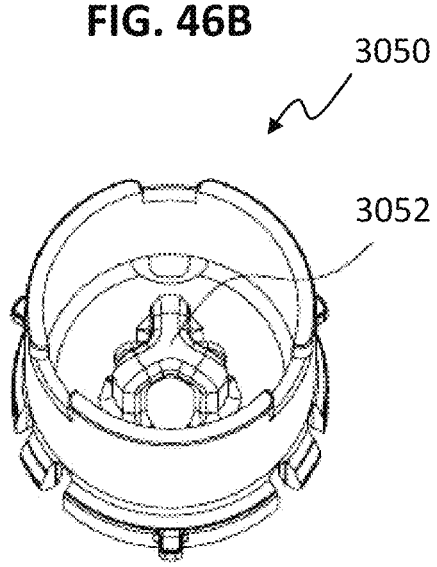
Figure 46D:
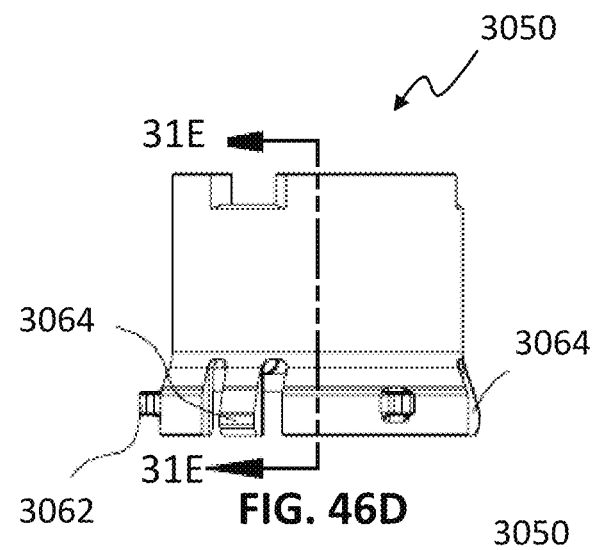
Figure 46E:
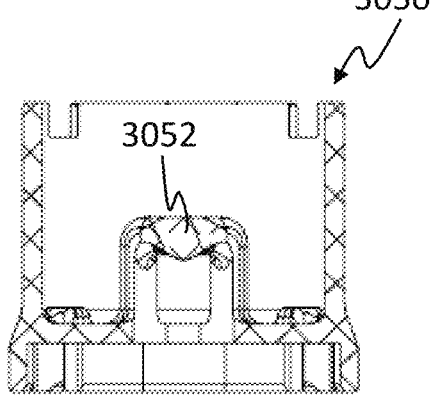
Figure 46C:
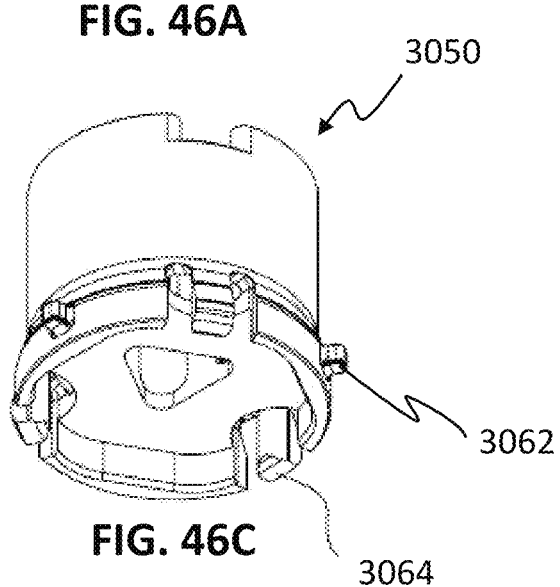

FIGS. 46A-46D depict an upper perspective view, a top view, a lower perspective view, and a side view, respectively, of a shuttle of an applicator. FIG. 46E depicts a cross-sectional view of the shuttle taken along the line 31E:31E shown in FIG. 46D.

Figure 47A:
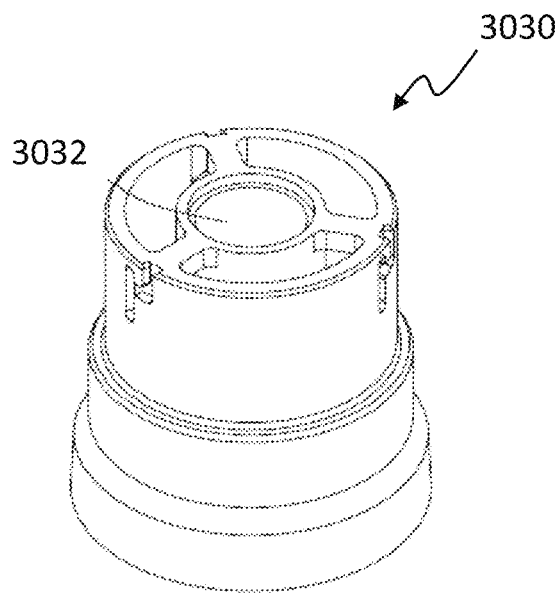
Figure 47C:
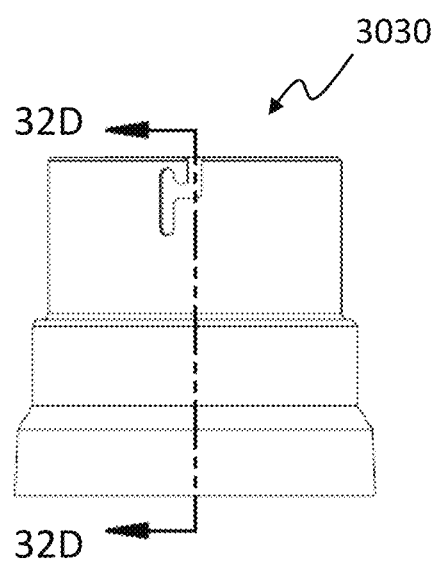
Figure 47B:
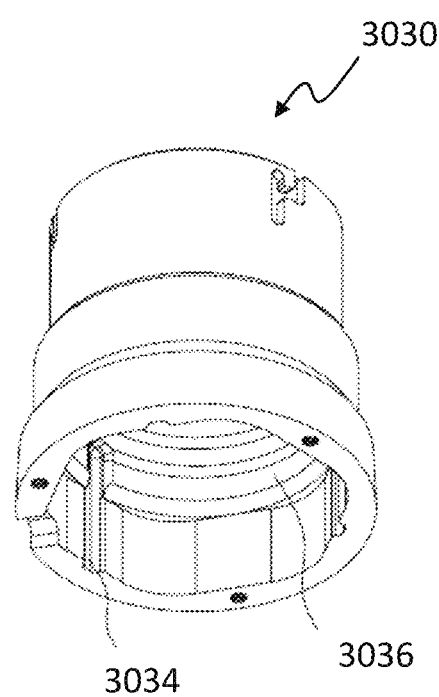
Figure 47D:
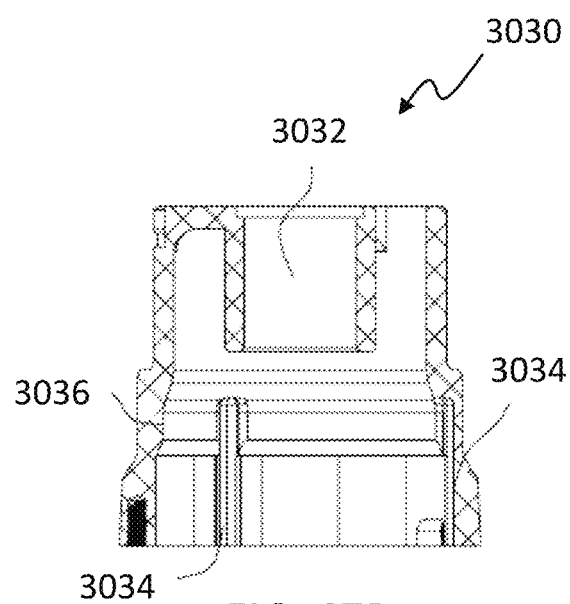

FIGS. 47A-47C depict an upper perspective view, a lower perspective view, and a side view, respectively, of a trigger of an applicator. FIG. 47D depicts a cross-sectional view of the trigger taken along the line 32D:32D shown in FIG. 47C.

Figure 48A:
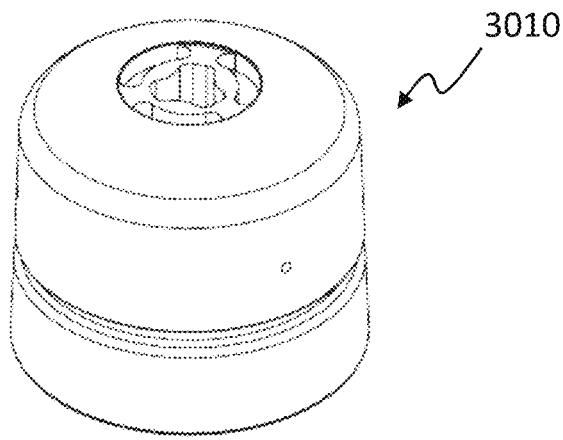
Figure 48B:
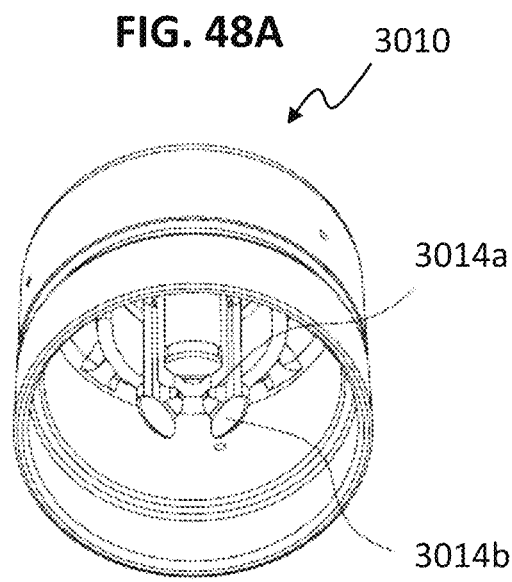
Figure 48D:
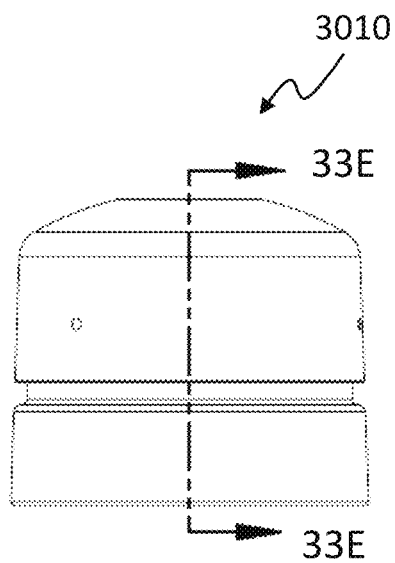
Figure 48C:
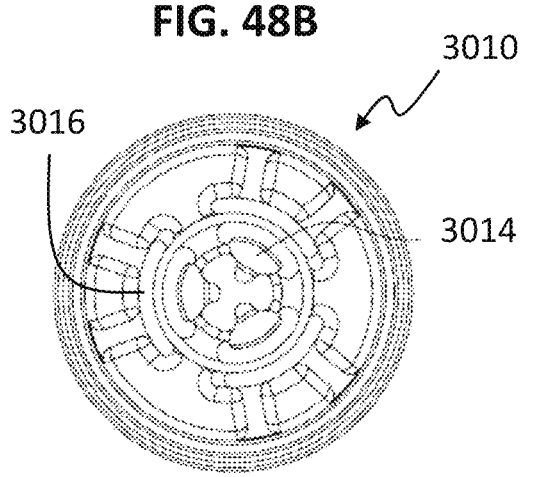
Figure 48E:
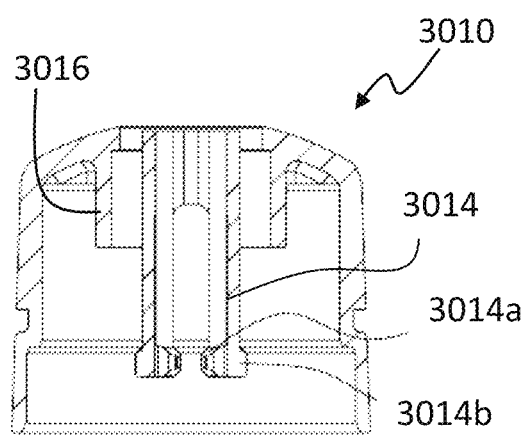

FIGS. 48A-48E depicts an upper perspective view, a lower perspective view, a bottom view, and a side view, respectively, of a housing of an applicator. FIG. 48E depicts a cross-sectional view of the housing taken along the line 33E:33E shown in FIG. 48D.

Figure 49:
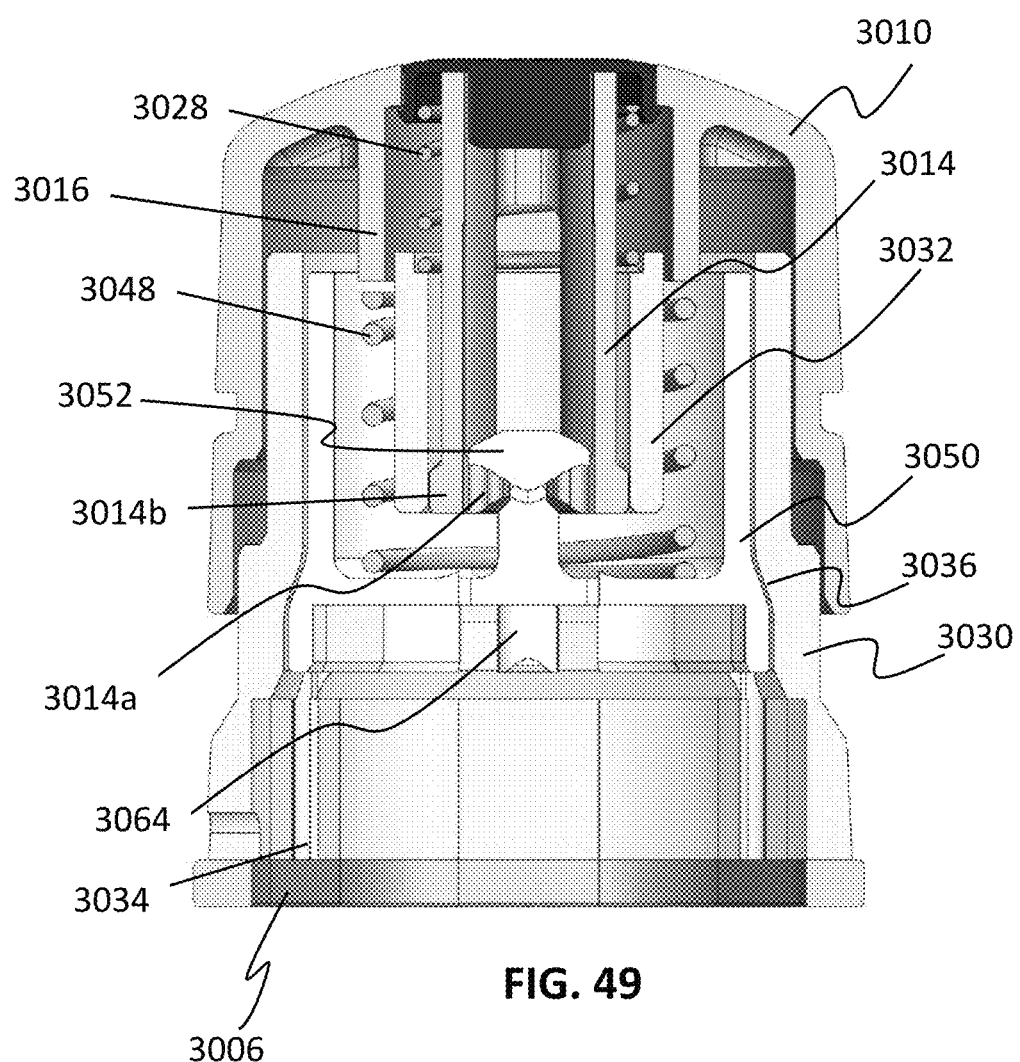

FIG. 49 depicts a cross-sectional view of an applicator in a loaded configuration for deploying an analyte monitoring device from the applicator.

FIG. 50 depicts a cross-sectional view of an applicator in a fired configuration for deploying an analyte monitoring device from the applicator.

Figure 51A:
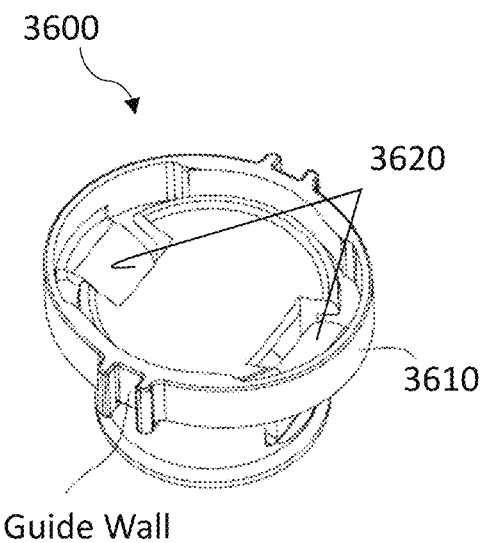
Figure 51D:
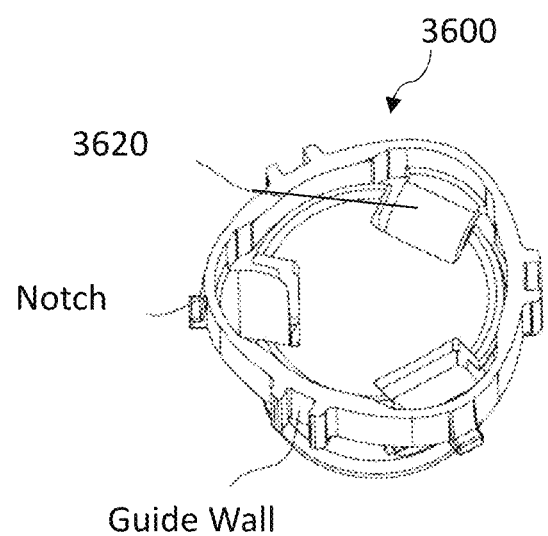
Figure 51B:
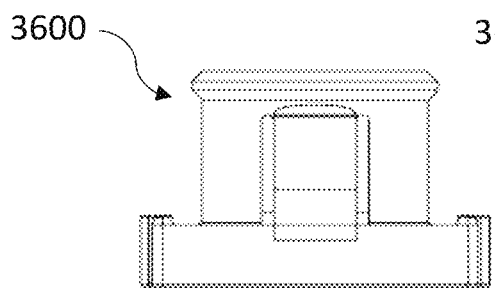
Figure 51E:
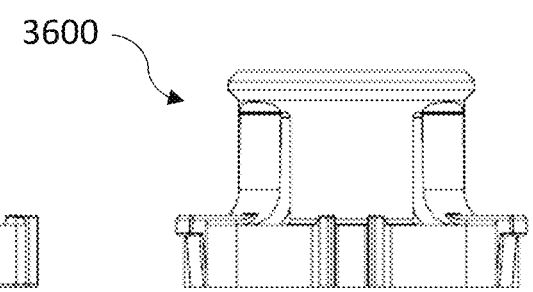
Figure 51C:
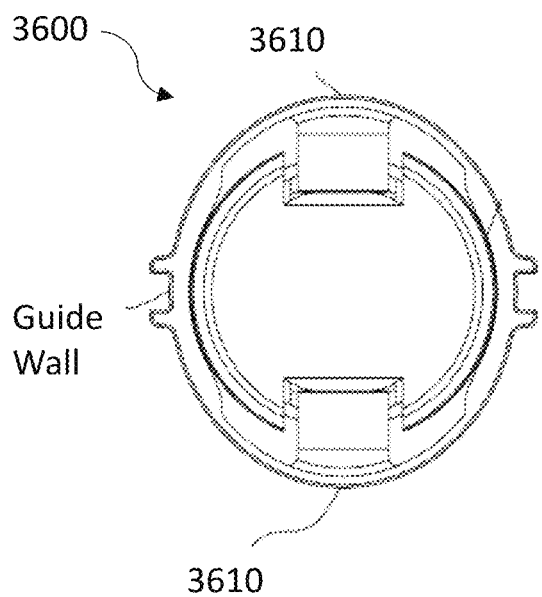

FIGS. 51A-51C depict a bottom perspective view, a side view, and a bottom view, respectively, of a shuttle of an applicator.

Figure 51F:
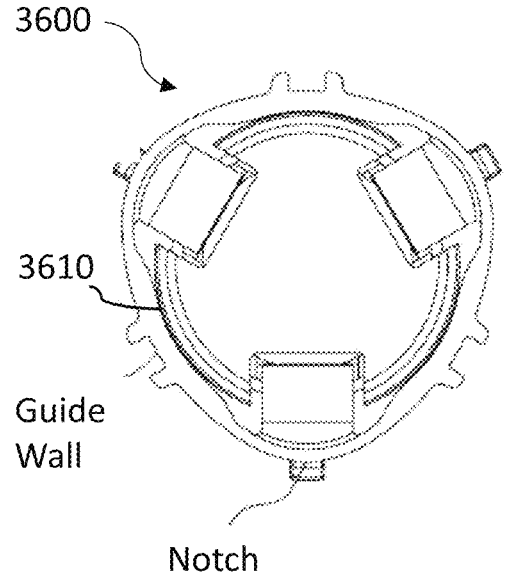

FIGS. 51D-51F depict a bottom perspective view, a side view, and a bottom view, respectively, of a shuttle of an applicator.

Figure 51G:
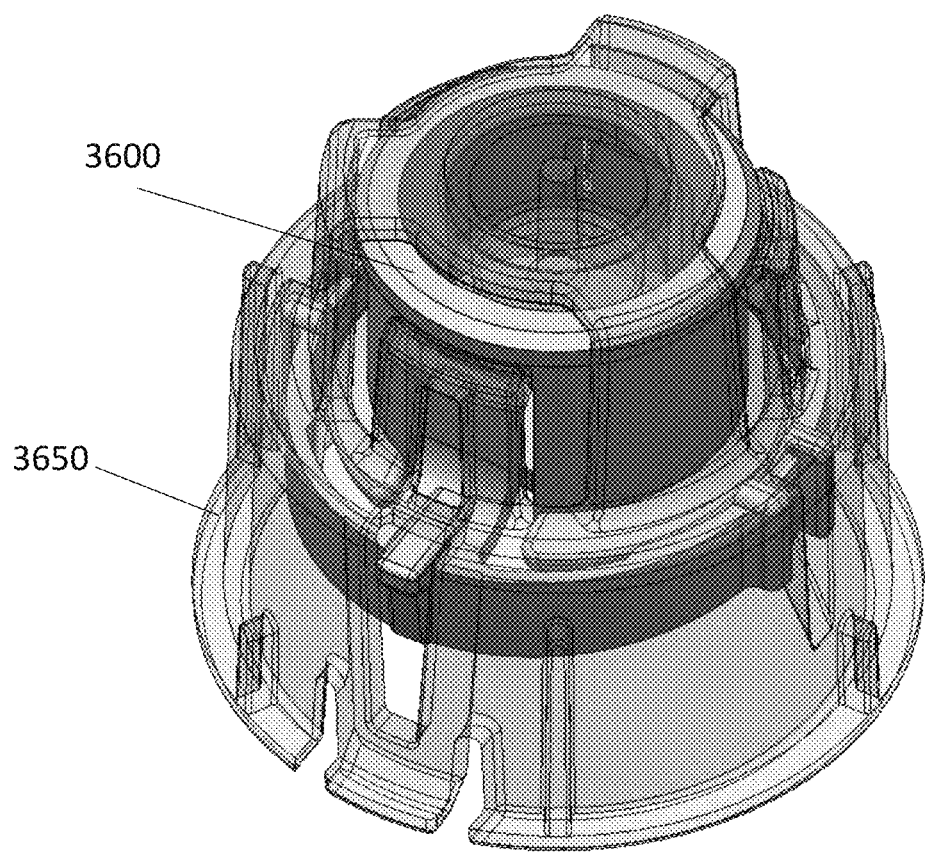
Figure 51H:
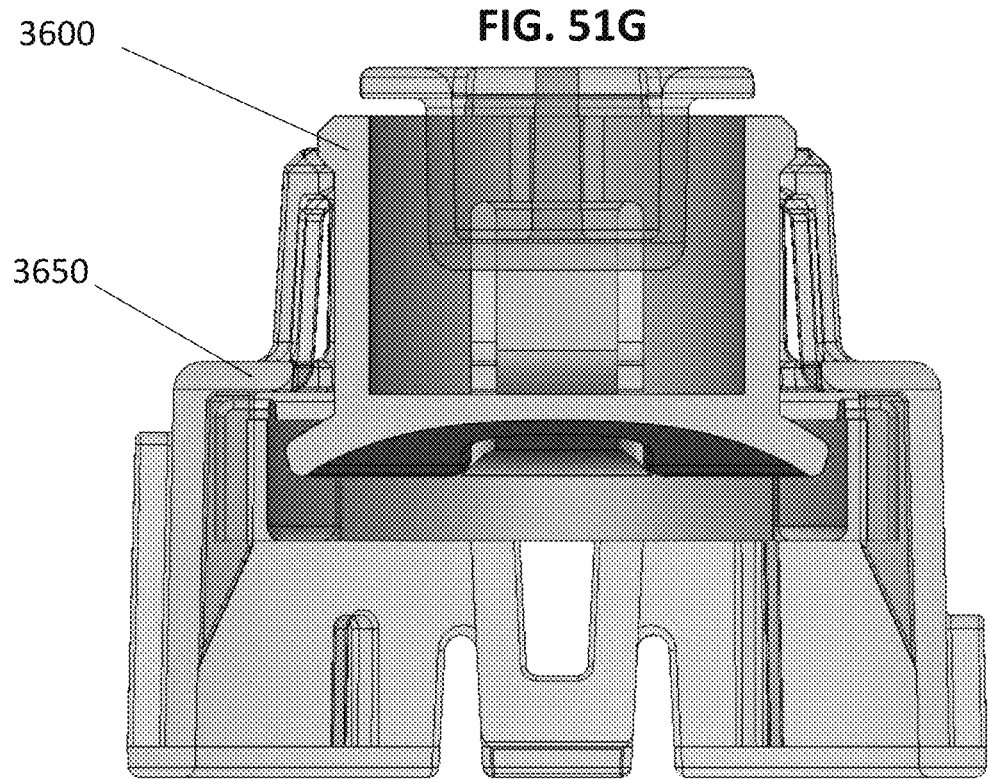
Figure 51I:
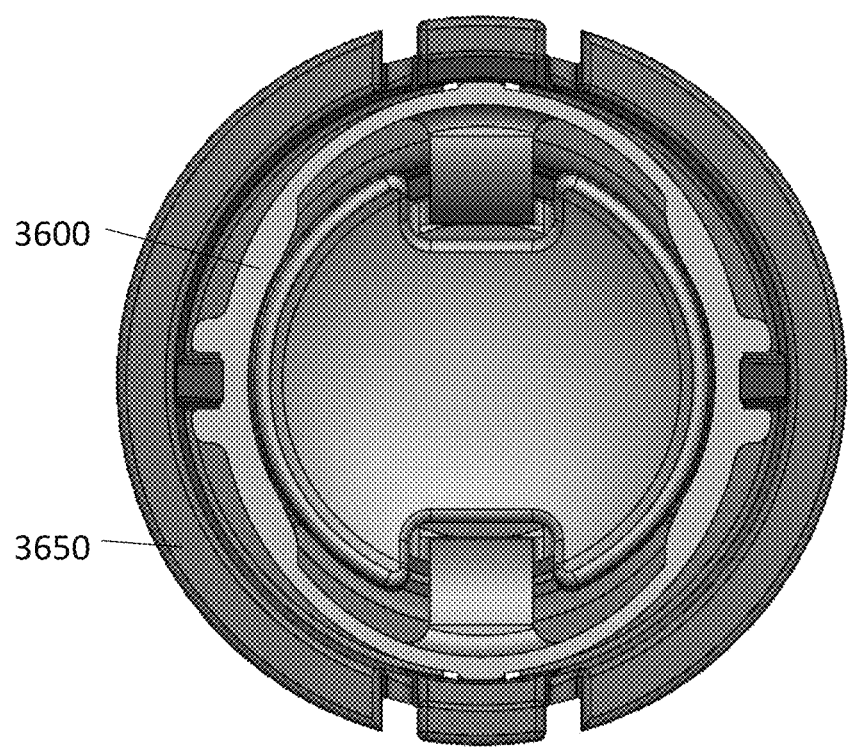

FIGS. 51G-51I depict an upper perspective view, a cross-sectional view, and a bottom view, respectively, of an applicator in a loaded configuration for deploying an analyte monitoring device from the applicator.

Figure 51J:
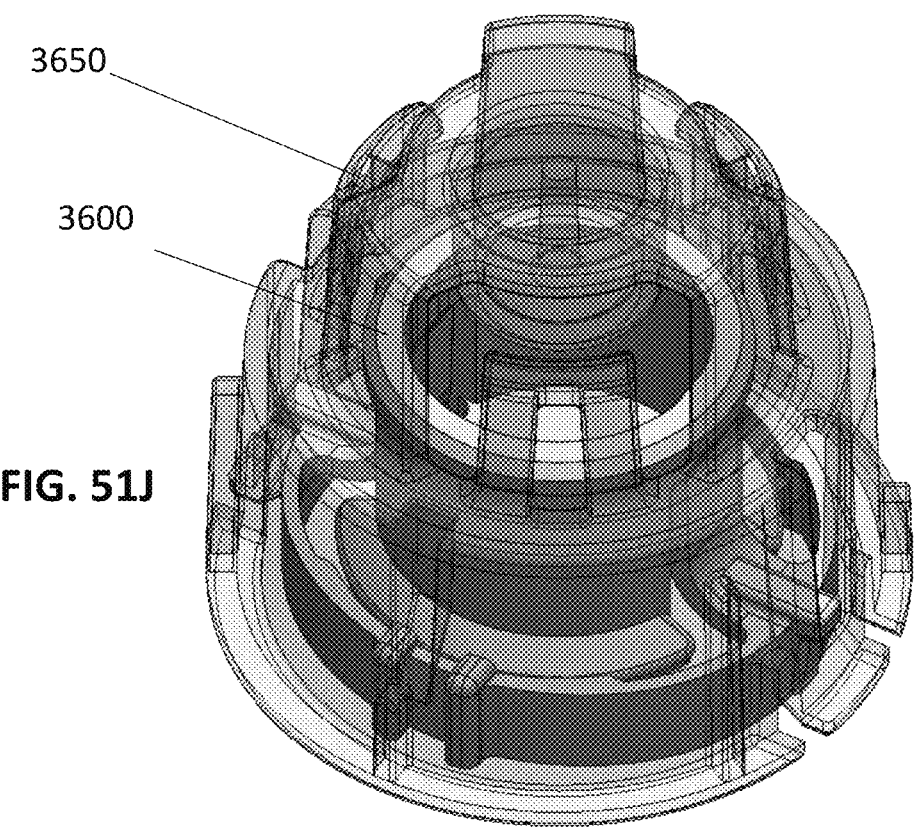
Figure 51K:
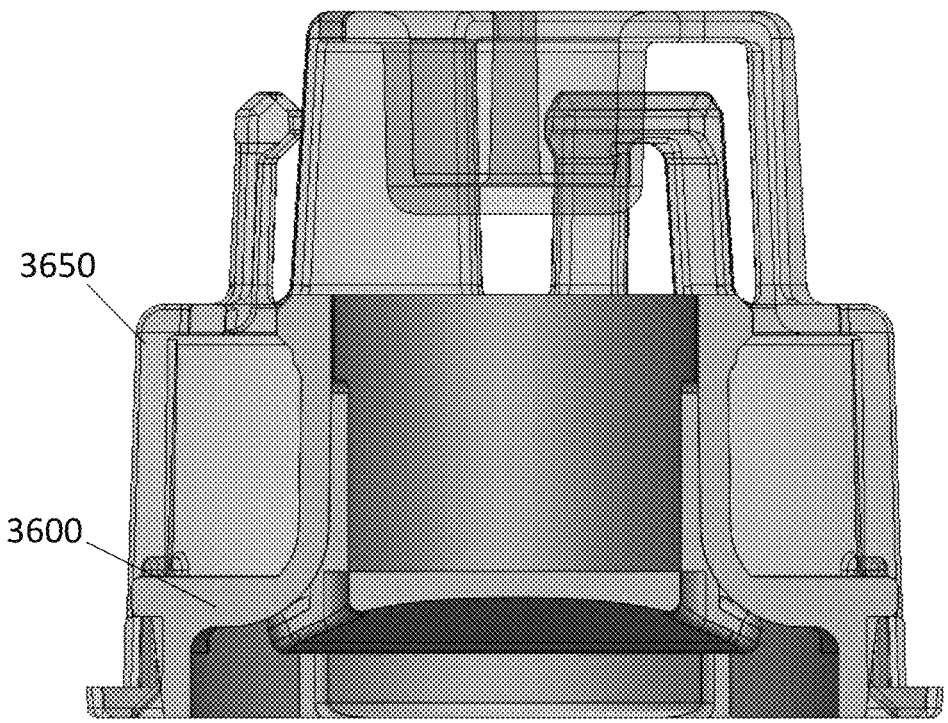
Figure 51L:
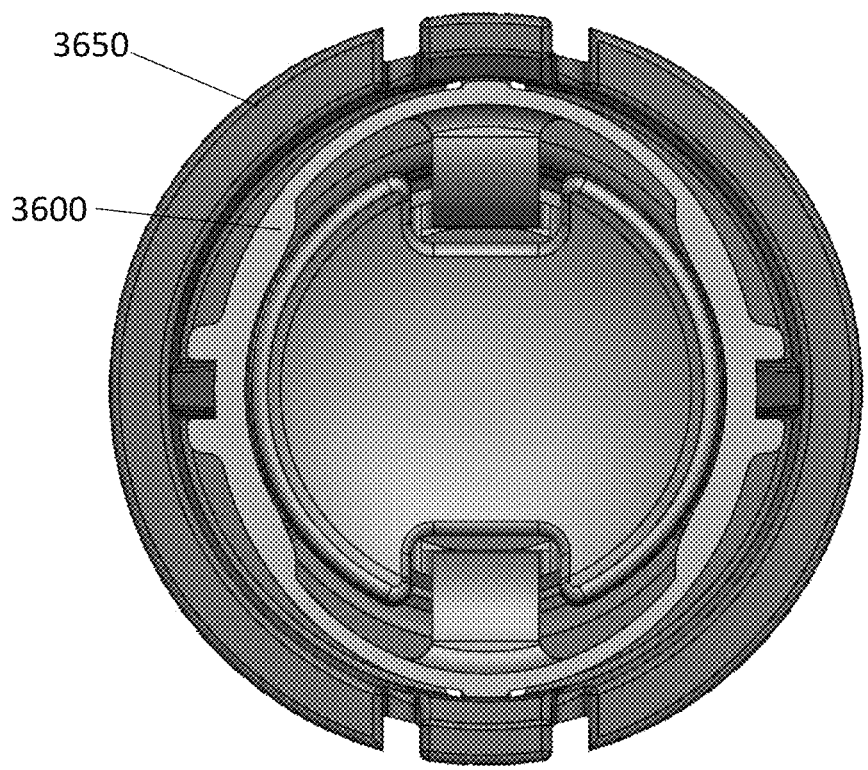

FIGS. 51J-51L depict an upper perspective view, a cross-section view, and a bottom view, respectively, of an applicator in a fired configuration for deploying an analyte monitoring device from the applicator.

Figure 51M:
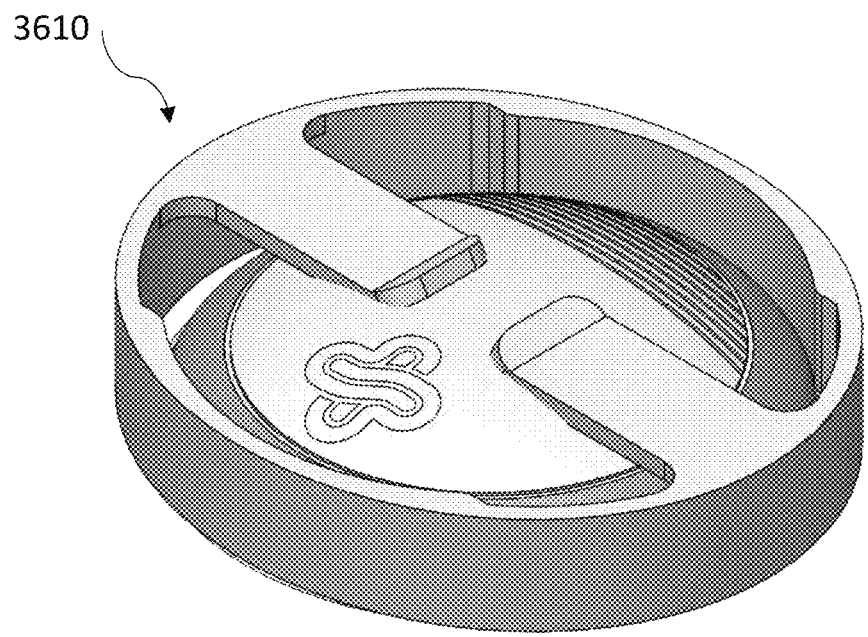
Figure 51N:
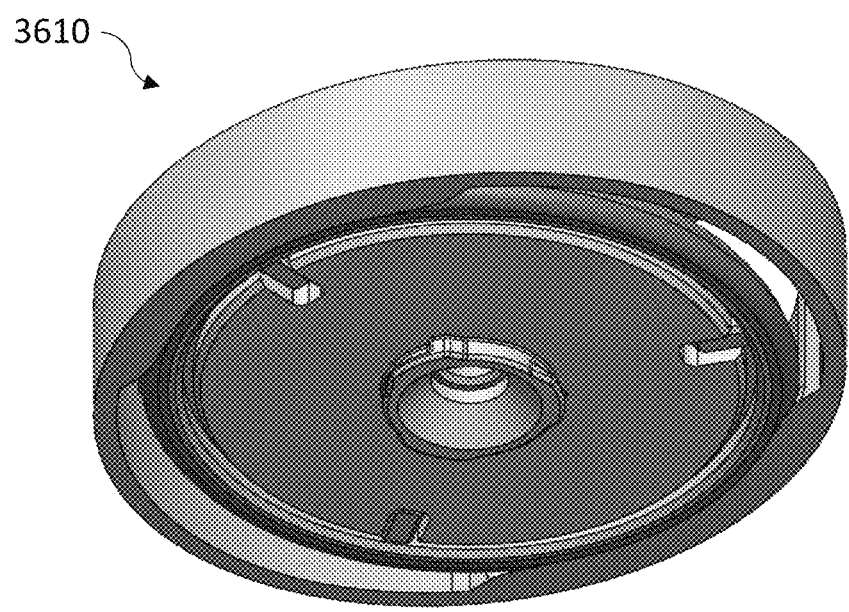

FIGS. 51M and 51N are an upper perspective view and a lower perspective view, respectively, of a shuttle of an applicator with an analyte monitoring device.

Figure 52A:
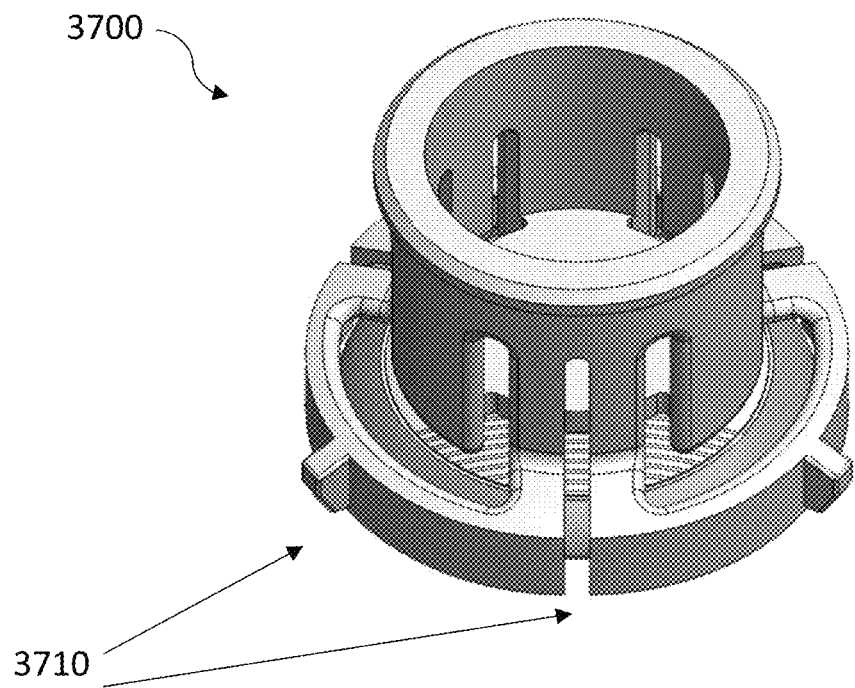
Figure 52B:
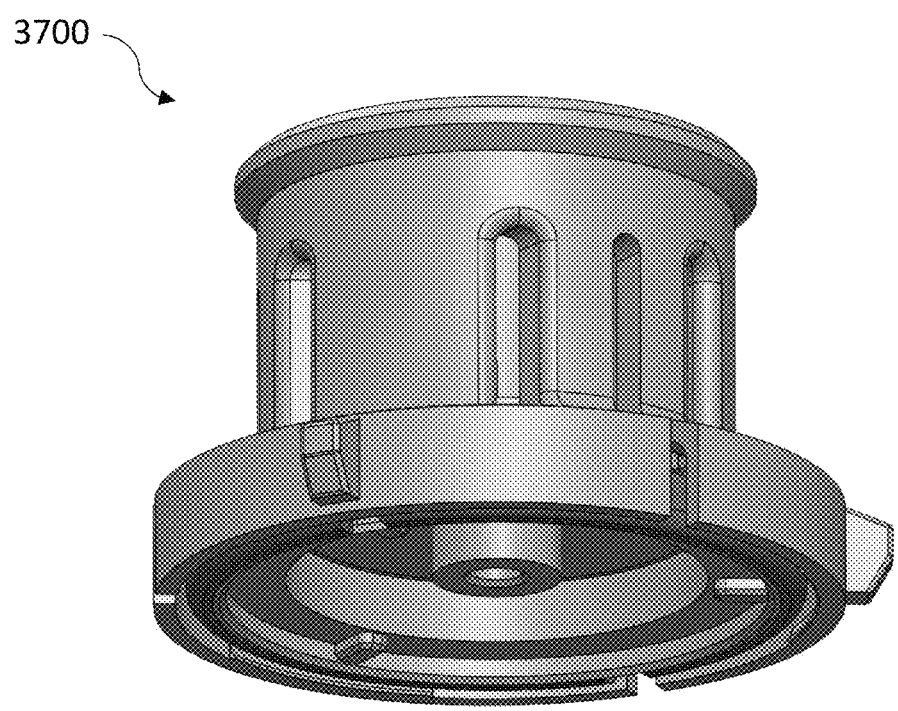

FIGS. 52A and 52B depict an upper perspective and a lower perspective view, respectively, of a shuttle of an applicator with an analyte monitoring device.

Figure 53A:
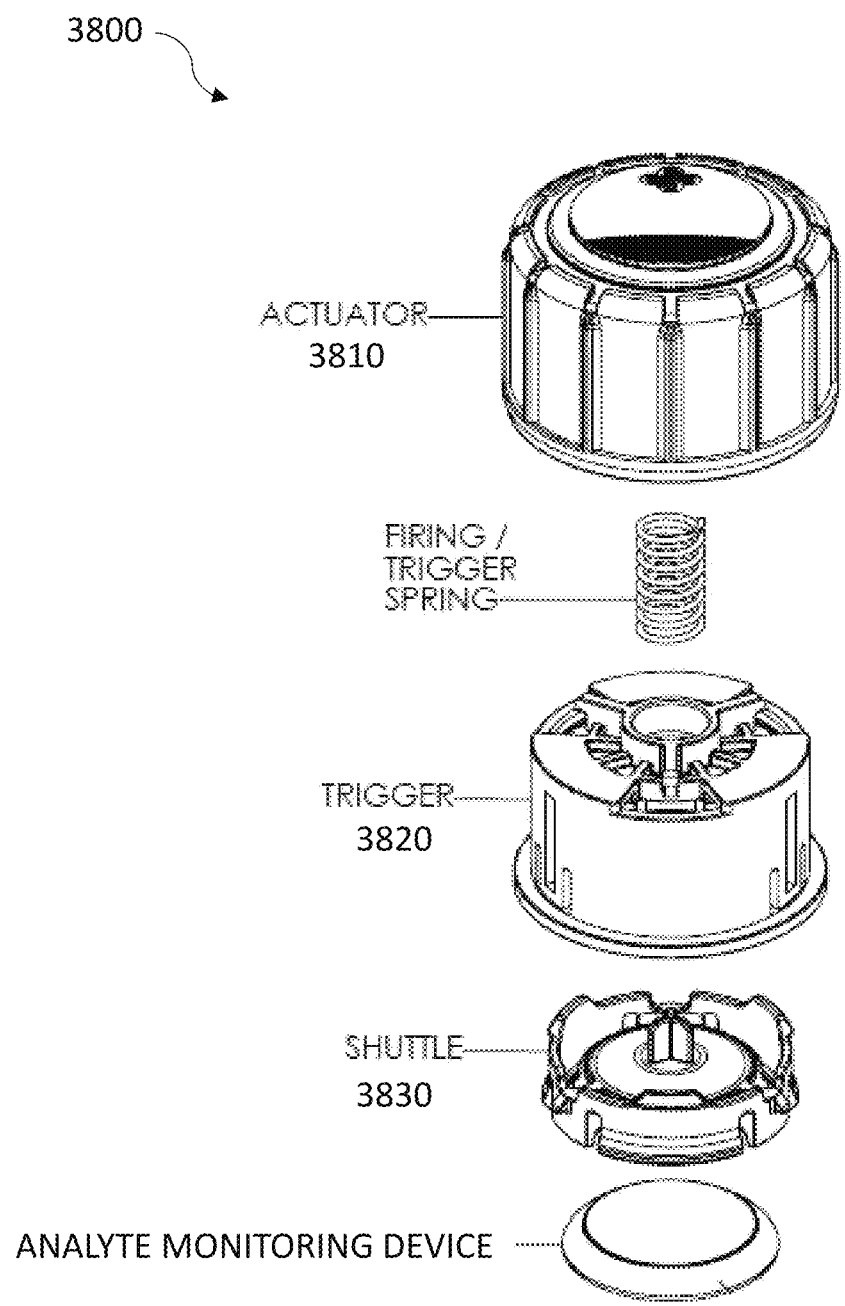

FIG. 53A depicts an exploded view of an applicator of an applicator.

FIGS. 53B-53E depict an upper perspective view, a top view, a lower perspective view, and a cross-sectional view, respectively, of a shuttle of an applicator.

FIGS. 53F-53H depict a lower perspective view, a bottom view, and an upper perspective view, respectively, of a trigger of an applicator.

Figure 53I:
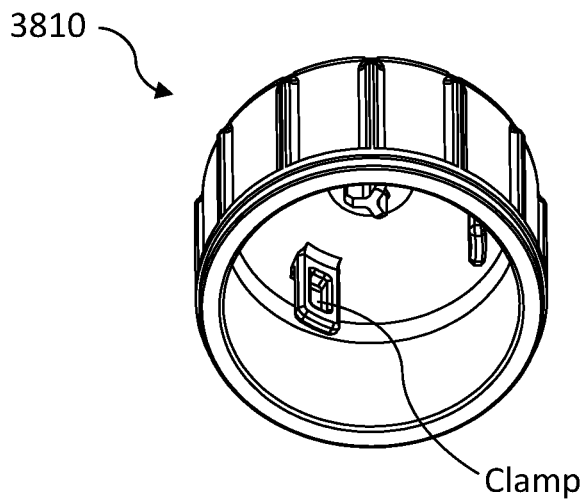
Figure 53J:
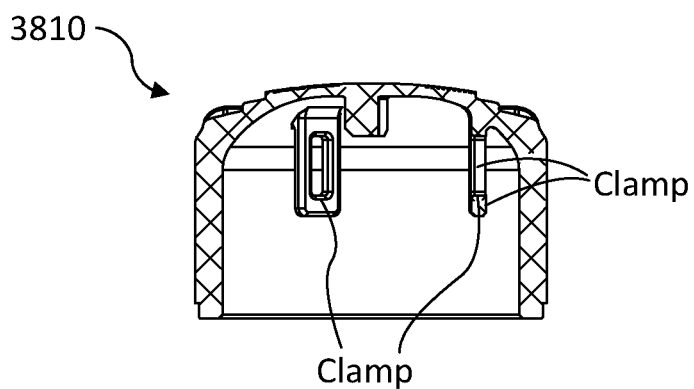
Figure 53K:
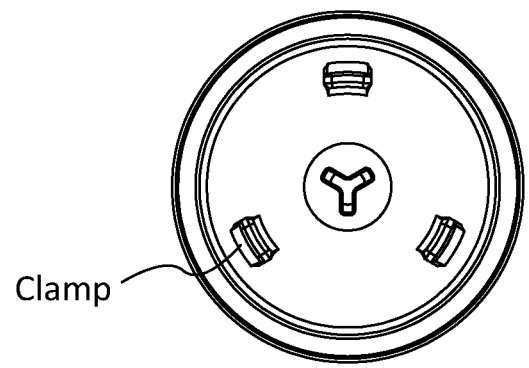

FIGS. 53I-53K depict a lower perspective view, a cross-sectional view, and a bottom view, respectively, of an actuator of an applicator.

FIGS. 54A and 54B depict a perspective view and an exploded view, respectively, of a shuttle of an applicator.

DETAILED DESCRIPTION

Non-limiting examples of various aspects and variations of the invention are described herein and illustrated in the accompanying drawings.

Aspects of the current subject matter are directed to a microneedle enclosure for providing a protective environment in which a microneedle array of an analyte monitoring device may be safely contained. The microneedle enclosure releasably attaches to the analyte monitoring device to protect the microneedle array prior to application of the analyte monitoring device and is removable from the analyte monitoring device to provide for application of the analyte monitoring device (e.g., insertion of the microneedle array).

Additional aspects of the current subject matter are directed to an applicator device (also referred to as an applicator) for application of an analyte monitoring device including one or more microneedle arrays to a target area of a user. The applicator device and variations described herein provide for safe and effective application of the analyte monitoring device to the user such that the microneedle array punctures the skin of the user for insertion into the skin, for example, the upper dermal region (e.g., papillary dermis and upper reticular dermis layers) of the skin.

Before providing additional details regarding aspects of the microneedle enclosure and the applicator device, the following provides a description of some examples of an analyte monitoring device that may be used with the microneedle enclosure and/or the applicator device described herein. The following descriptions are meant to be exemplary, and aspects related to the microneedle enclosure and the applicator device consistent with the current subject matter are not limited to the example analyte monitoring device described herein.

As generally described herein, an analyte monitoring system may include an analyte monitoring device that is worn by a user and includes one or more sensors for monitoring at least one analyte of a user. The sensors may, for example, include one or more electrodes configured to perform electrochemical detection of at least one analyte. The analyte monitoring device may communicate sensor data to an external computing device for storage, display, and/or analysis of sensor data.

Figure 1:
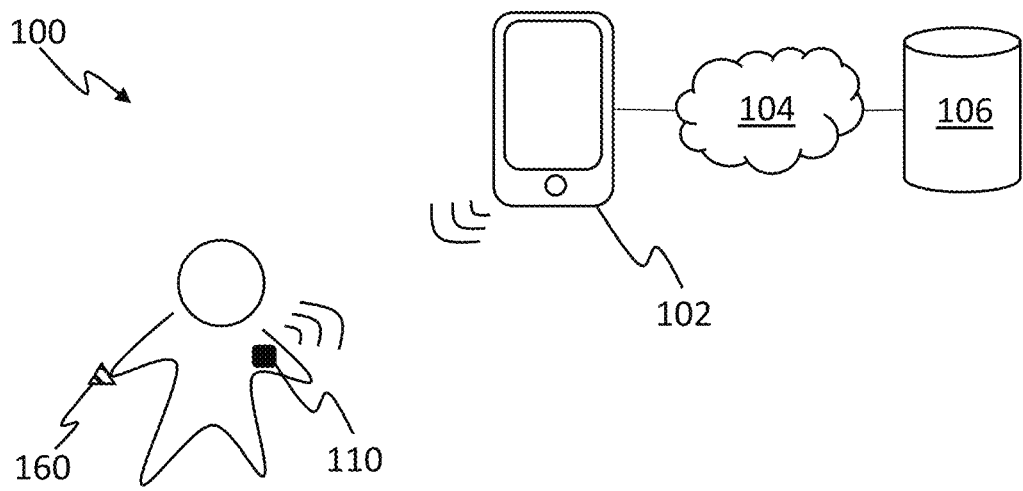
FIG. 1 depicts an illustrative schematic of an analyte monitoring system with a microneedle array.

For example, as shown in FIG. 1, an analyte monitoring system 100 may include an analyte monitoring device 110 that is worn by a user, and the analyte monitoring device 110 may be a continuous analyte monitoring device (e.g., continuous glucose monitoring device). The analyte monitoring device 110 may include, for example, a microneedle array comprising at least one electrochemical sensor for detecting and/or measuring one or more analytes in body fluid of a user. In some variations, the analyte monitoring device may be applied to the user using suitable applicator 160 (e.g., any of the applicators described herein). The analyte monitoring device 110 may include one or more processors for performing analysis on sensor data, and/or a communication module (e.g., wireless communication module) configured to communicate sensor data to a mobile computing device 102 (e.g., smartphone) or other suitable computing device. In some variations, the mobile computing device 102 may include one or more processors executing a mobile application to handle sensor data (e.g., displaying data, analyzing data for trends, etc.) and/or provide suitable alerts or other notifications related to the sensor data and/or analysis thereof. It should be understood that while in some variations the mobile computing device 102 may perform sensor data analysis locally, other computing device(s) may alternatively or additionally remotely analyze sensor data and/or communicate information related to such analysis with the mobile computing device 102 (or other suitable user interface) for display to the user. Furthermore, in some variations the mobile computing device 102 may be configured to communicate sensor data and/or analysis of the sensor data over a network 104 to one or more storage devices 106 (e.g., server) for archiving data and/or other suitable information related to the user of the analyte monitoring device.

The analyte monitoring devices described herein have characteristics that improve a number of properties that are advantageous for a continuous analyte monitoring device such as a continuous glucose monitoring (CGM) device. For example, the analyte monitoring device described herein have improved sensitivity (amount of sensor signal produced per given concentration of target analyte), improved selectivity (rejection of endogenous and exogenous circulating compounds that can interfere with the detection of the target analyte), and improved stability to help minimize change in sensor response over time through storage and operation of the analyte monitoring device. Additionally, compared to conventional continuous analyte monitoring devices, the analyte monitoring devices described herein have a shorter warm-up time that enables the sensor(s) to quickly provide a stable sensor signal following implantation, as well as a short response time that enables the sensors(s) to quickly provide a stable sensor signal following a change in analyte concentration in the user. Furthermore, as described in further detail below, the analyte monitoring devices described herein may be applied to and function in a variety of wear sites, and provide for pain-free sensor insertion for the user. Other properties such as biocompatibility, sterilizability, and mechanical integrity are also optimized in the analyte monitoring devices described herein.

Although the analyte monitoring systems described herein may be described with reference to monitoring of glucose (e.g., in users with Type 2 diabetes, Type 1 diabetes), it should be understood that such systems may additionally or alternatively be configured to sense and monitor other suitable analytes. As described in further detail below, suitable target analytes for detection may, for example, include glucose, ketones, lactate, and cortisol. One target analyte may be monitored, or multiple target analytes may be simultaneously monitored (e.g., in the same analyte monitoring device). For example, monitoring of other target analytes may enable the monitoring of other indications such as stress (e.g., through detection of rising cortisol and glucose) and ketoacidosis (e.g., through detection of rising ketones).

Figure 2A:
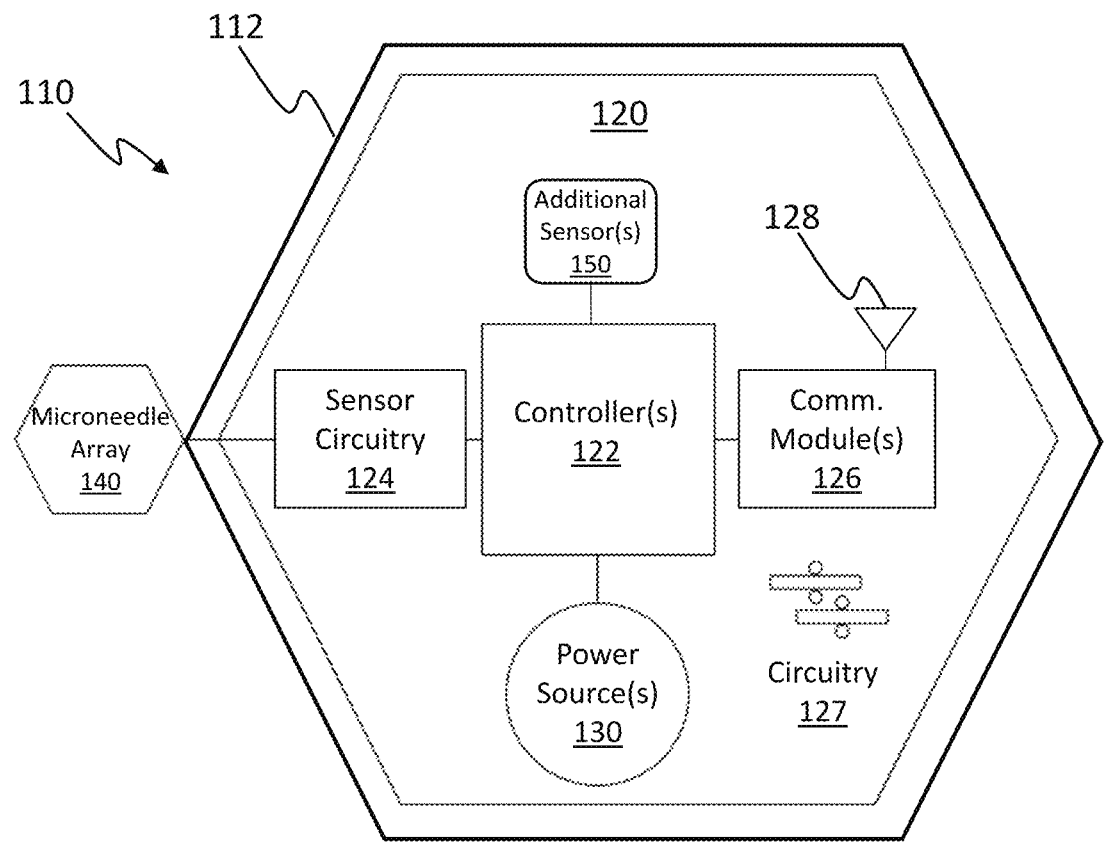
FIG. 2A depicts an illustrative schematic of an analyte monitoring device.

As shown in FIG. 2A, in some variations, an analyte monitoring device 110 may generally include a housing 112 and a microneedle array 140 extending outwardly from the housing. The housing 112, may, for example, be a wearable housing configured to be worn on the skin of a user such that the microneedle array 140 extends at least partially into the skin of the user. For example, the housing 112 may include an adhesive such that the analyte monitoring device 110 is a skin-adhered patch that is simple and straightforward for application to a user. The microneedle array 140 may be configured to puncture the skin of the user and include one or more electrochemical sensors (e.g., electrodes) configured for measuring one or more target analytes that are accessible after the microneedle array 140 punctures the skin of the user. In some variations, the analyte monitoring device 110 may be integrated or self-contained as a single unit, and the unit may be disposable (e.g., used for a period of time and replaced with another instance of the analyte monitoring device 110).

An electronics system 120 may be at least partially arranged in the housing 112 and include various electronic components, such as sensor circuitry 124 configured to perform signal processing (e.g., biasing and readout of electrochemical sensors, converting the analog signals from the electrochemical sensors to digital signals, etc.). The electronics system 120 may also include at least one microcontroller 122 for controlling the analyte monitoring device 110, at least one communication module 126, at least one power source 130, and/or other various suitable passive circuitry 127. The microcontroller 122 may, for example, be configured to interpret digital signals output from the sensor circuitry 124 (e.g., by executing a programmed routine in firmware), perform various suitable algorithms or mathematical transformations (e.g., calibration, etc.), and/or route processed data to and/or from the communication module 124. In some variations, the communication module 126 may include a suitable wireless transceiver (e.g., Bluetooth transceiver or the like) for communicating data with an external computing device 102 via one or more antennas 128. For example, the communication module 126 may be configured to provide uni-directional and/or bi-directional communication of data with an external computing device 102 that is paired with the analyte monitoring device 110. The power source 130 may provide power for the analyte monitoring device 110, such as for the electronics system. The power source 130 may include battery or other suitable source, and may, in some variations, be rechargeable and/or replaceable. Passive circuitry 127 may include various non-powered electrical circuitry (e.g., resistors, capacitors, inductors, etc.) providing interconnections between other electronic components, etc. The passive circuitry 127 may be configured to perform noise reduction, biasing and/or other purposes, for example. In some variations, the electronic components in the electronics system 120 may be arranged on one or more printed circuit boards (PCB), which may be rigid, semi-rigid, or flexible, for example. Additional details of the electronics system 120 are described further below.

In some variations, the analyte monitoring device 110 may further include one or more additional sensors 150 to provide additional information that may be relevant for user monitoring. For example, the analyte monitoring device 110 may further include at least one temperature sensor (e.g., thermistor) configured to measure skin temperature, thereby enabling temperature compensation for the sensor measurements obtained by the microneedle array electrochemical sensors.

Figure 2B:
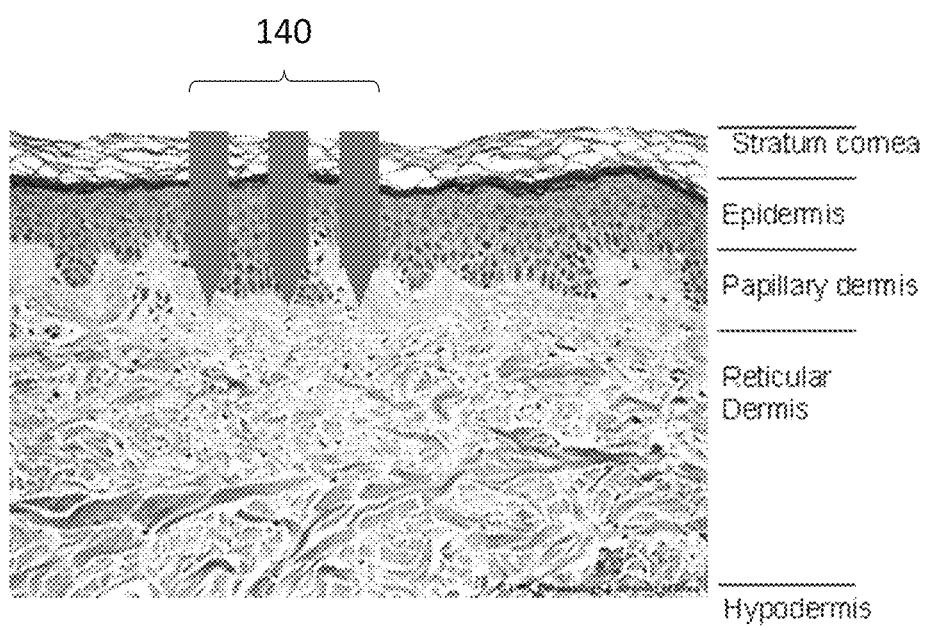
FIG. 2B depicts an illustrative schematic of microneedle insertion depth in an analyte monitoring device.

In some variations, the microneedle array 140 in the analyte monitoring device 110 may be configured to puncture skin of a user. As shown in FIG. 2B, when the device 110 is worn by the user, the microneedle array 140 may extend into the skin of the user such that electrodes on distal regions of the microneedles rest in the dermis. Specifically, in some variations, the microneedles may be designed to penetrate the skin and access the upper dermal region (e.g., papillary dermis and upper reticular dermis layers) of the skin, in order to enable the electrodes to access interstitial fluid that surrounds the cells in these layers. For example, in some variations, the microneedles may have a height generally ranging between at least 350 μm and about 515 μm. In some variations, one or more microneedles may extend from the housing such that a distal end of the electrode on the microneedle is located less than about 5 mm from a skin-interfacing surface of the housing, less than about 4 mm from the housing, less than about 3 mm from the housing, less than about 2 mm from the housing, or less than about 1 mm from the housing.

In contrast to traditional continuous analyte monitoring devices (e.g., CGM devices), which include sensors typically implanted between about 8 mm and about 10 mm beneath the skin surface in the subcutis or adipose layer of the skin, the analyte monitoring device 110 has a shallower microneedle insertion depth of about 0.25 mm (such that electrodes are implanted in the upper dermal region of the skin) that provides numerous benefits. These benefits include access to dermal interstitial fluid including one or more target analytes for detection, which is advantageous at least because at least some types of analyte measurements of dermal interstitial fluid have been found to closely correlate to those of blood. For example, it has been discovered that glucose measurements performed using electrochemical sensors accessing dermal interstitial fluid are advantageously highly linearly correlated with blood glucose measurements. Accordingly, glucose measurements based on dermal interstitial fluid are highly representative of blood glucose measurements.

Additionally, because of the shallower microneedle insertion depth of the analyte monitoring device 110, a reduced time delay in analyte detection is obtained compared to traditional continuous analyte monitoring devices. Such a shallower insertion depth positions the sensor surfaces in close proximity (e.g., within a few hundred micrometers or less) to the dense and well-perfused capillary bed of the reticular dermis, resulting in a negligible diffusional lag from the capillaries to the sensor surface. Diffusion time is related to diffusion distance according to $t=x^2/(2D)$ where t is the diffusion time, x is the diffusion distance, and D is the mass diffusivity of the analyte of interest. Therefore, positioning an analyte sensing element twice as far away from the source of an analyte in a capillary will result in a quadrupling of the diffusional delay time. Accordingly, conventional analyte sensors, which reside in the very poorly vascularized adipose tissue beneath the dermis, result in a significantly greater diffusion distance from the vasculature in the dermis and thus a substantial diffusional latency (e.g., typically 5-20 minutes). In contrast, the shallower microneedle insertion depth of the analyte monitoring device 110 benefits from low diffusional latency from capillaries to the sensor, thereby reducing time delay in analyte detection and providing more accurate results in real-time or near real-time. For example, in some embodiments, diffusional latency may be less than 10 minutes, less than 5 minutes, or less than 3 minutes.

Furthermore, when the microneedle array rests in the upper dermal region, the lower dermis beneath the microneedle array includes very high levels of vascularization and perfusion to support the dermal metabolism, which enables thermoregulation (via vasoconstriction and/or vasodilation) and provides a barrier function to help stabilize the sensing environment around the microneedles. Yet another advantage of the shallower insertion depth is that the upper dermal layers lack pain receptors, thus resulting in a reduced pain sensation when the microneedle array punctures the skin of the user, and providing for a more comfortable, minimally-invasive user experience.

Thus, the analyte monitoring devices and methods described herein enable improved continuous monitoring of one or more target analytes of a user. For example, as described above, the analyte monitoring device may be simple and straightforward to apply, which improves ease-of-use and user compliance. Additionally, analyte measurements of dermal interstitial fluid may provide for highly accurate analyte detection. Furthermore, compared to traditional continuous analyte monitoring devices, insertion of the microneedle array and its sensors may be less invasive and involve less pain for the user. Additional advantages of other aspects of the analyte monitoring devices and methods are further described below.

FIG. 3A-FIG. 3D depict aspects of the analyte monitoring device 110. FIGS. 3A-3D depict an upper perspective view, a side view, a bottom view, and an exploded view, respectively, of the analyte monitoring device 110.

The analyte monitoring device 110 may include a housing that at least partially surrounds or encloses other components (e.g., electronic components) of the analyte monitoring device 110, such as for protection of such components. For example, the housing may be configured to help prevent dust and moisture from entering the analyte monitoring device 110. In some variations, an adhesive layer may attach the housing to a surface (e.g., skin) of a user, while permitting the microneedle array 140 to extend outwardly from the housing and into the skin of the user. Furthermore, in some variations, the housing may generally include rounded edges or corners and/or be low-profile to reduce interference with clothing, etc. worn by the user.

For example, as shown in FIGS. 3A-3D, an example variation of the analyte monitoring device 110 may include a housing cover 320 and a base plate 330, configured to at least partially surround internal components of the analyte monitoring device 110. For example, the housing cover 320 and the base plate 330 may provide an enclosure for a sensor assembly 350 including the microneedle array 140 and electronic components. Once assembled, the microneedle array 140 extends outwardly from a portion of the base plate 330 in a skin-facing direction (e.g., an underside) of the analyte monitoring device 110.

The housing cover 320 and the base plate 330 may, for example, include one or more rigid or semi-rigid protective shell components that may couple together via suitable fasteners (e.g., mechanical fasteners), mechanically interlocking or mating features, and/or an engineering fit. The housing cover 320 and the base plate 330 may include radiused edges and corners and/or other atraumatic features. When coupled together, the housing cover 320 and the base plate 330 may form an internal volume that houses internal components, such as the sensor assembly 350. For example, the internal components arranged in the internal volume may be arranged in a compact, low-profile stack-up as the sensor assembly 350.

The analyte monitoring device 110 may include one or more adhesive layers to attach the analyte monitoring device 110 (e.g., the coupled together housing cover 320 and the base plate 330) to a surface (e.g., the skin) of a user. As shown in FIG. 3D, the one or more adhesive layers may include an inner adhesive layer 342 and an outer adhesive layer 344. The inner adhesive layer 342 may adhere to the base plate 330, and the outer adhesive layer 344 may adhere to the inner adhesive layer 342 and, on its outward facing side, provide an adhesive for adhering (e.g., temporarily) to the skin of the user. The inner adhesive layer 342 and the outer adhesive layer 344 together act as a double-sided adhesive for adhering the analyte monitoring device 110 to the skin of the user. The outer adhesive layer 344 may be protected by a release liner that the user removes to expose the adhesive prior to skin application. In some variations, a single adhesive layer is provided. In some variations, the outer adhesive layer 344, the inner adhesive layer 342, and/or the single adhesive layer may have a perimeter that extends farther than the perimeter or periphery of the housing cover 320 and the base plate 330. This may increase surface area for attachment and increase stability of retention or attachment to the skin of the user. The inner adhesive layer 342, the outer adhesive layer 344, and/or the single adhesive layer each have an opening that permits passage of the outwardly extending microneedle array 140, as further described below. The openings of the inner adhesive layer 342 and the outer adhesive layer 344 may generally align with one another but may, in some variations, differ in size such that one opening is smaller than the other opening. In some variations, the openings are substantially the same size.

The base plate 330 has a first surface (e.g., an outwardly exposed surface) opposite a second surface and serves as a support and/or connection structure and as a protective cover for the sensor assembly 350. The base plate 330 is sized and shaped to attach to the housing cover 320. The base plate 330 may be shaped to securely fit within the housing cover 320 such that outer edges of the base plate 330 align with corresponding edges of an opening of the housing cover 320. The alignment may be such that there is no gap between the outer edges of the base plate 330 and the corresponding edges of the opening of the housing cover 320.

A connection member 332 may be formed in a central or near central region of the first surface of the base plate 330. The connection member 332 is a protrusion (e.g., a projected hub) with sidewalls that extend from the first surface of the base plate 330 and with a first surface substantially parallel to the first surface of the base plate 330. Sidewalls extend from edges of the first surface of the connection member 332 to the first surface of the base plate 330. A remaining portion of the first surface of the base plate 330 surrounding the connection member 332 may be flat or substantially flat. One or more connector features 336 extend outwardly from the sidewalls of the connection member 332 to releasably engage with corresponding connectors of a microneedle enclosure, as further described below. The first surface and the sidewalls of the connection member 332 define, in part, a cavity. The cavity may be further defined through a portion of the base plate 330 adjacent (e.g., below) the connection member 332. The cavity has an opening, and is accessible, on the second surface of the base plate 330. An aperture 334 is formed through the first surface of the connection member 332. The aperture 334 may be sized and shaped such that the microneedle array 140 fits securely within and extends through the aperture 334. For example, sidewalls of the microneedle array 140 may align with corresponding sidewalls of the aperture 334. In some variations, the aperture 334 may be sized and shaped to correspond with an area surrounding the microneedle array 140. The openings in the inner adhesive layer 342 and the outer adhesive layer 344 (or the single adhesive layer) are sized such that the connection member 332 extends through the openings without interference with the adhesive layers. For example, the diameter of the opening of the inner adhesive layer 342 and the diameter of the opening of the outer adhesive layer 344 is larger than that of the connection member 332. In some variations, the opening of the inner adhesive layer 342 and/or the opening of the outer adhesive layer 344 (or that of the single adhesive layer) is in proximity with the sidewalls of the connection member 332 with a clearance to accommodate the one or more connector features 336. In some variations, one or more slits or notches may be formed in the inner adhesive layer 342, the outer adhesive layer 344, and/or the single adhesive layer, extending from the opening to aid in placement of the respective adhesive layer.

Although the housing cover 320 and the base plate 330 depicted in FIGS. 3A-3D are substantially circular with the housing cover 320 having a dome shape, in other variations, the housing cover 320 and the base plate 330 may have any suitable shape. For example, in other variations the housing cover 320 and the base plate 330 may be generally prismatic and have an elliptical, triangular, rectangular, pentagonal, hexagonal, or other suitable shape. The outer adhesive layer 344 (or the single adhesive layer) may extend outwardly from the housing cover 320 and the base plate 330 to extend beyond the perimeter of the housing cover 320. The outer adhesive layer 344 (or the single adhesive layer) may be circular, as shown in FIGS. 3A-3D or may have an elliptical, triangular, rectangular, pentagonal, hexagonal, or other suitable shape and need not be the same shape as the housing cover 320 and/or the base plate 330.

FIGS. 4A-4E depict aspects of the sensor assembly 350 of the analyte monitoring device 110 in a perspective exploded view, a side exploded view, a lower perspective view, a side view, and an upper perspective view, respectively.

The sensor assembly 350 includes microneedle array components and electronic components to implement analyte detection and processing aspects of the microneedle array-based continuous analyte monitoring device 110 for the detection and measuring of an analyte. In some variations, the sensor assembly 350 is a compact, low-profile stack-up that is at least partially contained within the internal volume defined by the housing cover 320 and the base plate 330.

In some variations, the sensor assembly 350 includes a microneedle array assembly 360 and an electronics assembly 370 that connect to one another to implement the microneedle array analyte detection and processing aspects further described herein. In some variations, the electronics assembly 370 includes a main printed circuit board (PCB) 450 on which electronic components are connected, and the microneedle array assembly 360 includes a secondary printed circuit board (PCB) 420 on which the microneedle array 140 is connected.

In some variations, the microneedle array assembly 360 includes, in addition to the secondary PCB 420 and the microneedle array 140, an epoxy skirt 410 and a secondary PCB connector 430. The microneedle array 140 is coupled to a top side (e.g., outer facing side) of the secondary PCB 420 so that the individual microneedles of the microneedle array 140 are exposed as described with reference to FIG. 3A-FIG. 3D. The secondary PCB connector 430 is coupled to a back side, opposite the top side, of the secondary PCB 420. The secondary PCB connector 430 may be an electromechanical connector and may communicatively couple to the primary PCB 450 through a primary PCB connector 470 on a top side (e.g., outer facing side) of the primary PCB 450 to allow for signal communication between the secondary PCB 420 and the primary PCB 450. For example, signals from the microneedle array 140 may be communicated to the primary PCB 450 through the secondary PCB 420, the secondary PCB connector 430, and the primary PCB connector 470.

The secondary PCB 420 may in part determine the distance to which the microneedle array 140 protrudes from the base plate 330 of the housing. Accordingly, the height of the secondary PCB 420 may be selected to help ensure that the microneedle array 140 is inserted properly into a user's skin. During microneedle insertion, the first surface (e.g., outer facing surface) of the connection member 332 of the base plate 330 may act as a stop for microneedle insertion. If the secondary PCB 420 has a reduced height and its top surface is flush or nearly flush with the first surface of the connection member 332, then the connection member 332 may prevent the microneedle array 140 from being fully inserted into the skin.

In some variations, other components (e.g., electronic components such as sensors or other components) may also be connected to the secondary PCB 420. For example, the secondary PCB 420 may be sized and shaped to accommodate electronic components on the top side or the back side of the secondary PCB 420.

In some variations, the epoxy skirt 410 may be deposited along the edges (e.g., the outer perimeter) of the microneedle array 140 to provide a secure fit of the microneedle array 140 within the aperture 334 formed in the connection member 332 of the base plate 330 and/or to relieve the sharp edges along the microneedle array 140, as shown in FIG. 3C and FIG. 3D. For example, the epoxy skirt 410 may occupy portions of the aperture 334 not filled by the microneedle array 140 and/or portions of the cavity defined in the base plate 330 not filled by the secondary PCB 420. The epoxy skirt 410 may also provide a transition from the edges of the microneedle array 140 to the edge of the secondary PCB 420. In some variations, the epoxy skirt 410 may be replaced or supplemented by a gasket (e.g., a rubber gasket) or the like.

The electronics assembly 370, having the primary PCB 450, includes a battery 460 coupled to a back side of the primary PCB 450, opposite the top side on which the primary PCB connector 470 is coupled. In some variations, the battery 460 may be coupled on the top side of the primary PCB 450 and/or in other arrangements.

Figure 4F:
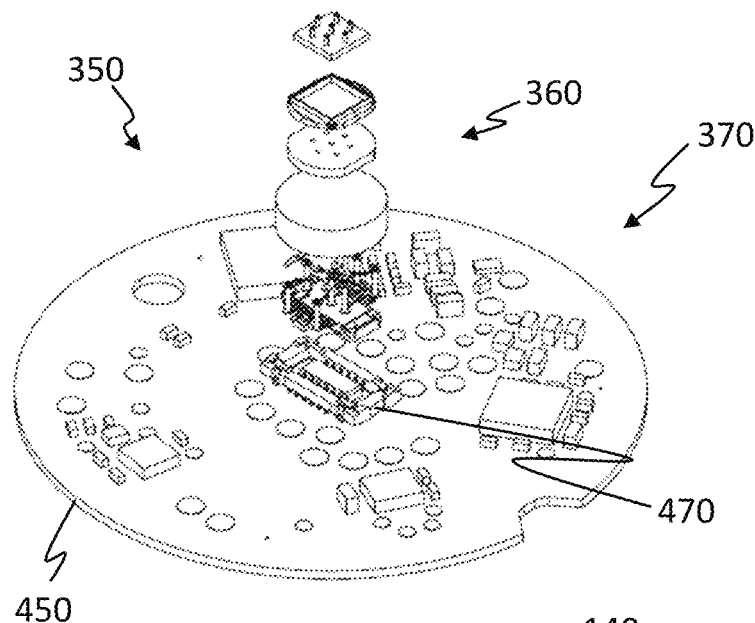
FIGS. 4F-4H depict a perspective exploded view, a side exploded view, and a side view, respectively, of a sensor assembly in an analyte monitoring device.
Figure 4G:
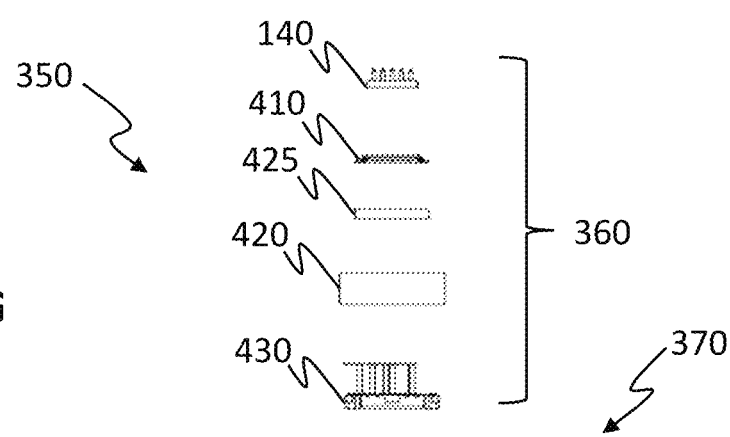
Figure 4H:
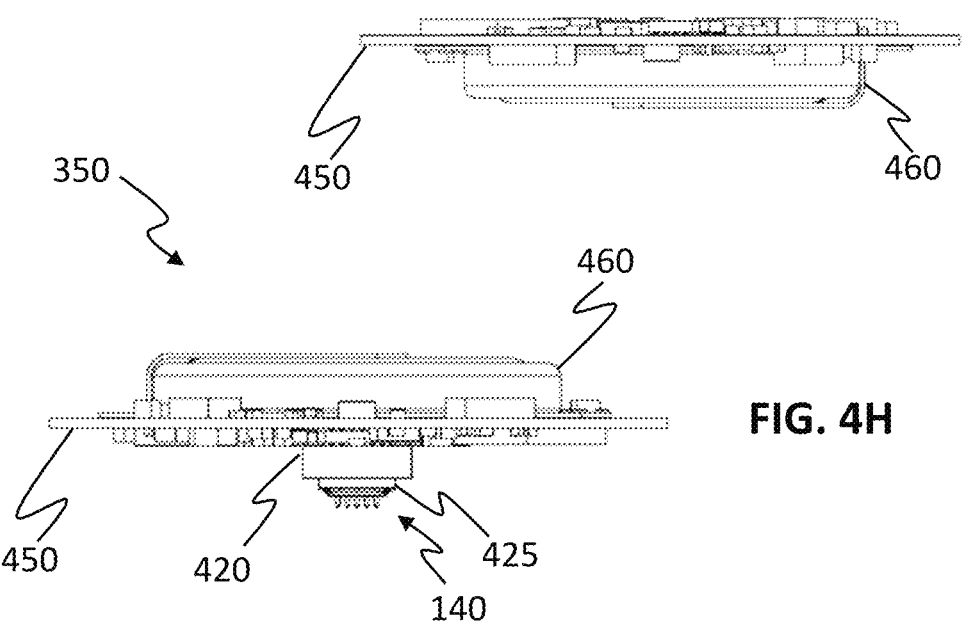

FIGS. 4F-4H depict aspects of an alternate variation of the sensor assembly 350 of the analyte monitoring device 110. A perspective exploded view, a side exploded view, and a side view of the sensor assembly 350 are provided, respectively, in FIGS. 4F-4H.

As shown, in the sensor assembly 350, an additional PCB component, an intermediate PCB 425, is incorporated. In some variations, the intermediate PCB 425 is part of the microneedle array assembly 360 and is positioned between and connected to the secondary PCB 420 and the microneedle array 140. The intermediate PCB 425 may be added to increase the height of the microneedle array assembly 360 such that the microneedle array 140 extends at a further distance from the base plate 330, which may aid in insertion of the microneedle array 140 into the skin of a user. The microneedle array 140 is coupled to a top side (e.g., outer facing side) of the intermediate PCB 425 so that the individual microneedles of the microneedle array 140 are exposed as described with reference to FIG. 3A-FIG. 3D. The secondary PCB 420 is coupled to a back side, opposite the top side, of the intermediate PCB 425, and the secondary PCB connector 430 is coupled to a back side, opposite the top side, of the secondary PCB 420. The epoxy skirt 410 (which may be replaced or supplemented by a gasket of the like) provides a transition from the edges of the microneedle array 140 to the edge of the intermediate PCB 425.

The intermediate PCB 425 with the secondary PCB 420 in part determine the distance to which the microneedle array 140 protrudes through the aperture 334 of the base plate 330. The incorporation of the intermediate PCB 425 provides an additional height to help ensure that the microneedle array 140 is properly inserted into a user's skin. In some variations, the top side (e.g., outer facing side) of the intermediate PCB 425 extends through and out of the aperture 334 so that the first surface (e.g., top, exposed surface) of the connection member 332 surrounding the aperture 334 does not prevent the microneedle array from being fully inserted into the skin. In some variations, the top side (e.g., outer facing side) of the intermediate PCB 425 does not extend out of the aperture 334 but the increased height (by virtue of incorporating the intermediate PCB 425) ensures that the microneedle array 140 protrudes at a sufficient distance from the base plate 330 of the housing.

In some variations, a microneedle enclosure may be provided for releasable attachment to the analyte monitoring device 110. The microneedle enclosure may provide a protective environment or enclosure in which the microneedle array 140 may be safely contained, thereby ensuring the integrity of the microneedle array 140 during certain stages of manufacture and transport of the analyte monitoring device 110, prior to application of the analyte monitoring device 110. The microneedle enclosure is releasable or removable from the analyte monitoring device 110 to allow for the microneedle array 140 to be exposed and ready for insertion into the skin of the user, as further described herein.

In some variations, the microneedle enclosure, by providing an enclosed and sealed environment in which the microneedle array 140 may be contained, provides an environment in which the microneedle array 140 may be sterilized. For example, the microneedle enclosure with the microneedle array 140 may be subjected to a sterilization process, during which the sterilization penetrates the microneedle enclosure so that the microneedle array 140 is also sterilized. As the microneedle array 140 is contained in an enclosed environment, the microneedle array 140 remains sterilized until removed from the enclosed environment.

FIGS. 5A-5D depict aspects of a microneedle enclosure 500 in an exploded view, first side and side cross-sectional views, second side and side cross-sectional views, and a bottom perspective view, respectively. The microneedle enclosure 500 includes a capsule 510, a clamp 520, and a biasing element 530 (e.g., a spring). In some variations, the microneedle enclosure 500 may further include a force concentrator 540.

The capsule 510 is a housing, an enclosure, or the like with sidewalls that surround and/or encase the microneedle array 140 and provide an enclosed, sealed environment for the microneedle array 140. The capsule 510 has an opening at a distal end through which the microneedle array 140 is positioned such that an inner portion of the sidewalls of the capsule 510 surround the microneedle array 140. A bumper 512 may be positioned at the distal end of the capsule 510 such that the bumper 512 surrounds the opening of the capsule 510 at the distal end. The bumper 512 may be a ring-shaped elastomeric bumper or the like that provides for a tight seal to be maintained around the distal end of the capsule 510. The bumper 512 may be sized to correspond to the size and shape of the opening of the capsule 510 at the distal end. An inner perimeter of the capsule 510 (e.g., the perimeter of the opening) may align or substantially align with a footprint of the microneedle array 140. For example, the inner perimeter of the capsule 510 may be sized and shaped to align with an outer perimeter of the microneedle array 140, providing for the microneedle array 140 to be fully contained within the capsule 510 with the microneedles extending into the capsule 510.

The clamp 520 includes a cavity defined by sidewalls of the clamp 520. The cavity may include a first cavity 522 and a second cavity 524, each defined by sidewalls of the clamp 520. The second cavity 524 is adjacent to the first cavity 522 in a region proximal to the first cavity 522, and the second cavity 524 is a proximal extension of the first cavity 522 such that the first cavity 522 and the second cavity 524 are fluidly connected. The first cavity 522 is sized and shaped to accommodate the capsule 510. An opening at a distal end of the clamp 520 provides an access point into the first cavity 522, permitting the capsule 510 to be fitted in the first cavity 522 through the opening. The second cavity 524 is sized and shaped to accommodate the biasing element 530. When the biasing element 530 and the capsule 510 are positioned within the clamp 520 (e.g., through the opening at the distal end of the clamp 520), the biasing element 530 is securely but movably contained within the second cavity 524, and outer sidewalls of the capsule 510 are aligned with and may abut against sidewalls of the first cavity 522. In some variations, one or more portions of the outer sidewalls of the capsule 510 contact a respective one or more portions of the first cavity 522 such that the capsule 510 is wedged or tightly fitted within the first cavity 522, causing the capsule 510 to be integral with the clamp 520. The biasing element 530 may generally correspond in size and shape to the second cavity 524 and extends in a distal direction from an upper region of the second cavity 524 to or near a top surface of the capsule 510. The diameter of the biasing element 530 may be slightly less than an inner diameter of the second cavity 524 to limit horizontal movement of the biasing element 530 within the clamp 520. The biasing element 530 may be a coiled metal spring, a plastic leaf spring, a coiled plastic spring, or any form of spring capable of providing a compliance between the clamp 520 and the capsule 510, as further described herein.

In some variations, the force concentrator 540 may be positioned within the biasing element 530 with a distal region extending out of the biasing element 530 and in contact with a top surface of the capsule 510. For example, the force concentrator 540 may include a shaft and a head. The shaft may fit within the biasing element 530, and the head may extend at a distal end through the biasing element 530 to contact the top surface of the capsule 510. The biasing element 530, and optionally the force concentrator 540, are incorporated to provide a sealing, downward force on the capsule 510 and the bumper 512 to maintain a sealed enclosure for the microneedle array 140 when the clamp 520 is engaged with the analyte monitoring device 110, as further described herein. The force concentrator 540 provides a downward force to the engaged top surface of the capsule 510 to eliminate transmission of torque to the bumper 512 during manufacturing and/or assembly processes. For example, the force concentrator 540 eliminates rotation of the bumper 512 during manufacturing and/or assembly processes.

Figure 5A:
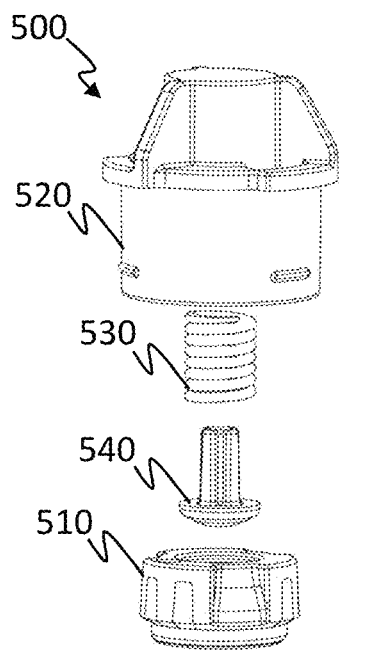
FIGS. 5A-5D depict aspects of a microneedle enclosure in an exploded view, first side and side cross-sectional views, second side and side cross-sectional views, and a bottom perspective view, respectively.
Figure 5D:
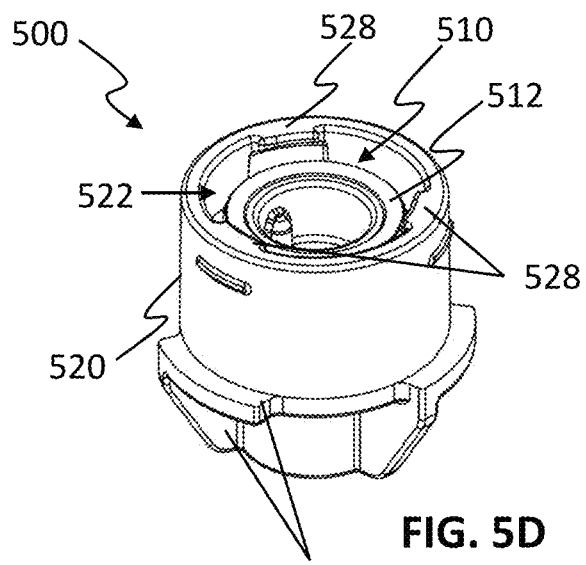
Figure 5B:
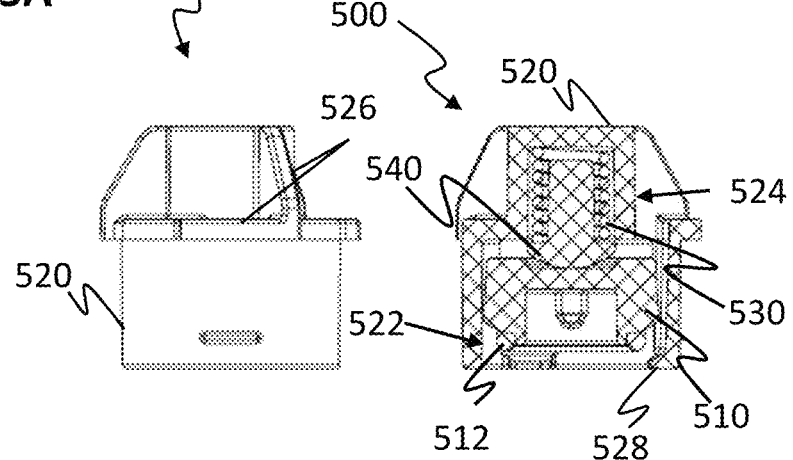
Figure 5C:
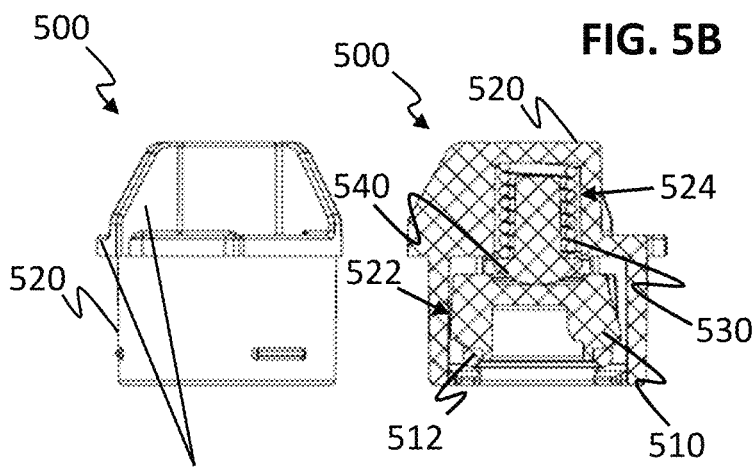

The clamp 520 further includes outer engagement features 526 and locking tabs 528. The outer engagement features 526 are configured to engage with a portion of an applicator device, as further described herein. The locking tabs 528 are formed on respective inner portions of the sidewalls of the clamp 520 at a distal end of the clamp 520, as best shown in FIG. 5D. The locking tabs 528 may be protrusions extending orthogonally outward from inner portions of the sidewalls of the clamp 520 and may be configured to releasably engage with the base plate 330, as further described below.

Figure 5E:
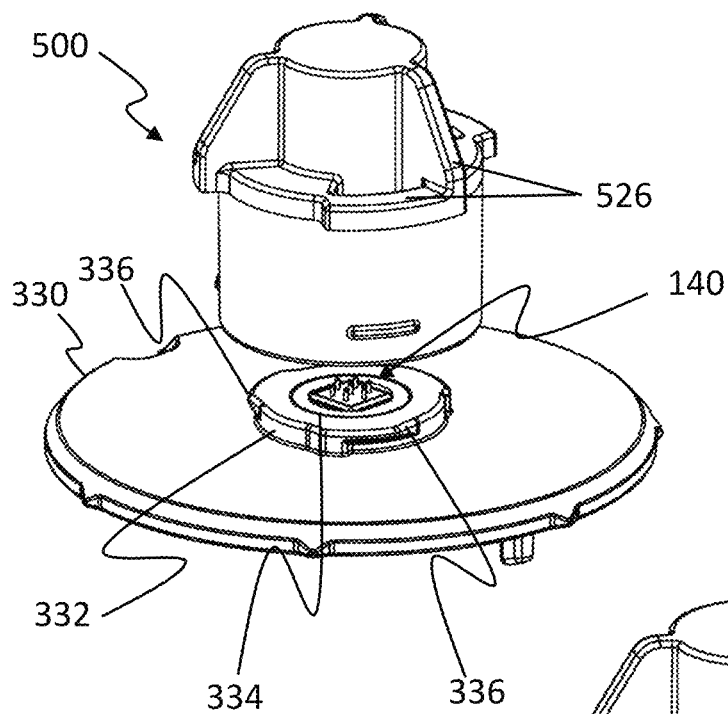
FIGS. 5E-5G depict aspects of a microneedle enclosure with a base plate of an analyte monitoring device in a perspective exploded view, a perspective view, and a side cross-sectional view, respectively.
Figure 5F:
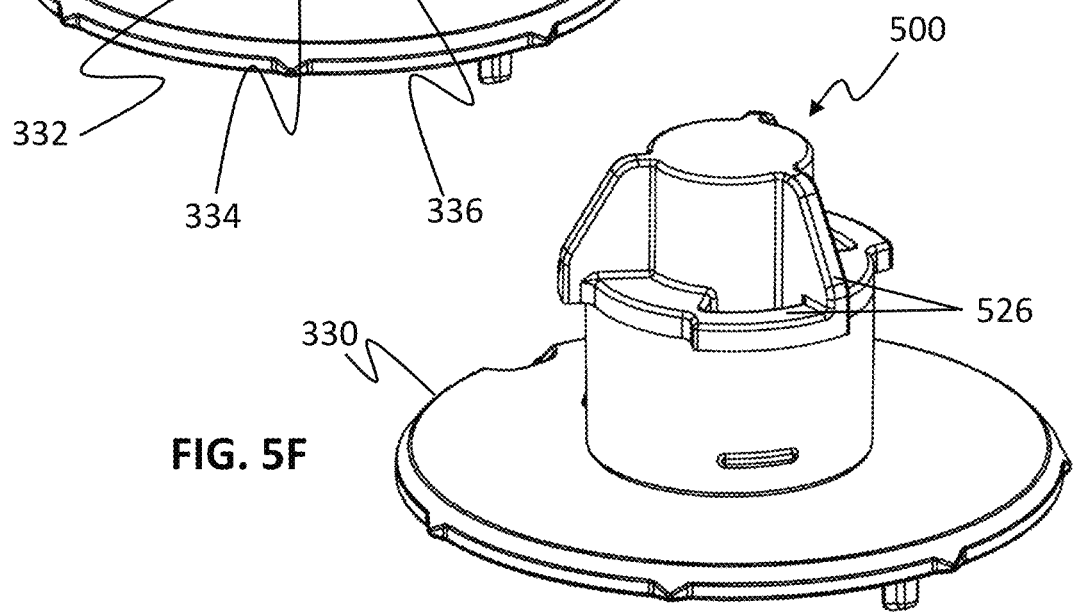
Figure 5G:
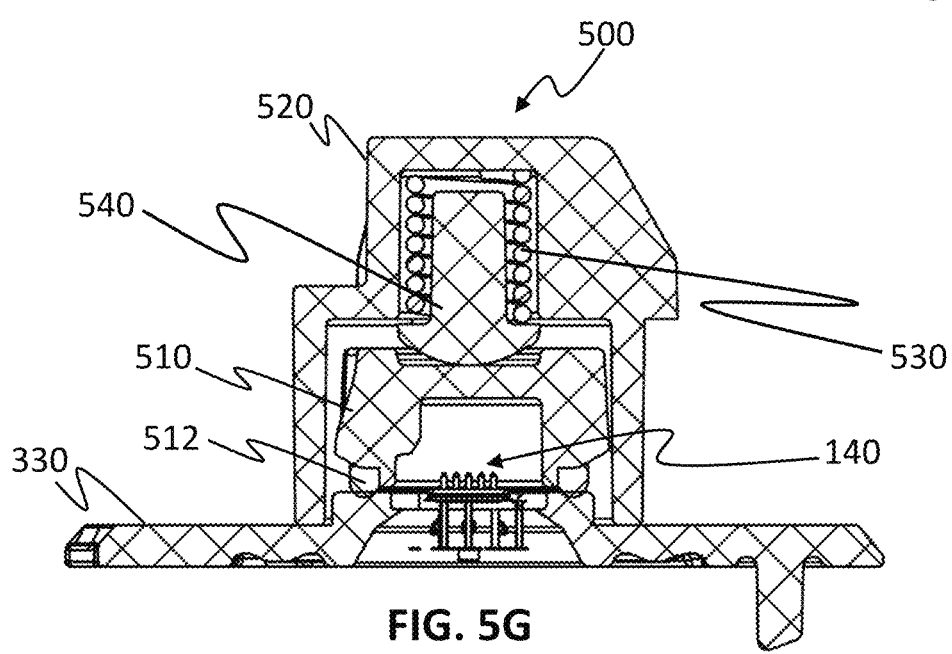

FIGS. 5E-5G depict aspects of the microneedle enclosure 500, the base plate 330 of the analyte monitoring device 110, and a releasable coupling there between. The microneedle enclosure 500 is configured to releasably attach or couple to the base plate 330 through engagement with the connection member 332. The microneedle array assembly 360 portion of the sensor assembly 350 is fitted within the cavity formed by the base plate 330 and the connection member 332, with the microneedle array 140 extending through the aperture 334 of the base plate 330. As shown in the side cross-sectional view of FIG. 5G, upon attachment of the microneedle enclosure 500 to the base plate 330, the microneedle array 140 is contained within the capsule 510 with the bumper 512 providing a seal between the capsule 510 and the base plate 330. In some variations, bottom edges of the sidewalls of the microneedle enclosure 500 interface and/or abut with the first surface of the base plate 330 around and/or adjacent to outer edges of the connection member 322. In some variations, bottom edges of the sidewalls of the capsule 510 and bottom edges of the bumper 512 interface and/or abut with the first surface of the connection member 332 around and/or adjacent to outer edges of the aperture 334. In some variations, the outer diameter of the capsule 510 is the same as or slightly less than the diameter of the first surface of the connection member 322. The diameter of the opening of the capsule 510 is of sufficient size to accommodate the aperture 334 without interfering with the microneedle array 140. Sidewalls of the opening of the capsule 510 may interface and/or abut with an edge surrounding the microneedle array 140 such that the sidewalls of the opening of the capsule 510 surround the edge of the microneedle array 140.

To form the releasable attachment or coupling between the base plate 330 and the microneedle enclosure 500, the connector features 336 of the connection member 332 releasably engage with the locking tabs 528 of the microneedle enclosure 500. In some variations, the connector features 336 may be bayonet connectors that engage and disengage the locking tabs 528 through a twisting or rotational motion. For example, the connector features 336 may include extension leaves that orthogonally protrude from an upper region of the connection member 332. Each extension leaf may terminate at one end with a stop feature (e.g., a vertical wall or vertically extending barrier) that extends from an upper edge of the respective extension leaf to the first surface of the base plate 330. The connector features 336 may be positioned circumferentially around the outer edge of the connection member 332, and each connector feature 336 may correspond to a respective locking tab 528 of the microneedle enclosure 500. The locking tabs 528 interface with the connector features 336 by sliding beneath the extension leaves and engaging the stop features upon rotation of the microneedle enclosure 500 with respect to the base plate 330. In some variations, the microneedle enclosure 500 is placed over the connection member 332 and rotated until further rotation is inhibited by the locking tabs 528 engaging the stop features of the connector features 336. Rotation in the opposite direction disengages the locking tabs 528 from the stop features, allowing the microneedle enclosure 500 to be disengaged from the connection member 332, at which point the microneedle enclosure 500 may be lifted or pulled off the base plate 330. Other types of connection members that form a releasable connection may be used. In some variations, three connector features 336 and locking tabs 528 may be incorporated. In other variations, one, two, four, or more pairs of connector features 336 and locking tabs 528 may be incorporated.

As depicted in FIG. 5G, when the microneedle enclosure 500 is connected to the base plate 330 including the microneedle array assembly 360, the capsule 510 is aligned around the microneedle array 140 on the first surface of the connection member 322. When the microneedle enclosure 500 is positioned over the connection member 322 and twisted to engage the one or more connector features 336, the biasing element 530 is biased to maintain a stabilizing connection between the capsule 510 and the clamp 520. The force concentrator 540 provides a downward force to the capsule 510 and the bumper 512 to eliminate transmission of torque to the bumper 512 so that the bumper 512 does not rotate during the twisting operation. The sterile barrier provided by the capsule 510 and the bumper 512 is thus maintained. The inner perimeter of the opening of the capsule 510 and the edge of the microneedle array 140 are tightly sealed such that that the clamp 520, the capsule 510, the bumper 512, the biasing element 530, and the force concentrator 540 provide a tight enclosure around the microneedle array 140.

The microneedle array assembly 360, including the microneedle array 140, fitted within the base plate 330 with the microneedle enclosure 500 coupled thereto, may be sterilized. For example, radiation sterilization methods may be applied. In some variations, the components are sterilized to a sterility assurance level (SAL) of $10^{-6}$. Notably, the sterilization is done without the microneedle array assembly 360 connected to the electronics assembly 370. After the sterilization process, the base plate 330 attaches to the housing cover 320 in which the electronics assembly 370 is positioned. The attachment includes establishing a connection between the microneedle array assembly 360 and the electronics assembly 370 through the respective PCB connectors 430 and 470. As the microneedle array 140 is contained within the sealed microneedle enclosure 500, the sterile environment in which the microneedle array 140 is contained is not compromised. The assembled analyte monitoring device 110, with the attached microneedle enclosure 500, may be contained in an applicator device, as further described herein.

The configuration of the microneedle enclosure 500 as described herein allows for large batch sterilization. For example, a plurality of assemblies including the microneedle array assembly 360, the base plate 330, and the microneedle enclosure 500 may be assembled as described herein. The plurality of assemblies may then be exposed to radiation to sterilize each microneedle array 140. In some variations, one or more trays, containers, or the like containing the plurality of assemblies may be placed in an enclosed environment or sterilization chamber to which radiation may be applied. This results in the plurality of assemblies being sterilized at the same time, thus enabling large scale manufacture of the analyte monitoring devices.

In some variations, the electronics system of the analyte monitoring device may include an analog front end. The analog front end may include sensor circuitry (e.g., sensor circuitry 124 as shown in FIG. 2A) that converts analog current measurements to digital values that can be processed by the microcontroller. The analog front end may, for example, include a programmable analog front end that is suitable for use with electrochemical sensors. For example, the analog front end may include a MAX30131, MAX30132, or MAX30134 component (which have 1, 2, and 4 channel, respectively), available from Maxim Integrated (San Jose, Calif.), which are ultra-low power programmable analog front ends for use with electrochemical sensors. The analog front end may also include an AD5940 or AD5941 component, available from Analog Devices (Norwood, Mass.), which are high precision, impedance and electrochemical front ends. Similarly, the analog front end may also include an LMP91000, available from Texas Instruments (Dallas, Tex.), which is a configurable analog front end potentiostat for low-power chemical sensing applications. The analog front end may provide biasing and a complete measurement path, including the analog to digital converters (ADCs). Ultra-low power may allow for the continuous biasing of the sensor to maintain accuracy and fast response when measurement is required for an extended duration (e.g. 7 days) using a body-worn, battery-operated device.

In some variations, the analog front end device may be compatible with both two and three terminal electrochemical sensors, such as to enable both DC current measurement, AC current measurement, and electrochemical impedance spectroscopy (EIS) measurement capabilities. Furthermore, the analog front end may include an internal temperature sensor and programmable voltage reference, support external temperature monitoring and an external reference source and integrate voltage monitoring of bias and supply voltages for safety and compliance.

In some variations, the analog front end may include a multi-channel potentiostat to multiplex sensor inputs and handle multiple signal channels. For example, the analog front end may include a multi-channel potentiostat such as that described in U.S. Pat. No. 9,933,387, which is incorporated herein in its entirety by this reference.

In some variations, the analog front end and peripheral electronics may be integrated into an application-specific integrated circuit (ASIC), which may help reduce cost, for example. This integrated solution may include the microcontroller described below, in some variations.

In some variations, the electronics system of the analyte monitoring device may include at least one microcontroller (e.g., controller 122 as shown in FIG. 2A). The microcontroller may include, for example, a processor with integrated flash memory. In some variations, the microcontroller in the analyte monitoring device may be configured to perform analysis to correlate sensor signals to an analyte measurement (e.g., glucose measurement). For example, the microcontroller may execute a programmed routine in firmware to interpret the digital signal (e.g., from the analog front end), perform any relevant algorithms and/or other analysis, and route processed data to and/or from the communication module. Keeping the analysis on-board the analyte monitoring device may, for example, enable the analyte monitoring device to broadcast analyte measurement(s) to multiple devices (e.g., mobile computing devices such as a smartphone or smartwatch, therapeutic delivery systems such as insulin pens or pumps, etc.) in parallel, while ensuring that each connected device has the same information.

In some variations, the microcontroller may be configured to activate and/or inactivate the analyte monitoring device on one or more detected conditions. For example, the device may be configured to power on the analyte monitoring device upon insertion of the microneedle array into skin. This may, for example, enable a power-saving feature in which the battery is disconnected until the microneedle array is placed in skin, at which time the device may begin broadcasting sensor data. Such a feature may, for example, help improve the shelf life of the analyte monitoring device and/or simplify the analyte monitoring device-external device pairing process for the user.

Figure 6A:
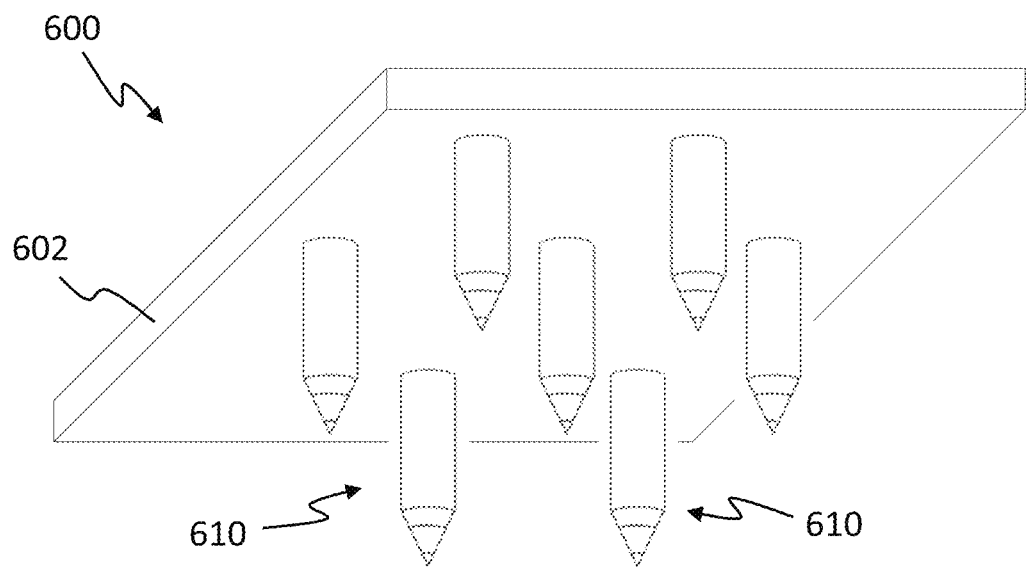
FIG. 6A depicts an illustrative schematic of a microneedle array.
Figure 6B:
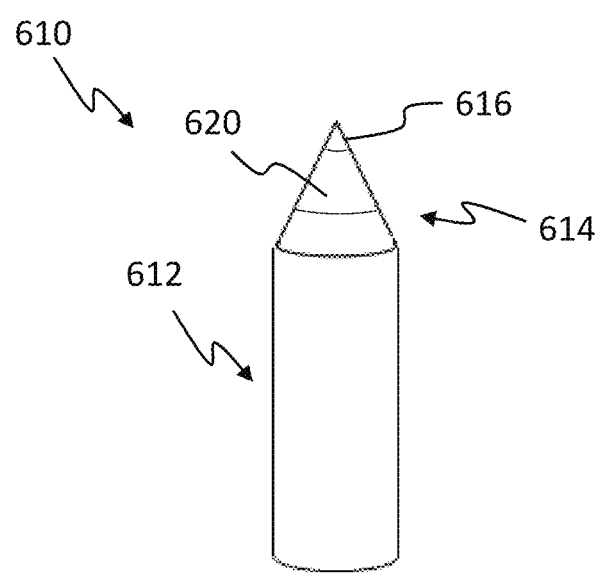
FIG. 6B depicts an illustrative schematic of a microneedle in the microneedle array depicted in FIG. 6A.

As shown in the schematic of FIG. 6A, in some variations, a microneedle array 600 for use in sensing one or more analytes may include one or more microneedles 610 projecting from a substrate surface 602. The substrate surface 602 may, for example, be generally planar and one or more microneedles 610 may project orthogonally from the planar surface. Generally, as shown in FIG. 6B, a microneedle 610 may include a body portion 612 (e.g., shaft) and a tapered distal portion 614 configured to puncture skin of a user. In some variations, the tapered distal portion 614 may terminate in an insulated distal apex 616. The microneedle 610 may further include an electrode 620 on a surface of the tapered distal portion. In some variations, electrode-based measurements may be performed at the interface of the electrode and interstitial fluid located within the body (e.g., on an outer surface of the overall microneedle). In some variations, the microneedle 610 may have a solid core (e.g., solid body portion), though in some variations the microneedle 610 may include one or more lumens, which may be used for drug delivery or sampling of the dermal interstitial fluid, for example. Other microneedle variations, such as those described below, may similarly either include a solid core or one or more lumens.

The microneedle array 600 may be at least partially formed from a semiconductor (e.g., silicon) substrate and include various material layers applied and shaped using various suitable microelectromechanical systems (MEMS) manufacturing techniques (e.g., deposition and etching techniques), as further described below. The microneedle array may be reflow-soldered to a circuit board, similar to a typical integrated circuit. Furthermore, in some variations the microneedle array 600 may include a three electrode setup including a working (sensing) electrode having an electrochemical sensing coating (including a biorecognition element such as an enzyme) that enables detection of a target analyte, a reference electrode, and a counter electrode. In other words, the microneedle array 600 may include at least one microneedle 610 that includes a working electrode, at least one microneedle 610 including a reference electrode, and at least one microneedle 610 including a counter electrode. Additional details of these types of electrodes are described in further detail below.

Figure 7:
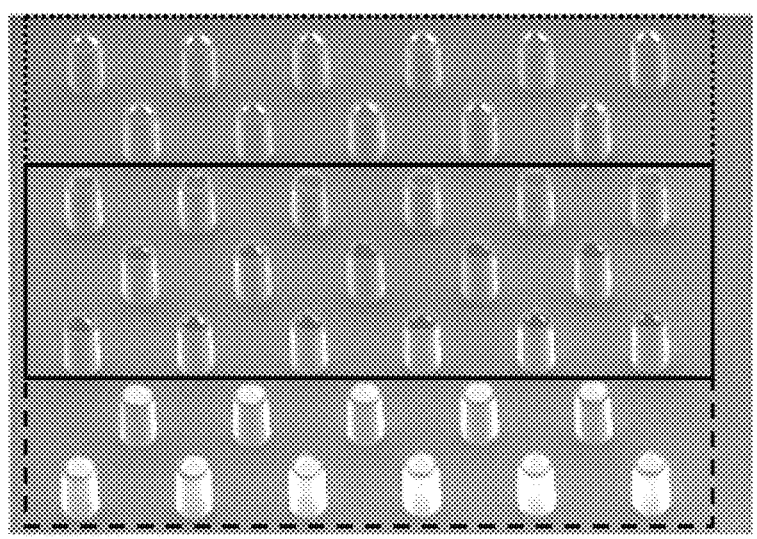
FIG. 7 depicts an illustrative schematic of a microneedle array used for sensing multiple analytes.

In some variations, the microneedle array 600 may include a plurality of microneedles that are insulated such that the electrode on each microneedle in the plurality of microneedles is individually addressable and electrically isolated from every other electrode on the microneedle array. The resulting individual addressability of the microneedle array 600 may enable greater control over each electrode's function, since each electrode may be separately probed. For example, the microneedle array 600 may be used to provide multiple independent measurements of a given target analyte, which improves the device's sensing reliability and accuracy. Furthermore, in some variations the electrodes of multiple microneedles may be electrically connected to produce augmented signal levels. As another example, the same microneedle array 600 may additionally or alternatively be interrogated to simultaneously measure multiple analytes to provide a more comprehensive assessment of physiological status. For example, as shown in the schematic of FIG. 7, a microneedle array may include a portion of microneedles to detect a first Analyte A, a second portion of microneedles to detect a second Analyte B, and a third portion of microneedles to detect a third Analyte C. It should be understood that the microneedle array may be configured to detect any suitable number of analytes (e.g., 1, 2, 3, 4, 5 or more, etc.). Suitable target analytes for detection may, for example, include glucose, ketones, lactate, and cortisol. For example, in some variations, ketones may be detected in a manner similar to that described in U.S. patent application Ser. No. 16/701,784, which is incorporated herein in its entirety by this reference. Thus, individual electrical addressability of the microneedle array 600 provides greater control and flexibility over the sensing function of the analyte monitoring device.

In some variations of microneedles (e.g., microneedles with a working electrode), the electrode 620 may be located proximal to the insulated distal apex 616 of the microneedle. In other words, in some variations the electrode 620 does not cover the apex of the microneedle. Rather, the electrode 620 may be offset from the apex or tip of the microneedle. The electrode 620 being proximal to or offset from the insulated distal apex 616 of the microneedle advantageously provides more accurate sensor measurements. For example, this arrangement prevents concentration of the electric field at the microneedle apex 616 during manufacturing, thereby avoiding non-uniform electro-deposition of sensing chemistry on the surface of the electrode 620 that would result in faulty sensing.

As another example, placing the electrode 620 offset from the microneedle apex further improves sensing accuracy by reducing undesirable signal artefacts and/or erroneous sensor readings caused by stress upon microneedle insertion. The distal apex of the microneedle is the first region to penetrate into the skin, and thus experiences the most stress caused by the mechanical shear phenomena accompanying the tearing or cutting of the skin. If the electrode 620 were placed on the apex or tip of the microneedle, this mechanical stress may delaminate the electrochemical sensing coating on the electrode surface when the microneedle is inserted, and/or cause a small yet interfering amount of tissue to be transported onto the active sensing portion of the electrode. Thus, placing the electrode 620 sufficiently offset from the microneedle apex may improve sensing accuracy. For example, in some variations, a distal edge of the electrode 620 may be located at least about 10 µm (e.g., between about 20 µm and about 30 µm) from the distal apex or tip of the microneedle, as measured along a longitudinal axis of the microneedle.

The body portion 612 of the microneedle 610 may further include an electrically conductive pathway extending between the electrode 620 and a backside electrode or other electrical contact (e.g., arranged on a backside of the substrate of the microneedle array). The backside electrode may be soldered to a circuit board, enabling electrical communication with the electrode 620 via the conductive pathway. For example, during use, the in-vivo sensing current (inside the dermis) measured at a working electrode is interrogated by the backside electrical contact, and the electrical connection between the backside electrical contact and the working electrode is facilitated by the conductive pathway. In some variations, this conductive pathway may be facilitated by a metal via running through the interior of the microneedle body portion (e.g., shaft) between the microneedle's proximal and distal ends. Alternatively, in some variations the conductive pathway may be provided by the entire body portion being formed of a conductive material (e.g., doped silicon). In some of these variations, the complete substrate on which the microneedle array 600 is built upon may be electrically conductive, and each microneedle 610 in the microneedle array 600 may be electrically isolated from adjacent microneedles 610 as described below. For example, in some variations, each microneedle 610 in the microneedle array 600 may be electrically isolated from adjacent microneedles 610 with an insulative barrier including electrically insulative material (e.g., dielectric material such as silicon dioxide) that surrounds the conductive pathway extending between the electrode 620 and backside electrical contact. For example, body portion 612 may include an insulative material that forms a sheath around the conductive pathway, thereby preventing electrical communication between the conductive pathway and the substrate. Other example variations of structures enabling electrical isolation among microneedles are described in further detail below.

Such electrical isolation among microneedles in the microneedle array permits the sensors to be individually addressable. This individually addressability advantageously enables independent and parallelized measurement among the sensors, as well as dynamic reconfiguration of sensor assignment (e.g., to different analytes). In some variations, the electrodes in the microneedle array can be configured to provide redundant analyte measurements, which is an advantage over conventional analyte monitoring devices. For example, redundancy can improve performance by improving accuracy (e.g., averaging multiple analyte measurement values for the same analyte which reduces the effect of extreme high or low sensor signals on the determination of analyte levels) and/or improving reliability of the device by reducing the likelihood of total failure.

In some variations, as described in further detail below with respective different variations of the microneedle, the microneedle array may be formed at least in part with suitable semiconductor and/or MEMS fabrication techniques and/or mechanical cutting or dicing. Such processes may, for example, be advantageous for enabling large-scale, cost-efficient manufacturing of microneedle arrays. For example, in some variations, the microneedle array may be formed at least in part using techniques described in U.S. patent application Ser. No. 15/913,709, which is incorporated herein in its entirety by this reference.

Described herein are multiple example variations of microneedle structure incorporating one or more of the above-described microneedle features for a microneedle array in an analyte monitoring device.

In some variations, a microneedle may have a generally columnar body portion and a tapered distal portion with an electrode. For example, FIGS. 8A-8C illustrate an example variation of a microneedle 800 extending from a substrate 802. FIG. 8A is a side cross-sectional view of a schematic of microneedle 800, while FIG. 8B is a perspective view of microneedle 800 and FIG. 8C is a detailed perspective view of a distal portion of the microneedle 800. As shown in FIGS. 7B and 8C, the microneedle 800 may include a columnar body portion 812, a tapered distal portion 814 terminating in an insulated distal apex 816, and an annular electrode 820 that includes a conductive material (e.g., Pt, Ir, Au, Ti, Cr, Ni, etc.) and is arranged on the tapered distal portion 814. As shown in FIG. 8A, the annular electrode 820 may be proximal to (or offset or spaced apart from) the distal apex 816. For example, the electrode 820 may be electrically isolated from the distal apex 816 by a distal insulating surface 815a including an insulating material (e.g., Sift). In some variations, the electrode 820 may also be electrically isolated from the columnar body portion 812 by a second distal insulating surface 815b. The electrode 820 may be in electrical communication with a conductive core 840 (e.g., conductive pathway) passing along the body portion 812 to a backside electrical contact 830 (e.g., made of Ni/Au alloy) or other electrical pad in or on the substrate 802. For example, the body portion 812 may include a conductive core material (e.g., highly doped silicon). As shown in FIG. 8A, in some variations, an insulating moat 813 including an insulating material (e.g., Sift) may be arranged around (e.g., around the perimeter) of the body portion 812 and extend at least partially through the substrate 802. Accordingly, the insulating moat 813 may, for example, help prevent electrical contact between the conductive core 840 and the surrounding substrate 802. The insulating moat 813 may further extend over the surface of the body portion 812. Upper and/or lower surfaces of the substrate 802 may also include a layer of substrate insulation 804 (e.g., Sift). Accordingly, the insulation provided by the insulating moat 813 and/or substrate insulation 804 may contribute at least in part to the electrical isolation of the microneedle 800 that enables individual addressability of the microneedle 800 within a microneedle array. Furthermore, in some variations the insulating moat 813 extending over the surface of the body portion 812 may function to increase the mechanical strength of the microneedle 800 structure.

The microneedle 800 may be formed at least in part by suitable MEMS fabrication techniques such as plasma etching, also called dry etching. For example, in some variations, the insulating moat 813 around the body portion 812 of the microneedle may be made by first forming a trench in a silicon substrate by deep reactive ion etching (DRIE) from the backside of the substrate, then filling that trench with a sandwich structure of $SiO_2$/polycrystalline silicon (poly-Si)/Sift by low pressure chemical vapor deposition (LPCVD) or other suitable process. In other words, the insulating moat 813 may passivate the surface of the body portion 812 of the microneedle, and continue as a buried feature in the substrate 802 near the proximal portion of the microneedle. By including largely compounds of silicon, the insulating moat 813 may provide good fill and adhesion to the adjoining silicon walls (e.g., of the conductive core 840, substrate 802, etc.). The sandwich structure of the insulating moat 813 may further help provide excellent matching of coefficient of thermal expansion (CTE) with the adjacent silicon, thereby advantageously reducing faults, cracks, and/or other thermally-induced weaknesses in the insulating moat 813.

The tapered distal portion may be fashioned out by an isotropic dry etch from the frontside of the substrate, and the body portion 812 of the microneedle 800 may be formed from DRIE. The frontside metal electrode 820 may be deposited and patterned on the distal portion by specialized lithography (e.g., electron-beam evaporation) that permits metal deposition in the desired annular region for the electrode 820 without coating the distal apex 816. Furthermore, the backside electrical contact 830 of Ni/Au may be deposited by suitable MEMS manufacturing techniques (e.g., sputtering).

The microneedle 800 may have any suitable dimensions. By way of illustration, the microneedle 800 may, in some variations, have a height of between about 300 μm and about 500 μm. In some variations, the tapered distal portion 814 may have a tip angle between about 60 degrees and about 80 degrees, and an apex diameter of between about 1 μm and about 15 μm. In some variations, the surface area of the annular electrode 820 may include between about 9,000 μm$^2$ and about 11,000 μm$^2$, or about 10,000 μm$^2$. FIG. 9 illustrates various dimensions of an example variation of a columnar microneedle with a tapered distal portion and annular electrode, similar to microneedle 800 described above.

FIGS. 10A-10F illustrate another example variation of a microneedle 1000 having a generally columnar body portion extending from a substrate 1002 having a top surface 1004. The microneedle 1000 may be similar to microneedle 800 as described above, except as described below. For example, as shown in FIG. 10B, like the microneedle 800, the microneedle 1000 may include a columnar body portion 1012, and a tapered distal portion arranged on a cylinder 1013 and terminating in an insulated distal apex 1016. The cylinder 1013 may be insulated and have a smaller diameter than the columnar body portion 1012. The microneedle 1000 may further include an annular electrode 1020 that includes a conductive material and is arranged on the tapered distal portion at a location proximal to (or offset or spaced apart from) the distal apex 1016. Other elements of microneedle 1000 as shown in FIGS. 10A-10F have numbering similar to corresponding elements of microneedle 800.

However, the electrode 1020 on the microneedle 1000 may include a tip contact trench 1022. This contact trench may be configured to help establish ohmic contact between the electrode 1020 and the underlying conductive core 1040 of the microneedle. In some variations, the shape of the tip contact trench 1022 may include an annular recess formed in the surface of the conductive core 1040 (e.g., into the body portion of the microneedle, or otherwise in contact with a conductive pathway in the body portion) such that when the electrode 1020 material is deposited onto the conductive core 1040, the electrode 1020 with the tip contact trench 1022 may have a stepped profile when viewed from the side. The tip contact trench 1022 may advantageously help provide a margin of error to ensure contact between the electrode 1020 and the underlying conductive core 1040. Any of the other microneedle variations described herein may also have a similar tip contact trench to help ensure contact between the electrode (which may be, for example, a working electrode, reference electrode, counter electrode, etc.) with a conductive pathway within the microneedle.

FIGS. 11A and 11B illustrate additional various dimensions of an example variation of a columnar microneedle with a tapered distal portion and annular electrode, similar to microneedle 1000 described above. For example, the variation of the microneedle shown in FIGS. 11A and 11B may have a tapered distal portion generally having a taper angle of about 80 degrees (or between about 78 degrees and about 82 degrees, or between about 75 degrees and about 85 degrees), and a cone diameter of about 140 μm (or between about 133 μm and about 147 μm, or between about 130 μm and about 150 μm). The cone of the tapered distal portion may be arranged on a cylinder such that the overall combined height of the cone and cylinder is about 110 μm (or between about 99 μm and about 116 μm, or between about 95 μm and about 120 μm). The annular electrode on the tapered distal portion may have an outer or base diameter of about 106 μm (or between about 95 μm and about 117 μm, or between about 90 μm and about 120 μm), and an inner diameter of about 33.2 μm (or between about 30 μm and about 36 μm, or between about 25 μm and about 40 μm). The length of the annular electrode, as measured along the slope of the tapered distal portion, may be about 57 μm (or between about 55 μm and about 65 μm), and the overall surface area of the electrode may be about 12,700 μm$^2$ (or between about 12,500 μm$^2$ and about 12,900 μm$^2$, or between about 12,000 μm$^2$ and about 13,000 μm$^2$). As shown in FIG. 11B, the electrode may furthermore have a tip contact trench extending around a central region of the cone of the tapered distal portion, where the contact may have a width of about 11 μm (or between about 5 μm and about 50 μm, between about 10 μm and about 12 μm, or between about 8 μm and about 14 μm) as measured along the slope of the tapered distal portion, and a trench depth of about 1.5 μm (or between about 0.1 μm and about 5, or between about 0.5 μm and about 1.5 μm, or between about 1.4 μm and about 1.6 μm, or between about 1 μm and about 2 μm). The microneedle has an insulated distal apex having a diameter of about 5.5 μm (or between about 5.3 μm and about 5.8 μm, or between about 5 μm and about 6 μm).

Details of example variations of microneedle array configurations are described in further detail below.

As described above, each microneedle in the microneedle array may include an electrode. In some variations, multiple distinct types of electrodes may be included among the microneedles in the microneedle array. For example, in some variations the microneedle array may function as an electrochemical cell operable in an electrolytic manner with three types of electrodes. In other words, the microneedle array may include at least one working electrode, at least one counter electrode, and at least one reference electrode. Thus, the microneedle array may include three distinct electrode types, though one or more of each electrode type may form a complete system (e.g., the system might include multiple distinct working electrodes). Furthermore, multiple distinct microneedles may be electrically joined to form an effective electrode type (e.g., a single working electrode may be formed from two or more connected microneedles with working electrode sites). Each of these electrode types may include a metallization layer and may include one or more coatings or layers over the metallization layer that help facilitate the function of that electrode.

Generally, the working electrode is the electrode at which oxidation and/or reduction reaction of interest occurs for detection of an analyte of interest. The counter electrode functions to source (provide) or sink (accumulate) the electrons, via an electrical current, that are required to sustain the electrochemical reaction at the working electrode. The reference electrode functions to provide a reference potential for the system; that is, the electrical potential at which the working electrode is biased is referenced to the reference electrode. A fixed, time-varying, or at least controlled potential relationship is established between the working and reference electrodes, and within practical limits no current is sourced from or sinked to the reference electrode. Additionally, to implement such a three-electrode system, the analyte monitoring device may include a suitable potentiostat or electrochemical analog front end to maintain a fixed potential relationship between the working electrode and reference electrode contingents within the electrochemical system (via an electronic feedback mechanism), while permitting the counter electrode to dynamically swing to potentials required to sustain the redox reaction of interest.

Multiple microneedles (e.g., any of the microneedle variations described herein, each of which may have a working electrode, counter electrode, or reference electrode as described above) may be arranged in a microneedle array. Considerations of how to configure the microneedles include factors such as desired insertion force for penetrating skin with the microneedle array, optimization of electrode signal levels and other performance aspects, manufacturing costs and complexity, etc.

For example, the microneedle array may include multiple microneedles that are spaced apart at a predefined pitch (distance between the center of one microneedle to the center of its nearest neighboring microneedle). In some variations, the microneedles may be spaced apart with a sufficient pitch so as to distribute force (e.g., avoid a "bed of nails" effect) that is applied to the skin of the user to cause the microneedle array to penetrate the skin. As pitch increases, force required to insert the microneedle array tends to decrease and depth of penetration tends to increase. However, it has been found that pitch only begins to affect insertion force at low values (e.g., less than about 150 μm). Accordingly, in some variations the microneedles in a microneedle array may have a pitch of at least 200 μm, at least 300 μm, at least 400 μm, at least 500 μm, at least 600 μm, at least 700 μm, or at least 750 μm. For example, the pitch may be between about 200 μm and about 800 μm, between about 300 μm and about 700 μm, or between about 400 μm and about 600 μm. In some variations, the microneedles may be arranged in a periodic grid, and the pitch may be uniform in all directions and across all regions of the microneedle array. Alternatively, the pitch may be different as measured along different axes (e.g., X, Y directions) and/or some regions of the microneedle array may include a smaller pitch while other may include a larger pitch.

Furthermore, for more consistent penetration, microneedles may be spaced equidistant from one another (e.g., same pitch in all directions). To that end, in some variations, the microneedles in a microneedle array may be arranged in a hexagonal configuration as shown in FIGS. 12A-12C, 13A-13B, and 14A-14J. Alternatively, the microneedles in a microneedle array may arranged in a rectangular array (e.g., square array), or in another suitable symmetrical manner Another consideration for determining configuration of a microneedle array is overall signal level provided by the microneedles. Generally, signal level at each microneedle is invariant of the total number of microneedle elements in an array. However, signal levels can be enhanced by electrically interconnecting multiple microneedles together in an array. For example, an array with a large number of electrically connected microneedles is expected to produce a greater signal intensity (and hence increased accuracy) than one with fewer microneedles. However, a higher number of microneedles on a die will increase die cost (given a constant pitch) and will also require greater force and/or velocity to insert into skin. In contrast, a lower number of microneedles on a die may reduce die cost and enable insertion into the skin with reduced application force and/or velocity. Furthermore, in some variations a lower number of microneedles on a die may reduce the overall footprint area of the die, which may lead to less unwanted localized edema and/or erythema. Accordingly, in some variations, a balance among these factors may be achieved with a microneedle array including 37 microneedles as shown in FIGS. 13A-13B or a microneedle array including seven microneedles as shown in FIGS. 12A-12C. However, in other variations there may be fewer microneedles in an array (e.g., between about 5 and about 35, between about 5 and about 30, between about 5 and about 25, between about 5 and about 20, between about 5 and about 15, between about 5 and about 100, between about 10 and about 30, between about 15 and about 25, etc.) or more microneedles in an array (e.g., more than 37, more than 40, more than 45, etc.).

Additionally, as described in further detail below, in some variations only a subset of the microneedles in a microneedle array may be active during operation of the analyte monitoring device. For example, a portion of the microneedles in a microneedle array may be inactive (e.g., no signals read from electrodes of inactive microneedles). In some variations, a portion of the microneedles in a microneedle array may be activated at a certain time during operation and remain active for the remainder of the operating lifetime of the device. Furthermore, in some variations, a portion of the microneedles in a microneedle array may additionally or alternatively be deactivated at a certain time during operation and remain inactive for the remainder of the operating lifetime of the device.

In considering characteristics of a die for a microneedle array, die size is a function of the number of microneedles in the microneedle array and the pitch of the microneedles. Manufacturing costs are also a consideration, as a smaller die size will contribute to lower cost since the number of dies that can be formed from a single wafer of a given area will increase. Furthermore, a smaller die size will also be less susceptible to brittle fracture due to the relative fragility of the substrate.

Furthermore, in some variations, microneedles at the periphery of the microneedle array (e.g., near the edge or boundary of the die, near the edge or boundary of the housing, near the edge or boundary of an adhesive layer on the housing, along the outer border of the microneedle array, etc.) may be found to have better performance (e.g., sensitivity) due to better penetration compared to microneedles in the center of the microneedle array or die. Accordingly, in some variations, working electrodes may be arranged largely or entirely on microneedles located at the periphery of the microneedle array, to obtain more accurate and/or precise analyte measurements.

FIGS. 13A and 13B depict an illustrative schematic of 37 microneedles arranged in an example variation of a microneedle array 1300. The 37 microneedles may, for example, be arranged in a hexagonal array with an inter-needle center-to-center pitch of about 750 μm (or between about 700 μm and about 800 μm, or between about 725 μm and about 775 μm) between the center of each microneedle and the center of its immediate neighbor in any direction. FIG. 13A depicts an illustrative schematic of an example variation of a die including the microneedle arrangement. Example dimensions of the die (e.g., about 4.4 mm by about 5.0 mm) and the microneedle array 1300 are shown in FIG. 13B.

FIGS. 12A and 12B depict perspective views of an illustrative schematic of seven microneedles 1210 arranged in an example variation of a microneedle array 1200. The seven microneedles 1210 are arranged in a hexagonal array on a substrate 1202. As shown in FIG. 12A, the electrodes 1220 are arranged on distal portions of the microneedles 1210 extending from a first surface of the substrate 1202. As shown in FIG. 12B, proximal portions of the microneedles 1210 are conductively connected to respective backside electrical contacts 1230 on a second surface of the substrate 1202 opposite the first surface of the substrate 1202. FIGS. 12C and 12D depict plan and side views of an illustrative schematic of a microneedle array similar to microneedle array 1200. As shown in FIGS. 12C and 12D, the seven microneedles are arranged in a hexagonal array with an inter-needle center-to-center pitch of about 750 μm between the center of each microneedle and the center of its immediate neighbor in any direction. In other variations the inter-needle center-to-center pitch may be, for example, between about 700 μm and about 800 μm, or between about 725 μm and about 775 μm. The microneedles may have an approximate outer shaft diameter of about 170 μm (or between about 150 μm and about 190 μm, or between about 125 μm and about 200 μm) and a height of about 500 μm (or between about 475 μm and about 525 μm, or between about 450 μm and about 550 μm).

Furthermore, the microneedle arrays described herein may have a high degree of configurability concerning where the working electrode(s), counter electrode(s), and reference electrode(s) are located within the microneedle array. This configurability may be facilitated by the electronics system.

Figure 14A:
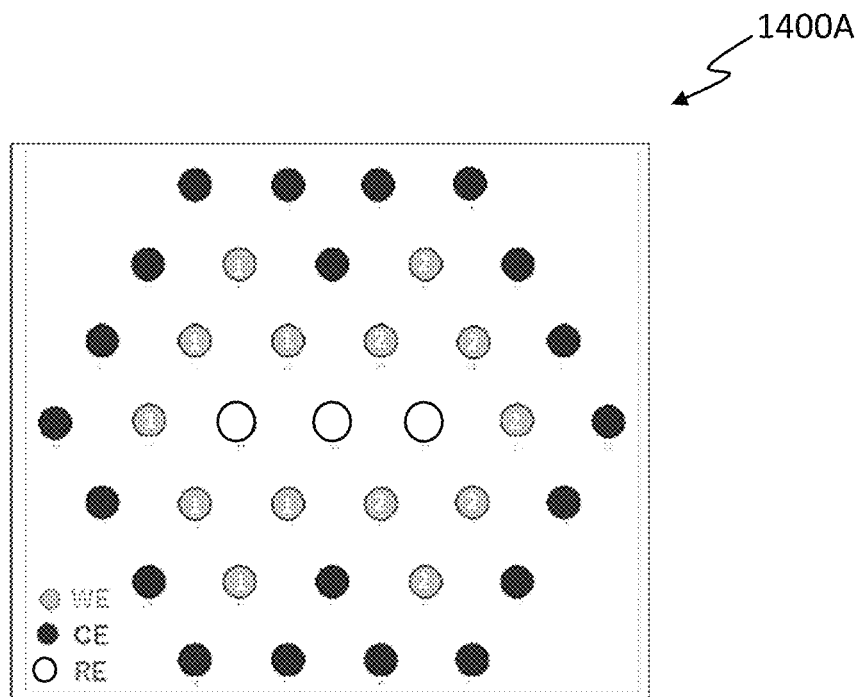

In some variations, a microneedle array may include electrodes distributed in two or more groups in a symmetrical or non-symmetrical manner in the microneedle array, with each group featuring the same or differing number of electrode constituents depending on requirements for signal sensitivity and/or redundancy. For example, electrodes of the same type (e.g., working electrodes) may be distributed in a bilaterally or radially symmetrical manner in the microneedle array. For example, FIG. 14A depicts a variation of a microneedle array 1400A including two symmetrical groups of seven working electrodes (WE), with the two working electrode groups labeled "1" and "2". In this variation, the two working electrode groups are distributed in a bilaterally symmetrical manner within the microneedle array. The working electrodes are generally arranged between a central region of three reference electrodes (RE) and an outer perimeter region of twenty counter electrodes (CE). In some variations, each of the two working electrode groups may include seven working electrodes that are electrically connected amongst themselves (e.g., to enhance sensor signal). Alternatively, only a portion of one or both of the working electrode groups may include multiple electrodes that are electrically connected amongst themselves. As yet another alternative, the working electrode groups may include working electrodes that are standalone and not electrically connected to other working electrodes. Furthermore, in some variations the working electrode groups may be distributed in the microneedle array in a non-symmetrical or random configuration.

Figure 14B:
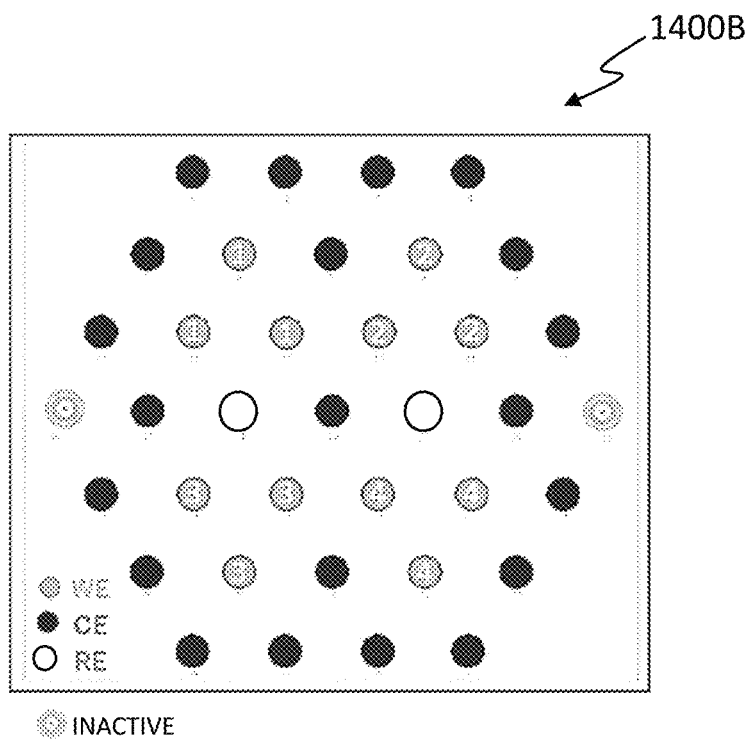

As another example, FIG. 14B depicts a variation of a microneedle array 1400B including four symmetrical groups of three working electrodes (WE), with the four working electrode groups labeled "1", "2", "3", and "4." In this variation, the four working electrode groups are distributed in a radially symmetrical manner in the microneedle array. Each working electrode group is adjacent to one of two reference electrode (RE) constituents in the microneedle array and arranged in a symmetrical manner. The microneedle array also includes counter electrodes (CE) arranged around the perimeter of the microneedle array, except for two electrodes on vertices of the hexagon that are inactive or may be used for other features or modes of operation.

Figure 14C:
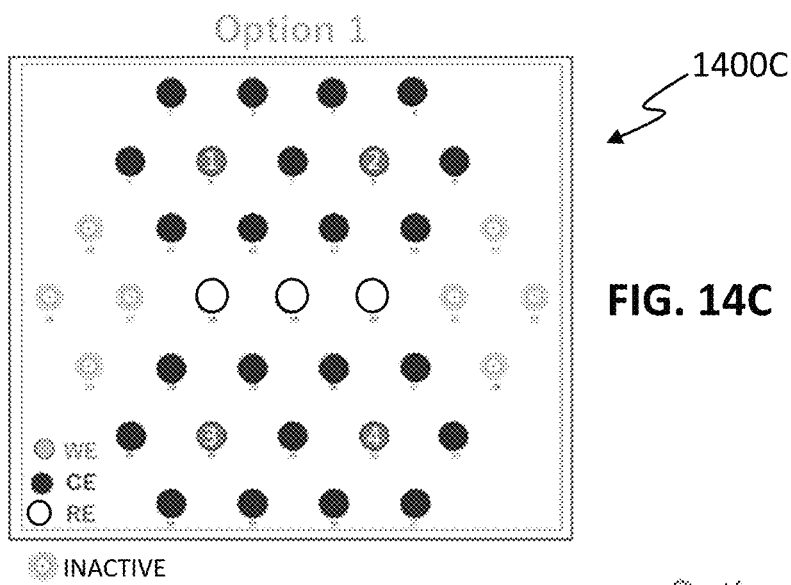

In some variations, only a portion of microneedle array may include active electrodes. For example, FIG. 14C depicts a variation of a microneedle array 1400C with 37 microneedles and a reduced number of active electrodes, including four working electrodes (labeled "1", "2", "3", and "4") in a bilaterally symmetrical arrangement, twenty-two counter electrodes, and three reference electrodes. The remaining eight electrodes in the microneedle array are inactive. In the microneedle array shown in FIG. 19C, each of the working electrodes is surrounded by a group of counter electrodes. Two groups of such clusters of working electrodes and counter electrodes are separated by a row of the three reference electrodes.

Figure 14D:
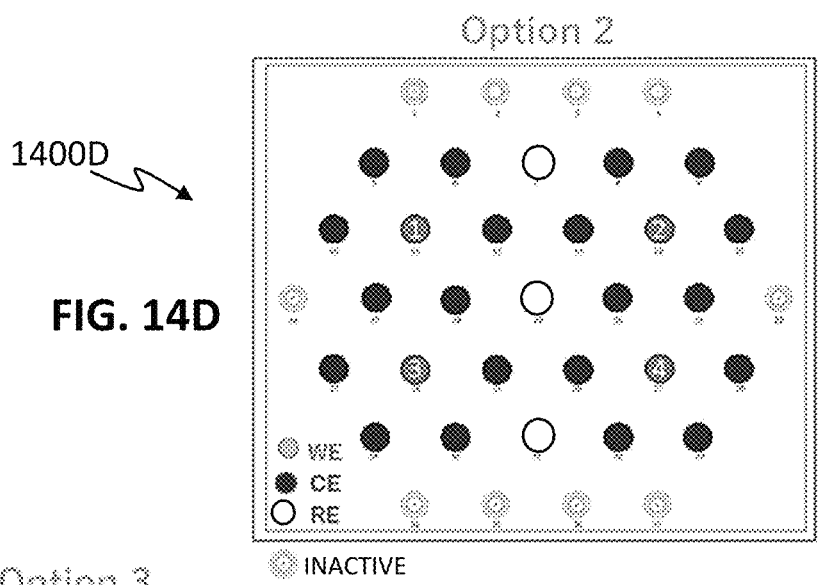

As another example, FIG. 14D depicts a variation of a microneedle array 1400D with 37 microneedles and a reduced number of active electrodes, including four working electrodes (labeled "1", "2", "3", and "4") in a bilaterally symmetrical arrangement, twenty counter electrodes, and three reference electrodes, where the remaining ten electrodes in the microneedle array are inactive.

Figure 14E:
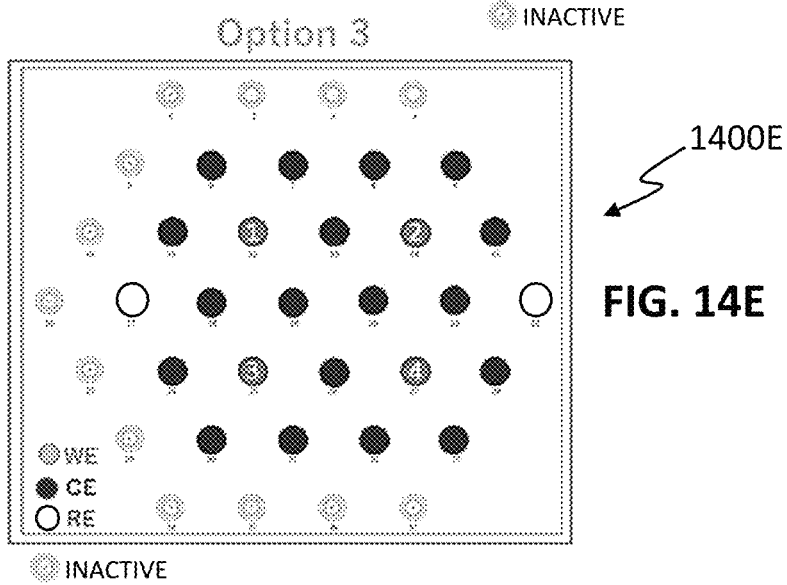

As another example, FIG. 14E depicts a variation of a microneedle array 1400E with 37 microneedles and a reduced number of active electrodes, including four working electrodes (labeled "1", "2", "3", and "4"), eighteen counter electrodes, and two reference electrodes. The remaining thirteen electrodes in the microneedle array are inactive. The inactive electrodes are along a partial perimeter of the overall microneedle array, thereby reducing the effective size and shape of the active microneedle arrangement to a smaller hexagonal array. Within the active microneedle arrangement, the four working electrodes are generally in a radially symmetrical arrangement, and each of the working electrodes is surrounded by a group of counter electrodes.

Figure 14F:
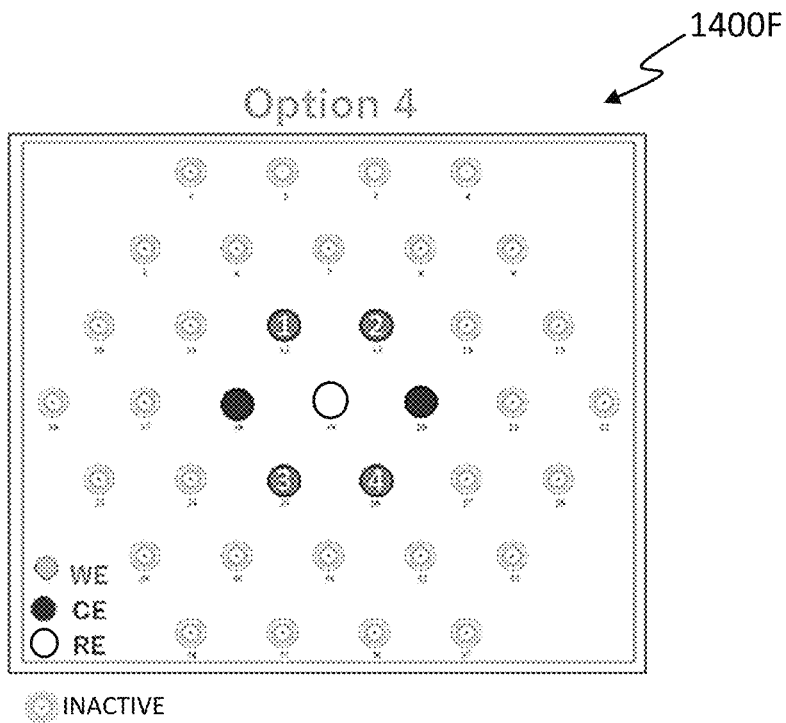

FIG. 14F depicts another example variation of a microneedle array 1400F with 37 microneedles and a reduced number of active electrodes, including four working electrodes (labeled "1", "2", "3", and "4"), two counter electrodes, and one reference electrode. The remaining thirty electrodes in the microneedle array are inactive. The inactive electrodes are arranged in two layers around the perimeter of the overall microneedle array, thereby reducing the effective size and shape of the active microneedle arrangement to a smaller hexagonal array centered around the reference electrode. Within the active microneedle arrangement, the four working electrodes are in a bilaterally symmetrical arrangement and the counter electrodes are equidistant from the central reference electrode.

Figure 14G:
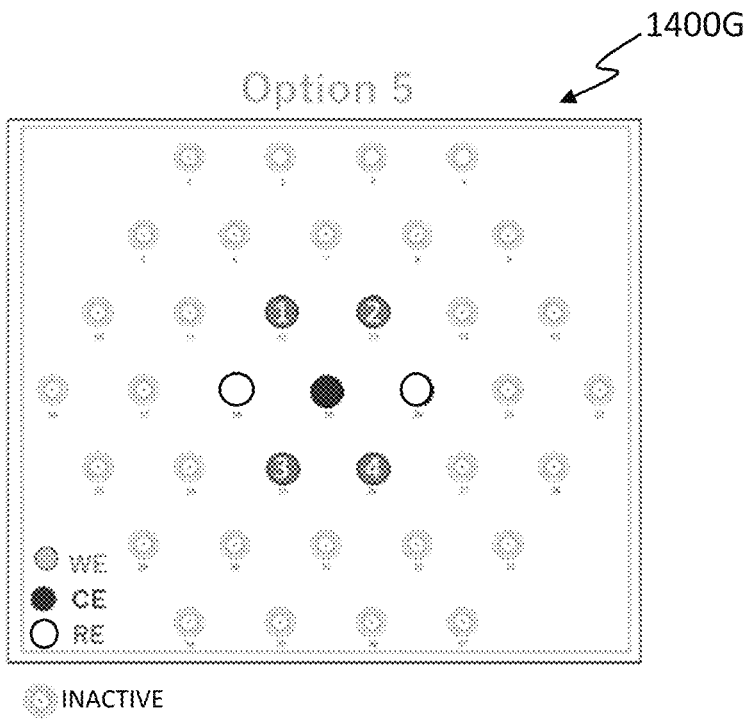

FIG. 14G depicts another example variation of a microneedle array 1400G with 37 microneedles and a reduced number of active electrodes. The active electrodes in microneedle array 1400G are arranged in a similar manner as that in microneedle array 1400F shown in FIG. 14F, except that the microneedle array 1400G includes one counter electrode and two reference electrodes, and the smaller hexagonal array of active microneedles is centered around the counter electrode. Within the active microneedle arrangement, the four working electrodes are in a bilaterally symmetrical arrangement and the reference electrodes are equidistant from the central counter electrode.

Figure 14J:
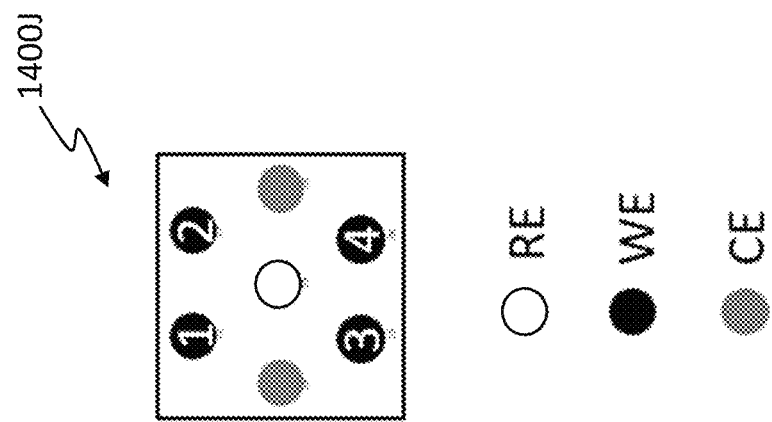
Figure 14I:
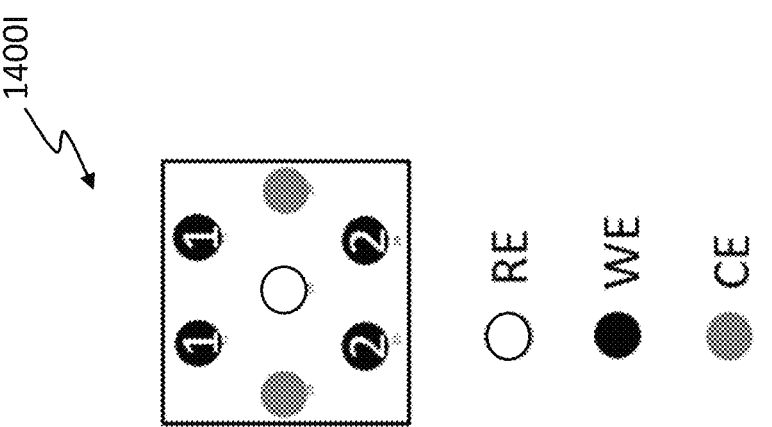
Figure 14H:
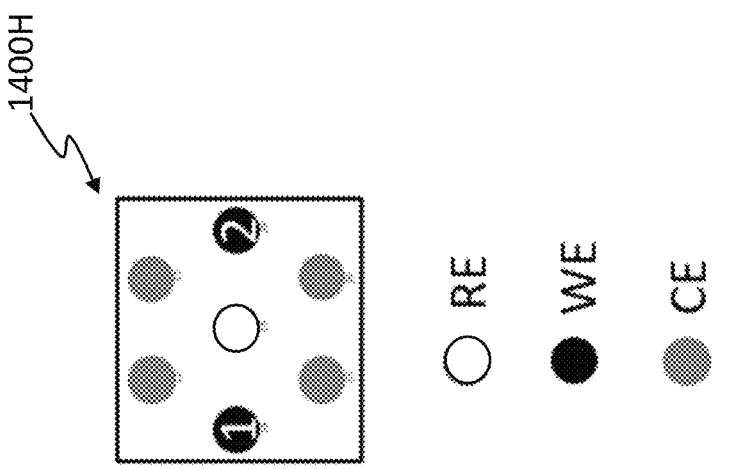

FIG. 14H depicts another example variation of a microneedle array 1400H with seven microneedles. The microneedle arrangement contains two microneedles assigned as independent working electrodes (1 and 2), a counter electrode contingent comprised of 4 microneedles, and a single reference electrode. There is bilateral symmetry in the arrangement of working and counter electrodes, which are equidistant from the central reference electrode. Additionally, the working electrodes are arranged as far as possible from the center of the microneedle array (e.g., at the periphery of the die or array) to take advantage of a location where the working electrodes are expected to have greater sensitivity and overall performance.

FIG. 14I depicts another example variation of a microneedle array 1400I with seven microneedles. The microneedle arrangement contains four microneedles assigned as two independent groupings (1 and 2) of two working electrodes each, a counter electrode contingent comprised of 2 microneedles, and a single reference electrode. There is bilateral symmetry in the arrangement of working and counter electrodes, which are equidistant from the central reference electrode. Additionally, the working electrodes are arranged as far as possible from the center of the microneedle array (e.g., at the periphery of the die or array) to take advantage of a location where the working electrodes are expected to have greater sensitivity and overall performance.

FIG. 14J depicts another example variation of a microneedle array 1400J with seven microneedles. The microneedle arrangement contains four microneedles assigned as independent working electrodes (1, 2, 3, and 4), a counter electrode contingent comprised of 2 microneedles, and a single reference electrode. There is bilateral symmetry in the arrangement of working and counter electrodes, which are equidistant from the central reference electrode. Additionally, the working electrodes are arranged as far as possible from the center of the microneedle array (e.g., at the periphery of the die or array) to take advantage of a location where the working electrodes are expected to have greater sensitivity and overall performance.

While FIGS. 14A-14J illustrate example variations of microneedle array configurations, it should be understood that these figures are not limiting and other microneedle configurations (including different numbers and/or distributions of working electrodes, counter electrodes, and reference electrodes, and different numbers and/or distributions of active electrodes and inactive electrodes, etc.) may be suitable in other variations of microneedle arrays.

As illustrated in FIG. 1, in some variations the analyte monitoring device 110 may be applied using a suitable applicator 160. The applicator may, for example, be configured to urge the analyte monitoring device 110 toward the skin of the user such that the microneedle array 140 is inserted into the skin (e.g., to the desired target depth) and the one or more adhesive layers are adhered to the skin to securely hold the analyte monitoring device 110 in place.

An applicator may include an actuatable housing (also referred to as an actuator and/or a housing) including a housing body that defines a cavity therein. The housing body has a distal opening, and the components of the applicator may be situated and/or positioned within the cavity of the housing body. The applicator components are aligned and configured to securely hold the analyte monitoring device 110 such that the analyte monitoring device 110 is positioned for insertion of the microneedle array 140 into the skin (e.g., with the microneedle array positioned such that the tips of the microneedles are oriented in a distally-facing direction). Moreover, the applicator components are aligned and configured to move the analyte monitoring device 110 at a velocity that allows for the microneedles of the microneedle array 140 to be inserted into the skin with sufficient force and to release the analyte monitoring device 110.

In some variations, an applicator may include the housing body, a cuff assembly, a shuttle, and a removable base (also referred to as a base). The housing body, the cuff assembly, the shuttle, and the base may be engaged with one another with one or more releasable coupling and/or engaging features. The base may be removed from an engagement with the housing body, causing the cuff assembly and the shuttle to be aligned and positioned in a configuration in which the analyte monitoring device 110, held by the shuttle, is ready for insertion into the skin. The shuttle and the cuff assembly are separately translatable relative to the housing body. In an application procedure, actuation of the housing body (e.g., manual actuation by a user, or with an additional external actuator) causes the shuttle and the analyte monitoring device 110 to move at a velocity that enables the microneedle array 140 to be inserted into the user's skin with a force that causes the microneedles of the microneedle array 140 to be inserted into the skin.

The housing, the cuff assembly, and the shuttle may be axially aligned (e.g., concentric) and/or nested together and/or telescopically arranged. The shuttle may releasably retain (e.g., grip, cradle, or otherwise carry) the analyte monitoring device 110. The applicator may transition from a first "collapsed" configuration to a second "extended" configuration to a third "released" configuration. In the collapsed configuration, the components of the applicator are locked with respect to one another such that the engagement between the various components of the applicator is fixed, the components cannot move with respect to each other, and the analyte monitoring device 110 cannot be deployed. In the collapsed configuration, the base is engaged with the housing. In the extended configuration, the components of the applicator are arranged and configured such that the analyte monitoring device may be deployed (e.g., released) from the applicator in response to actuation of the housing. The base is removed, and the shuttle is moved into firing position in the extended configuration. In the released configuration, the analyte monitoring device 110 is released from the applicator and inserted in the skin of the user. Each configuration and the transition therebetween is described in detail below.

The cuff assembly may be a single component, or, in some variations, two or more component may be incorporated to form the cuff assembly. For example, a cuff and a friction ring may engage and/or lock together, as further described herein.

In some variations, in the collapsed configuration, the analyte monitoring device 110 is retained within the shuttle, and the shuttle and a distal edge of the cuff are in a proximal most position. In the extended configuration, the distal edge of the cuff is in a distal most position and the shuttle is in an intermediate position. In the released configuration, the analyte monitoring device 110 is released from the shuttle, the distal edge of the cuff is in an intermediate position, and the shuttle is in a distal most position.

The housing may include a first retention surface or feature that is releasably coupled with a coupling member of the cuff assembly. The housing may also include a second retention surface or feature that is releasably engaged with an engaging member of the shuttle. In response to actuation of at least a portion of the housing toward the shuttle (e.g., the applicator may be placed in compression, such as against a skin surface of the user), the first retention surface of the housing may decouple from the coupling member of the cuff assembly, which may allow release of the engagement between the second retention surface of the housing and the engaging member of the shuttle. During axial movement of the shuttle, in response to the actuation of the housing, the shuttle may engage at least one shuttle flexion surface (e.g., a hard stop) of the cuff assembly. The engagement of the shuttle with the shuttle flexion surface may cause radially outward flexing of the shuttle, resulting in release of the analyte monitoring device 110 from the shuttle.

Furthermore, the applicator may include one or more biasing elements (e.g., springs) that are arranged to force adjacent components apart. For example, in some variations, the applicator may include a first biasing element arranged between the housing and the cuff assembly. The first biasing element may be loaded to store potential energy prior to actuation of the housing (e.g., the first biasing element may include a compression spring that is pre-compressed prior to actuation of the housing). Upon actuation of the housing during an application procedure, the first biasing element may provide a force to the cuff assembly that causes the first retention surface of the housing to decouple from the coupling member of the cuff assembly. Additionally or alternatively, the applicator may include a second biasing element that is arranged between the housing and the shuttle. The second biasing element may be loaded to store potential energy prior to actuation of the housing (e.g., the second biasing element may include a compression spring that is pre-compressed prior to actuation of the housing). Upon actuation of the housing during an application procedure when the shuttle disengages from the housing, the energy stored in the loaded second biasing element may be transferred to the shuttle to thereby drive the analyte monitoring device with a suitable application force (e.g., for suitable skin puncture by the microneedle array). The incorporation of two biasing elements for the deployment of the analyte monitoring device 110 allows for control of the actuation force and the velocity at which the shuttle moves in response to actuation of the housing (e.g., impact velocity). The dual biasing element design allows for control of the impact velocity independent from the force applied for actuation. In some variations, the force to the cuff assembly provided by the first biasing element may range from about 5 Newtons to about 45 Newtons. In some variations, a residual force provided by the second biasing element to the shuttle may range from about 5 Newtons to about 45 Newtons. The impact velocity may range from about 2 meters/second to about 10 meters/second. The forces provided by the first biasing element and the second biasing element and the resulting impact velocity may be controlled by adjustment of the compression and characteristics of the biasing elements.

The components of the applicator may be formed with any suitable manufacturing process, including injection molding, casting, 3D printing, machining techniques (e.g., with mill or lathe), and/or the like.

FIG. 15A-FIG. 15D depict an example variation of an applicator 1500 for an analyte monitoring device (e.g., the analyte monitoring device 110). FIGS. 15A and 15B are side views, FIG. 15C is a top perspective view, and FIG. 15D is a bottom perspective view of the applicator 1500. FIG. 15A and FIG. 15B depict the applicator 1500 in the collapsed configuration in which a base 1550 is engaged with a housing covered by an outer enclosure 1570.

FIG. 15C and FIG. 15D depict exploded views of the applicator 1500. As shown in FIG. 15C and FIG. 15D, the applicator 1500 includes a housing 1510, a cuff 1520, a friction ring 1530, a shuttle 1540, and the base 1550. The housing 1510 includes a housing body that defines a cavity therein. The housing body has a distal opening, and the components of the applicator may be situated and/or positioned within and/or connected to the cavity of the housing body through the distal opening.

The friction ring 1530 is axially aligned with and configured to be nested and arranged (e.g., telescopically arranged) within the cuff 1520. The cuff 1520 and the friction ring 1530 are axially aligned with and configured to be nested and arranged within the cavity of the housing body. The shuttle 1540 is axially aligned with and configured to be nested and arranged within the nested arrangement of the cuff 1520 and the friction ring 1530 in the cavity of the housing body.

The applicator 1500 also includes a base 1550 arranged to engage the housing body at the distal opening thereof. Locking members 1560, the outer enclosure 1570, and a top plug 1580 are also provided. In some variations, the outer enclosure 1570 and/or the top plug 1580 are optional and need not be included in the applicator 1500 for operation.

As further shown in FIG. 15C and FIG. 15D, a first biasing element 1582 (e.g., a first compression spring) may be arranged between the housing 1510 and the cuff 1520, and a second biasing element 1584 (e.g., a second compression spring) may be arranged between the housing 1510 and the shuttle 1540.

FIG. 15E and FIG. 15F depict aspects of the shuttle 1540 and the analyte monitoring device 110 with respect to one another in an exploded view and a perspective view, respectively. As shown in FIG. 15E and FIG. 15F, the analyte monitoring device 110 with the attached microneedle enclosure 500 may be retained in the shuttle 1540, with the microneedle array 140 (enclosed in the views of FIG. 15E and FIG. 15F by the microneedle enclosure 500) in a distal direction. When the shuttle 1540 is arranged in the cavity of the housing body, the analyte monitoring device 110 is at a distal end.

The base 1550 is removably coupled to the housing body to fully enclose the analyte monitoring device 110 within the cavity defined by the housing body (e.g., to preserve sterility of the device 110 prior to application as further described herein). The base 1550 is a removable distal cover or cap that is releasably engaged with the housing body when the applicator is in the collapsed configuration. The base 1550 couples to the microneedle enclosure 500 that provides a sterile environment for the microneedle array 140. In some variations, when the base 1550 is removed from the housing body, the microneedle enclosure 500 is removed with the base 1550, thereby making accessible the microneedle array 140 through the distal opening of the housing body. Additional details are provided herein.

FIG. 16A, FIG. 16B, FIG. 16C, and FIG. 16D depict aspects of the shuttle 1540 in more detail. FIG. 16A is a perspective view of the shuttle 1540, FIG. 16B a bottom view, FIG. 16C a side view, and FIG. 16D a cross-sectional side view along line A-A shown in FIG. 16C. The shuttle 1540 is configured to retain the analyte monitoring device 110 when the applicator 1500 is in the collapsed and extended configurations. The shuttle 1540 is configured to respond to actuation of the housing 1510 and to deploy the analyte monitoring device 110 with a velocity and force necessary to insert the microneedles of the microneedle array 140 into the skin of the user. In the released configuration of the applicator, the analyte monitoring device 110 is released from the shuttle 1540.

As shown, the shuttle 1540 includes a base portion 1610 and a shuttle shaft 1630. The shuttle shaft 1630 defines an inner cavity 1632 in which the second biasing element 1584 is arranged.

The shuttle 1540 may include an engaging member or feature for releasably engaging with a shuttle retention surface or feature of the housing 1510. The engaging member or feature may be formed at one or more portions around an outer periphery of the shuttle shaft 1630 and may be configured to releasably engage with a shuttle retention surface of the housing 1510. In some variations and as best seen in FIG. 16C, the engaging member may include a distal surface 1636 of a shelf 1634. The shelf 1634 may be a section of the shuttle shaft 1630 that extends horizontally outward from the shuttle shaft 1630. A span (e.g., a width or a diameter) of the shelf 1634 is longer than a span (e.g., a width or a diameter) of the shuttle shaft 1630, where the spans are measured in a direction orthogonal to that of the axial arrangement of the shuttle 1540 within the cavity of the housing body. The distal surface 1636 may be a surface, such as a ledge, that extends between the shelf 1634 and the shuttle shaft 1630. In some variations, the distal surface 1636 may be an angled surface. In some variations, the distal surface 1636 may be flat or substantially flat. As further described herein, the distal surface 1636 releasable engages with the housing 1510 at a shuttle retention surface.

The base portion 1610, at a distal end of the shuttle shaft 1630, includes one or more flexible leaves 1612 extending from the shuttle shaft 1630, one or more flexible support petals 1614 extending from the shuttle shaft 1630, and one or more tracking projections 1616 extending from outer sidewalls of the one or more flexible leaves 1612.

The configuration or orientation of the flexible leaves 1612 defines a configuration (e.g., a carrying configuration and a releasing configuration) of the shuttle 1540, as further described herein. The flexible leaves 1612 define a receptacle 1640 in which the analyte monitoring device 110 may be received. For example, as shown in FIG. 16A and FIG. 16B, each flexible leaf 1612 includes an arcuate or curved member extending from a flexible connection member that is attached at its proximal end to the shuttle shaft 1630. The flexible connection member allows for flexing of the flexible leaves 1612 with respect to the shuttle shaft 1630. For example, the flexible leaves 1612 are, in some variations, cantilevered arms that may be flexed radially outward. The flexible leaves 1612 may be circumferentially arranged around the shuttle shaft 1630 to define the receptacle 1640, approximating the footprint area of the analyte monitoring device 110 for cradling the analyte monitoring device 110. As shown in FIG. 16A and FIG. 16B, the receptacle 1640 may be substantially circular. The shuttle 1540 is in a carrying configuration, in which the analyte monitoring device 110 is cradled or retained in the receptacle 1640, when the flexible leaves 1612 are in a natural, unflexed state. In the carrying configuration, the analyte monitoring device 110 is held in the receptacle 1640 due to engagement of inner side walls of the flexible leaves 1612 with the outer periphery of the analyte monitoring device 110. External pressure may, for example, be applied to the flexible leaves 1612, causing the shuttle 1540 to transition to a releasing configuration. In the releasing configuration, the analyte monitoring device 110 is not being held by the flexible leaves 1612, and the analyte monitoring device 110 is able to be released from the receptacle 1640. The external pressure may be provided, at least in part, by the second biasing element 1584. For example, upon actuation of the housing 1510 during an application procedure, the shuttle 1540 is moved axially downward through the concentric (e.g., telescopic) arrangement within the cuff 1520, and the second biasing element 1584 is compressed within the inner cavity 1632. The tracking projections 1616 extending from the outer sidewalls of the flexible leaves 1612 of the shuttle 1540, during the axial movement of the shuttle 1540, engage and interfere with shuttle flexion surfaces (e.g., a hard stop) of the cuff 1520. The shuttle flexion surfaces of the cuff 1520 stop the axial movement of the shuttle 1540, and the energy stored in the second biasing element 1584 is transferred to the shuttle 1540 to thereby radially flex outward the flexible leaves 1612, driving out the analyte monitoring device 110 with a suitable application force (e.g., for suitable insertion of the microneedle array 140 into the skin of the user). The configuration of the flexible leaves 1612 is similar to and/or analogous with a collet configuration in which in a carrying configuration, collet arms are biased radially inward and engage and retain a component. At the end of a carrying path, the collet arms are released from their biased state, thereby disengaging the component.

In some variations, each of the flexible leaves 1612 may further include one or more optional coupling features arranged at a distal end of the flexible leaves 1612 and configured to assist in the cradling of the analyte monitoring device 110. For example, as shown in FIG. 16B and FIG. 16D, at least one flexible leaf 1612 may include a ledge 1622 or other projection or ledge-like support surface at a distal end of the arcuate or curved member of the flexible leaf 1612. The ledge 1622 or other projection or ledge-like support surface may extend inwardly at the distal end to help provide stabilizing support for a distal surface of the analyte monitoring device 110.

In some variations, each flexible support petal 1614 is a tab-like member extending from a flexible connection member that is attached at its proximal end to the shuttle shaft 1630. The flexible support petals 1614 may be circumferentially arranged around the shuttle shaft 1630 in an alternating configuration with the flexible leaves 1612. Each of the flexible support petals 1614 may have a radiused or curved distal surface to retain and/or support and/or stabilize a proximal surface of the analyte monitoring device 110. For example, in some variations, a portion of the proximal surface of the analyte monitoring device 110 fits snugly within the radiused configuration formed by the distal surfaces of the flexible support petals 1614.

Each of the flexible support petals 1614 may also include one or more optional coupling or gripping features. For example, a support grip 1624 in the form of a projection or extension of the tab-like member may be positioned at a distal end of one or more of the flexible support petals 1614. The support grip 1624 together with the radiused or curved distal surface of the flexible support petals 1614 helps to stabilize and retain the analyte monitoring device 110.

When the analyte monitoring device 110 is placed in the receptacle 1640, the ledges 1622 and/or the grip members 1624 provide additional support for cradling or retaining the analyte monitoring device 110. The engagement between the circumferential edges of the analyte monitoring device 110 and the ledges 1622 and/or the engagement between a proximal surface of the analyte monitoring device 110 and the grip members 1624 help to provide additional stability of the analyte monitoring device 110 within the receptacle 1640 when the shuttle 1540 is in the carrying configuration. When the flexible leaves 1612 are flexed radially outward (in the releasing configuration of the shuttle 1540), the ledges 1622 are not engaged with the analyte monitoring device 110, thus are not providing additional stability to and/or impeding release of the analyte monitoring device 110.

Although the shuttle 1540 is shown with four flexible leaves 1612 and four flexible support petals 1614, in other variations, the shuttle 1540 may have any suitable number of flexible leaves 1612 (e.g., one, two, three, five, six, or more) and any suitable number of flexible support petals 1614 (e.g., one, two, three, five, six, or more). In some variations, the flexible support petals 1614 are not included. In some variations, the number of flexible leaves 1612 may vary from the number of flexible support petals 1614. For example, the shuttle 1540 may include fewer or more flexible support petals 1614 than flexible leaves 1612.

Although the shuttle 1540 is shown with flexible leaves 1612 that are substantially equal in size and shape to one another, in other variations, one or more flexible leaves 1612 may vary in size and shape from one or more other flexible leaves 1612. For example, the shuttle 1540 may include two flexible leaves 1612 having a longer perimeter than two other flexible leaves 1612. Similarly, although the shuttle 1540 is shown with flexible support petals 1614 that are substantially equal in size and shape to one another, in other variations, one or more flexible support petals 1614 may vary in size and shape from one or more other flexible support petals 1614.

Although the receptacle 1640 is shown to have a round or substantially round footprint formed by the shape and configuration of the flexible leaves 1612 and the flexible support petals 1614, the receptacle 1640 may define a footprint of other shapes, such as square, elliptical, rectangular, etc., to account for the shape of the analyte monitoring device 110. The flexible leaves 1612 and the flexible support petals 1614 may have varying configurations (e.g., curvatures, dimensions, shapes, etc.) to provide for retaining and releasing an analyte monitoring device of any shape. In some variations, the curvature of the flexible support petals 1614 mirrors the curvature of the proximal surface of the analyte monitoring device such that the flexible support petals 1614 cradle the proximal surface.

With reference to FIGS. 16E and 16F, additional features of the shuttle 1540 are illustrated in a bottom perspective view and a bottom view, respectively. In some variations, a gripping layer 1650 may be provided on a distal surface of the flexible leaves 1612, the flexible support petals 1614, and the shuttle shaft 1630. The gripping layer 1650 may be an elastomeric layer deposited and/or applied to provide additional gripping capability between the analyte monitoring device 110 and the flexible leaves 1612, the flexible support petals 1614, and/or distal surface of the shuttle shaft 1630. In some variations, one or more proximal surfaces of the analyte monitoring device 110 may be a smooth or a substantially smooth surface, and the incorporation of the gripping layer 1650 helps to retain the analyte monitoring device 110 in the receptacle 1640 defined by the flexible leaves 1612. In some variations, the gripping layer 1650 is provided on one or more distal surfaces of the flexible leaves 1612, the flexible support petals 1614, and/or the shuttle shaft 1630 that contact the analyte monitoring device 110 when retained in the receptacle 1640. In some variations, the gripping layer 1650 is evenly distributed. In some variations, the gripping layer 1650 is unevenly distributed. In some variations, the gripping layer 1650 is provided at one or more points of contact between the analyte monitoring device 110 and the distal surfaces of the flexible leaves 1612, the flexible support petals 1614, and/or the shuttle shaft 1630.

FIG. 16G and FIG. 16H depict aspects of the shuttle 1540 with a variation to the shelf 1634 in a side view and a side cross-sectional view, respectively. Additional aspects and features of the shuttle 1540 may be the same as those shown in and described with reference to FIGS. 16A-16F.

In some variations, the shelf 1634 has a proximal surface 1638. The proximal surface 1638 may be a surface, such as a ledge, that extends between the shelf 1634 and the shuttle shaft 1630. In some variations, the proximal surface 1638 may be an angled surface. In some variations, the proximal surface 1638 may be flat or substantially flat. The proximal surface 1638 of the shelf 1634 may be used, in some variations, as a shuttle lockout feature. For example, it may be desirable to incorporate a feature that prevents the shuttle 1540 from being reloaded so that the applicator 1500 cannot be moved from the released configuration to the extended configuration. This may be desirable in situations in which sterility and/or condition of the analyte monitoring device 110 is unknown. For example, if the analyte monitoring device 110 has been released from the applicator 1500, the microneedle array 140 or other components of the analyte monitoring device 110 may be compromised. In response to axial movement of the shuttle 1540 toward a proximal end of the housing 1510 after disengagement of the distal surface 1636 of the shuttle 1540 and the housing 1510 at a shuttle retention surface, the axial movement of the shuttle 1540 is stopped by a distal end of the shuttle retention surface. In particular, the proximal surface 1638 will abut against the distal end of the shuttle retention surface, preventing the axial movement of the shuttle 1540 toward the proximal end of the housing 1510. The distal end of the shuttle retention surface may be a flat or substantially flat surface to prevent the proximal surface 1638 from pushing past the shuttle retention surface.

In some variations (e.g., such as those shown in and described with reference to FIGS. 16A-16D), the applicator 1500 may be reloaded and/or reusable. For example, the shuttle 1540 is reloadable to allow for the axial movement of the shuttle 1540 toward the proximal end of the housing 1510 such that the applicator components are reengaged in the extended configuration.

In some variations, alternate and/or additional shuttle lockout features may be incorporated. In one variation, spring finger features are nested within the shuttle shaft 1630 in a retaining column positioned within the shuttle shaft 1630. Distal ends of spring-loaded fingers are flexed inward to be held by the retaining column. A proximal end of the spring-loaded fingers are held at a proximal end of the cavity of the housing body. When the applicator 1500 transitions to the extended configuration and the shuttle 1540 moves toward the distal end of the housing body, the retaining column moves with the shuttle 1540 and the spring-loaded fingers expand to a larger radial configuration. The spring-loaded fingers, in the larger radial configuration, create a blocking surface for the shuttle 1540 if a shuttle reload or repositioning (e.g., moving the shuttle 1540 toward the proximal end of the housing body) is attempted.

In another variation, a lockout post is positioned within the shuttle shaft 1630. The lockout post includes spring-loaded fingers at a distal end that engage with interior surface features of the shuttle shaft 1630. At a proximal end, the lockout post is engaged within a footprint defined by lockout arms extending from a proximal end of the cavity of the housing body. The engagement of the lockout post within the footprint defined by the lockout arms causes outward deflection of the lockout arms. When the applicator 1500 transitions to the extended configuration and the shuttle 1540 moves toward the distal end of the housing body, the lockout post moves with the shuttle 1540 and the lockout arms deflect inward to a natural, unflexed state. A distal end of the lockout arms provides a blocking surface for the shuttle 1540 if a shuttle reload or repositioning is attempted.

FIGS. 17A-17E depict aspects of the cuff 1520 in more detail. FIG. 17A provides a top perspective view of the cuff 1520, FIG. 17B a bottom view, FIG. 17C a top view, FIG. 17D a first side and corresponding side cross-sectional view, and FIG. 17E a second side and corresponding side cross-sectional view.

The cuff 1520 is arranged in the cavity defined by the housing body and is configured to maintain the applicator 1500 in the collapsed configuration (in which the position of the housing 1510 and the position of the shuttle 1540 are fixed with respect to one another) when the base 1550 is engaged with the housing 1510. The cuff 1520 is further configured to disengage the base 1550 from the housing 1510 upon depression of the locking members 1560 and to transition the applicator 1500 to the extended configuration. The cuff 1520 interacts and engages with the friction ring 1530 to transition the shuttle 1540 in a firing position in the extended configuration, as further described herein. The shuttle 1540 may be substantially axially aligned and nested within the cuff 1520, and the shuttle 1540 may move axially within the cuff 1520. The cuff 1520, upon actuation of the housing 1510, functions to cause disengagement of the analyte monitoring device 110 from the shuttle 1540.

As shown in FIG. 17A, the cuff 1520 is a tubular structure with sidewalls and a lumen 1720 extending therethrough. The cuff 1520 has a proximal opening and a distal opening. The firing ring 1530 and the shuttle 1540 are axially aligned and axially move within the lumen 1720 through the proximal opening and/or the distal opening.

In some variations, the cuff 1520 is generally cylindrical with a circular or substantially circular cross-section along a plane orthogonal to a height of the cuff 1520. In some variations, the cuff 1520 may have other configurations. For example, the cuff 1520 may have a square, a rectangular, or an elliptical cross-section. The effective inner diameter or inner span between opposing sidewalls may be consistent along the height of the cuff 1520. In some variations, the effective inner diameter or inner span of the cuff 1520 may vary slightly along its height. An upper ledge 1722 is positioned at a proximal end of the cuff 1520 along the proximal opening and a bottom flange 1732 at a distal end of the cuff 1520 along the distal opening.

The cuff 1520 includes retention walls 1712 formed on outer sidewalls and generally extending along the height of the cuff 1520 at positions corresponding to respective ones of the locking members 1560. As shown, in some variations, the cuff 1520 has two retention walls 1712 corresponding to two locking members 1560. In some variations, the cuff 1520 has fewer or additional retention walls 1712 and corresponding locking members 1560. For example, in some variations, there may be one retention wall 1712 and one locking member 1560. Each retention wall 1712 is defined by a retention lip 1714 that extends around at least a portion of the perimeter of the retention wall 1712. Each retention wall 1712 may be sized and shaped to generally correspond to an outer perimeter of the locking member 1560 such that the retention lip 1714 closely conforms and/or aligns with the outer perimeter of the movable locking member 1560. The outer exposed surface of the retention wall 1712 may be flat or substantially flat. In some variations, an outer curvature of the cuff 1520 forms the outer exposed surface of the retention wall 1712.

A top edge of the retention lip 1714 is configured to engage with an upper edge of the corresponding locking member 1560. In the collapsed configuration of the applicator 1500, the locking member 1560 is positioned within the retention wall 1712 such that an upper edge of the locking member 1560 is engaged beneath the top edge of the retention lip 1714, preventing downward movement of the cuff 1520 with respect to the housing 1510. Upon depression of the locking members 1560, vertical movement of the cuff 1520 is no longer impeded due to the locking members 1560 being removed from the engagement with the top edge of the retention lips 1714. Additional details are further described herein.

Rotational alignment of the shuttle 1540 within the cuff 1520 may be guided by one or more tracking features. The one or more tracking features may also guide the axial movement of the shuttle 1540 within the cuff 1520. For example, the cuff 1520 may include one or more tracks 1716 that extend along at least a portion of the height of the cuff 1520 within which the one or more tracking projections 1616 on the shuttle 1540 may travel. The tracks 1716 may include open slots as shown in FIG. 17A, or other suitable structures (e.g., recessed grooves or channels) that the tracking projections 1616 on the shuttle 1540 may slidingly engage. The tracks 1716 may furthermore be configured to receive other suitable kinds of tracking features on the shuttle 1540 (e.g., ball bearings). The cuff 1520 and the shuttle 1540 may include any suitable number of tracking features (e.g., one, two, three, four or more) and the tracking features may be circumferentially distributed in an equal or unequal manner. For example, four tracking features may be equally distributed around the shuttle 1540 and the cuff 1520 at 90 degrees apart from one another. In some variations, two tracking features may be equally distributed 180 degrees apart from one another or directly opposing each other, three tracking features may be equally distributed 120 degrees apart from one another, etc.

Each track 1716 may culminate with a shuttle flexion surface 1718 at a bottom end of the track 1716. The shuttle flexion surface 1718 may be a portion of a bottom surface or the bottom flange 1732 of the cuff 1520 or another ledge-like surface that acts as a stop for the axial movement of the shuttle 1540 to aid in the radially outward flexing of the flexible leaves 1612 of the shuttle 1540. For example, the shuttle flexion surface 1718 of each track 1716 prevents further movement of the shuttle 1540 beyond the bottom edge of the cuff 1520.

The upper ledge 1722 of the cuff 1520 may include features for engaging with and locking to the friction ring 1530. In the collapsed configuration of the applicator 1500, the friction ring 1530 is collapsed within the lumen 1720 of the cuff 1520. In the transition to the extended configuration from the collapsed configuration, the friction ring 1530 telescopes and/or extends out of the proximal opening of the cuff 1520 at the proximal end. The collapsed arrangement of the friction ring 1530 within the cuff 1520 in the collapsed configuration of the applicator 1500 provides for a compact overall height of the applicator 1500. In some variations, the friction ring 1530 is not collapsed within the cuff 1520, resulting in an applicator having a greater height in the collapsed configuration. In some variations, the friction ring 1530 and the cuff 1520 are not separate components.

A ledge circumferentially formed around the top edge of the cuff 1520 may secure the engagement of the friction ring 1530 to the cuff 1520. In some variations, a portion of the upper ledge 1722 may include a sill 1724 with guide walls 1726. The sill 1724 may be a flat or substantially flat surface that extends outwards from a portion of the upper ledge 1722 such that the sill 1724 extends over a corresponding portion of the lumen 1720. Two guide walls 1726 may be arranged at either end of the sill 1724, the guide walls 1726 including vertically-extending members that extend upward from or adjacent the sill 1724. The sill 1724 provides a flat surface for engaging a flexible tab of the friction ring 1530, and the pair of guide walls 1726 secure the flexible tab on the sill 1724 by preventing rotational movement of the friction ring 1530. For example, the pair of guide walls 1726 are positioned at either end of the sill 1724 to lock in place the flexible tab on the sill 1724. The cuff 1520 may include more than one of the engaging and locking features for securing the engagement with the friction ring 1530, and the engaging and locking features may be circumferentially distributed in an equal or unequal manner around the upper ledge 1722. For example, as shown in FIGS. 17A, 17B, and 17C, three sills 1724 with corresponding pairs of guide walls 1726 are equally distributed around the upper ledge 1722 120 degrees apart from one another. In some variations, four sills 1724 with corresponding pairs of guide walls 1726 may be equally distributed at 90 degrees apart from one another, two sills 1724 with corresponding pairs of guide walls 1726 may be equally distributed 180 degrees apart from one another or directly opposing each other, etc.

An underside 1728 of the upper ledge 1722 may also interface with the friction ring 1530. For example, the underside 1728 may interface with a portion of a circumferential edge of the friction ring 1530 to maintain an axial position of the cuff 1520 with the friction ring 1530. Additional details related to the engaging and locking are further described herein.

Outer sidewalls of the cuff 1520 may have features for interfacing with the base 1550. For example, a base retention surface 1730 may be formed at one or more portions around an outer periphery and near or at a distal end of the cuff 1520. The base retention surface 1730 may be a rib protruding from the outer sidewall of the cuff 1520 and may be configured to provide a retention surface for one or more members of the base 1550, as further described herein.

FIG. 17F and FIG. 17G depict aspects of the cuff 1520 with a variation to the bottom flange 1732 in a bottom view and a side view, respectively. Additional aspects and features of the cuff 1520 may be the same as those shown in and described with reference to FIGS. 17A-17E. As shown in FIG. 17F and FIG. 17G, the bottom flange 1732 has an increased surface area compared to the bottom flange shown in, for example, FIGS. 17A-17C. During actuation of the applicator 1500, a distal end of the bottom flange 1732 is the contact area with the skin of the user at the insertion site for the analyte monitoring device 110. The increase in surface area of the bottom flange 1732 distributes the forces applied during actuation, making the application process a more comfortable experience for the user. With a bottom flange having a smaller surface area (e.g., 17A-17C), the forces applied during actuation are concentrated among the smaller area, resulting in a more pronounced force felt by the user at the distal end of the cuff 1520

The bottom flange 1732 having the increased surface area has cutouts 1734 formed therethrough for accommodating arms of the base 1550, as further described herein.

The bottom flange 1732 creates a contact surface area for insertion of the microneedle array 140 of the analyte monitoring device 110. The contact surface area along with the actuation force required to actuate the housing body causes the user's skin to dome convexly inside the perimeter of the bottom flange 1732, distal to the microneedle array 140 when the applicator 1500 is in the extended configuration. When the skin domes (in some variations, about 3-6 mm depending on skin type), the skin is stretched and tightened, providing a preferable insertion site for the microneedle array insertion as stretched/tightened skin improves insertion efficacy and consistency. The domed and convex shape of the skin reduces the well-known bed-of-nails effect that may occur with standard microneedle insertion. The result is that the microneedles in the center of the microneedle array may penetrate first, followed by the microneedles around the perimeter of the microneedle array, resulting in consistent and effective insertion.

Figure 18A:
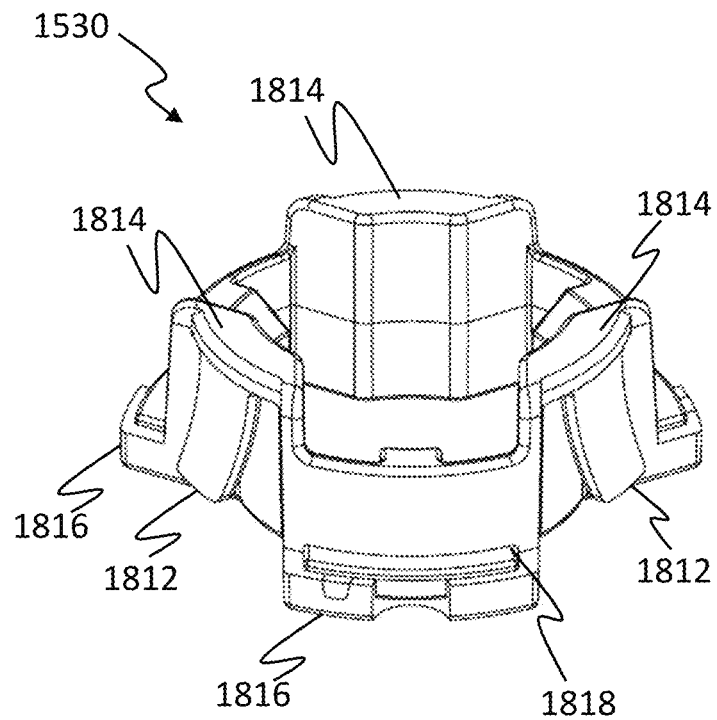

FIGS. 18A-18D depict aspects of the friction ring 1530 in more detail. FIG. 18A provides a first top perspective view of the friction ring 1530, FIG. 18B second top perspective view, FIG. 18C a first bottom perspective view, and FIG. 18D a second bottom perspective view.

The friction ring 1530 has a ring-shaped structure that is concentrically and axially arranged within the cuff 1520 and serves as an extension of the cuff 1520 for application of the analyte monitoring device 110. In the collapsed configuration of the applicator 1500, the friction ring 1530 is collapsed within the cuff 1520. The friction ring 1530 includes a coupling member that prevents firing of the shuttle 1540 until removal of the base 1550. In the transition from the collapsed configuration to the extended configuration of the applicator 1500 and upon removal of the base 1550, the cuff 1520 moves axially toward the distal opening of the housing body such that the friction ring 1530 extends and/or telescopes out of the proximal opening of and locks into the cuff 1520. During actuation of the housing 1510, the friction ring 1530 and the cuff 1520 are locked together as a single component and function to cause disengagement of the analyte monitoring device 110 from the shuttle 1540. The shuttle 1540 may be substantially axially aligned and nested within the friction ring 1530, and the shuttle 1540 may move axially within the friction ring 1530.

As shown in FIGS. 18A-18D, the friction ring 1530 has a ring-shaped core that defines a friction ring cavity 1810 that extends through the ring-shaped core. The shuttle 1540 is axially aligned and moves within the friction ring cavity 1810. Outer sidewalls of the ring-shaped core are axially aligned and move within and extend at least partially out of the cuff 1520.

Locking of the cuff 1520 to the friction ring 1530 may be achieved by one or more engagement and locking features. For example, the friction ring 1530 may include one or more features that engages with and locks to respective features of the cuff 1520. In some variations, the engagement and locking features may be circumferentially arranged around the ring-shaped core of the friction ring 1530. For example, a flexible tab 1812 may extend along at least a portion of the height of the outer sidewall of the ring-shaped core and be in circumferential alignment with the sill 1724 of the cuff 1520. A proximal or top end of the flexible tab 1812 is attached or secured at a top ledge 1814 of the friction ring 1530, and a distal or bottom end of the flexible tab 1812 is unsecured, allowing the distal end of the flexible tab 1812 to flex or move with respect to the secured proximal end. When the applicator 1500 is in the collapsed configuration, the proximal end of the flexible tab 1812 is aligned with a portion of an inner diameter of the upper ledge 1722 of the cuff 1520. During the transition from the collapsed configuration to the extended configuration of the applicator 1500, the cuff 1520 moves axially toward and through the distal opening of the housing body with respect to the friction ring 1530 along the length of the flexible tab 1812. The flexible tab 1812 is flexed or pushed inward until the cuff 1520 passes the distal end of the flexible tab 1812, at which point the flexible tab 1812 snaps onto the sill 1724 and is held between the pair of guide walls 1726.

The friction ring 1530 may include more than one flexible tab 1812, and the flexible tabs 1812 may be circumferentially distributed in an equal or unequal manner around the outer sidewall of the ring-shaped core. For example, as shown in FIGS. 18A-18D, three flexible tabs 1812 are equally distributed around the outer sidewall of the ring-shaped core 120 degrees apart from one another. In some variations, four flexible tabs 1812 may be equally distributed at 90 degrees apart from one another, two flexible tabs 1812 may be equally distributed 180 degrees apart from one another or directly opposing each other, etc. The number of flexible tabs 1812 generally corresponds to the number of sills 1724 and associated pair of guide walls 1726.

Figure 18B:
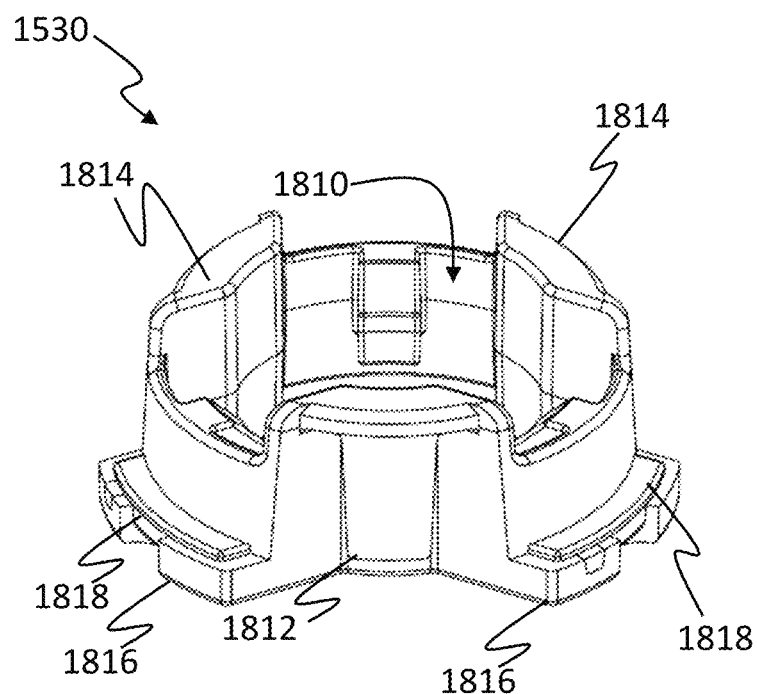

The friction ring 1530 may further include an outward extending surface for the engagement and locking with the cuff 1520. For example, the underside 1728 of the upper ledge 1722 of the cuff 1520 may interface with the friction ring 1530 at the outward extending surface. The interface between the underside 1728 of the cuff 1520 and the outward extending surface of the friction ring 1530 may serve to maintain an axial position of the cuff 1520 with respect to the friction ring 1530. For example, the friction ring 1530 may include a protruding circumferential edge 1816. The protruding circumferential edge 1816 may protrude outward at a distal end or region of the outer sidewall of the ring-shaped core, orthogonal to a height of the outer sidewall, as best shown in FIG. 18B. The protruding circumferential edge 1816 provides an interfacing or engagement point for the underside 1728 of the cuff 1520. As the cuff 1520 moves axially downward with respect to the friction ring 1530, during the transition from the collapsed configuration to the extended configuration of the applicator 1500, the underside 1728 abuts against the protruding circumferential edge 1816, which prevents further downward axial movement of the cuff 1520.

A dampening member 1818 may be positioned on an upper surface of the protruding circumferential edge 1816. The dampening member 1818 may be an elastomeric or rubber strip or the like that dampens the or softens the contact between the underside 1728 of the cuff 1520 and the protruding circumferential edge 1816.

The friction ring 1530 may include more than one protruding circumferential edge 1816, and the protruding circumferential edges 1816 may be circumferentially distributed in an equal or unequal manner around the outer sidewall of the ring-shaped core. For example, as shown in FIGS. 18A-18D, three protruding circumferential edges 1816 are equally distributed around the outer sidewall of the ring-shaped core 120 degrees apart from one another. In some variations, four protruding circumferential edges 1816 may be equally distributed at 90 degrees apart from one another, two protruding circumferential edges 1816 may be equally distributed 180 degrees apart from one another or directly opposing each other, etc.

The friction ring 1530 may include a coupling member that is releasably coupled to a ring retention surface of the housing 1510 to aid in locking the shuttle 1540 when the base 1550 is engaged with the housing 1510. For example, in some variations, in the collapsed configuration of the applicator 1500, the friction ring 1530 is collapsed within the cuff 1520 and prevents firing of the shuttle 1540 until removal of the base 1550.

For example, the housing 1510 may include at least one ring retention surface, and the friction ring 1530 may be arranged in cavity defined by the housing body and include a projection 1820 that is releasably coupled with the ring retention surface. In response to actuation of at least a portion of the housing 1510 toward the shuttle 1540 (e.g., the applicator may be placed in compression, such as against a skin surface of the user), the ring retention surface of the housing may decouple from the projection 1820, which may cause release of releasable coupling features coupling the shuttle 1540 and the housing 1510.

Figure 18C:
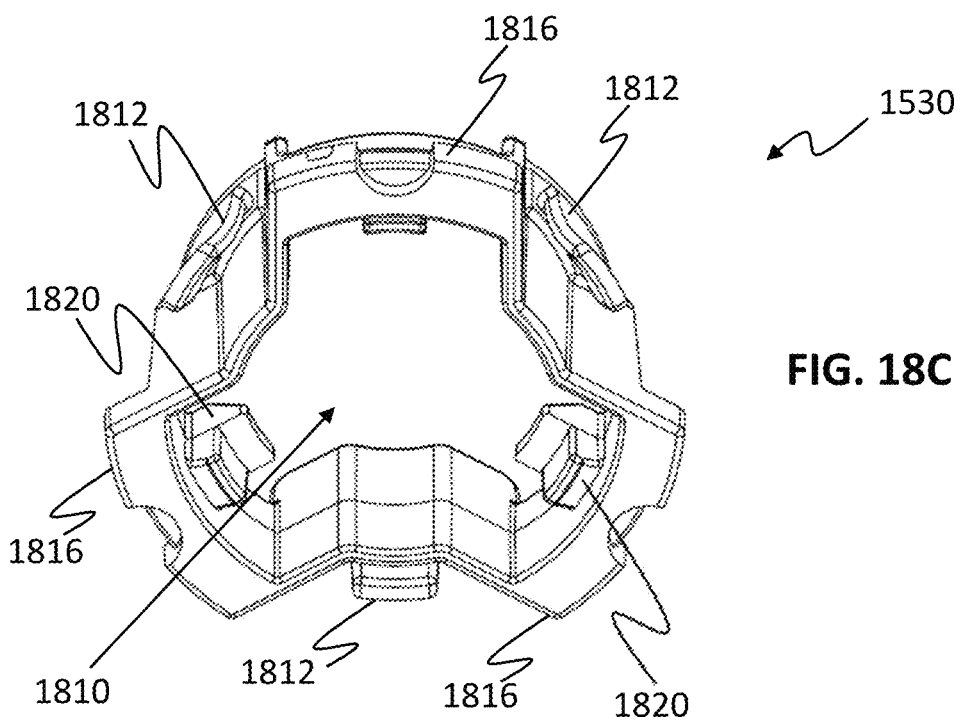
Figure 18D:
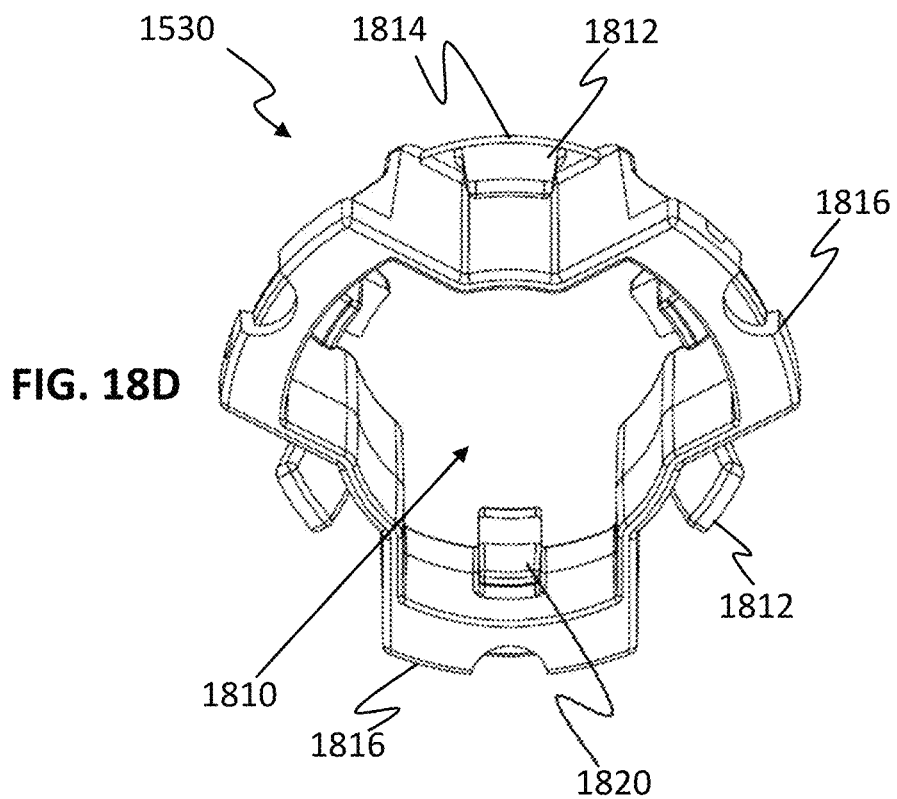

As best seen in FIG. 18C, the projection 1820 may be arranged on an inner sidewall of the ring-shaped core and extend into the friction ring cavity 1810. The projection 1820 may include a surface, such as a flat surface orthogonal or substantially orthogonal to the inner sidewall of the ring-shaped core, that forms the releasable engagement with the ring retention surface of the housing 1510, as further described herein.

The friction ring 1530 may include more than one projection 1820, and the projections 1820 may be circumferentially distributed in an equal or unequal manner around the inner sidewall of the ring-shaped core. For example, as shown in FIGS. 18A-18D, three projections 1820 are equally distributed around the inner sidewall of the ring-shaped core 120 degrees apart from one another. In some variations, four projections 1820 may be equally distributed at 90 degrees apart from one another, two projections 1820 may be equally distributed 180 degrees apart from one another or directly opposing each other, etc.

FIGS. 19A-19E depict aspects of a cuff-ring assembly 1900, including the cuff 1520 and the friction ring 1530 of the analyte monitoring device 1500. Shown in a top perspective view, a bottom view, a top view, a side view, a side cross-sectional view, and two detailed views, respectively in FIGS. 19A-19E, the cuff-ring assembly 1900 is in a locked state in which the cuff 1520 and the friction ring 1530 are locked together.

The cuff 1520 and the friction ring 1530 may be locked or secured to one another through one or more engagement and locking features. When the applicator 1500 is in the collapsed configuration, the friction ring 1530 is collapsed within the cuff 1520 and the engagement and locking features are not connected to one another. Upon removal of the base 1550 from the housing 1510, the applicator 1500 transitions from the collapsed configuration to the extended configuration. During this transition, the cuff 1520 is moved or pushed downward, during which the engagement and locking features become engaged, thereby locking the cuff 1520 and the friction ring 1530 to one another.

Figure 19A:
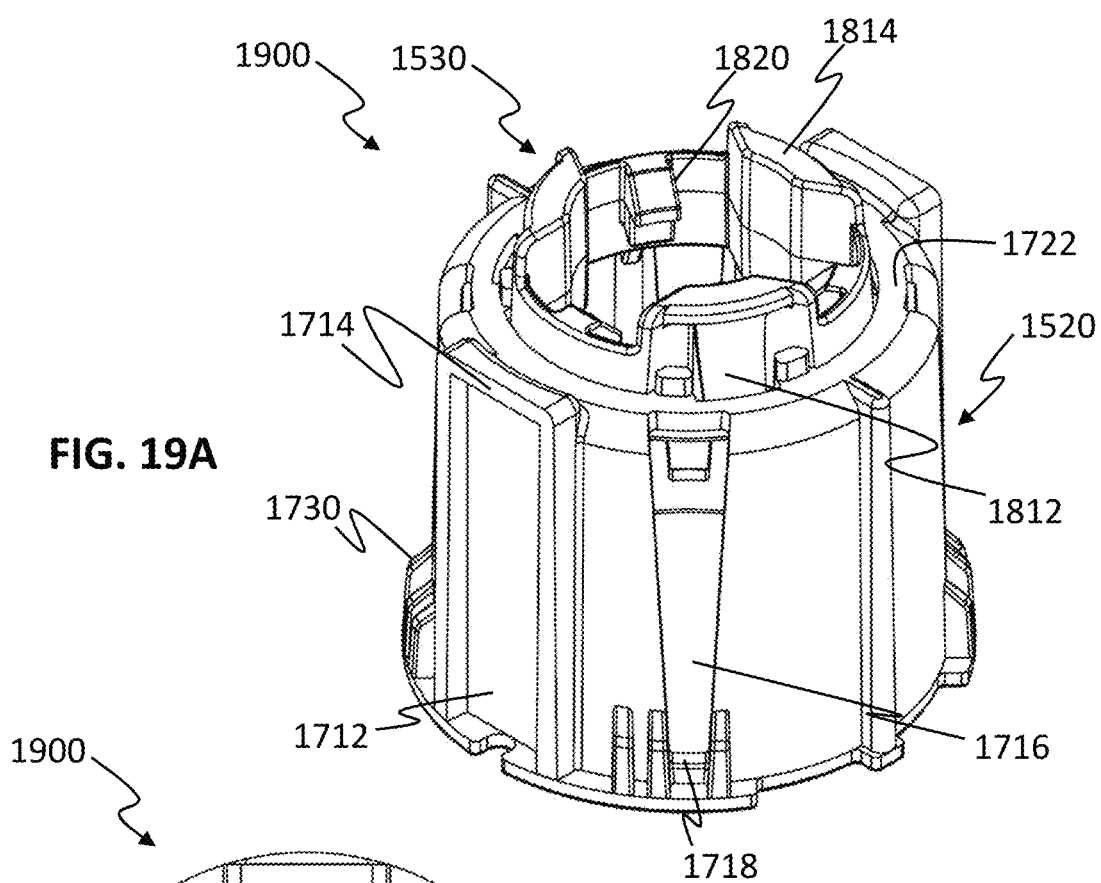
Figure 19B:
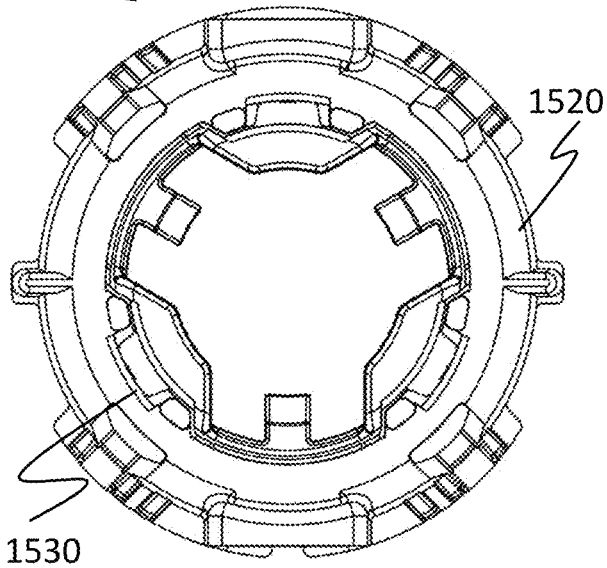
Figure 19C:
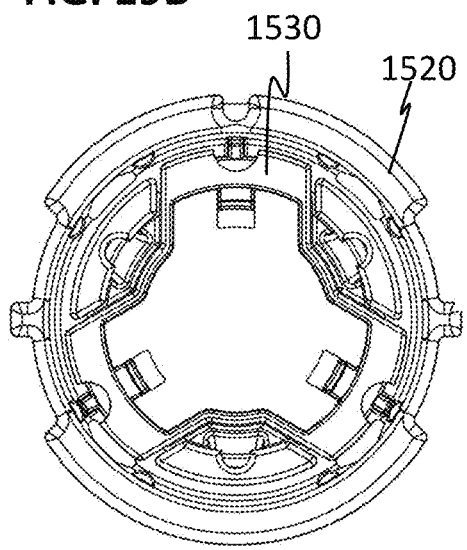

As best shown in FIGS. 19A, 19D, and 19E, when the cuff-ring assembly 1900 is in the locked state, a top portion of the friction ring 1530 telescopes upward and is exposed out of the proximal end of the cuff 1520 such that the upper ledge 1722 surrounds the top, exposed portion of the friction ring 1530.

The detailed views provided in FIG. 19E are close-up views illustrating portions of the engagement and locking features of the cuff 1520 and the friction ring 1530 in the locked state.

As shown the close-up view D, in the locked state, the underside 1728 of the upper ledge 1722 of the cuff 1520 is interfaced with the friction ring 1530 at the protruding circumferential edge 1816. This interface serves to maintain an axial position of the cuff 1520 with respect to the friction ring 1530. For example, the protruding circumferential edge 1816 acts as a stop for the cuff 1520. As shown in the close-up view C, the flexible tab 1812 is snapped onto the sill 1724 and is held in alignment between the pair of guide walls 1726.

FIGS. 20A-20F depict aspects of the housing 1510 of the applicator 1500 for the analyte monitoring device 110 according to some variations. Provided are a first top perspective view, a second top perspective view, a first bottom perspective view, a second bottom perspective view, a first side cross-sectional view, and a second side cross-sectional view in FIGS. 20A-20F, respectively. The housing 1510 is configured to be manipulated (e.g., manually by a user) to actuate the applicator 1500 to deploy the analyte monitoring device 110 releasably retained within the shuttle 1540. The housing 1510 has a housing body 2002 that defines a cavity 2010 that receives the cuff 1520, the friction ring 1530, and the shuttle 1540. The housing body 2002 has a distal opening 2004. The first biasing element 1582 (e.g., a first compression spring) may be arranged inside the cavity 2010 on or around a mount 2014 (e.g., a mounting or support structure) that extends downward through the cavity 2010 from a proximal surface 2012 of the housing body 2002. For example, the mount 2014 may extend from an underside of the proximal surface 2012 of the housing body 2002 so that the mount 2014 extends within the cavity 2010. The mount 2014 may be concentrically aligned or nested with the cuff 1520, the friction ring 1530, and the shuttle 1540. For example, the mount 2014 may extend through the locking friction ring cavity 1810 of the friction ring 1530, and the shuttle shaft 1630 may extend through at least a portion of the mount 2014.

In some variations, as shown in FIG. 20C-FIG. 20F, the mount 2014 includes a plurality of downward extending fingers 2016 arranged in a circumferential configuration. For example, the plurality of downward extending fingers 2016 are arranged such that the configuration defines a circular or generally circular footprint. The circular or generally circular footprint may correspond to the perimeter of the shuttle shaft 1630 such that the shuttle shaft 1630 (e.g., the upper portion of the shuttle shaft 1630) fits within the circular or generally circular footprint. Variations to the shape and configuration of the footprint defined by the downward extending fingers 2016 may be based on the shape and configuration of the shuttle shaft 1630 and/or the first biasing element 1582. Each of the downward extending fingers 2016 may be configured to flex or bend outward in response to a force along a portion of the length of the downward extending finger 2016.

One or more retention surfaces and/or features may be formed on the mount 2014. For example, each downward extending finger 2016 may have one or more retention members formed thereon. The retention surfaces and/or features may include a ring retention surface that includes a ledge 2018 for releasably coupling with the projection 1820 of the friction ring 1530 for preventing firing of the shuttle 1540 until removal of the base 1550. For example, the ledge 2018 may be formed along an outwardly facing (e.g., first) surface of the downward extending finger 2016 and may couple with the projection 1820 by a distal surface of the projection 1820 contacting or resting on the ledge 2018. In some variations, a ring retention slot (e.g., a groove or a channel) may be formed through or along the outwardly facing surface of the downward extending finger 2016, where the ring retention slot terminates at a distal end at the ledge 2018. The ring retention slot may be sized so that the projection 1820 smoothly but securely travels along its length. For example, the thickness of the projection 1820 may approximate the width of the ring retention slot. Upon actuation of the housing 1510, the housing 1510 is moved downward with respect to the cuff 1520 and the friction ring 1530. During this downward movement of the housing 1510, the ring retention slot slides downward along the projection 1820, and the coupling (e.g., contact) between the ledge 2018 and the projection 1820 is released.

The retention surfaces and/or features of each downward extending finger 2016 may also include a shuttle retention surface that includes a shoulder 2020 for releasably engaging the shelf 1634 of the shuttle 1540 for controlling axial movement of the shuttle 1540 in the release of the analyte monitoring device 110. For example, the shoulder 2020 may be formed along an inwardly facing (e.g., second) surface of the downward extending finger 2016, and the shoulder 2020 may engage the distal surface 1636 of the shelf 1634. The shelf 1634 and the distal surface 1636 may extend circumferentially along the shuttle shaft 1630. Upon actuation of the housing 1510, as the engagement between the ledge 2018 and the projection 1820 is released, downward movement of the shuttle 1540 toward the distal opening 2004 of the housing body 2002 causes the shelf 1634 to push past (e.g., deflect or bend) the shoulder 2020, which is no longer inhibited by the friction ring 1530.

Figure 20A:
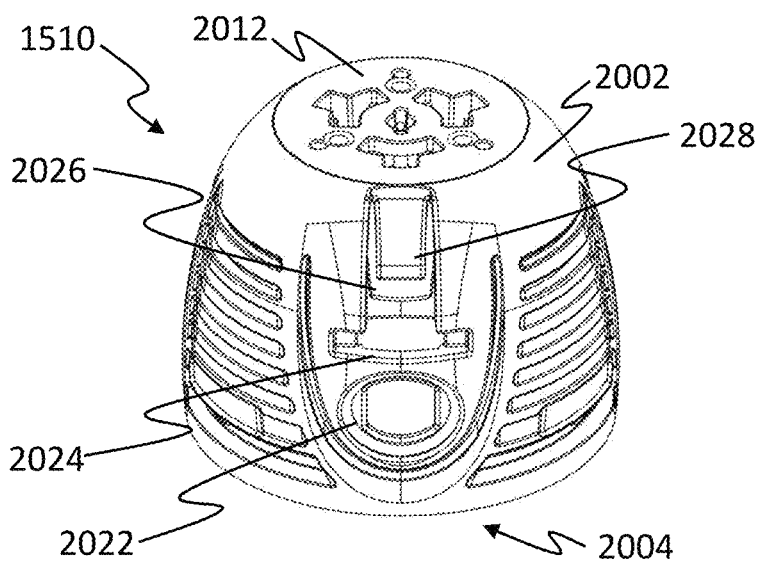
Figure 20B:
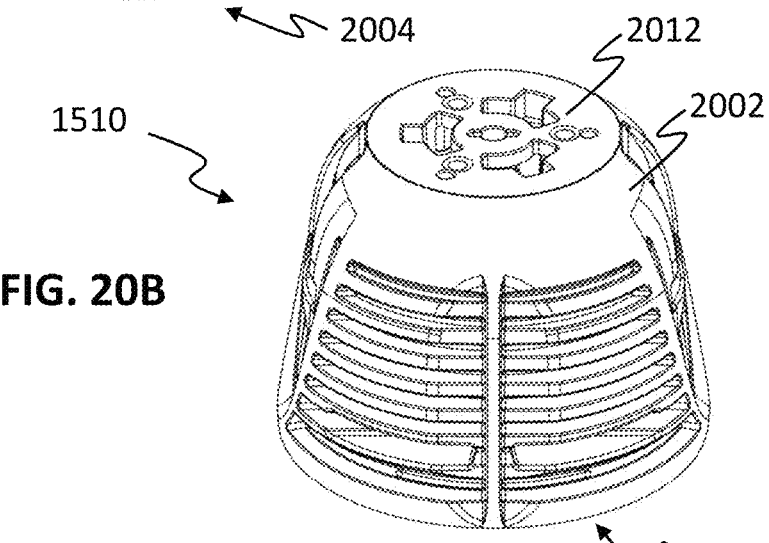
Figure 20C:
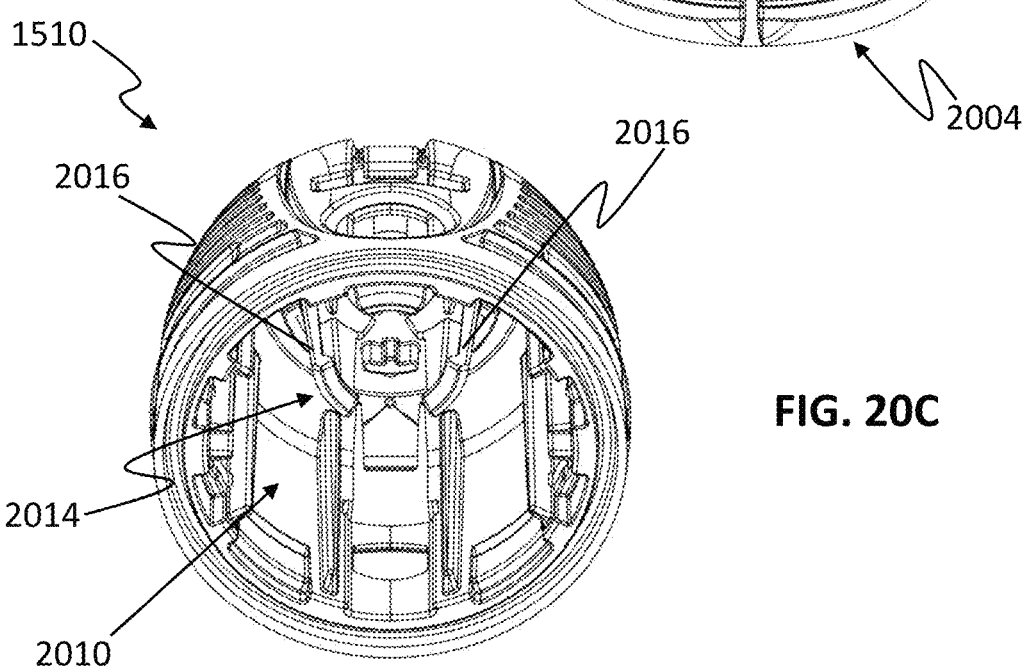
Figure 20D:
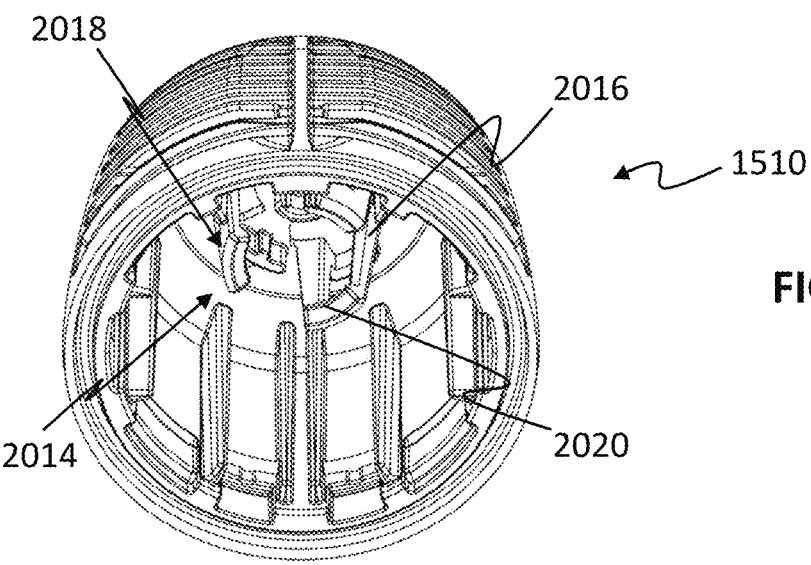
Figure 20E:
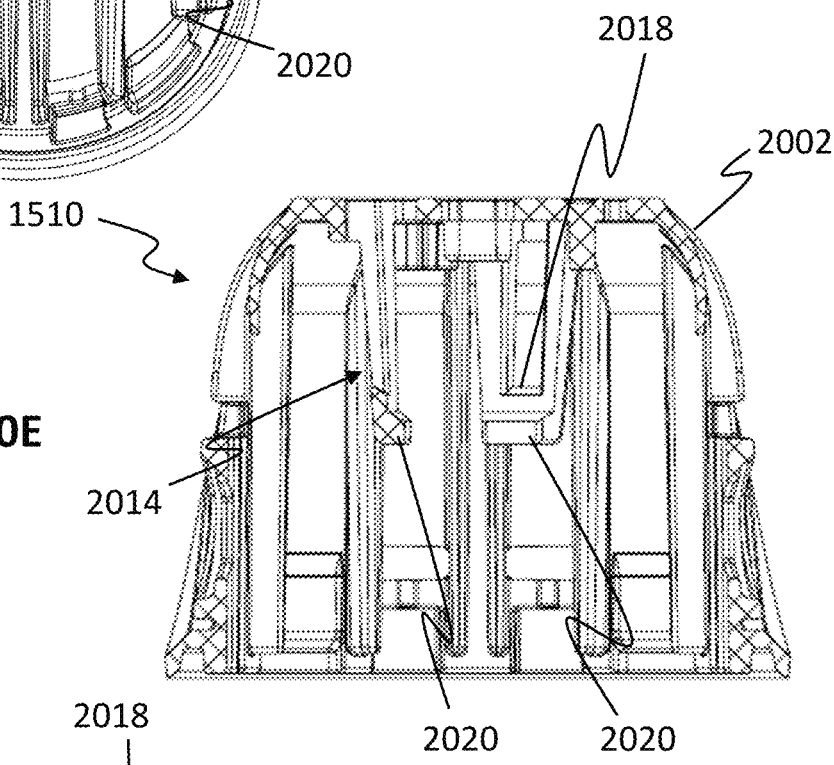
Figure 20F:
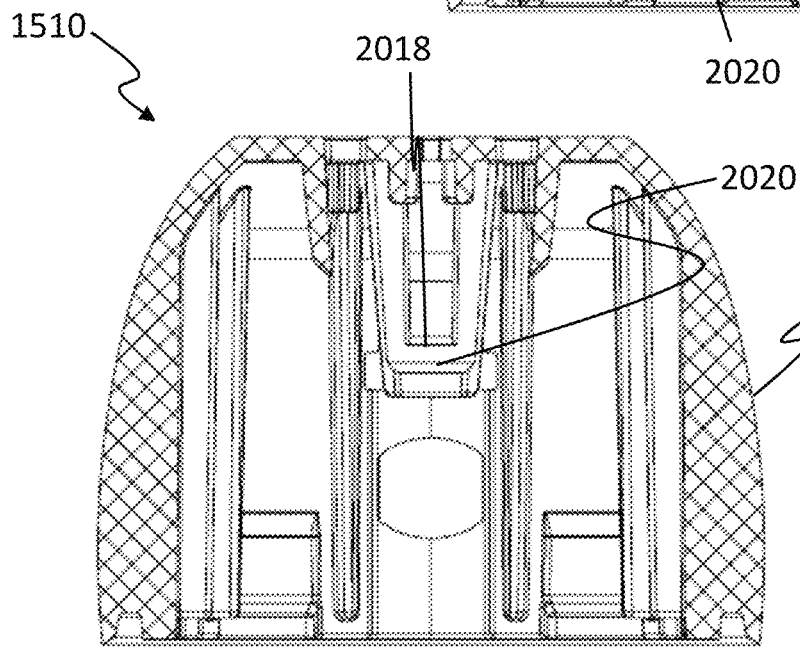

In some variations, each downward extending finger 2016 may include the ledge 2018 formed along an outwardly facing surface of the downward extending finger 2016 and the shoulder 2020 formed along an opposing inwardly facing surface of the downward extending finger 2016. The number of downward extending fingers 2016 may correspond to the number of projections 1820. The downward extending fingers 2016 may be circumferentially distributed in an equal or unequal manner. For example, as shown in FIG. 20D, three downward extending fingers 2016 are equally distributed within the cavity 2010 120 degrees apart from one another. In some variations, four downward extending fingers 2016 may be equally distributed at 90 degrees apart from one another, two downward extending fingers 2016 may be equally distributed 180 degrees apart from one another or directly opposing each other, etc.

In some variations, the housing 1510 may include one or more guide members along internal sidewalls of the housing body 2002 within the cavity 2010. For example, one or more ribs may extend along a length or a portion of the length of the internal sidewalls of the housing body 2002 and may interface with corresponding outward facing members arranged along a length or a portion of the length of the cuff 1520. The guide members may help to maintain the axial and rotational alignment of the cuff 1520 within the housing body 2002.

The housing 1510 may further include features for aligning with and holding, in a movable configuration, the locking members 1560. For example, a first side opening 2022 formed through the sidewall of the housing body 2002 may be sized and shaped to hold therein a depressible member of the locking member 1560. A pivot surface 2024 may be formed at a height above the first side opening 2022 and may provide a pivoting surface for the locking member 1560. For example, the pivot surface 2024 may provide a point along which the locking member 1560 may pivot to release the locking member 1560 from its engagement with the cuff 1520. At a height above the pivot surface 2024, a second side opening 2026 may be formed through the sidewall of the housing body 2002. The second side opening 2026 may be sized and shaped to hold therein a pivoting member of the locking member 1560. A flexible contact member 2028 may be formed at a height above the second side opening 2026. The flexible contact member 2028 may be secured at its proximal end to the sidewall of the housing body 2002. A distal end of the flexible contact member 2028 may be unsecured with respect to the sidewall of the housing body 2002 and may be configured to flex outwards from the sidewall in response to an applied force. For example, the distal end of the flexible contact member 2028 may be in engagement with a portion of the pivoting member of the locking member 1560. When the pivoting member pivots outward along the pivot bar 2024, the flexible contact member 2028 flexes outward in response to the pivoting movement but limits the outward pivoting or flexing movement of the locking member 1560.

In some variations, the housing 1510 may include features for interfacing with and/or securing the base 1550. For example, one or more recesses or slots may be formed in one or more portions at a distal end of the housing body 2002 to receive portions of base sidewalls of the base 1550, and/or one or more recesses or slots may be formed within inner sidewalls of the housing body 2002 to receive corresponding one or more arms of the base 1550, as further described herein.

In some variations, the housing 1510 may include or be coupled to an outer enclosure 1570. For example, the outer enclosure 1570 may be a grip that may include a sheath or ring that is slipped around the housing 1510 or coupled to the housing 1510 with suitable mechanical interfit such as threads, interference fit, etc. In some variations, the outer enclosure 1570 may be integrally formed with the housing 1510 (e.g., over molded) and/or the housing 1510 may include one or more grip features. In some variations, the outer enclosure 1570 may include one or more features to enhance the ability of a user to manipulate the housing 1510. For example, the outer enclosure 1570 may include one or more concave or otherwise recessed contours with finger-receiving surfaces to improve manual graspability. Additionally or alternatively, the outer enclosure 1570 may include one or more convex textural features (bumps, ridges, ribs, rings, etc.) to increase friction. Additionally or alternatively, the outer enclosure 1570 may include one or more materials with greater friction (e.g., silicone or other elastomer). In some variations, the outer enclosure 1570 is an elastomeric material that provides an environmental enclosure for the housing body 2002 (e.g., by substantially surrounding the housing body 2002) and components arranged within. The outer enclosure 1570 may also control acoustics (e.g., reduce sounds produced by the actuation of the applicator) and vibration (e.g., dampen vibrations between the user and the applicator components produced by the actuation of the applicator).

FIGS. 21A-21B depict aspects of the locking member 1560 of the applicator 1500 for the analyte monitoring device 110 in a front perspective view and a back perspective view, respectively. The movable locking member 1560 fits within the corresponding features of the housing body 2002 and is aligned with and at least partially fitted within the retention wall 1712 formed on the outer sidewalls of the cuff 1520. For example, the outer perimeter of the locking member 1560 at a back surface may be an elongated member that fits within the retention wall 1712 defined by the retention lip 1714. The locking member 1560 includes a depressible member 2110, a pivot bar 2112, and a pivoting member 2114 with a flat or substantially flat upper edge 2116. The depressible member 2110 may be in the form of a button or a nub and may have a configuration for fitting in and extending through the first side opening 2022 of the housing 1510. The depressible member 2110 is generally sized and shaped to allow for a user to contact and depress the depressible member 2110. The pivot bar 2112 is a bar-like member that extends through the second side opening 2026 of the housing 1510 and along the pivot surface 2024. For example, the pivot bar 2112 is in moveable engagement with the pivot surface 2024 such that when the depressible member 2110 is pressed inward (e.g., depressed), the locking member 1560 pivots at the interface between the pivot bar 2112 and the pivot surface 2024. The pivoting movement of the locking member 1560 causes the outward movement of the pivoting member 2114. That is, when the depressible member 2110 is pressed or pushed inward in the first opening 2022, the pivoting member 2114 moves outward from the second side opening 2026. The outward movement of the pivoting member 2114 is controlled or limited by the flexible contact member 2028 of the housing 1510.

The pivoting member 2114 has a flat or substantially flat upper edge 2116 that is in releasable engagement with the top edge of the retention lip 1714 that defines the retention wall 1712 of the cuff 1520. In the collapsed configuration of the applicator 1500, the locking member 1560 is positioned within the retention wall 1712 such that the upper edge 2116 of the movable locking member 1560 is engaged beneath the top edge of the retention lip 1714, preventing downward movement of the cuff 1520 with respect to the housing body 2002. Upon depression of the locking members 1560, vertical movement of the cuff 1520 is no longer impeded due to the outward movement of the pivoting member 2114 away from the top edge of the retention lips 1714.

The locking member 1560 is thus engaged with the cuff 1520 in a first configuration and disengaged from the cuff 1520 in a second configuration. In some variations, movement of the locking member 1560 from the first configuration to the second configuration releases the cuff 1520, thereby decoupling a proximal surface of the base 1550 from the housing body 2002, as further described herein.

In some variations, one locking member 1560 is provided. In some variations, two locking members 1560 are provided. The incorporation of two locking members 1560 provides for a locking system for the applicator 1500 that requires a deliberate and controlled user action (e.g., simultaneous or near simultaneous depression of the two locking members 1560) to unlock the applicator 1500 and transition the applicator 1500 from the collapsed configuration to the extended configuration for deployment of the analyte monitoring device 110.

FIGS. 22A-22G depict aspects of the base 1550 of the applicator 1500 for the analyte monitoring device 110, according to some variations. The base 1550 is shown in a top perspective view, a top view, a bottom view, a first side view, a first side cross-sectional view, a second side view, and a second side cross-sectional view, respectively in FIGS. 22A-22G. Generally, the base 1550 provides an enclosed area for the analyte monitoring device 110 before a user is ready to apply the analyte monitoring device 110. The base 1550 is removably coupled to the housing body 2002 at the distal opening 2004. The base 1550 is held into place through releasable engagement between features of the base 1550, the cuff 1520, and the housing body 2002, as further described herein. The base 1550 is removed from its releasable engagement with the cuff 1520 and the housing body 2002 upon movement of the locking members 1560 from the first configuration to the second configuration, followed by a removal force applied to the base 1550 by a user. The release of the locking members 1560 from the engagement with the top edge of the retention lip 1714 of the cuff 1520 allows the cuff 1520 to vertically translate toward the distal opening 2004 of the housing body 2002. The movement of the cuff 1520 toward the distal opening 2004 contacts and pushes the base 1550 in the same direction.

As the cuff 1520 progresses downward, the shuttle 1540 is moved into a position in which the shoulder 2020 of the one or more downward extending fingers 2016 is engaged with the shelf 1634 (e.g., at the distal surface 1636) formed on the shuttle shaft 1630. The cuff 1520 progresses further downward until stopped by the protruding circumferential edge 1816 of the friction ring 1530, and the friction ring 1530 is locked into the cuff 1520 via the engagement of the flexible tabs 1812 onto the sill 1724. While the cuff 1520 is moved axially downward, further movement of the shuttle 1540 is impeded by the shoulder 2020 of the one or more downward extending fingers 2016. Meanwhile, the further downward movement results in the base 1550 being pushed further downward such that lockout arms of the base 1550 prevent the base 1550 from being reattached, and retention arms of the base 1550 are in a position to cause release of the base 1550 by a user-applied removal force to the base 1550. Upon the user-applied removal force to the base 1550, the applicator 1500 is in the extended configuration in which the components of the applicator 1500 are aligned and ready to apply the analyte monitoring device 110 upon actuation of the housing 1510.

In some variations, as shown in FIGS. 22A-22G, the base 1550 has a proximal surface 2210 with base sidewalls 2212 extending upward from a portion of the proximal surface 2210. The proximal surface 2210 may have a substantially flat surface with curved edges that abut against bottom edges of the housing body 2002 and/or the outer enclosure 1570 to form a sealed enclosure therebetween. In some variations, the base sidewalls 2212 may extend continuously in a circular or substantially circular arrangement. In some variations, the base sidewalls 2212 may be separate and discrete members that together form a circular or substantially circular footprint. Upper edges of the base sidewalls 2212 may fit into corresponding recesses formed in a bottom edge of the housing body 2002 so that the base sidewalls 2212, when the applicator 1500 is in the collapsed configuration, are surrounded by the housing body 2002.

The base 1550 may be configured to form a secure attachment with the microneedle enclosure 500 connected to the analyte monitoring device 110. For example, an interior portion of the base 1550 may be sized and shaped such that the clamp 520 (of the microneedle enclosure 500) may be fitted and/or contained within the interior portion. In some variations, the base 1550 includes a receiving area or compartment that provides a surrounding enclosure for the microneedle enclosure 500. The microneedle enclosure 500 and the base plate 330 of the analyte monitoring device 110, when attached to one another via the locking tabs 528 and the connection member 332, may be contained within the receiving area of the base 1550. An engagement may be made between the outer engagement features 526 of the microneedle enclosure 500 and clamp engagement features formed within the receiving area of the base 1550, as further described herein.

FIG. 22H-FIG. 22J depict aspects of the base 1550 and the microneedle enclosure 500 enclosure in an exploded view, a top perspective view, and a side cross-sectional view, respectively, as further described herein.

In some variations, the receiving area may include enclosure sidewalls 2214 that extend upward from a center region of the proximal surface 2210, interior to the base sidewalls 2212. The enclosure sidewalls 2214 may form a perimeter that surrounds or interfaces with the outer periphery of the base plate 330 of the analyte monitoring device 110. Within the enclosure sidewalls 2214, clamp engagement features may include a plurality of upward extending flexible fingers 2216, each having a chamfered or beveled edge, and a plurality of walls 2217, each of which engage with the outer engagement features 526 of the clamp 520. The upward extending flexible fingers 2216 flex outward for receiving the microneedle enclosure 500, the chamfered or beveled edges secure the microneedle enclosure 500, and the walls 2217 limit rotational movement of the microneedle enclosure 500. The flexible fingers 2216 may be positioned in an alternating configuration with the walls 2217, and the flexible fingers 2216 and the walls 2217 may be positioned circumferentially around an inner perimeter of the enclosure sidewalls 2214 such that the flexible fingers 2216 and the walls 2217 form a footprint for the clamp 520.

For example, the outer engagement features 526 of the clamp 520 may include an extension surface that orthogonally protrudes from a mid-region of the clamp 520 and terminates at a fin that extends from the extension surface in an orthogonal direction to or near a proximal end of the clamp 520, as best shown in FIGS. 5E and 5F. The outer engagement features 526 of the clamp 520 may be positioned circumferentially around an outer edge of the clamp 520, and each outer engagement feature 526 (including an extension surface and a fin) may correspond to a respective flexible finger 2216 and wall 2217 of the base 1550. The extension surface of the clamp 520 may interface with the flexible finger 2216 such that upon application of pressure there between, the extension surface is secured beneath an upper edge of the flexible finger 2216 (e.g., the flexible finger 2216 flexes outward upon pressure to allow the extension surface to snap-fit beneath the chamfered or beveled upper edge of the flexible finger 2216).

Rotational movement of the clamp 520 is limited or restricted due to the interface between the fin of the clamp 520 and the wall 2217. For example, rotational movement of the clamp 520 is stopped upon contact between the fin of the clamp 520 and the wall 2217 of the base 1550. As the clamp 520 has a rotatable connection with the connection member 332 of the base plate 330 (as described above with reference to FIGS. 5E, 5F, and 5G), rotation of the clamp 520 while held within the clamp engagement features of the base 1550 may result in the disengagement of the clamp 520 and the base plate 330. For example, by rotating the clamp 520 such that the locking tabs 528 of the clamp are disengaged from the connector features 336 of the base plate 330, the microneedle enclosure 500 (held within the base 1550 by the clamp engagement features (e.g., the engagement of the flexible fingers 2216 and the extension surfaces of the clamp 520)) may be lifted off the base plate 330.

Thus, when the analyte monitoring device 110 with the microneedle enclosure 500 is fitted within the base 1550, the microneedle array 140 of the analyte monitoring device 110 is contained in the sterile environment provided by the capsule 510 until removal of the compressed engagement between the clamp 520 and the base plate 330. In some variations, once the microneedle enclosure 500 is attached to the base 1550 and the base 1550 is attached to the housing 1510, the rotational locking arrangement between the microneedle enclosure 500 and the base plate 330 may be disengaged through, for example, a manufacturing operation which retains the engagement between the flexible fingers 2216 and the microneedle enclosure 500. The microneedle array 140 then remains in its sterile environment, due to compression from the biasing elements 530, 1582, and 1584, until the base 1550 is disengaged from the housing 1510. The disengagement of the base 1550 results in removal of the microneedle enclosure 500 with the base 1550 as the microneedle enclosure 500 is rotationally disengaged from the base plate 330 (through the preceding manufacturing disengagement operation) and is secured in the base 1550 through the snap-fit attachment with the flexible fingers 2216.

In some variations, the base 1550 includes arms that assist in the engagement and release between the base 1550, the cuff 1520, and the housing body 2002. The base 1550 may include a lockout arm 2218 that extends from the proximal surface 2210 in an upward projecting configuration. The lockout arm 2218 may be configured to flex or snap into a lockout retention recess formed in the sidewalls of the housing body 2002 when the base 1550 is connected to the housing body 2002. For example, during assembly of the applicator 1500, the lockout arm 2218 may be flexed inward to allow for an outward protruding surface of the lockout arm 2218 to be positioned in (e.g., snapped into) the lockout retention recess and biased radially outward. During release of the base 1550 as the base 1550 is being pushed downward, the lockout arm 2218 is disengaged from (e.g., pulled out of) the lockout retention recess and pushed beyond, in the downward, axial movement of the base 1550, a walled surface formed in the sidewall of the housing body 2002. Once the lockout arm 2218 is moved beyond the walled surface, the user is prevented from reattaching the base 1550 to the housing body 2002 due to the walled surface blocking upward, axial movement of the lockout arm 2218.

In some variations, the base 1550 may include more than one lockout arm 2218, and the lockout arms 2218 may be circumferentially distributed and/or positioned in an equal or unequal manner around the proximal surface 2210. For example, as shown in FIG. 22A, the base 1550 includes four lockout arms 2218 distributed around the proximal surface 2210.

In some variations, the lockout arm 2218 may be flexed outward to allow for an outward protruding surface of the lockout arm 2218 to be positioned in (e.g., snapped into) the lockout retention recess and biased radially inward.

The base 1550 includes retention arms that releasably engage with a base retention surface of the cuff 1520. A configuration of the retention arms with the base retention surface of the cuff 1520 and with the housing body 2002 prevents the base 1550 from separating from its engagement with the cuff 1520 and the housing body 2002 when the applicator 1500 is in the collapsed configuration. For example, the base 1550 may include a retention arm 2220 that extends from the proximal surface 2210 in an upward projecting configuration. When the applicator 1500 is in the collapsed configuration, the retention arm 2220 may be sandwiched between an outer side surface of the cuff 1520 and an inner side surface of the housing body 2002. An inward protruding surface of the retention arm 2220 may be engaged with the base retention surface 1730 of the cuff 1520. This engaged or locked configuration prevents separation between the base 1550 and the housing body 2002. During release of the base 1550, the base 1550 is being pushed downward with the cuff 1520, and the engagement between the retention arm 2220 and the base retention surface 1730 is maintained. At the point at which the engagement point is beyond the housing body 2002, the base 1550 is in a configuration in which the base 1550 may be removed by a user-applied removal force.

In some variations, the base 1550 may include more than one retention arm 2220, and the releasable retention arms 2220 may be circumferentially distributed in an equal or unequal manner around the proximal surface 2210. For example, as shown in FIG. 22A, the base 1550 includes four releasable retention arms 2220 distributed around the proximal surface 2210.

In some variations, a length of the lockout arm 2218 is greater than a length of the retention arm 2220. In some variations, a length of the retention arm 2220 is greater than a length of the lockout arm 2218. In some variations, a length of the lockout arm 2218 is equal to or about equal to a length of the retention arm 2220.

FIG. 22K depicts, in a top perspective view, aspects of the base 1550 of the applicator engaged with the cuff 1520. As shown, cuff 1520 includes the bottom flange 1732 with the increased surface area and the cutouts 1734 formed therethrough for accommodating arms (e.g., lockout arms 2218 and retention arms 220) of the base 1550.

FIGS. 23A-23O depict, in cross-sectional and close-up views, views of the applicator 1500 in assembled form according to variations described herein. FIGS. 23A-23F illustrate the applicator 1500 in a collapsed configuration. FIGS. 23G-23K illustrate the applicator 1500 during the process of releasing the base 1550 from engagement with the housing body 2002, transitioning the applicator 1500 from the collapsed configuration to the extended configuration. FIGS. 23L-23O illustrate, sequentially, the applicator 1500 moving from the extend configuration, in which the analyte monitoring device 110 is ready to be released, to the released configuration, in which the analyte monitoring device 110 is released from the applicator 1500. The analyte monitoring device 110 is shown in some views in FIGS. 23A-23O. Where details of the analyte monitoring device 110 are not necessary for the particular aspect being illustrated, the analyte monitoring device 110 may be omitted from the view. The microneedle enclosure 500 is shown in some views in FIGS. 23A-23O but is omitted from other views where the details of the microneedle enclosure 500 are not necessary for the particular aspect being illustrated.

With reference to FIGS. 23A-23F, the applicator 1500 is depicted in the collapsed configuration in which the components are locked (e.g., fixed) with respect to one another, and the analyte monitoring device 110 cannot be deployed.

In the collapsed configuration, the friction ring 1530 is collapsed within the cuff 1520, and the locking member 1560 is engaged with the cuff 1520. The second biasing element 1584 is positioned in the inner cavity 1632 defined by the shuttle shaft 1630 and is compressed to a first compression of the second biasing element 1584. The first biasing element 1582 is positioned within the cavity 2010 defined by the housing body 2002 and is compressed to a first compression of the first biasing element 1582. The shelf 1634 (e.g., the distal surface 1636) of the shuttle shaft 1630 is positioned proximal to the shoulder 2020 (e.g., with a clearance therebetween) of the downward extending finger 2016. The analyte monitoring device 110 is retained by the shuttle 1540.

In the collapsed configuration of the applicator 1500, the locking tabs 528 of the microneedle enclosure and the connector features 336 of the base plate 330 are disengaged. The sterile seal provided by the microneedle enclosure 500 is maintained by the opposing forces of the microneedle enclosure biasing element 530 and that of the first and second biasing elements 1582, 1584. Additionally, as the analyte monitoring device 110 is maintained between these opposing forces, the analyte monitoring device 110 is able to move with respect to the components of the applicator 1500. This movement allows the bumper 512 (e.g., the seal around the capsule 510) to be reliably held in contact with the analyte monitoring device, thereby maintaining sterility through vibrations, temperature changes, and other environmental situations.

As shown in FIG. 23A, the microneedle enclosure 500 is contained in the base 1550 and connected to the analyte monitoring device 110. The outer engagement features 526 of the microneedle enclosure 500 are secured beneath the chamfered or beveled upper edge of the flexible finger 2216 formed in the base 1550, allowing the microneedle enclosure 500 to be removed upon the release of the base 1550 from the housing body 2002. As shown in FIG. 23A, in the collapsed configuration, the shuttle 1540 and a distal edge of the cuff 1520 are in a proximal most position and are positioned proximal of the distal opening 2004 of the housing body 2002. In some variations of the collapsed configuration, the shuttle 1540 and a distal edge of the cuff 1520 are positioned proximal of the distal opening 2004 of the housing body 2002.

With reference to FIG. 23B, a detailed view of the locking members 1560 fitted within the retention walls 1712 formed on the outer sidewalls of the cuff 1520 is provided. The close-up view depicts the upper edge 2116 of the locking member 1560 engaged beneath the top edge of the retention lip 1714 of the retention wall 1712. This engagement between the locking members 1560 and the cuff 1520 prevents downward movement of the cuff 1520 with respect to the housing body 2002. As the friction ring 1530 is collapsed within the cuff 1520 when the applicator 1500 is in the collapsed configuration, the engagement and locking features of the cuff 1520 and the friction ring 1530 are not connected to one another.

The friction ring 1530 arrangement within the cuff 1520 prevents firing of the shuttle 1540 in the collapsed configuration, as shown in FIGS. 23C and 23D. This is because the friction ring 1530 prevents vertical displacement of the shuttle 1540 toward the distal opening 2004 when the friction ring 1530 is collapsed within the cuff 1520 and sandwiched between the cuff 1520 and the mount 2014 of the housing 1510; the downward extending finger 2016 of the mount cannot be flexed a sufficient amount to allow the vertical displacement of the shuttle 1540 by virtue of the position of the friction ring 1530. In other words, when the applicator 1500 is in the collapsed configuration, the shuttle 1540 is locked in place due to the concentric arrangement of the mount 2014, the friction ring 1530, and the cuff 1520.

FIGS. 23E and 23F depict aspects of the base 1550 engaged with the housing body 2002 and the cuff 1520 when the applicator 1500 is in the collapsed configuration. Upper edges of the base sidewalls 2212 are fitted into corresponding recesses formed in a distal edge of the housing body 2002 so that the base sidewalls 2212 are surrounded by the housing body 2002. The lockout arm 2218 of the base 1550 is fitted into a lockout retention recess formed in the sidewalls of the housing body 2002, as shown in the close-up view of FIG. 23E. As shown in the close-up view of FIG. 23F, the retention arm 2220 of the base 1550 is sandwiched between an outer side surface of the cuff 1520 and an inner side surface of the housing body 2002. For example, the inward protruding surface of the retention arm 2220 is engaged with the base retention surface 1730 of the cuff 1520 to prevent separation between the base 1550 and the housing body 2002.

With reference to FIGS. 23G-23K, aspects relating to release of the base 1550 from engagement with the housing body 2002, transitioning the applicator 1500 from the collapsed configuration to the extended configuration, are illustrated. Upon depression of the locking members 1560 (e.g., when the depressible members 2110 are pressed inward to move from a first configuration to a second configuration), each locking member 1560 pivots at the interface between the pivot bar 2112 of the locking member 1560 and the pivot surface 2024 of the housing body 2002. The pivoting movement causes the pivoting member 2114 of the locking member 1560 to move outward in the second side opening 2026, and the upper edge 2116 of the pivoting member 2114 is no longer locked under the top edge of the retention lip 1714 of the cuff 1520. Thus, upon depression of the locking members 1560, vertical movement of the cuff 1520 is no longer impeded due to the outward movement of the pivoting member 2114 away from the top edge of the retention lips 1714. In the extended configuration of the applicator 1500, the distal edge of the cuff 1520 is in a distal most position and the shuttle 1540 is in an intermediate position. In some variations of the extended configuration, the distal edge of the cuff 1520 is positioned distal of the distal opening 2004 of the housing body 2002, and the shuttle 1540 is positioned proximal of the distal opening 2004 of the housing body 2002. In some variations of the extended configuration, the distal edge of the cuff 1520 is positioned distal of the distal opening 2004 of the housing body 2002, and the shuttle 1540 is positioned proximal of the distal opening 2004 of the housing body 2002.

FIG. 23G illustrates the disengagement between the cuff 1520 and the locking members 1560. The release of the locking members 1560 from the engagement with the top edge of the retention lip 1714 of the cuff 1520 allows the cuff 1520 to vertically translate in a downward direction, as shown in FIG. 23G. The downward movement of the cuff 1520 pushes the base 1550 (e.g., at the proximal surface 2210) in the same downward direction. The close-up view in FIG. 23G depicts the release of the locking members 1560 from the engagement with the top edge of the retention lip 1714 of the cuff 1520, and the outward movement of the pivoting member 2114 being limited by the flexible contact member 2028 of the housing body 2002.

FIG. 23H depicts details of the engagement between the cuff 1520 and the friction ring 1530. During the downward movement of the cuff 1520, the cuff 1520 moves axially such that the friction ring 1530 extends out of the top surface of and locks into the cuff 1520. More specifically, the cuff 1520 moves axially downward with respect to the friction ring 1530 along the length of the flexible tab 1812. The flexible tab 1812 is flexed or pushed inward until the cuff 1520 passes the distal end of the flexible tab 1812, at which point the flexible tab 1812 snaps onto the sill 1724 (and is held between the pair of guide walls 1726, not shown in FIG. 23H). Progress of the cuff 1520 further downward is stopped by the protruding circumferential edge 1816 of the friction ring 1530, which provides an interfacing or engagement point for the underside 1728 of the cuff 1520. The engagement between the cuff 1520 and the friction ring 1530 prevents the cuff 1520 from moving distally relative to the distal opening 2004 of the housing body 2002.

FIG. 23I depicts details of the microneedle enclosure 500 removed with the base 1550. The microneedle enclosure 500 is removed with the base 1550 due to the secured engagement of the outer engagement features 526 of the clamp 520 with the upper edge of the flexible finger 2216 formed in the base 1550. The close-up view of FIG. 23I depicts the interface between the extension surface (of the outer engagement features 526) and the flexible finger 2216. As shown and described herein, the flexible finger 2216 flexes outward upon pressure to allow the extension surface to snap-fit and be held beneath the chamfered or beveled upper edge of the flexible finger 2216. The axial displacement of the cuff 1520 pushes the base 1550, and the microneedle enclosure 500, secured beneath the flexible finger 2216, moves with the base 1550. This movement of the microneedle enclosure 500 breaks the sterile seal between the capsule 510 and the microneedle array 140. Thus, in the extended configuration, the microneedle enclosure 500 does not enclose the microneedle array 140.

FIGS. 23J and 23K depict aspects of the arms of the base 1550 as the base 1550 is pushed downward during the transition of the applicator 1500 to the extended configuration. FIG. 23J illustrates that the lockout arm 2218 is disengaged from the lockout retention recess of the housing body 2002. As shown in the close-up view of FIG. 23J, when the lockout arm 2218 is pushed beyond the lockout retention recess, the user is prevented from reattaching the base 1550 to the housing body 2002 due to the walled surface beneath the lockout retention recess blocking upward, axial movement of the lockout arm 2218. FIG. 23K illustrates that as the base 1550 is pushed downward with the cuff 1520, the engagement between the retention arm 2220 and the base retention surface 1730 is maintained. At the point at which the engagement point is beyond the housing body 2002, the base 1550 is in a configuration in which the base 1550 may be removed by a user-applied removal force. For example, the user may grasp the base 1550 and pull off the base 1550, with the force of the pull overcoming the engagement between the retention arm 2220 and the base retention surface 1730.

With reference to FIGS. 23L-23O, aspects relating to the applicator 1500 moving from the extended configuration to the released configuration are shown. In the extended configuration, the components of the applicator 1500 are arranged and configured such that the analyte monitoring device 110 may be deployed (e.g., released) from the applicator 1500 in response to actuation of the housing 1510. The base 1550 is removed, and the shuttle 1540 is moved into firing position in the extended configuration. In the released configuration, the analyte monitoring device 110 is released from the applicator 1500 and inserted in the skin of the user.

During actuation of the housing 1510, the friction ring 1530 and the cuff 1520 act as a single component and function to cause disengagement of the analyte monitoring device 110 from the shuttle 1540. The shuttle 1540 is axially aligned and nested within the friction ring 1530. FIG. 23L depicts details of the shuttle 1540 positioned in the extended configuration. In the extended configuration, the mount 2014 is releasably engaged with the friction ring 1530, and the mount 2014 is releasably engaged with the shuttle 1540. In this configuration, the shuttle 1540 is moved into a position in which the shoulder 2020 of the downward extending finger 2016 is engaged with the shelf 1634 of the shuttle shaft 1630, and the ledge 2018 of the downward extending finger 2016 is engaged with the projection 1820 of the friction ring 1530, as shown in the close-up view of FIG. 23L.

FIGS. 23M, 23N, and 23O illustrate details, in first, second, and third cross-sectional views, respectively, of the applicator 1500 in the released configuration. In particular, FIGS. 23M, 23N, and 23O depict arrangement of the applicator components when the applicator 1500 is in the released configuration in which the analyte monitoring device 110 is deployed from the shuttle 1540. As shown in FIGS. 23M, 23N, and 23O, the second biasing element 1584 is less compressed as the energy stored in the second biasing element 1584 when loaded has been transferred to the shuttle 1540 to drive the analyte monitoring device 110 with a suitable application force. In the released configuration, the analyte monitoring device 110 is released from the shuttle 1540. In the released configuration, the distal edge of the cuff 1520 is in an intermediate position, and the shuttle 1540 is in a distal most position. In some variations of the released configuration, the distal edge of the cuff 1520 and the shuttle 1540 are each positioned distal of the distal opening 2004 of the housing body 2002. In some variations of the released configuration, the distal edge of the cuff 1520 is positioned distal of the distal opening 2004 of the housing body 2002, and the shuttle 1540 is positioned distal of the distal opening 2004 of the housing body 2002.

FIG. 23M depicts details of the disengagement between the friction ring 1530 and the housing body 2002. More specifically, as shown in the close-up view of FIG. 23M, as the housing body 2002 is actuated (e.g., pushed downward), the projection 1820 of the friction ring 1530 is decoupled from the ledge 2018 of the housing 1510. As the downward movement causes the decoupling between the friction ring 1530 and the downward extending finger 2016 on which the ledge 2018 is formed, a release of the releasable coupling features between the shuttle 1540 and the downward extending finger 2016 occurs. More specifically, downward movement of the shuttle 1540 causes the shelf 1634 to push past the shoulder 2020, (e.g., the downward extending finger 2016 bends away from the shuttle 1540). This bending or flexing is possible because the downward extending finger 2016 is no longer inhibited or blocked by the projection 1820. Additionally, during actuation of the housing body 2002, as the housing body 2002 is moved downward with respect to the cuff 1520 and the friction ring 1530, the ring retention slot formed in the outward facing sidewall of the downward extending finger 2016, slides in a distal direction along the projection 1820.

FIG. 23N and FIG. 23O depict details of the tracks 1716 formed along the cuff 1520 through which the one or more tracking projections 1616 on the shuttle 1540 travel during the actuation of the housing body 2002. Each track 1716 culminates at a distal end with the shuttle flexion surface 1718 that acts as a stop for the axial movement of the shuttle 1540 to aid in the radially outward flexing of the flexible leaves 1612 of the shuttle 1540, as shown in the close-up view of FIG. 23O. With the radially outward flexing of the flexible leaves 1612, the analyte monitoring device 110 is released from the shuttle 1540. The second biasing element 1584 provides the external pressure for the radially outward flexing as the second biasing element 1584 is compressed within the inner cavity 1632 of the shuttle 1540. The shuttle flexion surfaces 1718 of the cuff 1520 stop the axial movement of the shuttle 1540, and the energy stored in the second biasing element 1584 is transferred to the shuttle 1540 to thereby radially flex outward the flexible leaves 1612, driving out the analyte monitoring device 110 with a suitable application force (e.g., for suitable insertion of the microneedle array 140 into the skin of the user). The adhesive layers (e.g., the outer adhesive layer 344) adhere the analyte monitoring device 110 to the skin of the user while the microneedle array 140 is inserted into the skin of the user. The analyte monitoring device 110 may be removed with sufficient force applied to overcome the adhesive layers.

FIG. 24 illustrates a process flowchart P2400 including the process of moving the applicator 1500 from a collapsed configuration to an extended configuration to move the analyte monitoring device 110 in a position to be released. The process flows sequentially along the lefthand side of the process flowchart from S2410 to S2420 to S2430 to S2440 and to S2450. The aspects connected by dashed lines and in dashed boxes depict different states and configurations of the applicator components following each of the process steps. The order in which the different states and configurations occur may vary and is not limited to that shown in FIG. 24.

At S2410, the locking member 1560 is depressed (e.g., moved from the first configuration to the second configuration). The depression of the locking member 1560 includes the locking member 1560 becoming disengaged from the cuff 1520.

At S2420, the cuff 1520 undergoes axial displacement toward the distal end 2004 of the housing body 2002. This axial displacement of the cuff 1520 causes the engagement between the cuff 1520 and the friction ring 1530. In particular, the flexible tab of the friction ring 1530 snaps onto the sill of the cuff 1520, and the protruding edge of the friction ring 1530 engages the underside of the proximal end of the cuff 1520. Moreover, the first biasing element 1582 moves from its first state of compression to a first biasing element second state of compression, less than the first state of compression.

At S2430, the base 1550 undergoes axial displacement as the cuff 1520 pushes against a proximal surface 2210 of the base. The axial displacement of the base 1550 causes the sterile seal provided by the microneedle enclosure 500 to be broken. The axial displacement of the base 1550 further causes the lockout arm of the base 1550 to disengage from the lockout recess of the housing body 2002.

At S2440, the shuttle 1540 drops into firing position. In the firing position, the shuttle 1540 is configured to fire or advance the analyte monitoring device 110 for insertion of the analyte monitoring device 110 into the skin of the user. As the shuttle 1540 drops into firing position, the shoulder 2020 of the downward extending finger engages the shelf 1634 of the shuttle shaft. The second biasing element 1584 moves from its first state of compression to a second biasing element second state of compression, which is slightly less than its first state of compression due to the axial displacement of the shuttle 1540 into the firing position.

At S2450, the base 1550 is pulled off. The base 1550 may be pulled off by the user applying an appropriate force. At this point, the applicator 1500 is in the extended configuration.

FIG. 25 illustrates a process flowchart P2500 including the process of moving the applicator 1500 from an extended configuration to a released configuration to insert the analyte monitoring device. The process flows sequentially along the lefthand side of the process flowchart from S2510 to S2520 to S2530 and to S2540. The aspects connected by dashed lines and in dashed boxes depict different states and configurations of the applicator components following each of the process steps. The order in which the different states and configurations occur may vary and is not limited to that shown in FIG. 25.

At S2510, the applicator 1500, in the extended configuration, is placed on the user. The distal end of the cuff 1520 is in contact with human skin at the insertion site at which the applicator 1500 is placed.

At S2520, the housing body 2002 is actuated (e.g., pushed downward for axial displacement). The actuation causes a clearance or decoupling between the projection 1820 and the friction ring 1530 and the ledge 2018 formed on the downward extending finger 2016. The decoupling is caused by the axial displacement of the downward extending finger 2016 due to the connection within the cavity 2010 of the housing body 2002. The shelf 1634 of the shuttle shaft pushes past the shoulder 2020 of the downward extending finger. The actuation further causes the first biasing element 1582 to move to a first biasing element third state of compression, which is greater than its second state of compression. In addition to the movements and/or changes to the applicator components upon actuation, actuation also results in doming of the human skin within the area defined by the distal edge of the cuff 1520.

At S2530, the shuttle 1540 is axially displaced toward the distal opening 2004 of the housing body 2002. The second biasing element 1584 moves to a second biasing element third state of compression, which is less than its second state of compression. The axial displacement of the shuttle 1540 causes the microneedle array 140 is contact the human skin and be inserted at the insertion site. The continued axial displacement of the shuttle 1540 causes the adhesive to adhere to the human skin at the insertion site.

At S2540, the tracking projections on the shuttle 1540 engage the shuttle flexion surface of the cuff 1520. The engagement between the tracking projections and the shuttle flexion surface causes the flexible leaves of the shuttle 1540 to splay or flex radially outward, thereby releasing the analyte monitoring device.

FIGS. 26A and 26B depict, in cross-sectional and close-up views, aspects of a shuttle lockout mechanism. As shown, the shelf 1634 formed on the shuttle shaft 1630 includes the distal surface 1636 and the proximal surface 1638. The proximal surface 1638 of the shelf 1634 may be used, in some variations, as a shuttle lockout feature. FIG. 26A illustrates the applicator 1500 in the extended configuration in which the distal surface 1636 of the shelf 1634 of the shuttle shaft 1630 is engaged with the shoulder 2020 of the downward extending finger 2016 to control movement of the shuttle 1540 toward the distal opening 2004 of the housing body 2002.

FIG. 26B illustrates how the proximal surface 1638 of the shelf 1634 prevents axial movement of the shuttle 1540 toward a proximal end of the housing body 2002. The axial movement toward the proximal end is prevented after the disengagement of the distal surface 1636 of the shelf 1634 and the shuttle retention surface (e.g., the shoulder 2020). The proximal surface 1638 abuts against the distal end of the shoulder 2020, preventing the axial movement of the shuttle 1540 toward the proximal end of the housing body 2002. The distal end of the shuttle retention surface may be a flat or substantially flat surface to prevent the proximal surface 1638 from pushing past the shuttle retention surface.

As described above, an analyte monitoring device may include a housing. The housing may at least partially surround or enclose other components of the analyte monitoring device (e.g., electronic components), such as for protection of such components. For example, the housing may be configured to help prevent dust and moisture from entering the analyte monitoring device. In some variations, an adhesive layer may attach the housing to a surface (e.g., skin) of a user, while permitting a microneedle array to extend outwardly from the housing and into the skin of the user. Furthermore, in some variations the housing may generally include rounded edges or corners and/or be low-profile so as to be atraumatic and reduce interference with clothing, etc. worn by the user.

For example, as shown in FIGS. 27A-27E, an example variation of an analyte monitoring device 300 may include a housing 310 configured to at least partially surround other various internal components of the device 300, and a microneedle array 331 that extends outwardly from a skin-facing surface (e.g., underside) of the housing 310.

The housing 310 may, for example, include one or more rigid or semi-rigid protective shell components that may couple together via suitable fasteners (e.g., mechanical fasteners), mechanically interlocking or mating features, and/or an engineering fit. For example, as shown in FIG. 27E, the housing may include a housing cover 310a and a housing base 310b, where the cover 310a and the base 310b may be secured together with one or more threaded fasteners (e.g., fasteners that engage threaded holes in the upper and/or lower housing portions). The cover 310a and the base 310b may include radiused edges and corners, and/or other atraumatic features. When coupled together, the cover 310a and the base 310b may form an internal volume that houses other internal components such as a device printed circuit board 351 (PCB), a sensor assembly 321, and/or other components such as a gasket 312. For example, the internal components arranged in the internal volume may be arranged in a compact, low profile stack-up as shown in FIG. 27E. While FIG. 27E illustrates a housing 310 include multiple housing components, in some variations the housing 310 may include a single component defining the internal volume for housing internal device components. In some embodiments, the housing 310 may be filled with a suitable potting compound (e.g., epoxy) to reduce deleterious environmental effects such as temperature, humidity, pressure, and light.

Furthermore, the analyte monitoring device 300 may include an adhesive layer 340 configured to attach the housing 310 to a surface (e.g., skin) of a user. The adhesive layer 340 may, for example, be attached to a skin-facing side of the housing 310 via a double-sided adhesive liner 345 as shown in in the variation depicted in FIG. 27D. Alternatively, the adhesive layer 340 may be coupled directly to the skin-facing side of the housing 310 with one or more suitable fasteners (e.g., adhesive, mechanical fasteners, etc.). The adhesive layer 340 may be protected by a release liner that the user removes prior to skin application, in order to expose the adhesive. In some variations, the analyte monitoring device may include 3M® 1504XL™ double-sided adhesive and 3M® 4076™ skin-facing adhesive, available from 3M®. These materials are selected for their: breathability, wearability, mean water vapor transmission rate (MWVTR), biocompatibility, compatibility with sensor sterilization method/strategy, appearance, durability, tackiness, and ability to retain said tackiness for the duration of sensor wear.

The adhesive layer 340 may, in some variations, have a perimeter that extends farther than the perimeter or periphery of the housing 310 (e.g., which may increase surface area for attachment and increase stability of retention, or the attachment to the skin of a user). Furthermore, in some variations, the adhesive layer 340 may include an opening 342 that permits passage of the outwardly extending microneedle array 331. The opening 342 may closely circumscribe the shape of the microneedle array 331 as shown in FIG. 27C (e.g., square opening closely corresponding in size and shape to a square microneedle array), or have another suitable size and shape that is larger than the footprint area of the microneedle array (e.g., circular opening larger than a square microneedle array).

Figure 28A:
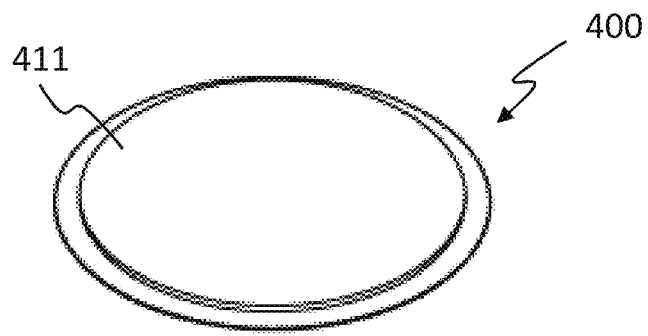
Figure 28B:
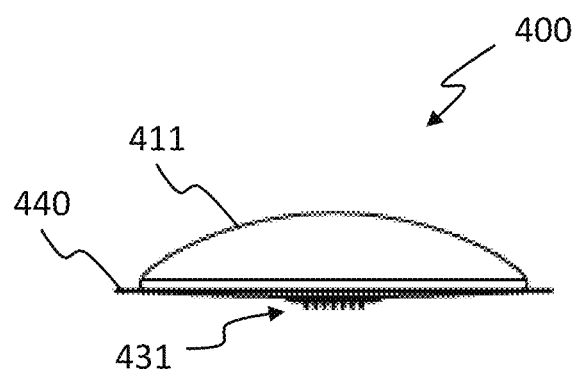
Figure 28C:
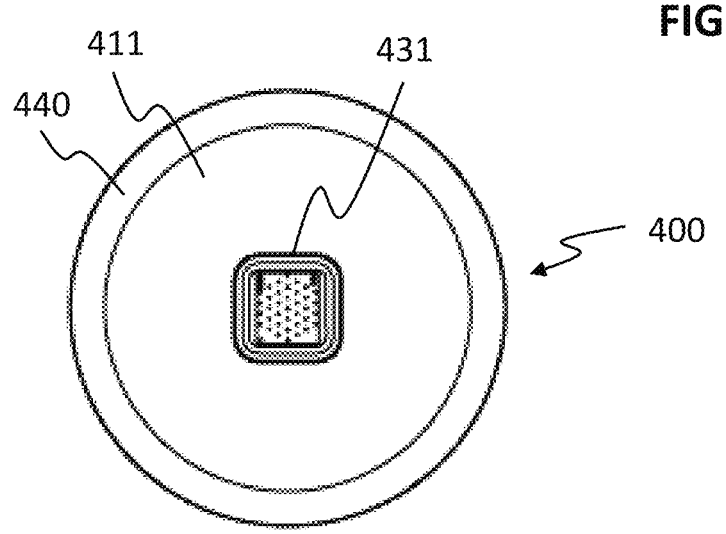

Although the housing 310 depicted in FIGS. 27A-27E is hexagonal shaped and generally prismatic, it should be understood that in other variations, the housing 310 may have any suitable shape. For example, in other variations the housing may be generally prismatic and have a base that has an elliptical (e.g., circular), triangular, rectangular, pentagonal, or other suitable shape. As another example, FIGS. 28A-28C illustrate an example variation of an analyte monitoring device 400 including a dome-shaped housing 411. While the dome-shaped housing 411 depicted in FIGS. 28A-28C is generally circular, in other variations the dome-shaped housing may have a base that has another suitable elliptical shape or polygonal shape.

Figure 28D:
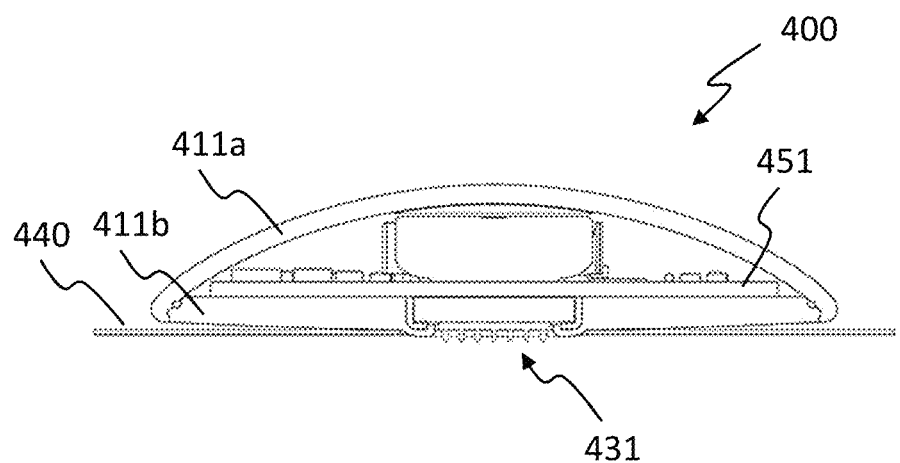
Figure 28E:
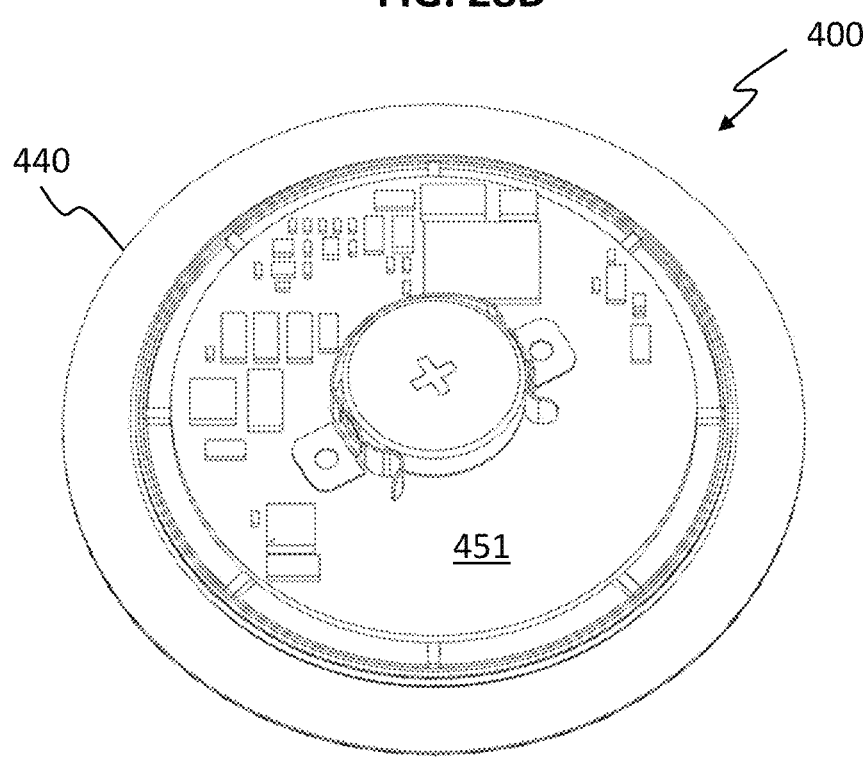

Similar to the housing 310, the housing 411 may include an internal volume configured to at least partially surround other components of the analyte monitoring device 400. For example, as shown in the cross-sectional view of FIG. 28D, the housing 411 may include a domed cover 411a coupled to a base 411b, so as to form an internal volume within which a device PCB 451 and a sensor assembly with a microneedle array 431 may be arranged. Additionally, the housing 411 may be configured to couple to a surface via an adhesive layer 440, and the microneedle array 431 may extend outwardly from the housing and beyond the adhesive layer 440. Furthermore, as shown in FIGS. 28D and 28E, the adhesive layer 440 may extend beyond the perimeter of the housing 411.

In some variations, an analyte monitoring system may provide user status, analyte monitoring device status, and/or other suitable information directly via a user interface (e.g., display, indicator lights, etc. as described below) on the analyte monitoring device. Thus, in contrast to analyte monitoring systems that may solely communicate information to a separate peripheral device (e.g., mobile phone, etc.) that in turn communicates the information to a user, in some variations such information may be directly provided by the analyte monitoring device. Advantageously, in some variations, such a user interface on the analyte monitoring device may reduce the need for a user to constantly maintain a separate peripheral device in order to monitor user status and/or analyte monitoring device status (which may be impractical due to cost, inconvenience, etc.). Additionally, the user interface on the analyte monitoring device may reduce risks associated with loss of communication between the analyte monitoring device and a separate peripheral device, such as a user having an inaccurate understanding of their current analyte levels (e.g., leading the user to assume their analyte levels are high when they are actually low, which could, for example, result in the user self-administering an inaccurate dose of drug or withholding a therapeutic intervention when it is medically necessary).

Additionally, the ability to communicate information to a user via the analyte monitoring device itself, independently of a separate peripheral device, may reduce or eliminate the need to maintain compatibility between the analyte monitoring device and separate peripheral devices as such peripheral devices are upgraded (e.g., replaced with new device models or other hardware, run new versions of operating systems or other software, etc.).

Accordingly, in some variations, the housing may include a user interface, such as an interface to provide information in a visual, audible, and/or tactile manner to provide information regarding user status and/or status of the analyte monitoring device, and/or other suitable information. Examples of user status that may be communicated via the user interface include information representative of analyte measurement in the user (e.g., below a predetermined target analyte measurement threshold or range, within a predetermined target analyte measurement range, above a predetermined target analyte measurement threshold or range, increase or decrease of analyte measurement over time, rate of change of analyte measurement, other information relating to trend of analyte measurements, other suitable alerts associated with analyte measurement, etc.). Examples of analyte monitoring device status that may be communicated via the user interface include device operation mode (e.g., associated with device warm-up state, analyte monitoring state, battery power status such as low battery, etc.), a device error state (e.g., operational error, pressure-induced sensing attenuation, fault, failure mode, etc.), device power status, device life status (e.g., anticipated sensor end-of-life), status of connectivity between device and a mobile computing device, and/or the like.

FIG. 29 illustrates another example variation of a microneedle 900 having a generally columnar body portion. The microneedle 900 may be similar to microneedle 700 as described above, except as described below. For example, like the microneedle 700, the microneedle 900 may include a columnar body portion 912, and a tapered distal portion 914 terminating in an insulated distal apex 916. The microneedle 900 may further include an annular electrode 920 that includes a conductive material and is arranged on the tapered distal portion 914 at a location proximal to (or offset from or spaced apart from) the distal apex 916. Other elements of microneedle 900 have numbering similar to corresponding elements of microneedle 700.

However, compared to the microneedle 700, the microneedle 900 may have a sharper tip at the distal apex 916 and a modified insulating moat 913. For example, the distal apex 916 may have a sharper tip angle, such as between about 25 degrees and about 45 degrees, and an apex radius of less than about 100 nm, which provides a sharper microneedle profile that may penetrate skin with greater ease, lower velocity, less energy, and/or less trauma. Furthermore, in contrast to the insulating moat 713 (which extends through the substrate 702 and along the height of the microneedle body portion 712 as shown in FIG. 33A), the modified insulating moat 913 may extend only through the substrate 902 such that the sandwich structure filling the trench (e.g., created by DRIE as described above) forms only the buried feature in the substrate. Although the sidewall of the microneedle 900 is shown in FIG. 29 as extending generally orthogonal to the substrate surface, it should be understood that because the modified insulating moat 913 need not extend the entire height of the microneedle body portion 712, in some variations the sidewall of the microneedle 900 may be angled at non-orthogonal angles relative to the substrate (e.g., the sidewall may have a slight positive taper of between about 1 degree to about 10 degrees, or between about 5 degrees and about 10 degrees).

In some variations, the rest of the microneedle surface 900 (aside from the annular electrode 920) may include an insulating material extending from substrate insulation 904. For example, a layer of an insulating material (e.g., $SiO_2$) may extend from a frontside surface of the substrate 902 to provide a body portion insulation 918, and may further extend up over a proximal edge of the electrode 920 as shown in FIG. 29. Another region of insulating material may similarly cover a distal edge of the electrode 920 and insulate the distal apex 916. Such region of insulating material and/or modified insulating moat 913 may help prevent electrical contact between the conductive core 940 and the surrounding substrate 902. Accordingly, like the microneedle 700, the microneedle 900 may maintain electrical isolation for individual addressability within a microneedle array. In some variations, the process to form microneedle 900 may result in higher yield and/or provide lower production cost compared to the process to form microneedle 700.

The microneedle 900 may have any suitable dimensions. By way of illustration, the microneedle 900 may, in some variations, include a height of between about 400 μm and about 600 μm, or about 500 μm. In some variations, the tapered distal portion 914 may have a tip angle of between about 25 degrees and about 45 degrees, with a tip radius of less than about 100 nm. Furthermore, the microneedle may have a shaft diameter of between about 160 μm and about 200 μm. FIG. 30 illustrates additional various dimensions of an example variation of a columnar microneedle with a tapered distal portion and annular electrode, similar to microneedle 900 described above.

While FIGS. 31A-31C illustrate example variations of microneedle array configurations, it should be understood that these figures are not limiting and other microneedle configurations (including different numbers and/or distributions of working electrodes, counter electrodes, and reference electrodes, and different numbers and/or distributions of active electrodes and inactive electrodes, etc.) may be suitable in other variations of microneedle arrays.

As shown in the schematic of FIG. 2A of an analyte monitoring device 110, the electronics system 120 may be integrated within the housing 112, such that the electronics system 120 may be combined with sensing elements (e.g., microneedle array) as part of a single unit, in contrast to traditional CGM systems, which typically incorporate components in multiple physically distinct units. Further details of an example variation of an electronics system 120 are described below.

In some variations, the analyte monitoring device may include one or more PCBs. For example, the analyte monitoring device may include at least one PCB in the sensor assembly 321 that includes the microneedle array, and at least one device PCB 351 as shown in FIG. 27E.

For example, as shown in FIGS. 27F-27I, a sensor assembly 321 may include a sensor standoff PCB 322 coupled to a connecting PCB 324. The microneedle array 331 may be attached to the sensor standoff PCB 322 (e.g., FR-4, PTFE, Rogers 4350B), such as through a soldering process combined with an epoxy underfill for mechanical strength. In some variations, an epoxy skirt may be deposited along the edges of the silicon microneedle array 331 to relieve the sharp edges from the silicon dicing processes described above. The epoxy may also provide a transition from the edge of the silicon substrate of the microneedle array silicon to the edge of the PCB 322. Alternatively, this epoxy may be replaced or supplemented by a rubber gasket or the like.

As shown in FIG. 27J, the sensor standoff PCB 322 may function as a standoff that at least in part determines the desired distance to which the microneedle array 331 protrudes from the housing 310. Accordingly, the standoff height of the sensor standoff PCB 322 may be selected to help ensure that the microneedle array 331 is inserted properly into a user's skin. During needle insertion, the bottom surface of the housing 310 will act as a stop for needle insertion. If the sensor standoff PCB 322 has a reduced height and its lower surface is flush or nearly flush with the bottom surface of the housing, then the housing 310 may prevent the microneedle array 331 from being fully inserted into the skin. However, increasing the standoff height may lead to more pressure of the microneedle array on the skin during microneedle insertion, which can lead to dermatological irritation and/or erythema (redness of the skin).

The sensor standoff PCB 322 may be secured to the housing 310 and/or secured within the stack up inside the housing, such as with suitable fasteners or the like. For example, as shown in FIGS. 27H-27J, the sensor standoff PCB 322 (with the microneedle array 331) may be coupled to a first side of the connecting PCB 324, while a second opposite side of the connecting PCB 324 may in turn be coupled to an interposer PCB connector 326. As shown in FIG. 27J, the interposer PCB connector 326 may be communicatively coupled to the device PCB 351, such as for signal processing as described below. Accordingly, signals from the microneedle array 331 may be communicated through the sensor standoff PCB 322 and to the device PCB via the sensor standoff PCB 322, connecting PCB 324, and interposer PCB connector 326. However, in some variations the analyte monitoring device may include fewer PCBs. For example, in some variations, the sensor assembly 321 may omit the sensor standoff PCB 322, such that the microneedle array 331 may directly communicate electrically to the connecting PCB 324 (or directly to the device PCB 351).

Additionally or alternatively, in some variations at least one of the PCBs in the sensor assembly 321 may include or be coupled to one or more additional sensors in combination with the microneedle array 331. For example, the sensor assembly 321 may include a temperature sensor (e.g., thermistor, resistance temperature detector, thermocouple, bandgap reference, non-contact temperature sensor, etc.). In some variations, temperature measurement may additionally or alternatively be performed by one or more analyte-insensitive electrodes in the microneedle array.

In some variations, the sensor standoff PCB 322 may be between about 0.05 inches and about 0.15 inches, or between about 0.093 inches and about 0.127 inches in thickness. The sensor standoff PCB 322, in some variations, may include one or a plurality of conductive through-substrate vias configured to route electrical signals from an anterior surface of the PCB to a posterior surface of the PCB. In some variations, the sensor standoff PCB 322 may comprise a semiconductor (e.g., silicon) with conductive through-substrate vias configured to route electrical signals from an anterior surface of the semiconductor to a posterior surface of the semiconductor. In yet other variations, the microneedle array 331 may be mounted directly to the PCB 324, without the sensor standoff PCB 322.

In some variations, the electronics system of the analyte monitoring device may include an analog front end. The analog front end may include sensor circuitry (e.g., sensor circuitry 124 as shown in FIG. 2A) that converts analog current measurements to digital values that can be processed by the microcontroller. The analog front end may, for example, include a programmable analog front end that is suitable for use with electrochemical sensors. For example, the analog front end may include a MAX30131, MAX30132, or MAX30134 component (which have 1, 2, and 4 channel, respectively), available from Maxim Integrated (San Jose, Calif.), which are ultra-low power programmable analog front ends for use with electrochemical sensors. The analog front end may also include an AD5940 or AD5941 component, available from Analog Devices (Norwood, Mass.), which are high precision, impedance and electrochemical front ends. Similarly, the analog front end may also include an LMP91000, available from Texas Instruments (Dallas, Tex.), which is a configurable analog front end potentiostat for low-power chemical sensing applications. The analog front end may provide biasing and a complete measurement path, including the analog to digital converters (ADCs). Ultra-low power may allow for the continuous biasing of the sensor to maintain accuracy and fast response when measurement is required for an extended duration (e.g. 7 days) using a body-worn, battery-operated device.

In some variations, the analog front end device may be compatible with both two and three terminal electrochemical sensors, such as to enable both DC current measurement, AC current measurement, and electrochemical impedance spectroscopy (EIS) measurement capabilities. Furthermore, the analog front end may include an internal temperature sensor and programmable voltage reference, support external temperature monitoring and an external reference source and integrate voltage monitoring of bias and supply voltages for safety and compliance.

In some variations, the analog front end may include a multi-channel potentiostat to multiplex sensor inputs and handle multiple signal channels. For example, the analog front end may include a multi-channel potentiostat such as that described in U.S. Pat. No. 9,933,387, which is incorporated herein in its entirety by this reference.

In some variations, the analog front end and peripheral electronics may be integrated into an application-specific integrated circuit (ASIC), which may help reduce cost, for example. This integrated solution may include the microcontroller described below, in some variations.

In some variations, the electronics system of the analyte monitoring device may include at least one microcontroller (e.g., controller 122 as shown in FIG. 2A). The microcontroller may include, for example, a processor with integrated flash memory. In some variations, the microcontroller in the analyte monitoring device may be configured to perform analysis to correlate sensor signals to an analyte measurement (e.g., glucose measurement). For example, the microcontroller may execute a programmed routine in firmware to interpret the digital signal (e.g., from the analog front end), perform any relevant algorithms and/or other analysis, and route processed data to and/or from the communication module. Keeping the analysis on-board the analyte monitoring device may, for example, enable the analyte monitoring device to broadcast analyte measurement(s) to multiple devices (e.g., mobile computing devices such as a smartphone or smartwatch, therapeutic delivery systems such as insulin pens or pumps, etc.) in parallel, while ensuring that each connected device has the same information.

In some variations, the electronics system of the analyte monitoring device may include at least one communication module (e.g., communication module 126 as shown in FIG. 2A), such as a wireless communication module to communicate with one or more devices. For example, the communication module may include a wireless transceiver that is integrated into the microcontroller device. However, the electronics system may additionally or alternatively include a communication module that is separate from the microcontroller device. In some variations, the communication module may communicate via wireless network (e.g., through Bluetooth, NFC, WiFi, RFID, or any type of data transmission that is not connected by cables). For example, devices may directly communicate with each other in pairwise connection (1:1 relationship, i.e. unicasting), or in a hub-spoke or broadcasting connection ("one to many" or 1:m relationship, i.e. multicasting). As another example, the devices may communicate with each other through mesh networking connections (e.g., "many to many", or m:m relationships, or ad-hoc), such as through Bluetooth mesh networking. Wireless communication may use any of a plurality of communication standards, protocols, and technologies, including but not limited to, Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (WiFi) (e.g., IEEE 802.11a, IEEE 802.11b, IEEE 802.11g, IEEE 802.11n, and the like), or any other suitable communication protocol. Some wireless network deployments may combine networks from multiple cellular networks or use a mix of cellular, Wi-Fi, and satellite communication. In an example variation, the communication module may include a wireless transceiver integrated into the microcontroller and including a Bluetooth Low Energy compatible radio that complies with the Bluetooth Special Interest Group 5.0 specification.

The communication module may further include or be coupled to one or more antennas (e.g., antenna 128 as shown in FIG. 2A). For example, the electronics system may include a chip antenna mounted on the PCB, or an antenna implemented directly onto the PCB, which may provide better range while reducing cost and complexity. In some variations, a user wearing the analyte monitoring device 110 may function as an antenna (e.g., antenna 128). For example, the antenna input/output 128 of the communication module 126 may be electrically connected to a single microneedle or plurality of microneedles, which are inserted into the wearer's skin (e.g., similar to microneedle array 140 shown in FIG. 2B). This may increase the effective cross-sectional area of the antenna, provide for an adequate impedance match between the antenna input/output of the communication module and free space, and/or help improve operational metrics such as antenna gain, antenna diversity, omni-directionality, and communication module receiver sensitivity/transmitter efficiency.

Devices can come in and out of range from the communication module to connect and reconnect so that the user is able to seamlessly connect and transfer information between devices. In some variations, the microcontroller on each analyte monitoring device may have a unique serial number, which enables tracking of specific analyte monitoring devices during production and/or field use.

As described above, in some variations, the analyte monitoring device may include one or more sensors in addition the microneedle array. For example, the analyte monitoring device may include one or more temperature sensors configured to measure skin temperature, thereby enabling temperature compensation for the analyte sensor(s). For example, in some variations, a temperature sensor (e.g., thermistor, RTD, semiconductor junction, bimetallic sensor, thermopile sensor) may be coupled to the device PCB within the housing such that the temperature sensor is arranged near a skin-facing portion or bottom portion of the housing 112. The housing may be thinned to reduce thermal resistance and improve heat transfer and hence measurement accuracy. Additionally or alternatively, a thermally conductive material may thermally couple a surface-mount temperature sensor to the user's skin. In variations in which the temperature sensor is coupled to the device PCB near the microneedle array die substrate, the thermally conductive material may, for example, be molded as a skirt to relieve the sharp edges of the die and wrap along the edges of the die and along the surface of the main PCB.

In some variations, the temperature sensor may be employed to develop a glucose interpolation characteristic based on measured current and an a priori sensitivity (e.g., nA/mM or pA/mg/dL). In the temperature-invariant case, the electrical current characteristic can be modeled by the following relation: $y=m_G[G]$ where y is the measured current, $m_G$ is the glucose sensitivity, and [G] is the interpolated glucose concentration. In some cases, such as the incorporation of an analyte insensitive channel b, the background signal may be incorporated into the equation above: $y=m_G[G]+b$. Incorporating the measurements from a temperature sensor, the electrical current characteristic can be represented by the following relation: $y=m_G[G]+m_T[T]+b$ where $M_T$ is the temperature sensitivity (e.g., pA/° C.), T is the measured temperature, and b is the background signal (e.g., pA). In other operating scenarios, the electrical current characteristic is modeled by the following relation: $y=m_1[G][T]+b$ where $m_1$ is a weighting factor determined a priori. In other operating scenarios, the electrical current characteristic can be modeled as a convolution of temperature and glucose: $y=\{m_T[T]+m_2\}[G]+b$ where $m_2$ is a weighting factor determined a priori. In yet other operating scenarios, the electrical current characteristic is provided by the following relation: $y=\{m_G[G]+m_2\}[T][G]+b$. In yet other operating scenarios, the electrical current characteristic is given by the following nonlinear relation: $y=\{m_{G2}[G]^2+m_G[G]\}[T]+b$ where $m_{G2}$ is a nonlinear weighting factor. In yet other operating scenarios, the electrical current characteristic is given by the following Gaussian relation: $y=m_G[G]\exp\{-([T]-[T_{OPT}])^2/(2\sigma^2)\}+b$ where $T_{OPT}$ is the optimal temperature for maximal catalytic turnover of the enzyme and $\sigma$ is the operating temperature range of the enzyme.

In some variations, the analyte monitoring device may include at least one microneedle with an electrode configured to function as an analyte insensitive channel (e.g., glucose insensitive channel) having a known temperature sensitivity, where such a known temperature sensitivity may be used to compensate for temperature. For example, one advantage of using a glucose insensitive channel includes proximity to the glucose sensor (e.g., resulting in less error from thermal gradients) and cost (e.g., by reducing external components and specialized processes to thermally couple the sensor to the skin). In some variations, the analyte monitoring device may include both an analyte insensitive channel along with a thermistor, with an algorithm that utilizes information from both. Additionally or alternatively, the analyte monitoring device may include an additional sensor(s) that measures ambient temperature, which may also be useful in the temperature compensation algorithm.

In some variations, the analyte insensitive channel may be used to perform differential measurements and/or subtract background noise levels from the analyte-sensitive channel(s) to improve signal fidelity and/or signal-to-noise ratio. The analyte insensitive channel may be sensitive to common mode signals that also arise on the analyte-sensitive channel(s) (e.g., endogenous and pharmacologic interference, pressure attenuations, etc.).

Additionally or alternatively, in some variations, the analyte monitoring device may include at least one kinetic sensor. The kinetic sensor may, for example, comprise an accelerometer, gyroscope, and/or inertial measurement unit to capture positional, displacement, trajectory, velocity, acceleration, and/or device orientation values. For example, such measurements may be used to infer the wearer's physical activity (e.g., steps, intense exercise) over a finite duration. Additionally or alternatively, in some variations, the kinetic sensor(s) may be employed to enable detection of wearer interactions with the analyte monitoring device such as touch or tapping. For example, touch or tap detection can be employed to silence or snooze notifications, alerts, and alarms, control a wirelessly connected mobile computing device, or to activate/deactivate a user interface on the analyte monitoring device (e.g., an embedded display or indicator light). Touching or tapping may be performed in a defined sequence and/or for a predetermined duration (e.g., at least 3 seconds, at least 5 seconds) to elicit certain actions (e.g., display or indicator light deactivation/activation). Additionally or alternatively, in some variations, the analyte monitoring device may enter into a power saving mode upon detection of limited motion or activity (e.g., absence of significant acceleration) for at least a predetermined period of time (e.g., 15 minutes, 30 minutes, 45 minutes, 1 hour, or other suitable of time), as measured by the kinetic sensor(s).

Additionally, or alternatively, in some variations, the analyte monitoring device may include at least one real-time clock (RTC). The real-time clock may be employed to track absolute time (e.g., Coordinated Universal Time, UTC, or local time) when the analyte monitoring device is in storage or during use. In some variations, synchronization to absolute time may be performed following manufacturing of the analyte monitoring device. The real-time clock may be employed to time-stamp analyte measurements (e.g., glucose measurements) during operation of the analyte monitoring device in order to create a time-series data set that is communicated to a connected peripheral device (e.g., mobile computing device), cloud storage, or other suitable data storage device, such as for later review by the user (e.g., wearer of the analyte monitoring device), their support network, or their healthcare provider, etc.

As shown in FIG. 2A, the analyte monitoring device may include one or more power sources 130 (e.g., battery) in the housing 112 configured to provide power to other components. For example, the analyte monitoring device may include an AgO battery, which has a high energy density and is more environmentally friendly than lithium batteries. In some variations, a primary (e.g., non-rechargeable) battery may be used. Furthermore, in some variations, a secondary (e.g., rechargeable) battery may be used. However, any suitable power source may be used, including a lithium-based battery.

In some variations, the power source may be coupled to the device PCB using a low profile holder or mount that reduces the overall height of the electronics, thereby minimizing the height or profile of the analyte monitoring device. For example, whereas traditional battery holders apply force to the topside of the battery using a conductive metal with a spring force, in some variations a lateral mounted battery holder may contact the sides of the battery to complete the electrical circuit. In some variations, the housing may be sized and/or shaped with suitable tolerances so as to apply vertical or downward force on the battery toward the device PCB, in order to keep the battery in contact with the PCB.

In some variations, the analyte monitoring device may be applied manually. For example, a user may remove a protective film on the adhesive layer, and manually press the device onto his or her skin on a desired wear site. Additionally or alternatively, as illustrated in FIG. 1, in some variations the analyte monitoring device may be applied to the skin using a suitable applicator 160. The applicator 160 may, for example, be configured to urge the analyte monitoring device 110 toward the skin of the user such that the microneedle array 140 of the analyte monitoring device 110 may be inserted into the skin (e.g., to the desired target depth). Below are described various example variations of an applicator for applying an analyte monitoring device.

In some variations, an applicator may include an actuatable housing, a trigger, and a shuttle. The shuttle may releasably receive (e.g., grip, cradle, or otherwise carry) the analyte monitoring device. Generally, the housing, trigger, and shuttle may be engaged with one another with one or more releasable coupling features, such that in an application procedure, actuation of the housing (e.g., direct or indirect manual actuation by a user, or with an additional external actuator) may cause a state change in the trigger, which in turn may cause a state change in the shuttle to release the analyte monitoring device from the shuttle. For example, the housing, trigger, and shuttle may be axially aligned (e.g., concentric) and/or nested together. The components of the applicator may be formed with any suitable manufacturing process, including injection molding, casting, 3D printing, machining techniques (e.g., with mill or lathe), and/or the like.

For example, the housing may include at least one trigger retention surface, and the trigger may be arranged in the housing and include at least one trigger member that is releasably engaged with the trigger retention surface. The shuttle may be releasably engaged with the trigger with one or more releasable coupling features and may be configured to receive the analyte monitoring device. The shuttle may have a first "carrying" configuration or form in which the shuttle holds the analyte monitoring device, and a second "releasing" configuration or form in which the shuttle releases the analyte monitoring device. In response to actuation of at least a portion of the housing toward the shuttle (e.g., the applicator may be placed in compression, such as against a patient surface), the trigger member may disengage from the trigger retention surface of the housing, which may cause release of the releasable coupling feature(s) coupling the shuttle and trigger. As a result, the shuttle may transition from its carrying configuration to its releasing configuration, thereby allowing for deployment of the analyte monitoring device from the applicator.

Furthermore, in some variations such as those described below, the applicator may include one or more biasing elements (e.g., spring) that are arranged to urge adjacent components apart. For example, in some variations the applicator may include at least one biasing element arranged between the actuatable housing and the trigger, such that upon actuation of the housing during an application procedure, this biasing element may provide a trigger force to the trigger that causes the trigger to disengage from the trigger retention surface of the housing. Additionally or alternatively, the applicator may include at least one biasing element that is arranged between the trigger and the shuttle. This biasing element may be loaded to store potential energy prior to actuation of the housing (e.g., the biasing element may include a compression spring that is pre-compressed prior to actuation of the housing). Upon actuation of the housing during an application procedure when the shuttle disengages from the trigger, the energy stored in the loaded biasing element may be transferred to the shuttle to thereby drive the analyte monitoring device with a suitable application force (e.g., for suitable skin puncture).

FIGS. 31A-31D depict an example variation of an applicator 1600 for an analyte monitoring device. The applicator 1600 includes an actuatable housing 1620, a trigger 1631 arranged in the housing 1620, and a shuttle 1651 arranged in the trigger 1631. As shown in FIG. 31D, a first biasing element 1628 (e.g., compression spring) may be arranged between the housing 1620 and the trigger 1631, and a second biasing element 1648 (e.g., compression spring) may be arranged between the trigger 1631 and the shuttle 1651. As described above and shown in FIG. 31C, an analyte monitoring device 10 may be received in the shuttle 1651, with a microneedle array in a distal direction oriented away from the housing 1620. A cap 1608 may be removably coupled to the housing 1620 to fully enclose the analyte monitoring device 10 within the housing (e.g., to preserve sterility of the device 10 prior to application).

Figure 32A:
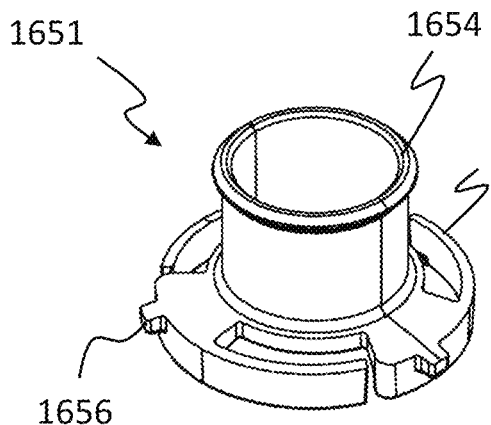
Figure 32B:
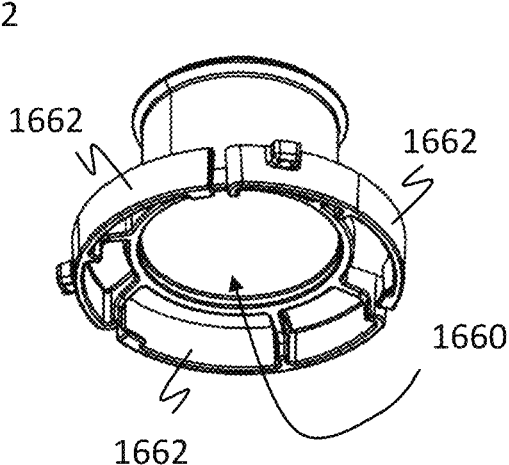
Figure 32C:
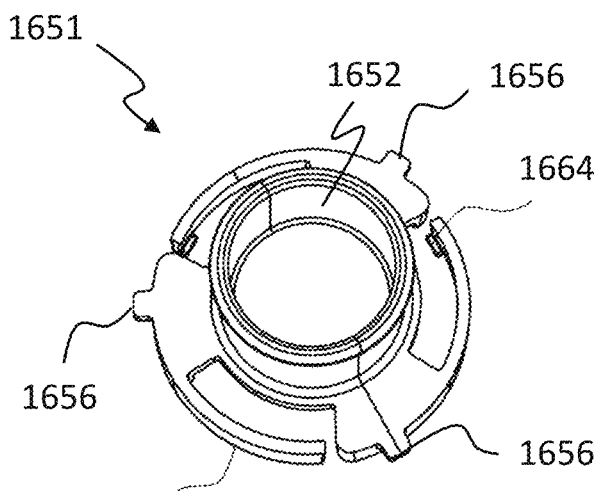
Figure 32D:
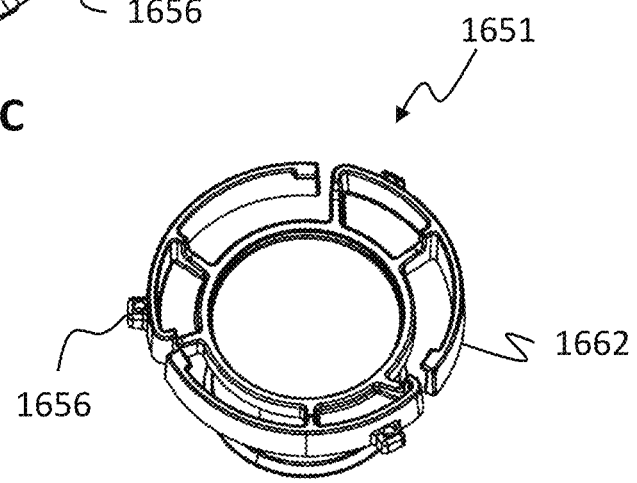
Figure 32E:
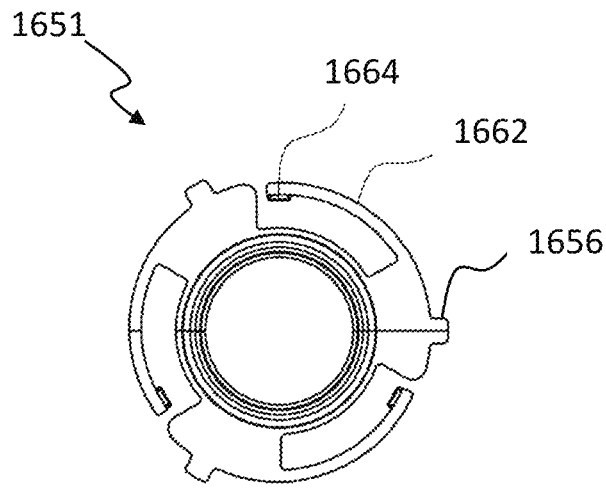
Figure 32F:
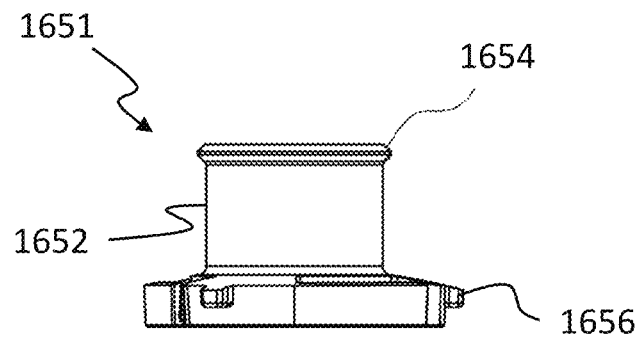
Figure 32G:
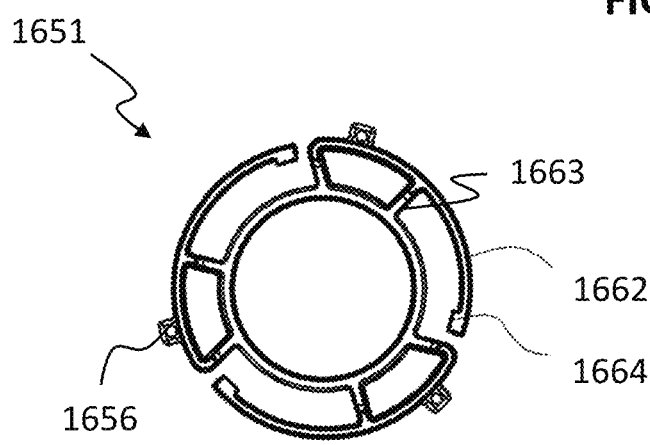

With reference to FIGS. 32A-32G depicting the shuttle 1651 in more detail, the shuttle 1651 may include a base portion with one or more bendable members 1662 extending from a shuttle core 1652, where the bendable members 1662 define a receptacle 1660 in which the analyte monitoring device 10 may be received. For example, as shown in FIG. 32C, the bendable members 1662 include arcuate or spiraling members that are attached at their proximal ends to the shuttle core 1652. The bendable members 1662 may be circumferentially arranged around the shuttle core 1652 to define a substantially circular receptacle 1660 approximating the footprint area of the analyte monitoring device 10 for cradling the analyte monitoring device 10. Although the shuttle 1651 is shown with three bendable members 1662, it should be understood that in other variations, the shuttle 1651 may have any suitable number of bendable members (e.g., one, two, four, five, six, or more).

Each of the bendable members 1662 may further include one or more coupling features (e.g., arranged at a distal end of the bendable member 1662) each configured to mate with a corresponding coupling feature on the analyte monitoring device 10. For example, as shown in FIG. 32C, at least one bendable member may include a tab 1664 or other projection that may be inserted into a corresponding opening 12 (shown in FIG. 31D) on an analyte monitoring device when the analyte monitoring device 10 is placed in the receptacle 1660. Such engagement between the bendable member(s) 1662 and the analyte monitoring device may thereby securely engage the analyte monitoring device within the receptacle 1660, when the bendable members 1662 are flexed sufficiently radially inward ("carrying configuration" of the shuttle) and the tabs 1664 are mated with their corresponding openings 12 on the analyte monitoring device. When the distal ends of bendable members 1662 flex sufficiently radially outward ("releasing configuration" of the shuttle), the tabs 1664 may disengage from the openings 12 of the analyte monitoring device. As described in further detail below, such disengagement of the coupling features on the shuttle and the analyte monitoring device may enable release of the analyte monitoring device from the applicator.

Although FIGS. 32A-32G depict a shuttle with tabs as coupling features for securing the analyte monitoring device to the shuttle, it should be understood that the shuttle may additionally or alternatively include other types of coupling features. For example, while FIGS. 32A-32G depict a substantially rectangular-shaped tab on the bendable members, the tabs may have any suitable shape (e.g., triangular, circular, semi-circular, etc.) and/or suitable cross-sectional profile (e.g., a tab may have substantially uniform thickness, or may be thinner at a radially outward side compared to a radially inward side attached to the bendable member 1662 such that the tab more easily self-aligns and mates with an opening 12 on the analyte monitoring device). As another example, in some variations a bendable member 1662 may include an opening on its distal end that is configured to receive a tab or other outward projection on the analyte monitoring device (not shown).

While FIGS. 32A-32G depict a coupling scheme in which coupling features on the bendable members 1662 are radially inward facing to engage a side edge of the analyte monitoring device, a coupling feature on a bendable member may be oriented in any suitable direction to engage the analyte monitoring device. For example, in some variations, at least a portion of a bendable member 1662 may include a shoulder along its length, forming a ledge-like surface that supports a lower (e.g., skin-facing) surface of the analyte monitoring device resting on the shoulder. In these variations, similar to the variation shown in FIGS. 32A-32G, when the shoulder portions of the bendable members 1662 flex radially outward, the shoulder portions may disengage from the lower surface of the analyte monitoring device, thereby enabling release of the analyte monitoring device from the applicator.

Furthermore, different kinds of coupling features may be combined in a single shuttle design. For example, a shuttle may include at least one bendable member having a tab similar to tab 1664 that engages an opening on the analyte monitoring device, at least one bendable member having an opening that receives a tab on the analyte monitoring device, at least one bendable member having a shoulder, or any combination thereof.

FIGS. 33A-33F depict detailed views of the trigger 1631, which may be configured to engage the shuttle 1651 received therein, as shown in FIG. 31C. For example, the shuttle 1651 may be substantially axially aligned and nested within the trigger 1631, and the shuttle 1651 may move axially within the trigger 1631. The trigger 1631, when activated by actuation of the housing, functions to cause disengagement of the analyte monitoring device from the shuttle 1651.

Figure 33G:
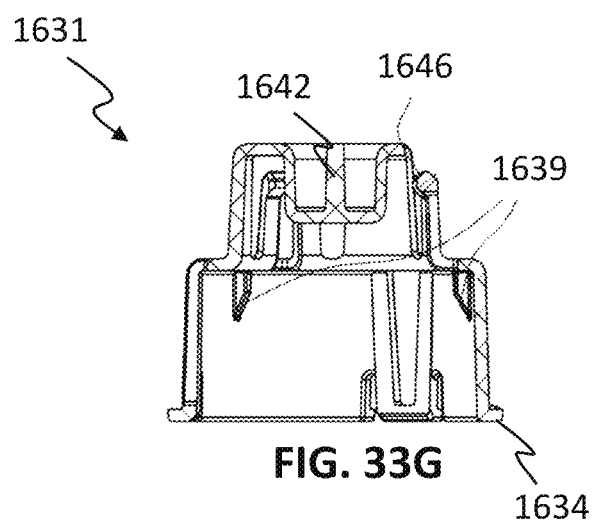

As shown in FIG. 33A, the trigger 1631 may include a base portion 1633. The bendable members 1662 of the shuttle (when the shuttle is placed in the trigger) may be generally biased outward toward the interior of the base portion 1633. However, the effective inner diameter of the base portion 1633 may vary along the height of the base portion, which controls the permitted extent of outward flexure of the bendable members 1662. For example, the interior of the trigger 1631 may include one or more sloped edges against which the bendable members 1662 engage. The sloped edges may, for example, be located on one or more angled trigger ribs 1639 as best shown in FIG. 33G, where an outwardly angled ramp or slope on the trigger ribs 1639 allows the bendable members 1662 to flex radially outward when the shuttle moves away from the housing (e.g., downward in the orientation shown in FIG. 33G). As such, if the shuttle moves in a direction away from the housing, the bendable members 1662 may gradually flex outward and gradually transition the shuttle from its carrying configuration to its releasing configuration.

Rotational alignment of the shuttle 1651 within the trigger 1631 may be guided by one or more tracking features. For example, the trigger 1631 may include one or more tracks 1637 within which outward tracking features 1656 on the shuttle may travel. The tracks 1637 may include open slots as shown in FIGS. 33A-33G, or other suitable structures (e.g., recessed grooves or channels) that the tracking features 1656 on the shuttle may slidingly engage. The tracks 1637 may furthermore be configured to receive other suitable kinds of tracking features on the shuttle (e.g., ball bearings). Additionally or alternatively, the shuttle 1651 may instead include one or more tracks within which outward tracking features on the trigger may travel. The shuttle 1651 and/or the trigger 1631 may each include any suitable number of tracking features (e.g., one, two, three, four or more) and the tracking features may be circumferentially distributed in an equal or unequal manner. For example, a shuttle may have two tracking features equally distributed around the shuttle (180 degrees apart from one another, or directly opposing each other), or three tracking features equally distributed around the shuttle (120 degrees apart from one another), or four tracking features equally distributed around the shuttle (90 degrees apart from one another), etc.

A crown portion 1641 of the trigger 1631 may be configured to control when the shuttle is able to move axially within the trigger. For example, as shown in FIG. 37A, a crown portion 1641 of the trigger 1631 may receive and engage with the shuttle core 1652, with a firing biasing element 1648 (e.g., spring) arranged inside the shuttle core 1652 and loaded between the shuttle and the trigger. The crown portion 1641 may include one or more trigger members 1644 having a catch 1646 (e.g., hook, lip, and/or the like) that may engage a shuttle lip 1654 extending at least partially around the shuttle core 1652. A trigger member 1644 may include an elongated structure that has a proximal end that is fixed to the base portion 1633 and a distal free end that extends into the crown portion 1641. As shown in FIG. 33A, for example, a trigger member 1644 may include a trigger retention slot 1644 (or channel, etc.) along its longitudinal length that engages with a retention member 1617 of the housing. In some variations, one or more of the trigger members 1644 may have an arcuate transverse cross-section that has a radius of curvature similar to a radius of curvature of the rest of the crown portion 1641. The trigger 1631 may include any suitable number of trigger members 1644 (e.g., one, two, three, four or more), and the trigger members may be circumferentially distributed in an equal or unequal manner. For example, a trigger may have two trigger members equally distributed around the trigger (180 degrees apart from one another, or directly opposing each other), or three trigger members equally distributed around the trigger (120 degrees apart from one another), or four trigger members equally distributed around the trigger (90 degrees apart from one another), etc.

FIGS. 34A-34G depict a housing 1620 of the applicator 1600. The housing 1620 may include a housing cavity that receives the trigger 1631 and the shuttle 1651. As shown in FIG. 37A, a first biasing element 1628 (e.g., spring) may be arranged inside the housing cavity and on a mount 1642 and/or similar mount inside the housing cavity. The housing 1620 may be configured to be manipulated (e.g., manually by a user) to actuate the applicator 1600 to deploy the analyte monitoring device loaded within the shuttle 1651.

The housing 1620 may include one or more retention members 1617 within the housing cavity. The one or more retention members 1617 may include at least one trigger retention surface for releasably engaging the trigger member(s) 1644 of the trigger 1631 and maintaining the trigger in a loaded (unfired) state until the housing 1620 is actuated during an application procedure. For example, a retention member 1617 may include a wall that extends radially inward from an interior surface of the housing 1620 and engages (e.g., inserts into) the trigger retention slot 1644 as described above. As such, the thickness of the retention member (as measured in a circumferential direction around the housing 1620) may approximate the width of the trigger retention slot 1644. In some variations, a retention member 1617 may have a stepped profile, with one step configured to engage with a trigger member 1644 when the trigger is in a loaded state, and another step configured to engage with the trigger member 1644 after the trigger has been activated and is in the fired state, as further described below.

In some variations, the housing 1620 may include or be coupled to a grip 1613. For example, the grip 1613 may include a sheath or ring that is slipped around the housing 1620, or coupled to the housing 1620 with suitable mechanical interfit such as threads, interference fit, etc. For example, as shown in FIG. 34B, the housing may include one or more ribs 1611a configured to engage and rotationally align with the grip 1613 and/or a shoulder 1611b configured to engage and axially align the grip 1613. In some variations, the grip 1613 may be integrally formed with the housing 1620 (e.g., overmolded) and/or the housing 1620 may include one or more of the grip features described herein. In some variations, the grip 1613 may include one or more features to enhance the ability of a user to manipulate the housing 1620. For example, the grip may include one or more concave or otherwise recessed contours with finger-receiving surfaces to improve manual graspability, as on housing 1620 shown in FIG. 34A or housing 1620' shown in FIG. 34H. Additionally or alternatively, the grip may include one or more convex textural features (bumps, ridges, ribs, rings, etc.) to increase friction, as on housing 1620" shown in FIG. 34I. Additionally or alternatively, the grip 1613 may include one or more materials with greater friction (e.g., silicone or other elastomer). The overall shape of the housing may vary. For example, the housing may be generally prismatic or dome-shaped and/or have a circular or polygonal cross-section, or any other suitable shape.

Furthermore, in some variations, as described above with respect to FIG. 31D, the applicator may include an applicator cap 1608 coupled to the housing to enclose the analyte monitoring device 10 within the applicator and help preserve sterility of the analyte monitoring device 10 until its application to a user. Examples of further techniques to preserve the sterility of the analyte monitoring device 10 and that may be used in conjunction with the applicator are described in U.S. Patent App. No. 63/249,399, which is incorporated herein by this reference. In some variations, the cap 1608 may be coupled to the housing 1620 via mechanical interfit (e.g., threads, snap fit) and/or other suitable means (e.g., epoxy that may be overcome with sufficient applied separation force). Furthermore, in some variations the coupling of the cap 1608 and the housing 1620 may include one or more seals (e.g., gasket). Similar to the grip 1613, the cap 1608 may include one or more feature to enhance the ability of a user to manipulate the cap (e.g., to separate the cap from the housing prior to use of the applicator). For example, as shown in FIG. 34H, cap 1608' may include ribs to increase friction and graspability of the cap. As another example, as shown in FIG. 34I, cap 1608" may include concave features and polygonal edges to enhance graspability of the cap.

Turning now to the use of the applicator 1600, FIGS. 35A-35B and FIGS. 36A-36C illustrate an example method for loading the analyte monitoring device 10 into the applicator 1600, such as during a manufacturing process. The analyte monitoring device 10 may be inserted into or otherwise received by the shuttle 1651, as described above. Specifically, as shown in greater detail in FIGS. 35A and 35B depicting the underside of the applicator, the analyte monitoring device 10 may be placed between the bendable members 1662 of the shuttle (with the microneedle array pointing away from the housing). The analyte monitoring device 10 may be rotationally oriented so as to align its openings 12 with tabs 1664 on the bendable members 1662, and the tabs 1664 may collectively be inserted into the openings 12 (or recesses, etc.) in order to carry the analyte monitoring device 10 in the space between the bendable members 1662.

As shown in FIG. 36A, the shuttle 1651 with the analyte monitoring device 10 may be pushed into the interior of the trigger 1631 while the trigger 1631 is arranged within the housing 1620. As shown in the detailed view of FIG. 36A, as the shuttle 1651 is pushed further into the trigger 1631, the shuttle lip 1654 (which may be an outward projection located around at least a portion of the shuttle core) may push into at least one trigger catch 1646 of the trigger. Due at least in part to the sloped nature of the interfacing surfaces of the shuttle lip 1654 (e.g., 1654' shown in FIG. 37C) and the trigger catch 1646, advancing the shuttle lip 1654 into the trigger may push the trigger catch 1646 up past a lower step (1617a shown in FIG. 37C) of the stepped retention member 1617 of the housing (FIG. 36B). As the trigger catch 1646 is pushed up past this lower step, the trigger member may flex radially outward, allowing the shuttle lip 1654 to bypass the trigger catch 1646. Once the shuttle lip 1654 is pushed further into the trigger and passes the trigger catch 1646, the trigger catch 1646 is allowed to fall back into place onto the lower step of the retention member 1617 (FIG. 36C). Once the trigger catch 1646 is re-engaged with the lower step of the retention member 1617, the shuttle lip 1654 is secured over the trigger catch 1646, thereby locking the shuttle in place within the trigger and housing in the shuttle's carrying configuration, simultaneously locking the analyte monitoring device 10 in the shuttle.

Additional cross-sectional views of the coupling between the shuttle, trigger, and housing when the analyte monitoring device is loaded in the applicator are shown in FIGS. 37A-37E and further described below. An underside view of the analyte monitoring device 10 as loaded in the applicator is also depicted in FIG. 35B, showing that the bendable members 1662 are engaged with the openings 12 of the analyte monitoring device 10, and also locked into a radially inward flexure position (the shuttle's carrying form) to secure the analyte monitoring device 10 in the applicator.

As described above, the analyte monitoring device 10 may be oriented with its openings 12 aligned with tabs 1664 on the bendable members 1662, and the tabs 1664 may be inserted into the openings 12 in order to carry the analyte monitoring device 10 in the space between the bendable members 1662. When the shuttle is locked in place within the trigger as described above with respect to FIGS. 36A-36C, the bendable members 1662 additionally are urged radially inwards by the trigger ribs 1639 on the interior of the trigger (FIG. 37E) such that the tabs 1664 are locked into the openings 12 of the analyte monitoring device 10.

Furthermore, as shown in FIG. 37A, a first biasing element 1628 (e.g., compression spring) may be arranged in a relaxed or unloaded state between the trigger and the housing. The first biasing element 1628, in this state, may urge the trigger and the housing apart, and transfer an actuation force to the trigger when the housing is pushed into the trigger. Additionally, a second biasing element 1648 may be arranged in a compressed or loaded state between the shuttle and the trigger, storing energy for forcefully ejecting the shuttle away from the trigger to deploy the analyte monitoring device 2. Although the first and second biasing elements 1628 and 1648 are shown as compression springs in FIG. 37A, it should be understood that other biasing elements (e.g., spring arms, leaf springs, etc.) may additionally or alternatively be used to function as the first biasing element 1628 and/or the second biasing elements 1648.

During an application procedure, at least a portion of the housing 1620 may be actuated toward the shuttle 1651 (or toward the trigger 1631). For example, at least a portion of the housing 1620 may be pushed or compressed. Alternatively, at least a portion of the housing 1620 may be rotated, tilted, or actuated in any manner to move the housing 1620 toward the shuttle and/or trigger. The entire housing may be actuated, or may include a pushable button (or other suitable actuator) to accomplish an appropriate mechanical force transfer similar to that described below. With reference to FIG. 37B, as the housing 1620 is pushed toward the shuttle 1651 or trigger 1631, the first biasing element 1628 compresses, which communicates or provides a trigger force to the trigger members 1644. This trigger force may cause the trigger members 1644 to become disengaged from the trigger retention surfaces 1617a on the lower step of the retention members 1617 and flex radially outward to move into a clearance to rest on the second step 1617b of the retention members 1617 in the housing. This outward movement of the trigger members 1644 results in the disengagement of the shuttle lip 1654 from the trigger members 1644, which unlocks the shuttle 165 and allows it to move axially within the trigger 1631. When the shuttle 1651 is unlocked in this manner, the second biasing element 1648 relaxes and releases its stored energy to accelerate or forcefully eject the shuttle 1651 axially downward (in the orientation shown in FIG. 38). The shuttle 1651 continues to move axially until the tracking features 1656 engaged in slots of tracks 1637 reach the lower edge of the slots of tracks 1637. Simultaneously, as the shuttle 1651 moves axially downwards, its bendable members 1662 gradually are allowed to flex radially outward from the shuttle's carrying configuration to the shuttle's releasing configuration, as permitted by the outwardly sloped or ramped surfaces on the trigger ribs 1639. When the bendable members 1662 are sufficiently radially outwardly flexed, the bendable members 1662 disengage from the analyte monitoring device 10 to allow the analyte monitoring device 10 to be fully separated from the applicator 1600. The longer the length of the outwardly sloped or ramped surfaces on the trigger ribs 1639, the later the outward flexure of the bendable members 1662 and ultimate release of the analyte monitoring device 10. As such, longer sloped or ramped surfaces on the trigger ribs 1639 may help ensure that the analyte monitoring device 10 is held in a secure position for longer duration as the shuttle is released. During the application procedure, the analyte monitoring device 10 is ejected from the shuttle and thus from the applicator, but the shuttle 1651 remains in the trigger 1631 at least in part due to the continued engagement of the shuttle lip 1654 within slots of the trigger members 1644.

FIGS. 39A-39D depict an example variation of an applicator 2400 similar to applicator 1600 described above, with certain differences as described below. For example, the applicator 2400 may include a housing 2410 (which may include or be coupled to a grip 2412), a trigger 2430, and a shuttle 2450 that are coupled to one another. A first biasing element 2428 may be arranged between the housing 2410 and the trigger 2430 to provide a trigger force, and a second biasing element 2448 may be arranged between the trigger 2430 and the shuttle 2450 to provide a firing force, similar to first and second biasing elements described above with respect to applicator 1600. The applicator 2400 may further include a cap 2408 removably coupled to the housing 2410, and the cap 2408 may be similar to the cap 1608 described above with respect to applicator 1600.

With reference to features shown in the detailed views of the shuttle 2450 shown in FIGS. 40A and 40B, the trigger 2430 shown in FIGS. 41A-41E, and the housing 2410 shown in FIGS. 42A-42E, below is a description of operation of the applicator 2400. FIG. 43 depicts the applicator 2400 in a loaded state in which an analyte monitoring device 10 (not pictured) may be carried in the shuttle 2450 in a receptacle defined at least in part by one or more coupling members 2464 and/or an annular rim (or partially annular rim) within or upon which the analyte monitoring device may rest. The shuttle 2450 may be engaged with the trigger 2430 such that outer periphery of the shuttle 2450 may interfere with (e.g., press radially outwardly against) an inner side wall surface of the trigger 2430, and the trigger side wall urges the shuttle 2450 into a carrying configuration with coupling members 2464 locked around the analyte monitoring device 10. In some variations, the periphery of shuttle 2450 may include one or more outwardly projecting members 2462 that engage and track within corresponding tracks 2416 (e.g., slots, recesses) in the sidewall of the trigger 2430, such as to maintain rotational alignment between the shuttle 2450 and the trigger 2430. The shuttle 2450 may include a shuttle stem 2452 extending from a central portion of the shuttle 2450 and configured to engage with a central opening between collet arm-like leaflets 2432 of the trigger 2430. The leaflets 2432 may be circumferentially arranged around the trigger 2430. Each leaflet 2432 may have a proximal end integrated with or otherwise attached to a periphery of the trigger 2430 (e.g., around the annular or partially annular base 2439, or at a sidewall of the trigger) to support the leaflet. Additionally, each leaflet 2432 may have a free distal end that extends towards the center of the trigger 2430 and has a surface 2432a to engage with a surface 2452a of the shuttle stem. Although the trigger 2430 is shown in the figures to include three leaflets, it should be understood that the trigger 2430 may include any suitable number of leaflets (e.g., one, two, four, or more, etc.). The leaflets may be arranged circumferentially in an equal or unequal manner. For example, a trigger may have two leaflets equally distributed around the trigger (180 degrees apart from one another, or directly opposing each other), or three leaflets equally distributed around the trigger (120 degrees apart from one another), or four leaflets equally distributed around the trigger (90 degrees apart from one another), etc.

The trigger 2430, in turn, may engage the interior of the housing 2410. As shown in FIG. 43. Trigger nubs 2436 are arranged around the exterior of the leaflets 2438 and project radially outwards such that the interior side surface of the housing 2410 interferes with the nubs 2436 and urge the leaflets 2438 inwards. This radially inward-directed force urges the leaflets 2438 in a closed configuration around the shuttle stem 2452 and further axially lock the shuttle 2450 in engagement with the trigger 2430 at a location where second biasing element 2448 (e.g., spring) is compressed or otherwise loaded with energy for firing the shuttle 2450 in response to trigger activation. Furthermore, similar to applicator 1600, a first biasing element 2428 may be arranged between the housing 2410 and the trigger 2430 to provide a trigger force.

FIG. 44 depicts the applicator 2400 in a fired state after the trigger 2430 has been activated (e.g., by actuating the housing 2410 toward the shuttle 2450 and/or trigger 2430). For example, when at least a portion of the housing 2410 is pushed and actuated toward the shuttle 2450 and/or trigger 2430, the housing 2410 moves toward the shuttle and/or trigger and the nubs 2436 on the trigger leaflets 2432 slip into the tracks 2416 in the housing. When the trigger leaflets 2432 are seated in the tracks 2416, this relieves the centrally-directed pressure on the trigger leaflets 2432 and permits the leaflets 2432 to expand radially outwards, thereby causing the central opening to widen and release the shuttle stem 2452. Once the shuttle stem 2452 is released, the shuttle 2450 is free to move axially with the trigger (downward, in the orientation shown in FIG. 44) to a point where the inner diameter of the trigger widens and allows the coupling members 2464 to flex radially outward and release the analyte monitoring device 10 in the shuttle's releasing configuration. This axial motion of the shuttle 2450 may be accelerated by the second biasing element 2448, which urges the shuttle 2450 and the analyte monitoring device 10 carried within downward, until the outwardly projecting members 2462 on the shuttle reach the lowest edge of the tracks 2416 in which the outwardly projecting members 2462 are engaged. The analyte monitoring device 10 is thus ejected from the applicator 2400, and the fired shuttle 2450 is retained within the trigger 2430.

FIGS. 45A-45D depict an example variation of an applicator 3000 similar to applicator 1600 described above, with certain differences as described below. For example, the applicator 3000 may include a housing 3010, a trigger 3030, and a shuttle 3050 that are coupled to one another. A first biasing element 3028 may be arranged between the housing 3010 and the trigger 3030 to provide a trigger force, and a second biasing element 3048 may be arranged between the trigger 3030 and the shuttle 3050 to provide a firing force, similar to first and second biasing elements described above with respect to applicator 1600. The applicator 3000 may further include a base ring 3006 that may be coupled to the housing 3010 (e.g., with one or more fasteners).

With reference to features depicted in the detailed views of the shuttle 3050 shown in FIGS. 46A-46E, the trigger 3030 shown in FIGS. 47A-47D, and the housing 3010 shown in FIGS. 48A-48E, below is a description of operation of the applicator 3000. FIG. 49 depicts the applicator 3000 in a loaded state in which an analyte monitoring device (not shown) may be carried in the shuttle 3050 in a receptacle defined at least in part by one or more coupling members 3064 and/or an annular rim (or partially annular rim) within or upon which the analyte monitoring device may rest. The shuttle 3050 may be arranged in the interior of the trigger 3030, with the receptacle portion (carrying the analyte monitoring device) engaging the inner side wall surface 3036 of the trigger 3030. Nubs 3062 of the shuttle 3050 may engage tracks 3034 (e.g., grooves, channels) within the inner side wall surface 3036, such as to maintain rotational alignment between the shuttle 3050 and the trigger 3030. The shuttle 3050 may have also a shuttle mating connector 3052 that is centrally located in the shuttle and extends upward (in the orientation shown in FIG. 49) from the receptacle portion of the shuttle 3050 carrying the analyte monitoring device. The shuttle 3050 may engage with the housing 3010 via actuator members 3014 that extend longitudinally within a central portion of the housing 3010. Each actuator member 3014 may have an inner catch 3014a that extends through a respective opening in the shuttle mating connector 3052 and engages with the shuttle mating connector 3052. Additionally, each actuator member 3014 may have an outer catch 3014b that engages with a trigger retaining cylinder 3032, such that the actuator members 3014 may be constrained between the shuttle mating connector 3052 and the trigger retaining cylinder 3032. As such, the actuator members 3014 in this locked position maintains the shuttle 3030 in a loaded position in which the shuttle's carrying form holds the analyte monitoring device (with the receptacle portion engaged against the inner side wall surface 3036, as described above).

FIG. 50 depicts the applicator 3000 in a fired state and the trigger 3030 has been activated (e.g., by activating the housing 3010 toward the shuttle 3050 and/or trigger 3030). For example, when at least a portion of the housing 3010 is pushed and actuated toward the shuttle 3050 and/or trigger 3030, the housing 3010 moves toward the shuttle and/or trigger and the actuator members 3014 are freed from the trigger retaining cylinder 3032. The freed actuator members 3014 are permitted to flex radially outward, which causes the inner catches 3014a to disengage from the shuttle mating connector 3052. Once the shuttle mating connector 3052 is disengaged and unlocked from the actuator members 3014, the shuttle 3050 is free to move axially within the trigger (downward, in the orientation shown in FIG. 50) to a point where the inner side wall surface 3036 widens and allows the coupling members 3064 (hidden behind analyte monitoring device 10 in FIG. 50) to flex radially outward and release the analyte monitoring device 10 in the shuttle's releasing form.

This axial motion of the shuttle 3050 is accelerated by the second biasing element 3048, which urges the shuttle 3050 and the analyte monitoring device 10 carried within downward, until shuttle nubs 3062 on the periphery of the shuttle reach the lowest edge of the tracks 3034 in which the nubs 3062 are engaged. The analyte monitoring device 10 is thus ejected from the applicator 3000, and the fired shuttle 3050 is retained within the trigger 3030.

Applicator variations as described above (e.g., applicator 1600, applicator 2400, and applicator 3000) may each include a certain combination of variations of a housing, a trigger, and a shuttle that interact with one another. However, it should be understood that one or more features of the housing, trigger, and/or shuttle variations described herein may be combined in any suitable manner. Furthermore, one or more features of the housing, trigger, and/or shuttle variations described herein may be combined with other housing, trigger, and/or shuttle designs not described herein. As such, any of the shuttle features described herein may be implemented with various implementations of the trigger and/or housing. Similarly, any of the trigger features described herein may be implemented with various implementations of the shuttle and/or the housing, and any of the housing features described herein may be implemented with various implementations of the shuttle and/or the trigger.

For example, described below are additional shuttle variations, which may be combined with any of the housing and/or trigger variations described above, or any suitable housing and/or trigger variations.

With reference to FIG. 51A-FIG. 51N, another shuttle variation 3600 comprising a deformable ring is depicted. Aspects of a shuttle 3600 are depicted in FIG. 51A-FIG. 51F. FIG. 51A, FIG. 51B, and FIG. 51C depict a bottom perspective view, a side view, and a bottom view of a first implementation of the shuttle 3600. FIG. 51D, FIG. 51E, and FIG. 51F depict a bottom perspective view, a side view, and a bottom view of a second implementation of the shuttle 3600.

A bottom ring portion 3610 of the shuttle 3600 may be configured to retain an analyte monitoring device in a constrained (e.g., closed, stored or otherwise carrying) configuration. The bottom ring portion 3610 may be configured to release the analyte monitoring device in an expanded (e.g., opened or releasing) configuration.

In the first implementation, shown in FIGS. 51A, 51B, and 51C, the bottom ring portion 3610 may be generally elliptical or oval in shape in the constrained configuration. In the expanded configuration, the bottom ring portion may be generally circular. In the constrained configuration, the analyte monitoring device may contact inner side walls of the bottom ring portion 3610, while in the expanded configuration, the analyte monitoring device has no contact with the inner side walls of the bottom ring portion 3610, thereby allowing for the analyte monitoring device to be released.

In the second implementation, shown in FIGS. 51D, 51E, and 51F, the bottom ring portion 3610 may be generally triangular in the constrained configuration; for example, the bottom ring portion 3610 may have a tri-lobular shape. In the expanded configuration, the bottom ring portion may be generally circular. The triangular shape provides for three points of contact between the wearable device and the inner side walls of the bottom ring portion 3610 when the bottom ring portion 3610 is in the constrained configuration.

The shuttle 3600 has two or more movable ribs 3620 that facilitate movement of the bottom ring 3610 between the constrained configuration and the expanded configuration. The two or more ribs 3620 connect between the bottom ring portion 3610 and a spring retention cavity of the shuttle 3600. The spring retention member forms a recess in which a firing spring is contained and interfaces with a trigger for deployment of the wearable device from the shuttle 3600.

FIG. 51G-FIG. 51I depict the shuttle 3600 engaged with a trigger 3650 in a loaded position. In the loaded position, the bottom ring portion 3610 is in the constrained configuration. FIG. 51J-FIG. 51L depict the shuttle 3600 engaged with the trigger 3650 in a deployed position. In the deployed position, the bottom ring portion 3610 is in the expanded configuration.

The shuttle 3600 may have one or more pairs of guide walls on an outer wall of the bottom ring portion 3610. Each of the one or more pairs of shuttle guide walls may interface (e.g., align and/or engage) with a corresponding one of a trigger wall ramp. The one or more trigger wall ramps are formed on an internal side wall of the trigger 3650. The shuttle 3600 may additionally include one or more shuttle notches that interface (e.g., align and/or engage) with corresponding channels of the trigger 3650. The trigger channels may be formed through the sidewalls of the trigger 3650. Each of the shuttle notches may be formed on a corresponding portion of the ribs 3620.

In the loaded position, the pairs of shuttle guide walls are interfaced with the trigger wall ramps, and the shuttle notches are interfaced with the trigger channels. In the deployed position, the pairs of shuttle guide walls are no longer interfaced with the trigger wall ramps, allowing for the bottom ring portion 3610 to move from the constrained configuration to the expanded configuration, thereby releasing the wearable device.

FIG. 51M and FIG. 51N depict an alternative implementation of the bottom wall portion 3610 of the shuttle 3600. In this implementation two upper extensions extend across a top portion of the bottom wall portion 3610, which assists with retention of the wearable device in the bottom wall portion 3610.

FIG. 52A and FIG. 52B depict yet another shuttle variation. A shuttle 3700 includes three or more retention walls 3710 that move from a constrained position to an expanded position. In the constrained position, the retention walls engage an analyte monitoring device such that the analyte monitoring device is held within inner side portions of the retention walls 3710. In the expanded position, the retention walls are moved such that the engagement between the inner side portions of the retention walls 3710 and the analyte monitoring device is broken. This allows for the deployment of the analyte monitoring device from the shuttle 3700.

The shuttle 3700 has a spring retention cavity for containing therein the firing spring, which interfaces with a trigger for deployment of the analyte monitoring device from the shuttle 3700 as described in accordance with other implementations herein.

In some implementations, each retention wall 3710 may have a corresponding notch that interfaces with a first opening of the trigger in the constrained configuration and that interfaces with a second opening of the trigger in the expanded configuration. The first opening is positioned at a lateral height above the second opening, and a lateral circumference along the first openings is smaller than a lateral circumference along the second openings. When the shuttle 3700 is released, the notches move from the first openings to the second openings, allowing the retention walls 3710 to move from the constrained configuration to the expanded configuration.

According to another, alternate or additional implementation, one or more wedges may be provided along a bottom portion of the trigger to move the retention walls from the constrained configuration to the expanded configuration. In some implementations, each wedge may correspond to a groove or opening between adjacent ones of the retention walls 3710.

Aspects of an applicator 3800 with an actuatable housing 3810, trigger 3820, and shuttle 3830 are depicted in FIG. 53A-FIG. 53K. FIG. 53A is an expanded view of the applicator 3800, illustrating the alignment of the housing 3810, the trigger 3820, and the shuttle 3830. The housing 3810 is the outermost component and defines an interior cavity into which the trigger 3820 is removably fitted. The trigger 3820 is generally concentric with the housing 3810. The trigger 3820 defines an interior cavity into which the shuttle 3830 is removably fitted. The shuttle 3830 includes a mechanism for holding and releasing an analyte monitoring device.

A trigger spring and a firing spring (not shown) are provided. The trigger spring provides a trigger force and is positioned between an inner surface of the actuator 3810 and an outer surface of the trigger 3820. A firing spring provides a deployment force and is positioned between an inner surface of the trigger 3820 and an outer surface of the shuttle 3830. FIG. 53A also illustrates an example analyte monitoring device that may be contained within the applicator 3800 for deployment and insertion into the dermis of a user.

FIG. 53B-FIG. 53E illustrate aspects of the shuttle 3830. The shuttle includes a spring post for the firing spring and three or more retention walls that move from a constrained position to an expanded position. In the constrained position, the retention walls engage an analyte monitoring device such that the analyte monitoring device is held within inner side portions of the retention walls. In the expanded position, the retention walls are moved such that the engagement between the inner side portions of the retention walls and the analyte monitoring device is broken. This allows for the deployment of the analyte monitoring device from the shuttle 3830.

FIG. 53F-FIG. 53H depict aspects of the trigger 3820. The trigger 3820 may interact with the shuttle 3830 according to the various implementations described herein. The trigger 3820 has one or more retention walls on an upper surface of the trigger 3820.

FIG. 53I-FIG. 53K depicts aspects of the housing 3810. On an internal top surface of the housing 3810 are one or more clamps. The one or more clamps are configured to interface and/or engage with the trigger retention walls. When the actuator is pressed downwards, the retention walls are moved within the clamps so that the trigger 3820 causes downward movement of the shuttle 3830, resulting in deployment of the analyte monitoring device.

FIG. 54A and FIG. 54B depict yet another shuttle variation. A shuttle 3900 includes a ring that interfaces with a deploy mechanism. The deploy mechanism has external side walls that interface with internal engagement features of the ring such that the deploy mechanism is movable within the ring. The ring is configured to retain an analyte monitoring device. The deploy mechanism, when deployed by a trigger, moves in a downward direction within the ring and engages the analyte monitoring device, thereby deploying the analyte monitoring device from the ring.

In some variations, some or all components of the analyte monitoring system may be provided in a kit (e.g., to a user, to a clinician, etc.). For example, a kit may include at least one analyte monitoring device 110 and/or at least one applicator 160. In some variations, a kit may include multiple analyte monitoring devices 110, which may form a supply of analyte monitoring devices sufficient that is for a predetermined period of time (e.g., a week, two weeks, three weeks, a month, two months, three months, six months, a year, etc.). The kit may include any suitable ratio of applicators to analyte monitoring devices (e.g., 1:1, lower than 1:1, greater than 1:1). For example, the kit may include the same number of applicators as analyte monitoring devices, such as if each applicator is single-use and is configured to be disposed after its use in applying a respective analyte monitoring device to the user. As another example, the kit may include a number of applicators that is lower than the number of analyte monitoring devices in the kit (e.g., one applicator per two or three analyte monitoring devices), such as if an applicator is intended to be reused for applying multiple analyte monitoring devices or if multiple analyte monitoring devices are loaded into a single applicator for repeated applications. As another example, the kit may include a number of applicators that is higher than the number of analyte monitoring devices in the kit (e.g., two applicators per analyte monitoring device), such as to provide extra or redundant applicators in case of applicator loss or breakage, etc.

In some variations, the kit may further include user instructions for operating the analyte monitoring device and/or applicator (e.g., instructions for applying the analyte monitoring device manually or with the applicator, instructions for pairing the analyte monitoring device with one or more peripheral devices (e.g., computing devices such as a mobile phone), etc.).

Described below is an overview of various aspects of a method of use and operation of the analyte monitoring system, including the analyte monitoring device and peripheral devices, etc.

As described above, the analyte monitoring device is applied to the skin of a user such that the microneedle array in the device penetrates the skin and the microneedle array's electrodes are positioned in the upper dermis for access to dermal interstitial fluid. For example, in some variations, the microneedle array may be geometrically configured to penetrate the outer layer of the skin, the stratum corneum, bore through the epidermis, and come to rest within the papillary or upper reticular dermis. The sensing region, confined to the electrode at the distal extent of each microneedle constituent of the array (as described above) may be configured to rest and remain seated in the papillary or upper reticular dermis following application in order to ensure adequate exposure to circulating dermal interstitial fluid (ISF) without the risk of bleeding or undue influence with nerve endings.

In some variations, the analyte monitoring device may include a wearable housing or patch with an adhesive layer configured to adhere to the skin and fix the microneedle array in position. While the analyte monitoring device may be applied manually (e.g., removing a protective film on the adhesive layer, and manually pressing the patch onto the skin on a desired wear site), in some variations the analyte monitoring device may be applied to the skin using a suitable applicator, such as any of the applicators described above. For example, any of the applicators described above (with base removed, if applicable) may be placed in contact against a patient surface, with the microneedle array directed toward the patient surface. The housing of the applicator may be actuated toward the patient surface (e.g., by pushing at least a portion of the housing toward the patient surface), thereby causing a shuttle carrying the analyte monitoring device to transition between a first configuration and a second configuration to release the analyte monitoring device.

The analyte monitoring device may be applied in any suitable location, though in some variations it may be desirable to avoid anatomical areas of thick or calloused skin (e.g., palmar and plantar regions), or areas undergoing significant flexion (e.g., olecranon or patella). Suitable wear sites may include, for example, on the arm (e.g., upper arm, lower arm), shoulder (e.g., over the deltoid), back of hands, neck, face, scalp, torso (e.g., on the back such as in the thoracic region, lumbar region, sacral region, etc. or on the chest or abdomen), buttocks, legs (e.g., upper legs, lower legs, etc.), and/or top of feet, etc.

Once the analyte monitoring device is inserted and warm-up and any calibration has completed, the analyte monitoring device may be ready for providing sensor measurements of a target analyte. The target analyte (and any requisite co-factor(s)) diffuses from the biological milieu, through the biocompatible and diffusion-limiting layers on the working electrode, and to the biorecognition layer including the biorecognition element. In the presence of a co-factor (if present), the biorecognition element may convert the target analyte to an electroactive product.

A bias potential may be applied between the working and reference electrodes of the analyte monitoring device, and an electrical current may flow from the counter electrode to maintain the fixed potential relationship between the working and reference electrodes. This causes the oxidation or reduction of the electroactive product, causing a current to flow between the working electrodes and counter electrodes. The current value is proportional to the rate of the redox reaction at the working electrode and, specifically, to the concentration of the analyte of interest according to the Cottrell relation as described in further detail above.

The electrical current may be converted to a voltage signal by a transimpedance amplifier and quantized to a digital bitstream by means of an analog-to-digital converter (ADC). Alternatively, the electrical current may be directly quantized to a digital bitstream by means of a current-mode ADC. The digital representation of the electrical current may be processed in the embedded microcontroller(s) in the analyte monitoring device and relayed to the wireless communication module for broadcast or transmission (e.g., to one or more peripheral devices). In some variations, the microcontroller may perform additional algorithmic treatment to the data to improve the signal fidelity, accuracy, and/or calibration, etc.

In some variations, the digital representation of the electrical current, or sensor signal, may be correlated to an analyte measurement (e.g., glucose measurement) by the analyte monitoring device. For example, the microcontroller may execute a programmed routine in firmware to interpret the digital signal and perform any relevant algorithms and/or other analysis. Keeping the analysis on-board the analyte monitoring device may, for example, enable the analyte monitoring device to broadcast analyte measurement(s) to multiple devices in parallel, while ensuring that each connected device has the same information. Thus, generally, the user's target analyte (e.g., glucose) values may be estimated and stored in the analyte monitoring device and communicated to one or more peripheral devices.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to explain the principles of the invention and its practical applications, they thereby enable others skilled in the art to utilize the invention and various embodiments with various modifications as are suited to the particular use contemplated. It is intended that the following claims and their equivalents define the scope of the invention.

NUMBERED EMBODIMENTS OF THE INVENTION

Notwithstanding the appended claims, the disclosure sets forth the following numbered embodiments:

Embodiment I-1. An applicator for an analyte monitoring device, the applicator comprising a housing comprising a body defining a cavity therein, wherein the housing body comprises a distal opening, a cuff received within the cavity and comprising a lumen therethrough, and a shuttle slidably received within the lumen and configured to releasably retain the analyte monitoring device, wherein the applicator is movable between a collapsed configuration, an extended configuration, and a released configuration, and wherein in the collapsed configuration, the analyte monitoring device is retained within the shuttle, and the shuttle and a distal edge of the cuff are in a proximal most position, in the extended configuration, the distal edge of the cuff is in a distal most position and the shuttle is in an intermediate position, and in the released configuration, the analyte monitoring device is released from the shuttle, the distal edge of the cuff is in an intermediate position, and the shuttle is in a distal most position.

Embodiment I-2. The applicator of embodiment I-1, wherein in the collapsed configuration, the shuttle and a distal edge of the cuff are positioned proximal of the distal opening of the housing body, in the extended configuration, the distal edge of the cuff is positioned distal of the distal opening of the housing body, and the shuttle is positioned proximal of the distal opening of the housing body, and in the released configuration, the distal edge of the cuff and the shuttle are each positioned distal of the distal opening of the housing body.

Embodiment I-3. The applicator of any one of the preceding embodiments, wherein, when the applicator is in the collapsed configuration, a position of the distal edge of the cuff is fixed relative to a position of the shuttle.

Embodiment I-4. The applicator of any one of the preceding embodiments, further comprising a base configured to removably couple to the housing body at the distal opening.

Embodiment I-5. The applicator of any one of the preceding embodiments, further comprising a friction ring releasably engageable with the cuff.

Embodiment I-6. The applicator of any one of the preceding embodiments, wherein the housing body further comprises a recess formed in a distal surface of the housing body and the base further comprises a wall circumferentially disposed around a microneedle enclosure releasably coupled to a proximal surface of the base.

Embodiment I-7. The applicator of any one of the preceding embodiments, wherein the housing body further comprises a mount that extends from a proximal end of the housing body toward the distal opening of the housing body.

Embodiment I-8. The applicator of any one of the preceding embodiments, further comprising a locking member at least partially received in at least one side opening of the housing body and releasably engageable with the cuff.

Embodiment I-9. The applicator of any one of the preceding embodiments, wherein the applicator is locked when it is in the collapsed configuration.

Embodiment I-10. The applicator of any one of the preceding embodiments, further comprising a locking member, wherein the applicator is unlocked when the locking member is actuated.

Embodiment I-11. The applicator of any one of the preceding embodiments, wherein, when the applicator is in the collapsed configuration, the locking member is engaged with the cuff, thereby preventing the cuff from moving distally toward the distal opening of the housing body.

Embodiment I-12. The applicator of any one of the preceding embodiments, wherein engagement between the locking member and the cuff comprises contact between an upper edge of the locking member and a retention lip of the cuff.

Embodiment I-13. The applicator of any one of the preceding embodiments, wherein the cuff comprises one or more tracks within which a corresponding one or more tracking projections on the shuttle may be slidably engaged, thereby maintaining alignment of the cuff with the shuttle when the applicator is moved from the collapsed configuration to the extended configuration and to the released configuration.

Embodiment I-14. The applicator of any one of the preceding embodiments, wherein actuation of the locking member releases the engagement between the locking member and the cuff, thereby allowing the cuff to move toward the distal opening of the housing body and the applicator to move from the collapsed configuration to the extended configuration.

Embodiment I-15. The applicator of any one of the preceding embodiments, wherein, when the locking member is actuated, the shuttle moves towards the distal opening of the housing body.

Embodiment I-16. The applicator of any one of the preceding embodiments, further comprising a base configured to removably couple to the housing body at the distal opening, wherein movement of the cuff toward the distal opening of the housing body axially displaces the base relative to the housing body.

Embodiment I-17. The applicator of any one of the preceding embodiments, further comprising a base configured to removably couple to the housing body at the distal opening, wherein a distal surface of the cuff pushes a proximal surface of the base during movement of the cuff toward the distal opening of the housing body, thereby axially displacing the base relative to the housing body.

Embodiment I-18. The applicator of any one of the preceding embodiments, wherein the distal surface of the cuff is a bottom surface of a bottom flange of the cuff.

Embodiment I-19. The applicator of any one of the preceding embodiments, wherein, when the applicator is in the collapsed configuration, the base wall is received within the recess of the housing body.

Embodiment I-20. The applicator of any one of the preceding embodiments, further comprising a microneedle enclosure releasably coupled to a proximal surface of the base, the microneedle enclosure comprising a cavity and a capsule slidably-received therein, the capsule enclosing a microneedle array of the analyte monitoring device when the applicator is in the collapsed configuration.

Embodiment I-21. The applicator of any one of the preceding embodiments, wherein, when the applicator is in the collapsed configuration, enclosure of the microneedle array by the capsule maintains sterility of the microneedle array.

Embodiment I-22. The applicator of any one of the preceding embodiments, wherein the housing body further comprises a mount that extends from a proximal end of the housing body toward the distal opening of the housing body, and wherein, when the applicator is in the extended configuration, the mount is releasably-engaged with the shuttle.

Embodiment I-23. The applicator of any one of the preceding embodiments, wherein engagement between the mount and the shuttle comprises contact between a retention surface of at least one downward extending finger of the mount and a shelf on an outer surface of the shuttle.

Embodiment I-24. The applicator of any one of the preceding embodiments, wherein the base comprises a lockout arm configured to be releasably received in a recess in the housing body.

Embodiment I-25. The applicator of any one of the preceding embodiments, wherein the lockout arm is biased radially outward toward the housing body when received in the recess in the housing body.

Embodiment I-26. The applicator of any one of the preceding embodiments, wherein the lockout arm is configured to prevent reattachment of the base to the housing body when the applicator is in the extended configuration.

Embodiment I-27. The applicator of any one of the preceding embodiments, wherein the base further comprises a plurality of lockout arms circumferentially positioned on a proximal surface of the base.

Embodiment I-28. The applicator of any one of the preceding embodiments, wherein the base further comprises a retention arm configured to be received between the cuff and an inner surface of the housing body.

Embodiment I-29. The applicator of any one of the preceding embodiments, wherein the retention arm is configured to releasably engage a retention surface on the cuff.

Embodiment I-30. The applicator of any one of the preceding embodiments, wherein, when the applicator is in the extended configuration, the retention arm is engaged with the retention surface on the cuff, thereby inhibiting further separation between the base and the cuff.

Embodiment I-31. The applicator of any one of the preceding embodiments, wherein, when the applicator is in the extended configuration, the base wall is outside of the recess of the housing body.

Embodiment I-32. The applicator of any one of the preceding embodiments, wherein at least a portion of the cuff is extended beyond the distal opening of the housing body when the applicator is in the extended configuration.

Embodiment I-33. The applicator of any one of the preceding embodiments, further comprising a microneedle enclosure releasably coupled to a proximal surface of the base and configured to enclose a microneedle array of the analyte monitoring device when the applicator is in the collapsed configuration, wherein, when the applicator is in the extended configuration, the microneedle enclosure does not enclose the microneedle array.

Embodiment I-34. The applicator of any one of the preceding embodiments, wherein, when the applicator is in the extended configuration, the friction ring is engaged with the cuff, thereby preventing the cuff from moving distally relative to the distal opening of the housing body.

Embodiment I-35. The applicator of any one of the preceding embodiments, wherein, when the applicator is in the extended configuration, a protruding circumferential edge of the friction ring is engaged with an underside of a ledge of the cuff, thereby preventing the cuff from moving distally relative to the distal opening of the housing body.

Embodiment I-36. The applicator of any one of the preceding embodiments, wherein the friction ring further comprises at least one flexible tab extending distally from a top ledge of the friction ring, wherein, when the applicator moves from the collapsed configuration to the extended configuration, the at least one flexible tab engages a corresponding sill proximate an upper ledge of the cuff.

Embodiment I-37. The applicator of any one of the preceding embodiments, wherein the friction ring and the cuff are locked together after the applicator is moved to the extended configuration.

Embodiment I-38. The applicator of any one of the preceding embodiments, wherein engagement between the at least one flexible tab of the friction ring and the corresponding sill of the cuff prevents proximal movement of the cuff relative to the friction ring.

Embodiment I-39. The applicator of any one of the preceding embodiments, wherein, when the applicator is in the extended configuration, the mount is releasably engaged with the friction ring.

Embodiment I-40. The applicator of any one of the preceding embodiments, wherein engagement between the mount and the friction ring comprises contact between a friction ring retention surface of at least one downward extending finger of the mount and a projection of the friction ring.

Embodiment I-41. The applicator of any one of the preceding embodiments, wherein, when the applicator is in the extended configuration, the mount is releasably engaged with the shuttle.

Embodiment I-42. The applicator of any one of the preceding embodiments, wherein engagement between the mount and the shuttle comprises contact between a shuttle retention surface of at least one downward extending finger of the mount and a shelf on an outer surface of the shuttle.

Embodiment I-43. The applicator of any one of the preceding embodiments, wherein engagement between the mount and the shuttle prevents the cuff from moving proximally relative to the distal opening of the housing body.

Embodiment I-44. The applicator of any one of the preceding embodiments, wherein the applicator is moved from the extended configuration to the released configuration after the base is removed from the housing.

Embodiment I-45. The applicator of any one of the preceding embodiments, wherein, when the applicator moves to the released configuration, the friction ring retention surface of the at least one downward extending finger of the mount disengages from the projection of the friction ring.

Embodiment I-46. The applicator of any one of the preceding embodiments, wherein, when the applicator moves to the released configuration, the shuttle retention surface of the at least one downward extending finger of the mount disengages from the shelf on the outer surface of the shuttle.

Embodiment I-47. The applicator of any one of the preceding embodiments, wherein, when the applicator moves to the released configuration, disengagement of the friction ring from the mount causes the at least one downward extending finger of the mount to bend away from the shuttle, thereby releasing the shuttle retention surface of the at least one downward extending finger from the shuttle member of the shuttle.

Embodiment I-48. The applicator of any one of the preceding embodiments, wherein a biasing member urges the shuttle toward the distal opening of the housing when the shuttle retention surface of the at least one downward extending finger is released from the shelf of the shuttle.

Embodiment I-49. The applicator of any one of the preceding embodiments, wherein, when the applicator is in the released configuration, a distal end of the shuttle is proximate a bottom flange of the cuff.

Embodiment I-50. The applicator of any one of the preceding embodiments, wherein, when the applicator is in the released configuration, one or more tracking projections on the shuttle are engaged with a shuttle flexion surface of the cuff, thereby preventing further movement of the shuttle relative to the cuff and away from a proximal end of the housing body.

Embodiment I-51. The applicator of any one of the preceding embodiments, wherein the applicator comprises a first intermediate configuration between the collapsed configuration and the extended configuration.

Embodiment I-52. The applicator of any one of the preceding embodiments, wherein, when the applicator is in the first intermediate configuration, the cuff is moved away from a proximal end of the housing body and the shuttle is moved away from the proximal end of the housing body and into engagement with the mount.

Embodiment I-53. The applicator of any one of the preceding embodiments, wherein the base is moved away from the proximal end of the housing body and from the distal opening of the housing body when the cuff is axially displaced.

Embodiment I-54. The applicator of any one of the preceding embodiments, wherein the housing body further comprises a recess formed in a distal surface of the housing body, and the base further comprises a wall circumferentially disposed on a proximal surface of the base, and wherein removal of the base wall from the recess comprises displacement of the base wall from within the corresponding recess in the distal surface of the housing body.

Embodiment I-55. The applicator of any one of the preceding embodiments, wherein the applicator is configured to move from the extended configuration to the released configuration following removal of the base from the housing.

Embodiment I-56. The applicator of any one of the preceding embodiments, wherein the applicator comprises a second intermediate configuration between the extended configuration and the released configuration.

Embodiment I-57. The applicator of any one of the preceding embodiments, wherein, when the applicator is in the second intermediate configuration, the base is removed from the housing.

Embodiment I-58. The applicator of any one of the preceding embodiments, wherein the base further comprises a retention arm configured to be received between the cuff and an inner surface of the housing body, the retention arm being configured to releasably engage a retention surface on the cuff, and wherein, when the applicator is in the second intermediate configuration, the retention arm is disengaged from the retention surface of the cuff.

Embodiment I-59. The applicator of any one of the preceding embodiments, wherein disengagement of the retention arm from the retention surface of the cuff comprises movement of the retention arm beyond the retention surface and away from a proximal end of the housing body.

Embodiment I-60. An applicator for an analyte monitoring device, the applicator comprising a housing comprising a body defining a cavity therein, wherein the housing body comprises a distal opening, a cuff received within the cavity and comprising a lumen therethrough, and a shuttle slidably received within the lumen and configured to releasably retain the analyte monitoring device, wherein the applicator is movable between a collapsed configuration, an extended configuration, and a released configuration, and wherein in the collapsed configuration, the analyte monitoring device is retained within the shuttle, the shuttle and a distal edge of the cuff are positioned proximal of the distal opening of the housing body, in the extended configuration, the distal edge of the cuff is positioned distal of the distal opening of the housing body, and the shuttle is positioned proximal of the distal opening of the housing body, and in the released configuration, the analyte monitoring device is released from the shuttle, the distal edge of the cuff is positioned distal of the distal opening of the housing body, and the shuttle is positioned distal of the distal opening of the housing body.

Embodiment I-61. A method of applying an analyte monitoring device to a skin surface of a user, the method comprising providing an applicator in a collapsed configuration, wherein the applicator comprises a shuttle releasably retaining an analyte monitoring device, the shuttle being slidably received within a trigger cavity of a cuff, the cuff being received within a cavity of a housing comprising a body defining the cavity, the housing body comprising a distal opening, transitioning the applicator from the collapsed configuration to an extended configuration, and transitioning the applicator from the extended configuration to a released configuration, and wherein in the collapsed configuration, the shuttle and a distal edge of the cuff are in a proximal most position, in the extended configuration, the distal edge of the cuff is in a distal most position, and the shuttle is in an intermediate position, and in the released configuration, the analyte monitoring device is released from the shuttle, the distal edge of the cuff is in an intermediate position, and the shuttle is in a distal most position.

Embodiment I-62. The method of Embodiment I-61, wherein transitioning the applicator from the extended configuration to the released configuration comprises applying a force to the housing body of the applicator.

Embodiment I-63. The method of any one of Embodiment I-61 through Embodiment I-62, wherein the applicator further comprises a base configured to removably couple to the housing body at the distal opening.

Embodiment I-64. The method of any one of Embodiment I-61 through Embodiment I-63, wherein the applicator further comprises a friction ring releasably engageable with the cuff.

Embodiment I-65. The method of any one of Embodiment I-61 through Embodiment I-64, wherein the housing body further comprises a recess formed in a distal surface of the housing body and the base further comprises a wall circumferentially disposed around a microneedle enclosure releasably coupled to a proximal surface of the base.

Embodiment I-66. The method of any one of Embodiment I-61 through Embodiment I-65, wherein the housing body further comprises a mount that extends from a proximal end of the housing body toward the distal opening of the housing body.

Embodiment I-67. The method of any one of Embodiment I-61 through Embodiment I-66, wherein the applicator further comprises a locking member at least partially received in at least one side opening of the housing body, and where the method further comprises transitioning the applicator between a locked state and an unlocked stock by actuating the locking member via the at least one side opening.

Embodiment I-68. The method of any one of Embodiment I-61 through Embodiment I-67, wherein, when the applicator is in the collapsed configuration, the method further comprises engaging the locking member with the cuff, thereby preventing the cuff from moving distally toward the distal opening of the housing body.

Embodiment I-69. The method of any one of Embodiment I-61 through Embodiment I-68, wherein engagement between the locking member and the cuff comprises contact between an upper edge of the locking member and a retention lip of the cuff.

Embodiment I-70. The method of any one of Embodiment I-61 through Embodiment I-69, wherein transitioning from the collapsed configuration to the extended configuration comprises actuating the locking member to release the engagement between the locking member and the cuff, thereby allowing the cuff to move toward the distal opening of the housing body.

Embodiment I-71. The method of any one of Embodiment I-61 through Embodiment I-70, wherein the housing body further comprises a mount that extends from a proximal end of the housing body toward the distal opening of the housing body, and wherein, when the applicator is in the extended configuration, the mount is releasably-engaged with the shuttle.

Embodiment I-72. The method of any one of Embodiment I-61 through Embodiment I-71, wherein the transitioning the applicator from the collapsed configuration to the extended configuration comprises releasing a microneedle enclosure from a portion of the analyte monitoring device, the microneedle enclosure being configured to enclose a microneedle array of the analyte monitoring device, wherein, when the microneedle enclosure is released, the microneedle enclosure does not enclose the microneedle array.

Embodiment I-73. The method of any one of Embodiment I-61 through Embodiment I-72, wherein the transitioning the applicator from the collapsed configuration to the extended configuration comprises sliding the cuff relative to the friction ring such that at least one flexible tab extending substantially distally from a top ledge of the friction ring engages a corresponding sill proximate an upper ledge of the cuff.

Embodiment I-74. The method of any one of Embodiment I-61 through Embodiment I-73, wherein the friction ring and the cuff are locked together upon transitioning the applicator to the extended configuration.

Embodiment I-75. The method of any one of Embodiment I-61 through Embodiment I-74, wherein the transitioning the applicator from the extended configuration to the released configuration comprises removing the base from the housing.

Embodiment I-76. The method of any one of Embodiment I-61 through Embodiment I-75, wherein during the transitioning of the applicator from the extended configuration to the released configuration, a friction ring retention surface of at least one downward extending finger of the mount disengages from the projection of the friction ring.

Embodiment I-77. The method of any one of Embodiment I-61 through Embodiment I-76, wherein the transitioning the applicator to the released configuration comprises disengaging a shuttle retention surface of at least one downward extending finger of the mount from the shelf on the outer surface of the shuttle.

Embodiment I-78. The method of any one of Embodiment I-61 through Embodiment I-77, wherein transitioning the applicator to the released configuration comprises disengaging the friction ring from the mount such that at least one downward extending finger of the mount bends away from the shuttle, thereby releasing the shuttle retention surface of the at least one downward extending finger from the shuttle member of the shuttle.

Embodiment I-79. The method of any one of Embodiment I-61 through Embodiment I-78, further comprising transitioning the applicator to a first intermediate configuration between the collapsed configuration and the extended configuration.

Embodiment I-80. The method of any one of Embodiment I-61 through Embodiment I-79, further comprising moving the cuff away from a proximal end of the housing body and into engagement with the mount.

Embodiment I-81. The method of any one of Embodiment I-61 through Embodiment I-80, further comprising moving the cuff away from a proximal end of the housing, thereby moving the base away from the proximal end of the housing body and the distal opening of the housing body.

Embodiment I-82. The method of any one of Embodiment I-61 through Embodiment I-81, wherein the transitioning the applicator from the extended configuration to the released configuration comprises removing the base from the housing.

Embodiment I-83. The method of any one of Embodiment I-61 through Embodiment I-82, further comprising transitioning the applicator to a second intermediate configuration between the extended configuration and the released configuration.

Embodiment I-84. The method of any one of Embodiment I-61 through Embodiment I-83, wherein, when the applicator is in the second intermediate configuration, the base is removed from the housing.

Embodiment I-85. An applicator for an analyte monitoring device, the applicator comprising: a. a housing comprising a body defining a cavity therein, wherein the housing body comprises a distal opening and a side opening; b. a cuff received within the cavity; c. a shuttle received within the cavity and configured to releasably retain the analyte monitoring device; d. a locking member at least partially received in the side opening of the housing body, wherein the locking member is engaged with the cuff in a first configuration and disengaged from the cuff in a second configuration; and e. a base configured to removably couple to the housing body at the distal opening, wherein the base comprises a proximal surface, f wherein movement of the locking member from the first configuration to the second configuration releases the cuff thereby decoupling the proximal surface from the housing body.

Embodiment I-86. The applicator of Embodiment I-85, wherein movement of the locking member from the first configuration to the second configuration allows for axial displacement of the cuff relative to the housing body.

Embodiment I-87. The applicator of any one of Embodiment I-85 through Embodiment I-86, wherein the axial displacement of the cuff axially displaces the base relative to the housing body.

Embodiment I-88. The applicator of any one of Embodiment I-85 through Embodiment I-87, wherein a distal surface of the cuff pushes the proximal surface of the base during the axial displacement of the cuff, thereby separating the proximal surface from the housing body.

Embodiment I-89. The applicator of any one of Embodiment I-85 through Embodiment I-88, wherein the distal surface of the cuff is a bottom surface of a distal flange of the cuff.

Embodiment I-90. The applicator of any one of Embodiment I-85 through Embodiment I-89, wherein the base comprises a lockout arm configured to be releasably received in a recess in the housing body.

Embodiment I-91. The applicator of any one of Embodiment I-85 through Embodiment I-90, wherein the lockout arm is biased radially outward or inward toward the housing body when received in the recess in the housing body.

Embodiment I-92. The applicator of any one of Embodiment I-85 through Embodiment I-91, wherein the lockout arm is configured to prevent reattachment of the base to the housing body after the lockout arm is released from the recess of the housing body.

Embodiment I-93. The applicator of any one of Embodiment I-85 through Embodiment I-92, wherein the base comprises a plurality of lockout arms, wherein the plurality of lockout arms are circumferentially positioned around the proximal surface.

Embodiment I-94. The applicator of any one of Embodiment I-85 through Embodiment I-93, wherein the base comprises a retention arm configured to be received between the cuff and an inner surface of the housing body.

Embodiment I-95. The applicator of any one of Embodiment I-85 through Embodiment I-94, wherein the retention arm is configured to releasably engage a retention surface on the cuff.

Embodiment I-96. The applicator of any one of Embodiment I-85 through Embodiment I-95, wherein when the retention arm is engaged with the retention surface on the cuff, the retention arm prevents separation between the base and the cuff.

Embodiment I-97. The applicator of any one of Embodiment I-85 through Embodiment I-96, wherein the retention surface is on an outer surface of the cuff.

Embodiment I-98. The applicator of any one of Embodiment I-85 through Embodiment I-97, wherein engagement between the retention arm and the retention surface of the cuff is maintained during decoupling of the proximal surface from the housing body.

Embodiment I-99. The applicator of any one of Embodiment I-85 through Embodiment I-98, wherein the base comprises a plurality of retention arms, each of the plurality of the retention arms configured to be received between the cuff and an inner surface of the housing body.

Embodiment I-100. The applicator of any one of Embodiment I-85 through Embodiment I-99, wherein the plurality of retention arms are circumferentially positioned around the proximal surface.

Embodiment I-101. The applicator of any one of Embodiment I-85 through Embodiment I-100, wherein the base comprises a retention arm configured to prevent separation between the base and the housing body and a lockout arm configured to prevent reattachment of the base to the housing body.

Embodiment I-102. The applicator of any one of Embodiment I-85 through Embodiment I-101, wherein a length of the lockout arm is greater than a length of the retention arm.

Embodiment I-103. The applicator of any one of Embodiment I-85 through Embodiment I-102, wherein the base comprises a plurality of retention arms and a plurality of lockout arms.

Embodiment I-104. The applicator of any one of Embodiment I-85 through Embodiment I-103, wherein the base comprises sidewalls, and wherein upper edges of the sidewalls are received in a recess in the housing body when the locking member is in the first configuration.

Embodiment I-105. The applicator of any one of Embodiment I-85 through Embodiment I-104, wherein the upper edges of the sidewalls are outside of the recess in the housing body when the locking member is in the second configuration.

Embodiment I-106. The applicator of any one of Embodiment I-85 through Embodiment I-105, wherein the cuff comprises a retention lip, and wherein the locking member is engaged with the retention lip in the first configuration and disengaged from the retention lip in the second configuration.

Embodiment I-107. The applicator of any one of Embodiment I-85 through Embodiment I-106, wherein the locking member is configured to transition from the first configuration to the second configuration upon depression of a portion of the locking member.

Embodiment I-108. The applicator of any one of Embodiment I-85 through Embodiment I-107, wherein the locking member is configured to pivot upon depression of the portion of the locking member.

Embodiment I-109. The applicator of any one of Embodiment I-85 through Embodiment I-108, wherein the housing body comprises a flexible contact member configured to limit movement of the locking member.

Embodiment I-110. The applicator of any one of Embodiment I-85 through Embodiment I-109, wherein a first end of the flexible contact member is coupled to the housing body and a second end is coupled to the locking member.

Embodiment I-111. The applicator of any one of Embodiment I-85 through Embodiment I-110, wherein the cuff comprises a lumen, and wherein the shuttle is positioned within the lumen.

Embodiment I-112. The applicator of any one of Embodiment I-85 through Embodiment I-111, wherein the shuttle is configured to move axially within the lumen of the cuff.

Embodiment I-113. The applicator of any one of Embodiment I-85 through Embodiment I-112, wherein the base is configured to preserve sterility of the analyte monitoring device when the locking member is in the first configuration.

Embodiment I-114. The applicator of any one of Embodiment I-85 through Embodiment I-113, wherein the housing comprises a guide member configured to maintain axial alignment and rotational alignment between the housing body and the cuff.

Embodiment I-115. The applicator of any one of Embodiment I-85 through Embodiment I-114, further comprising a first biasing element arranged between the housing body and the cuff and a second biasing element arranged between the housing body and the shuttle.

Embodiment I-116. A method of using an applicator for an analyte monitoring device, the method comprising transitioning a locking member of an applicator from a first configuration to a second configuration, wherein the applicator comprises a housing body defining a cavity therein, a cuff and a shuttle each received within the cavity, and a base removably coupled to the housing body, wherein the shuttle releasably retains the analyte monitoring device, and wherein transitioning the locking member disengages the locking member from the cuff, thereby allowing the cuff to move relative to the housing body and displace a base of the applicator relative to the housing body.

Embodiment I-117. An applicator for an analyte monitoring device, the applicator comprising a housing comprising a body defining a cavity therein, a cuff received within the cavity and comprising a lumen, and a shuttle received within the lumen, wherein the shuttle comprises a shaft; and a base portion at a distal end of the shaft, wherein the base portion comprises a plurality of flexible leaves extending from the shaft and a plurality of petals extending from the shaft, and wherein the plurality of flexible leaves define a receptacle to retain the analyte monitoring device.

Embodiment I-118. The applicator of Embodiment I-117, wherein at least one flexible leaf of the plurality of flexible leaves comprises an arcuate member.

Embodiment I-119. The applicator of any one of Embodiment I-117 through Embodiment I-118, wherein the at least one flexible leaf of the plurality of flexible leaves further comprises a flexible connector coupling the arcuate member to the core.

Embodiment I-120. The applicator of any one of Embodiment I-117 through Embodiment I-119, wherein the arcuate member comprises a support surface configured to engage the analyte monitoring device when the analyte monitor device is received within the receptacle.

Embodiment I-121. The applicator of any one of Embodiment I-117 through Embodiment I-120, wherein the support surface extends inwardly at a distal end of the arcuate member.

Embodiment I-122. The applicator of any one of Embodiment I-117 through Embodiment I-121, wherein each flexible leaf of the plurality of flexible leaves is configured to flex radially outward.

Embodiment I-123. The applicator of any one of Embodiment I-117 through Embodiment I-122, wherein each flexible leaf of the plurality of flexible leaves is configured to move relative to the shaft.

Embodiment I-124. The applicator of any one of Embodiment I-117 through Embodiment I-123, wherein the plurality of flexible leaves are circumferentially arranged about the shaft.

Embodiment I-125. The applicator of any one of Embodiment I-117 through Embodiment I-124, wherein a distal surface of at least one support petal of the plurality of support petals comprises a radiused surface.

Embodiment I-126. The applicator of any one of Embodiment I-117 through Embodiment I-125, wherein the at least one support petal further comprises a flexible connector coupling the radiused surface to the shaft.

Embodiment I-127. The applicator of any one of Embodiment I-117 through Embodiment I-126, wherein a free end of the radiused surface comprises a support grip configured to engage the analyte monitoring device when the analyte monitoring device is retained in the receptacle.

Embodiment I-128. The applicator of any one of Embodiment I-117 through Embodiment I-127, wherein the support grip is configured to engage a proximal surface of the analyte monitoring device when the analyte monitoring device is retained in the receptacle.

Embodiment I-129. The applicator of any one of Embodiment I-117 through Embodiment I-128, wherein the plurality of support petals are configured to stabilize the analyte monitoring device when the analyte monitoring device is retained in the receptacle.

Embodiment I-130. The applicator of any one of Embodiment I-117 through Embodiment I-129, wherein the plurality of flexible leaves and the plurality of petals are arranged in an alternating configuration around the shaft.

Embodiment I-131. The applicator of any one of Embodiment I-117 through Embodiment I-130, wherein at least one flexible leaf of the plurality of flexible leaves comprises a tracking projection extending radially outward from an outer surface of the at least one flexible leaf.

Embodiment I-132. The applicator of any one of Embodiment I-117 through Embodiment I-131, wherein the tracking projection is configured to engage with a surface of the cuff to stop axial movement of the shuttle.

Embodiment I-133. The applicator of any one of Embodiment I-117 through Embodiment I-132, wherein the shaft comprises an inner cavity.

Embodiment I-134. The applicator of any one of Embodiment I-117 through Embodiment I-133, wherein the applicator further comprises a biasing element positioned within the inner cavity.

Embodiment I-135. The applicator of any one of Embodiment I-117 through Embodiment I-134, wherein the biasing element is configured to transfer stored energy to the shuttle to displace each leaf of the plurality of flexible leaves radially outward.

Embodiment I-136. The applicator of any one of Embodiment I-117 through Embodiment I-135, wherein the displacement of each leaf of the plurality of flexible leaves radially outward is configured to release the analyte monitoring device from the receptacle when retained therein.

Embodiment I-137. The applicator of any one of Embodiment I-117 through Embodiment I-136, wherein the shuttle is configured to prevent reinsertion of the analyte monitoring device into the receptacle after it is released therefrom.

Embodiment I-138. An applicator for an analyte monitoring device, the applicator comprising a housing comprising a housing body and a mount, a cuff-ring assembly comprising a cuff and a friction ring coupled to the cuff, and a shuttle configured to releasably retain the analyte monitoring device, wherein the shuttle and the cuff-ring assembly are separately translatable relative to the housing body, and wherein each of the shuttle and the cuff-ring assembly are releasably coupled to the mount.

Embodiment I-139. The applicator of Embodiment I-138, wherein the mount comprises a plurality of fingers extending from an internal surface of a proximal end of the housing body into the cavity.

Embodiment I-140. The applicator of any one of Embodiment I-138 through Embodiment I-139, wherein the plurality of fingers define a round footprint.

Embodiment I-141. The applicator of any one of Embodiment I-138 through Embodiment I-140, wherein at least one finger of the plurality of fingers comprises a ring retention surface releasably coupled to the friction ring.

Embodiment I-142. The applicator of any one of Embodiment I-138 through Embodiment I-141, wherein the friction ring comprises a ring core and a projection extending inwardly from an internal surface of the ring core, wherein the ring retention surface is releasably coupled to the projection.

Embodiment I-143. The applicator of any one of Embodiment I-138 through Embodiment I-142, wherein the ring retention surface comprises a ledge formed on an outwardly facing surface of the at least one finger of the plurality of fingers of the mount.

Embodiment I-144. The applicator of any one of Embodiment I-138 through Embodiment I-143, wherein at least one finger of the plurality of fingers comprises a shuttle retention surface releasably engaged with the shuttle.

Embodiment I-145. The applicator of any one of Embodiment I-138 through Embodiment I-144, wherein the shuttle comprises an angled surface, and wherein the shuttle retention surface releasably engages the angled surface.

Embodiment I-146. The applicator of any one of Embodiment I-138 through Embodiment I-145, wherein the shuttle retention surface comprises a shoulder formed along an inwardly facing surface of the at least one finger of the plurality of fingers.

Embodiment I-147. The applicator of any one of Embodiment I-138 through Embodiment I-146, wherein the shuttle comprises a shaft comprising a shelf having a distal angled surface, and wherein the shoulder releasably engages the distal angled surface.

Embodiment I-148. The applicator of any one of Embodiment I-138 through Embodiment I-147, wherein at least one finger of the plurality of fingers comprises a ring retention surface releasably coupled with the friction ring and a shuttle retention surface releasably engaged with a distal angled surface on an outer surface of a shaft of the shuttle.

Embodiment I-149. The applicator of any one of Embodiment I-138 through Embodiment I-148, wherein the ring retention surface is on an outwardly facing surface of the at least one finger of the plurality of fingers and the shuttle retention surface is on an inwardly facing surface of the finger of the plurality of fingers.

Embodiment I-150. The applicator of any one of Embodiment I-138 through Embodiment I-149, wherein the ring retention surface and the friction ring are configured to decouple during actuation of the housing.

Embodiment I-151. The applicator of any one of Embodiment I-138 through Embodiment I-150, wherein the shuttle retention surface and the distal angled surface of the shaft of the shuttle are configured to disengage during actuation of the housing.

Embodiment I-152. The applicator of any one of Embodiment I-138 through Embodiment I-151, wherein during actuation of the housing, the ring retention surface is configured to decouple from the friction ring before the shuttle retention surface is configured to disengage from the angled surface of the shuttle shaft.

Embodiment I-153. The applicator of any one of Embodiment I-138 through Embodiment I-152, wherein the shuttle is configured to move axially toward a distal end of the housing body after disengagement of the shuttle retention surface and the distal angled surface of the shuttle shaft.

Embodiment I-154. The applicator of any one of Embodiment I-138 through Embodiment I-153, wherein the shuttle shaft further comprises a proximal angled surface, wherein a distal end of the shuttle retention surface engages the proximal angled surface of the shuttle shaft in response to axial movement of the shuttle toward a proximal end of the housing and after disengagement of the shuttle retention surface and the distal angled surface of the shuttle shaft.

Embodiment I-155. The applicator of any one of Embodiment I-138 through Embodiment I-154, wherein the distal end of the shuttle retention surface comprises a flat surface.

Embodiment I-156. An applicator for an analyte monitoring device, the applicator comprising a housing comprising a housing body defining a cavity therein and a mount extending from an internal surface of a proximal end of the housing body into the cavity, a cuff-ring assembly comprising a cuff having a lumen and a proximal opening, and a friction ring positioned within the lumen and extending through the proximal opening, wherein the cuff-ring assembly is positioned around the mount, and a shuttle configured to releasably retain the analyte monitoring device, wherein a portion of the shuttle extends through the mount.

Embodiment I-157. The applicator of Embodiment I-156, wherein the mount comprises a plurality of fingers extending from the internal surface of the proximal end of the housing body into the cavity.

Embodiment I-158. The applicator of any one of Embodiment I-156 through Embodiment I-157, wherein the plurality of fingers define a round footprint.

Embodiment I-159. The applicator of any one of Embodiment I-156 through Embodiment I-158, wherein at least one finger of the plurality of fingers comprises a ring retention surface releasably coupled to the friction ring.

Embodiment I-160. The applicator of any one of Embodiment I-156 through Embodiment I-159, wherein the friction ring comprises a ring core and a projection extending inwardly from an internal surface of the ring core, wherein the ring retention surface is releasably coupled to the projection.

Embodiment I-161. The applicator of any one of Embodiment I-156 through Embodiment I-160, wherein the ring retention surface comprises a ledge formed on an outwardly facing surface of the at least one finger of the plurality of fingers of the mount.

Embodiment I-162. The applicator of any one of Embodiment I-156 through Embodiment I-160, wherein at least one finger of the plurality of fingers comprises a shuttle retention surface releasably engaged with the shuttle.

Embodiment I-163. The applicator of any one of Embodiment I-156 through Embodiment I-162, wherein the shuttle comprises an angled surface, and wherein the shuttle retention surface releasably engages the angled surface.

Embodiment I-164. The applicator of any one of Embodiment I-156 through Embodiment I-163, wherein the shuttle retention surface comprises a shoulder formed along an inwardly facing surface of the at least one finger of the plurality of fingers.

Embodiment I-165. The applicator of any one of Embodiment I-156 through Embodiment I-164, wherein the shuttle comprises a shaft comprising a shelf having a distal angled surface, and wherein the shoulder releasably engages the distal angled surface.

Embodiment I-166. The applicator of any one of Embodiment I-156 through Embodiment I-165, wherein at least one finger of the plurality of fingers comprises a ring retention surface releasably coupled with the friction ring and a shuttle retention surface releasably coupled with an angled surface on a shaft of the shuttle.

Embodiment I-167. The applicator of any one of Embodiment I-156 through Embodiment I-166, wherein the ring retention surface is on an outwardly facing surface of the at least one finger of the plurality of fingers and the shuttle retention surface is on an inwardly facing surface of the finger of the plurality of fingers.

Embodiment I-168. The applicator of any one of Embodiment I-156 through Embodiment I-167, wherein the ring retention surface and the friction ring are configured to decouple during actuation of the housing.

Embodiment I-169. The applicator of any one of Embodiment I-156 through Embodiment I-168, wherein the shuttle retention surface and the shuttle are configured to disengage during actuation of the housing.

Embodiment I-170. The applicator of any one of Embodiment I-156 through Embodiment I-169, wherein during actuation of the housing, the ring retention surface is configured to decouple from the friction ring before the shuttle retention surface is configured to disengage from the shuttle.

Embodiment I-171. The applicator of any one of Embodiment I-156 through Embodiment I-170, wherein the shuttle is configured to move axially toward a distal end of the housing body after disengagement of the shuttle retention surface and shuttle.

Embodiment I-172. The applicator of any one of Embodiment I-156 through Embodiment I-171, wherein the shuttle comprises a shaft including a proximal angled surface and a distal angled surface, wherein a distal end of the shuttle retention surface engages the proximal angled surface of the shuttle shaft in response to axial movement of the shuttle toward a proximal end of the housing and after disengagement of the shuttle retention surface and the distal angled surface of the shuttle shaft.

Embodiment I-173. An applicator for an analyte monitoring device, the applicator comprising a housing comprising a housing body defining a cavity therein and a mount extending into the cavity, a cuff-ring assembly comprising a cuff and a friction ring coupled to the cuff, a shuttle configured to releasably retain the analyte monitoring device, and a base removably coupled to the housing, wherein the mount is configured to 1) releasably engage the friction ring to prevent axial movement of the shuttle before removal of the base from the housing and 2) releasably engage with the shuttle to control axial movement of the shuttle after removal of the base from the housing.

Embodiment I-174. The applicator of Embodiment I-173, wherein the mount comprises a first retention feature releasably engaged with the friction ring to prevent axial movement of the shuttle before removal of the base from the housing, and a second retention feature releasably engaged with the shuttle to control axial movement of the shuttle after removal of the base from the housing.

Embodiment I-175. The applicator of any one of Embodiment I-173 through Embodiment I-174, wherein the first retention feature is on first side of the mount and the second retention feature is on a second, opposite side of the mount.

Embodiment I-176. A method of applying an analyte monitoring device to a skin surface using an applicator, the method comprising providing an applicator comprising a housing defining a cavity, a cuff, and a shuttle, wherein the cuff and the shuttle are each received within the cavity, wherein the shuttle retains the analyte monitoring device, applying a distal surface of the cuff of the applicator to the skin surface, advancing the housing toward the skin surface, wherein advancing the housing moves the housing relative to the cuff and the shuttle, and disengages one or more retention features preventing movement of the shuttle independently of the housing, wherein disengagement of the one or more retention features releases the shuttle and advances the shuttle with the analyte monitoring device toward the skin surface, and releasing the analyte monitoring device from the shuttle.

Embodiment I-177. The method of Embodiment I-176, wherein releasing the analyte monitoring device from the shuttle comprises engaging a tracking projection of the shuttle with a flexion surface of the cuff.

Embodiment I-178. The method of any one of Embodiment I-176 through Embodiment I-177, wherein the shuttle comprises a plurality of flexible leaves and wherein engaging the tracking projection of the shuttle with the flexion surface of the cuff flexes the flexible leaves radially outward.

Embodiment I-179. The method of any one of Embodiment I-176 through Embodiment I-178, wherein advancing the housing toward the skin surface comprises puncturing the skin surface with a microneedle array of the analyte monitoring device.

Embodiment I-180. The method of any one of Embodiment I-176 through Embodiment I-179, wherein advancing the housing toward the skin surface comprises adhering the analyte monitoring device to the skin surface.

Embodiment I-181. The method of any one of Embodiment I-176 through Embodiment I-180, further comprising removing a base of the applicator from the housing prior to applying the distal surface of the cuff to the skin surface.

Embodiment I-182. The method of any one of Embodiment I-176 through Embodiment I-181, wherein removing the base from the applicator further comprises breaking a sterile seal around a microneedle array of the analyte monitoring device.

Embodiment I-183. The method of any one of Embodiment I-176 through Embodiment I-182, further comprising transitioning a locking member of the applicator from a first configuration to a second configuration.

Embodiment I-184. The method of any one of Embodiment I-176 through Embodiment I-183, wherein transitioning the locking member disengages the locking member from the cuff, thereby allowing the cuff to move relative to the housing.

Embodiment I-185. The method of any one of Embodiment I-176 through Embodiment I-184, wherein movement of the cuff relative to the housing upon disengagement of the locking member from the cuff moves a base of the applicator relative to the housing.

Embodiment I-186. The method of any one of Embodiment I-176 through Embodiment I-185, wherein movement of the base relative to the housing breaks a sterile seal between a microneedle enclosure coupled to the base and the analyte monitoring device.

Embodiment I-187. The method of any one of Embodiment I-176 through Embodiment I-186, further comprising removing the base from the applicator.

Embodiment I-188. An applicator for an analyte monitoring device, the applicator comprising a housing comprising a body defining a cavity therein and a distal opening, a cuff slidably received within the cavity and comprising a lumen therethrough, a shuttle slidably received within the lumen and configured to releasably retain the analyte monitoring device, a first biasing element arranged between the housing and the cuff, a second biasing element arranged between the housing and the shuttle, a microneedle enclosure releasably engaged with the analyte monitoring device and configured to enclose a portion of the analyte monitoring device when engaged, the microneedle enclosure comprising a third biasing element, and a base releasably engaged with the housing and coupled to the microneedle enclosure.

Embodiment I-189. The applicator of Embodiment I-188, wherein the first biasing element is configured to bias the cuff toward the distal opening.

Embodiment I-190. The applicator of any one of Embodiment I-188 through Embodiment I-189, wherein the second biasing element is configured to bias the shuttle toward the distal opening.

Embodiment I-191. The applicator of any one of Embodiment I-188 through Embodiment I-190, wherein the microneedle enclosure maintains sterility of the analyte monitoring device when engaged.

Embodiment I-192. The applicator of any one of Embodiment I-188 through Embodiment I-191, wherein the shuttle is configured to slide relative to the cuff and to the housing body.

Embodiment I-193. The applicator of any one of Embodiment I-188 through Embodiment I-192, wherein the cuff is configured to slide relative to the shuttle and to the housing body.

Embodiment I-194. The applicator of any one of Embodiment I-188 through Embodiment I-193, wherein the microneedle enclosure comprises a cavity and a capsule slidably-received therein, the cavity comprising the third biasing element, the capsule enclosing the portion of the analyte monitoring device when the microneedle enclosure and the analyte monitoring device are engaged.

Embodiment I-195. The applicator of any one of Embodiment I-188 through Embodiment I-194, wherein the third biasing element biases the capsule toward the analyte monitoring device.

Embodiment I-196. The applicator of any one of Embodiment I-188 through Embodiment I-195, wherein the microneedle enclosure further comprises a force concentrator arranged within the cavity, the force concentrator comprising a shaft and a head, the shaft being disposed within the third biasing element, wherein the force concentrator and the third biasing element are incorporated to bias the capsule toward the analyte monitoring device to maintain the enclosure for the analyte monitoring device.

Embodiment I-197. The applicator of any one of Embodiment I-188 through Embodiment I-196, wherein the shuttle and the cuff are telescopically-arranged within the housing body.

Embodiment I-198. The applicator of any one of Embodiment I-188 through Embodiment I-197, wherein the first biasing element, the second biasing element, and the third biasing element are each selected from the group consisting of: a coiled metal spring, a plastic leaf spring, and a coiled plastic spring.

Embodiment I-199. The applicator of any one of Embodiment I-188 through Embodiment I-198, wherein the analyte monitoring device comprises a microneedle array oriented away from a proximal end of the housing body.

Embodiment I-200. The applicator of any one of Embodiment I-188 through Embodiment I-199, wherein the first biasing element is further arranged around a mount that extends from a proximal end of the housing body toward the distal opening of the housing body.

Embodiment I-201. The applicator of any one of Embodiment I-188 through Embodiment I-200, wherein the mount comprises at least one downward extending finger configured to releasably engage the shuttle.

Embodiment I-202. The applicator of any one of Embodiment I-188 through Embodiment I-201, further comprising a friction ring arranged around the mount and around a shaft of the shuttle, the shuttle shaft extending away from the analyte monitoring device and toward the proximal end of the housing body.

Embodiment I-203. The applicator of any one of Embodiment I-188 through Embodiment I-202, wherein the mount comprises at least one downward extending finger configured to releasably engage the friction ring.

Embodiment I-204. The applicator of any one of Embodiment I-188 through Embodiment I-203, further comprising a locking member at least partially received within a side opening of the housing body and releasably engaged with the cuff.

Embodiment I-205. The applicator of any one of Embodiment I-188 through Embodiment I-204, wherein actuation of the locking member releases engagement between the locking member and the cuff, thereby permitting the cuff to move.

Embodiment I-206. The applicator of any one of Embodiment I-188 through Embodiment I-205, wherein the microneedle enclosure comprises locking tabs configured to engage connector features of the analyte monitoring device.

Embodiment I-207. The applicator of any one of Embodiment I-188 through Embodiment I-206, wherein the base comprises a retention arm configured to be received between the cuff and an inner surface of the housing body.

Embodiment I-208. The applicator of any one of Embodiment I-188 through Embodiment I-207, wherein the retention arm is configured to releasably engage a retention surface on the cuff.

Embodiment I-209. The applicator of any one of Embodiment I-188 through Embodiment I-208, wherein the retention arm prevents separation between the base and the cuff when the retention arm is engaged with the retention surface on the cuff.

Embodiment I-210. The applicator of any one of Embodiment I-188 through Embodiment I-209, wherein the base comprises a plurality of retention arms, each of the plurality of the retention arms configured to be received between the cuff and the inner surface of the housing body.

Embodiment I-211. The applicator of any one of Embodiment I-188 through Embodiment I-210, wherein the base comprises a lockout arm configured to be releasably received in a recess in the housing body.

Embodiment I-212. The applicator of any one of Embodiment I-188 through Embodiment I-211, wherein the lockout arm is biased radially outward toward the housing body when received in the recess in the housing body.

Embodiment I-213. The applicator of any one of Embodiment I-188 through Embodiment I-212, wherein the base comprises a plurality of lockout arms, and wherein the plurality of lockout arms are circumferentially positioned around the base.

Embodiment I-214. The applicator of any one of Embodiment I-188 through Embodiment I-213, wherein the cuff comprises one or more tracks within which a corresponding one or more tracking projections on the shuttle may be slidably engaged.

Embodiment I-215. The applicator of any one of Embodiment I-188 through Embodiment I-214, wherein the one or more tracks are circumferentially disposed around the cuff and the corresponding one or more tracking projections are circumferentially disposed at corresponding positions around the shuttle.

Embodiment I-216. The applicator of any one of Embodiment I-188 through Embodiment I-215, wherein the housing body comprises one or more guides on an inner surface thereof and the cuff comprises a corresponding one or more guided projections on an outer surface thereof, the corresponding one or more guided projections being slidably engageable with the one or more guides.

The invention claimed is:

1. An applicator for an analyte monitoring device, the applicator comprising:
a housing comprising a body defining a cavity therein, wherein the housing body comprises a distal opening;
a cuff received within the cavity and comprising a lumen therethrough; and
a shuttle slidably received within the lumen and configured to releasably retain the analyte monitoring device,
wherein the applicator is movable between a collapsed configuration, an extended configuration, and a released configuration, and wherein
in the collapsed configuration, the analyte monitoring device is retained within the shuttle, and the shuttle and a distal edge of the cuff are in a proximal most position,
in the extended configuration, the distal edge of the cuff is in a distal most position and the shuttle is in an intermediate position, and
in the released configuration, the analyte monitoring device is released from the shuttle, the distal edge of the cuff is in an intermediate position, and the shuttle is in a distal most position.

2. The applicator of claim 1, wherein
in the collapsed configuration, the shuttle and the distal edge of the cuff are positioned proximal of the distal opening of the housing body,
in the extended configuration, the distal edge of the cuff is positioned distal of the distal opening of the housing body, and the shuttle is positioned proximal of the distal opening of the housing body, and
in the released configuration, the distal edge of the cuff and the shuttle are each positioned distal of the distal opening of the housing body.

3. The applicator of claim 1, further comprising a base configured to removably couple to the housing body at the distal opening.

4. The applicator of claim 3, wherein the housing body further comprises a recess formed in a distal surface of the housing body and the base further comprises a wall circumferentially disposed around a microneedle enclosure releasably coupled to a proximal surface of the base.

5. The applicator of claim 3, further comprising a microneedle enclosure releasably coupled to a proximal surface of the base, the microneedle enclosure comprising a cavity and a capsule slidably-received therein, the capsule enclosing a microneedle array of the analyte monitoring device when the applicator is in the collapsed configuration.

6. The applicator of claim 3, wherein the base comprises a lockout arm configured to be releasably received in a recess in the housing body.

7. The applicator of claim 3, wherein the base further comprises a retention arm configured to be received between the cuff and an inner surface of the housing body.

8. The applicator of claim 3, further comprising a microneedle enclosure releasably coupled to a proximal surface of the base and configured to enclose a microneedle array of the analyte monitoring device when the applicator is in the collapsed configuration, wherein, when the applicator is in the extended configuration, the microneedle enclosure does not enclose the microneedle array.

9. The applicator of claim 3, wherein the applicator is moved from the extended configuration to the released configuration after the base is removed from the housing.

10. The applicator of claim 1, further comprising a friction ring releasably engageable with the cuff.

11. The applicator of claim 10, wherein the housing body further comprises a mount that extends from a proximal end of the housing body toward the distal opening of the housing body.

12. The applicator of claim 11, wherein, when the applicator is in the extended configuration, the mount is releasably engaged with the friction ring.

13. The applicator of claim 12, wherein engagement between the mount and the friction ring comprises contact between a ring retention surface of at least one downward extending finger of the mount and a projection of the friction ring.

14. The applicator of claim 13, wherein, when the applicator moves to the released configuration, the ring retention surface of the at least one downward extending finger of the mount disengages from the projection of the friction ring.

15. The applicator of claim 11, wherein, when the applicator is in the extended configuration, the mount is releasably engaged with the shuttle.

16. The applicator of claim 15, wherein engagement between the mount and the shuttle comprises contact between a shuttle retention surface of at least one downward extending finger of the mount and a shelf on an outer surface of the shuttle.

17. The applicator of claim 16, wherein, when the applicator moves to the released configuration, the shuttle retention surface of the at least one downward extending finger of the mount disengages from the shelf on the outer surface of the shuttle.

18. The applicator of claim 17, wherein, when the applicator moves to the released configuration, disengagement of the friction ring from the mount causes the at least one downward extending finger of the mount to bend away from the shuttle, thereby releasing the shuttle retention surface of the at least one downward extending finger from the shuttle member of the shuttle.

19. The applicator of claim 10, wherein, when the applicator is in the extended configuration, the friction ring is engaged with the cuff, thereby preventing the cuff from moving distally relative to the distal opening of the housing body.

20. The applicator of claim 1, further comprising a locking member at least partially received in at least one side opening of the housing body and releasably engageable with the cuff.

21. The applicator of claim 20, wherein, when the applicator is in the collapsed configuration, the locking member is engaged with the cuff, thereby preventing the cuff from moving distally toward the distal opening of the housing body.

22. The applicator of claim 21, wherein engagement between the locking member and the cuff comprises contact between an upper edge of the locking member and a retention lip of the cuff.

23. The applicator of claim 20, wherein actuation of the locking member releases the engagement between the locking member and the cuff, thereby allowing the cuff to move toward the distal opening of the housing body and the applicator to move from the collapsed configuration to the extended configuration.

24. The applicator of claim 23, wherein, when the locking member is actuated, the shuttle moves towards the distal opening of the housing body.

25. The applicator of claim 24, further comprising a base configured to removably couple to the housing body at the distal opening, wherein movement of the cuff toward the distal opening of the housing body axially displaces the base relative to the housing body.

26. The applicator of claim 1, wherein the cuff comprises one or more tracks within which a corresponding one or more tracking projections on the shuttle may be slidably engaged, thereby maintaining alignment of the cuff with the shuttle when the applicator is moved from the collapsed configuration to the extended configuration and to the released configuration.

27. The applicator of claim 1, wherein, when the applicator is in the released configuration, one or more tracking projections on the shuttle are engaged with a shuttle flexion surface of the cuff, thereby preventing further movement of the shuttle relative to the cuff and away from a proximal end of the housing body.

28. An applicator for an analyte monitoring device, the applicator comprising:
  a housing comprising a body defining a cavity therein, wherein the housing body comprises a distal opening;
  a cuff received within the cavity and comprising a lumen therethrough; and
  a shuttle slidably received within the lumen and configured to releasably retain the analyte monitoring device,
  wherein the applicator is movable between a collapsed configuration, an extended configuration, and a released configuration, and wherein
    in the collapsed configuration, the analyte monitoring device is retained within the shuttle, the shuttle and a distal edge of the cuff are positioned proximal of the distal opening of the housing body,
    in the extended configuration, the distal edge of the cuff is positioned distal of the distal opening of the housing body, and the shuttle is positioned proximal of the distal opening of the housing body, and
    in the released configuration, the analyte monitoring device is released from the shuttle, the distal edge of the cuff is positioned distal of the distal opening of the housing body, and the shuttle is positioned distal of the distal opening of the housing body.

29. A method of applying an analyte monitoring device to a skin surface of a user, the method comprising:
  providing an applicator in a collapsed configuration, wherein the applicator comprises a shuttle releasably retaining an analyte monitoring device, the shuttle being slidably received within a trigger cavity of a cuff, the cuff being received within a cavity of a housing comprising a body defining the cavity, the housing body comprising a distal opening;
  transitioning the applicator from the collapsed configuration to an extended configuration; and
  transitioning the applicator from the extended configuration to a released configuration;
  and wherein
    in the collapsed configuration, the shuttle and a distal edge of the cuff are in a proximal most position,
    in the extended configuration, the distal edge of the cuff is in a distal most position, and the shuttle is in an intermediate position, and
    in the released configuration, the analyte monitoring device is released from the shuttle, the distal edge of the cuff is in an intermediate position, and the shuttle is in a distal most position.

* * * * *